(12) United States Patent
Takaku et al.

(10) Patent No.: US 9,728,726 B2
(45) Date of Patent: Aug. 8, 2017

(54) ORGANIC ELECTROLUMINESCENT ELEMENT, MATERIAL FOR ORGANIC ELECTROLUMINESCENT ELEMENT AND LIGHT EMITTING DEVICE, DISPLAY DEVICE, AND ILLUMINATION DEVICE, EACH EMPLOYING ORGANIC ELECTROLUMINESCENT ELEMENT

(71) Applicant: UDC Ireland Limited, Dublin (IE)

(72) Inventors: Koji Takaku, Kanagawa (JP); Yasunori Yonekuta, Kanagawa (JP); Masaru Kinoshita, Kanagawa (JP); Wataru Sotoyama, Kanagawa (JP); Toshihiro Ise, Kanagawa (JP); Kuniyuki Kaminaga, Kanagawa (JP); Heijiro Hirayama, Kanagawa (JP)

(73) Assignee: UDC Ireland Limited, Dublin (IE)

(*) Notice: Subject to any disclaimer, the term of this patent is extended or adjusted under 35 U.S.C. 154(b) by 510 days.

(21) Appl. No.: 14/350,745

(22) PCT Filed: Nov. 1, 2012

(86) PCT No.: PCT/IB2012/002186
§ 371 (c)(1),
(2) Date: Jun. 23, 2014

(87) PCT Pub. No.: WO2013/064881
PCT Pub. Date: May 10, 2013

(65) Prior Publication Data
US 2014/0291660 A1    Oct. 2, 2014

(30) Foreign Application Priority Data

Nov. 2, 2011    (JP) .................. 2011-241629
Mar. 30, 2012    (JP) .................. 2012-080177

(51) Int. Cl.
H01L 51/00    (2006.01)
H01L 51/50    (2006.01)
(Continued)

(52) U.S. Cl.
CPC ........ *H01L 51/0056* (2013.01); *C07B 59/001* (2013.01); *C07C 211/56* (2013.01);
(Continued)

(58) Field of Classification Search
None
See application file for complete search history.

(56) References Cited

U.S. PATENT DOCUMENTS

2002/0132134 A1    9/2002  Hu et al.
2004/0131880 A1*   7/2004  Zheng .................. C08G 61/02
                                              428/690
(Continued)

FOREIGN PATENT DOCUMENTS

JP    2011-204843    10/2011
WO    03/060956    7/2003
(Continued)

*Primary Examiner* — J. L. Yang
(74) *Attorney, Agent, or Firm* — Riverside Law LLP

(57) ABSTRACT

This application relates in part to an organic electroluminescent element including a substrate, a pair of electrodes including an anode and a cathode, disposed on the substrate, and an organic layer(s) including a light emitting layer, in which the organic layer(s) contains a compound represented by the following formula (1), in which $R^1$ to $R^8$ are each hydrogen or a substituent, at least one of $R^1$ to $R^4$ and at least one of $R^5$ to $R^8$ are each a substituent represented by the formula (2); $R^9$ to $R^{12}$, $Z^1$ to $Z^4$, $Ar^1$, $Ar^2$, and $L^1$ are as defined herein.

(Continued)

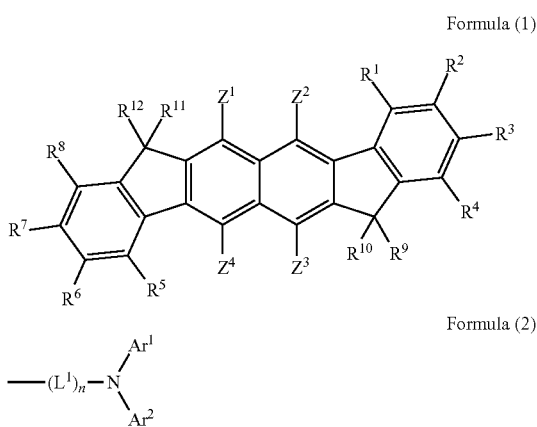

Formula (1)

Formula (2)

32 Claims, 1 Drawing Sheet

(51) Int. Cl.
*C07D 213/74* (2006.01)
*C07C 255/58* (2006.01)
*C07D 219/14* (2006.01)
*C07C 211/56* (2006.01)
*C07C 211/61* (2006.01)
*C07D 239/42* (2006.01)
*C07D 471/06* (2006.01)
*C07D 487/06* (2006.01)
*C07D 493/06* (2006.01)
*C07D 209/86* (2006.01)
*C07B 59/00* (2006.01)
*C07F 7/08* (2006.01)
*C09K 11/06* (2006.01)
*H05B 33/10* (2006.01)
*C09B 57/00* (2006.01)
*C09B 1/00* (2006.01)

(52) U.S. Cl.
CPC .......... *C07C 211/61* (2013.01); *C07C 255/58* (2013.01); *C07D 209/86* (2013.01); *C07D 213/74* (2013.01); *C07D 219/14* (2013.01); *C07D 239/42* (2013.01); *C07D 471/06* (2013.01); *C07D 487/06* (2013.01); *C07D 493/06* (2013.01); *C07F 7/0807* (2013.01); *C09B 1/00* (2013.01); *C09B 57/00* (2013.01); *C09B 57/008* (2013.01); *C09K 11/06* (2013.01); *H01L 51/006* (2013.01); *H05B 33/10* (2013.01); *C07B 2200/05* (2013.01); *C07C 2103/54* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1096* (2013.01); *H01L 51/0052* (2013.01); *H01L 51/0072* (2013.01); *H01L 51/0074* (2013.01); *H01L 51/5012* (2013.01)

(56) References Cited

U.S. PATENT DOCUMENTS

| | | |
|---|---|---|
| 2005/0202279 A1 | 9/2005 | Zheng et al. |
| 2009/0066225 A1 | 3/2009 | Kimura et al. |
| 2011/0260604 A1 | 10/2011 | Ise |
| 2012/0181922 A1 | 7/2012 | Kawamura et al. |
| 2015/0031896 A1 | 1/2015 | Vestweber et al. |

FOREIGN PATENT DOCUMENTS

| | | |
|---|---|---|
| WO | 2004/061048 | 7/2004 |
| WO | 2011/074231 | 6/2011 |

* cited by examiner

ORGANIC ELECTROLUMINESCENT ELEMENT, MATERIAL FOR ORGANIC ELECTROLUMINESCENT ELEMENT AND LIGHT EMITTING DEVICE, DISPLAY DEVICE, AND ILLUMINATION DEVICE, EACH EMPLOYING ORGANIC ELECTROLUMINESCENT ELEMENT

CROSS-REFERENCE TO RELATED APPLICATIONS

This application is a national stage entry of International Patent Application No. PCT/IB2012/002186, filed 1 Nov. 2012, which in turn claims priority to, and the benefit of, Japanese Patent Application Nos. 2011-241629, filed 2 Nov. 2011, and 2012-080177, filed 30 Mar. 2012, all of which are incorporated herein by reference in their entireties.

TECHNICAL FIELD

The present invention relates to an organic electroluminescent element and a material for an organic electroluminescent element used therefor. The present invention further relates to a light emitting device, a display device, or an illumination device each using the organic electroluminescent element.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have an organic layer between a pair of electrodes, and utilize, for light emitting, energy of the exciton generated as a result of recombination of the electron injected from a cathode and the hole injected from an anode in the organic layer. Since the organic electroluminescent elements can be provided as an element having diverse light emitting wavelengths, and have a high response speed and are relatively thin and light-weight, it is expected that they can be employed in a wide range of applications. Above all, it is important to develop an organic electroluminescent element having high color purity and high luminous efficiency in applications with full-color displays and the like, and the results of studies on various research and development have been reported.

As such a material for an organic electroluminescent element, a compound having a skeleton in which 2,6-diphenylnaphthalene is subjected to saturated ring fusion via a linking group having quaternary carbon atoms is known to be an excellent blue fluorescent material (see, for example PTLs 1 and 2). PTL 1 mentions that from such a fluorescent material, a fluorescent material having high efficiency and controlled color is obtained. In addition, PTL 2 mentions that from such a fluorescent material, a fluorescent material capable of controlling a wide range of light emission and having a high charge transporting property is obtained.

On the other hand, PTL 3 describes a compound having a skeleton in which 2,6-diphenylnaphthalene is subjected to saturated ring fusion via a linking group having O, S, or N atoms as an organic transistor material, but the literature does not mention the use of the compound for an organic electroluminescent element and does not disclose a skeleton in which 2,6-diphenylnaphthalene is subjected to saturated ring fusion via a linking group having quaternary carbon atoms.

CITATION LIST

Patent Literature

PTL 1: US2005/202279
PTL 2: US2002/132134
PTL 3: WO2011/074231

SUMMARY OF INVENTION

Technical Problem

In such a circumstance, the present inventors have investigated, using the compounds described in PTLs 1 and 2 as a light emitting material for an organic electroluminescent element, and as a result, it is thought that the compound described in PTL 1 performs control of light emitting wavelength and inhibition of light sub-emission through the inhibition of association by incorporating a long-chain alkyl group having 6 or more carbon atoms as a substituent in a moiety of a linking group having quaternary carbon atoms, in which 2,6-diphenylnaphthalene is subjected to saturated ring fusion, but it could be seen that the orientation properties are lowered and the number of the molecules of the light emitting material having a transition moment parallel to a substrate decreases, and accordingly, sufficient light emitting properties are not obtained. Further, PTL 2 describes a fluorescent material having a structure in which 2,6-diphenylnaphthalene is subjected to saturated ring fusion, but it could be seen that since the fluorescent material does not contain a donating group as a substituent in a phenyl group, sufficient light emitting characteristics are not obtained, and since the inhibition of association is not performed, the chromaticity is changed by the concentration of the compound.

The present invention aims to solve the foregoing problems. That is, it is an object of the present invention to provide an organic electroluminescent element having sufficient luminous efficiency and excellent chromaticity by solving the aforementioned problems.

Solution to Problem

The present inventors have conducted extensive investigations to solve the problems, and as a result, they have found that both inhibition of association and orientation properties can be satisfied by reducing the number of carbon atoms in an alkyl group or reducing the number of carbon atoms of an alkyl group which may be optionally contained in an aryl group as for the aryl group, to a certain number, in a moiety of a linking group having quaternary carbon atoms, in which 2,6-diphenylnaphthalene is subjected to saturated ring fusion. Based on this, the present inventors have thus seen that sufficient performance as a light emitting material can be provided.

The present invention which is a specific means for solving the problems described above is as follows.

[1] An organic electroluminescent element including a substrate, a pair of electrodes including an anode and a cathode, disposed on the substrate, and at least one organic layer including a light emitting layer, disposed between the electrodes, in which the organic layer(s) contains a compound represented by the following general formula (1).

[Chem. 1]

General Formula (1)

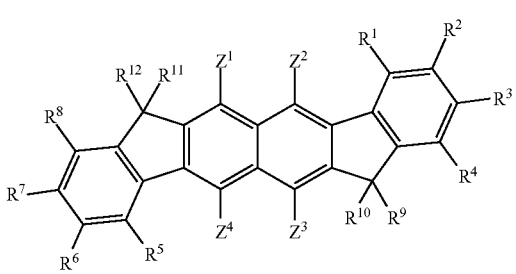

(In the general formula (1), $R^1$ to $R^8$ each independently represent a hydrogen atom or a substituent, these may be bonded to each other to form a ring, and at least one of $R^1$ to $R^8$ is a substituent represented by the following general formula (2).

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Z^1$ and $Z^2$ and $Z^3$ and $Z^4$ may be respectively bonded to each other to form a ring, but they do not form an aromatic ring in any case.

In the case where $Z^1$ and $Z^2$ and $Z^3$ and $Z^4$ are respectively bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group, or an aryl group.)

In the case where $Z^1$ and $Z^2$ and $Z^3$ and $Z^4$ are each not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

[Chem. 2]

General Formula (2)

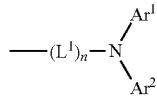

(In the general formula (2), $Ar^1$ and $Ar^2$ each independently represent an alkyl group, an aryl group, or a heteroaryl group and may be bonded to each other to form a ring. $L^1$ represents an arylene group or a heteroarylene group. $Ar^1$ and $Ar^2$, and $L^1$ and $Ar^1$ and/or and $Ar^2$ may be bonded to each other to form a ring. n represents 0 or 1, and when n is 0, $L^1$ represents a single bond.)

[2] In the organic electroluminescent element described in [1], at least one of $R^1$ to $R^4$ and at least one of $R^5$ to $R^8$ in the general formula (1) are each preferably a substituent represented by the general formula (2).

[3] In the organic electroluminescent element as described in [1] or [2], the compound represented by the general formula (1) is preferably a compound represented by the following general formula (3).

[Chem. 3]

General Formula (3)

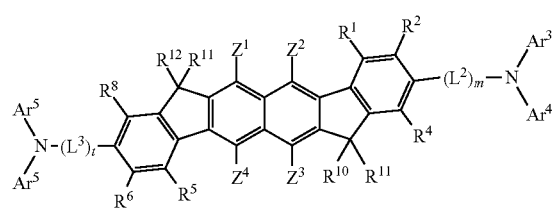

(In the general formula (3), $R^1$, $R^2$, $R^4$ to $R^6$, and $R^8$ each independently represent a hydrogen atom or a substituent, and these may be bonded to each other to form a ring.

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring.

$L^2$ and $L^3$ each independently represent an arylene group or a heteroarylene group. $Ar^3$ and $Ar^4$, $L^2$ and $Ar^3$ and/or $L^2$ and $Ar^4$, $Ar^5$ and $Ar^6$, and $L^3$ and $Ar^5$ and/or $L^3$ and $Ar^6$ may be bonded to each other to form a ring.

m and t each independently represent 0 or 1, and when m and t are 0, each of $L^2$ and $L^3$ represents a single bond.

$Z^2$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

[4] In the organic electroluminescent element as described in any one of [1] to [3], the compound represented by the general formula (3) is preferably a compound represented by the following general formula (4).

[Chem. 4]

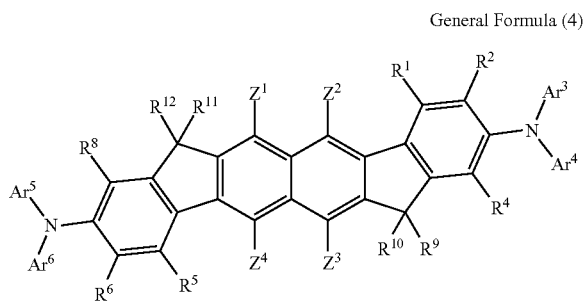

General Formula (4)

(In the general formula (4), $R^1$, $R^2$, $R^4$ to $R^6$, and $R^8$ each independently represent a hydrogen atom or a substituent, and these may be bonded to each other to form a ring.

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring.

$Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

[5] In the organic electroluminescent element as described in [4], $Z^1$ and $Z^2$ and $Z^3$ and $Z^4$ in the general formula (4) are preferably not respectively bonded to each other to form a ring, and $Z^1$ to $Z^4$ are each independently preferably a hydrogen atom (including a deuterium atom), an alkyl group, a fluorine atom, a silyl group, or a cyano group.

[6] In the organic electroluminescent element as described in any one of [1] to [3], the compound represented by the general formula (1) is preferably a compound represented by the following general formula (5).

[Chem. 5]

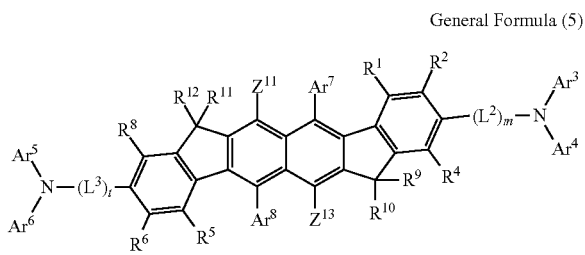

General Formula (5)

(In the general formula (5), $R^1$, $R^2$, $R^4$ to $R^6$, and $R^8$ each independently represent a hydrogen atom or a substituent, and these may be bonded to each other to form a ring.

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring.

$Ar^7$ and $Ar^8$ each independently represent an aryl group or a heteroaryl group.

$L^2$ and $L^3$ each independently represent an arylene group or a heteroarylene group.

m and t each independently represent 0 or 1, and when m and t are 0, each of $L^2$ and $L^3$ represents a single bond.

$Z^{11}$ and $Ar^7$ and $Z^{13}$ and $Ar^8$ may be respectively bonded to each other to form a ring, but they do not form an aromatic ring in any case. In the case where $Z^{11}$ and $Ar^7$ and $Z^{13}$ and $Ar^8$ are respectively bonded to each other to form a ring, $Z^{11}$ and $Z^{13}$ each independently represent an alkyl group, an aryl group, a heteroaryl group, a silyl group, —O—, or —NY— (provided that Y is an alkyl group or an aryl group). In the case where $Z^{11}$ and $Ar^7$ and $Z^{13}$ and $Ar^8$ are not respectively bonded to each other to form a ring, $Z^{11}$ and $Z^{13}$ each independently represent a hydrogen atom (including a deuterium atom), an alkyl group, an aryl group, a heteroaryl group, a fluorine atom, a silyl group, or a cyano group.)

[7] In the organic electroluminescent element as described in any one of [1] to [4] and [6], the compound represented by the general formula (1) is preferably a compound represented by the following general formula (6).

[Chem. 6]

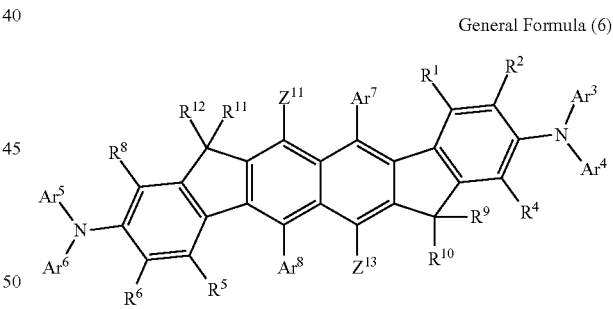

General Formula (6)

(In the general formula (6), $R^1$, $R^2$, $R^4$ to $R^6$, and $R^8$ each independently represent a hydrogen atom or a substituent, and these may be bonded to each other to form a ring.

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring.

$Ar^7$ and $Ar^8$ each independently represent an aryl group or a heteroaryl group.

$Z^{11}$ and $Ar^7$ and $Z^{13}$ and $Ar^8$ may be respectively bonded to each other to form a ring, but they do not form an aromatic ring in any case. In the case where $Z^{11}$ and $Ar^7$ and $Z^{13}$ and $Ar^8$ are respectively bonded to each other to form a ring, $Z^{11}$ and $Z^{13}$ each independently represent an alkyl group, an aryl group, a heteroaryl group, a silyl group, —O—, or —NY— (provided that Y is an alkyl group or an aryl group). In the case where $Z^{11}$ and $Ar^7$ and $Z^{13}$ and $Ar^8$ are not respectively bonded to each other to form a ring, $Z^{11}$ and $Z^{13}$ each independently represent a hydrogen atom (including a deuterium atom), an alkyl group, an aryl group, a heteroaryl group, a fluorine atom, a silyl group, or a cyano group.)

[8] In the organic electroluminescent element as described in [6] or [7], $Z^{11}$ and $Ar^7$ and $Z^{13}$ and $Ar^8$ in the general formulae (5) and (6) are preferably respectively not bonded to each other to form a ring.

[9] In the organic electroluminescent element as described in any one of [6] to [8], $Ar^3$ to $Ar^8$ in the general formulae (5) and (6) preferably each independently represent an aryl group having 6 to 20 carbon atoms.

[10] In the organic electroluminescent element as described in any one of [6] to [9], at least two or more of $Ar^3$ to $Ar^8$ in the general formulae (5) and (6) are preferably an alkyl group having 1 to 5 carbon atoms, an aryl group having 6 to 12 carbon atoms, a silyl group having 3 to 18 carbon atoms, or an aryl group having a fluorine atom as a substituent.

[11] In the organic electroluminescent element as described in any one of [6] to [10], $Ar^7$ to $Ar^8$ in the general formulae (5) and (6) are preferably an alkyl group having 1 to 5 carbon atoms, an aryl group having 6 to 12 carbon atoms, a silyl group having 3 to 18 carbon atoms, or an aryl group having a fluorine atom as a substituent.

[12] In the organic electroluminescent element as described in any one of [6] to [11], $Ar^7$ to $Ar^8$ in the general formulae (5) and (6) are preferably an aryl group having a fluorine atom as a substituent.

[13] In the organic electroluminescent element as described in any one of [4] to [12], at least one of $Ar^3$ to $Ar^6$ in the general formulae (3) to (6) is preferably an alkyl group having 1 to 5 carbon atoms, an aryl group having 6 to 12 carbon atoms, a silyl group having 3 to 18 carbon atoms, or an aryl group having a fluorine atom as a substituent.

[14] In the organic electroluminescent element as described in any one of [4] to [12], at least one of $Ar^3$ to $Ar^6$ in the general formulae (3) to (6) is preferably a substituted or unsubstituted β-naphthyl group or biphenyl group.

[15] In the organic electroluminescent element as described in any one of [1] to [14], at least one layer of the organic layer(s) containing the compound represented by the general formula (1) is preferably a light emitting layer.

[16] In the organic electroluminescent element as described in [15], the light emitting layer preferably contains an anthracene-based host material.

[17] In the organic electroluminescent element as described in [16], the anthracene-based host material is preferably represented by the following general formula (An-1).

[Chem. 7]

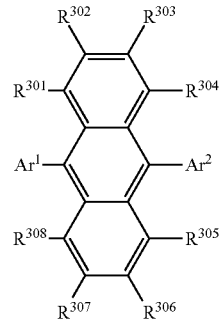

General Formula (An-1)

(In the general formula (An-1), $Ar^1$ and $Ar^2$ each independently represent an aryl group or a heteroaryl group, and $R^{301}$ to $R^{308}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be bonded to each other to form a ring.)

[18] In the organic electroluminescent element as described in [17], the compound represented by the general formula (An-1) is preferably a compound represented by the following general formula (An-2).

[Chem. 8]

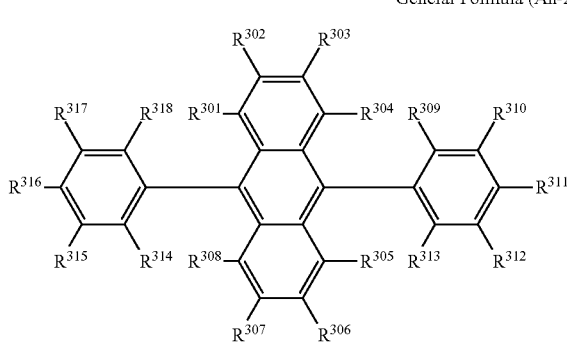

General Formula (An-2)

(In the general formula (An-2), $R^{301}$ to $R^{318}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{313}$ and $R^{314}$, $R^{315}$ and $R^{316}$, $R^{316}$ and $R^{317}$, and $R^{317}$ and $R^{318}$ may be bonded to each other to form a ring.)

[19] In the organic electroluminescent element as described in any one of [1] to [18], at least one of the organic layer(s) preferably contains a compound represented by the following general formula (P).

[Chem. 9]

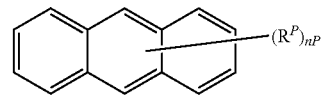

General Formula (P)

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), and these may have a substituent selected from the above-described Substituent Group A. nP represents an integer of 1 to 10, and in the case where there are a plurality of $R^P$s, they may be the same as or different from each other. At least one of $R^P$s is a substituent represented by any of the following general formulae (P-1) to (P-5).)

[Chem. 10]

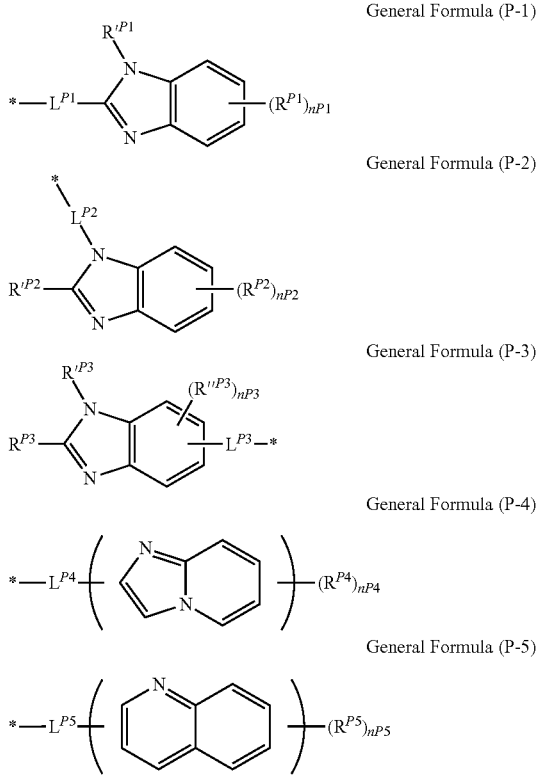

General Formula (P-1)

General Formula (P-2)

General Formula (P-3)

General Formula (P-4)

General Formula (P-5)

(In the general formulae (P-1) to (P-5), $R^{P1}$ to $R^{P5}$, $R^{\prime P1}$ to $R^{\prime P3}$, $R^{\prime P5}$, and $R^{\prime\prime P3}$ each represent an alkyl group (preferably having carbon atoms 1 to 8), an aryl group (preferably having carbon atoms 6 to 30), or a heteroaryl group (preferably having carbon atoms 4 to 12), and these may have a substituent selected from the above-described Substituent Group A. $n^{P1}$ to $n^{P2}$, $n^{P4}$, and $n^{P5}$ represents an integer of 0 to 4, $n^{P3}$ and $n^{P5}$ each represent an integer of 0 to 2, and in the case where there are a plurality of $R^{P1}$ to $R^{P5}$, $R^{\prime P1}$ to $R^{\prime P3}$, $R^{\prime P5}$, and $R^{\prime\prime P3}$, they may be the same as or different from each other. $L^{P1}$ to $L^{P5}$ represents any one of divalent linking groups consisting of a single bond, an aryl ring, and a heteroaryl ring. * represents a binding position with an anthracene ring of the general formula (P).)

[20] In the organic electroluminescent element as described in [19], the compound represented by the general formula (P) is preferably a compound having a substituent represented by the general formula (P-1) as at least one of $R^P$s.

[21] In the organic electroluminescent element as described in [19], the compound represented by the general formula (P) is preferably a compound having a substituent represented by the general formula (P-2) as at least one of $R^P$s.

[22] In the organic electroluminescent element as described in [19], the compound represented by the general formula (P) is preferably a compound having a substituent represented by the general formula (P-3) as at least one of $R^P$s.

[23] In the organic electroluminescent element as described in [19], the compound represented by the general formula (P) is preferably a compound having a substituent represented by the general formula (P-4) as at least one of $R^P$s.

[24] In the organic electroluminescent element as described in [19], the compound represented by the general formula (P) is preferably a compound having a substituent represented by the general formula (P-5) as at least one of $R^P$s.

[25] In the organic electroluminescent element as described in any one of [1] to [24], the light emitting layer is preferably formed by a vacuum deposition process.

[26] In the organic electroluminescent element as described in any one of [1] to [24], the light emitting layer is preferably formed by a wet type process.

[27] A light emitting device using the organic electroluminescent element as described in any one of [1] to [26].

[28] A display device using the organic electroluminescent element as described in any one of [1] to [26].

[29] An illumination device using the organic electroluminescent element as described in any one of [1] to [26].

[30] A material for an organic electroluminescent element represented by the following general formula (1).

[Chem. 11]

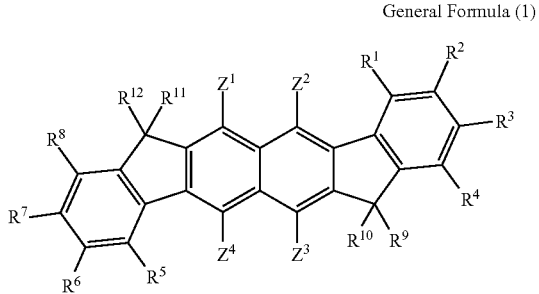

General Formula (1)

(In the general formula (1), $R^1$ to $R^8$ each independently represent a hydrogen atom or a substituent, these may be bonded to each other to form a ring, and at least one of $R^1$ to $R^8$ is a substituent represented by the following general formula (2).

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are respectively bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not respectively bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

[Chem. 12]

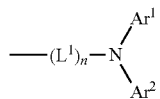

General Formula (2)

(In the general formula (2), $Ar^1$ and $Ar^2$ each independently represent an alkyl group, an aryl group, or a heteroaryl group and may be bonded to each other to form a ring. $L^1$ represents an arylene group or a heteroarylene group. $L^1$ and $Ar^1$, and/or $L^1$ and $Ar^2$ may be bonded to each other to form a ring. n represents 0 or 1, and when n is 0, $L^1$ represents a single bond.)

[31] In the material for an organic electroluminescent element as described in [30], at least one of $R^1$ to $R^4$ and at least one of $R^5$ to $R^8$ in the general formula (1) are preferably a substituent represented by the general formula (2).

[32] The material for an organic electroluminescent element as described in [30] or [31] is preferably represented by the following general formula (3).

[Chem. 13]

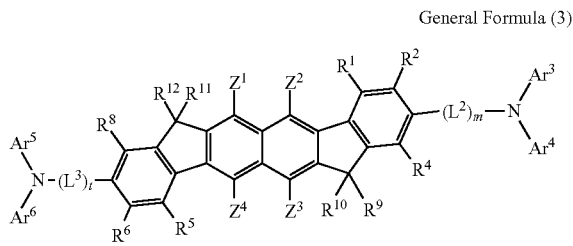

General Formula (3)

(In the general formula (3), $R^1$, $R^2$, $R^4$ to $R^6$, and $R^8$ each independently represent a hydrogen atom or a substituent, and these may be bonded to each other to form a ring.

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8.

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring.

$L^2$ and $L^3$ each independently represent an arylene group or a heteroarylene group. $L^2$ and $Ar^3$ and/or $L^2$ and $Ar^4$, and $L^3$ and $Ar^5$ and/or $L^3$ and $Ar^6$ may be bonded to each other to form a ring.

m and t each independently represent 0 or 1, and when m and t are 0, each of $L^2$ and $L^3$ represents a single bond.

$Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

Advantageous Effects of Invention

The organic electroluminescent element of the present invention has sufficient luminous efficiency and excellent chromaticity. Further, by using the material for an organic electroluminescent element of the present invention having good light emitting wavelength and satisfying both inhibition of association and control of orientation properties, the organic electroluminescent element of the present invention having sufficient luminous efficiency and excellent chromaticity can be easily prepared. In addition, the light emitting device, the display device, and the illumination device of the present invention have advantageous effects in that the power consumption is low and the chromaticity is excellent.

DESCRIPTION OF EMBODIMENTS

Figure 1:
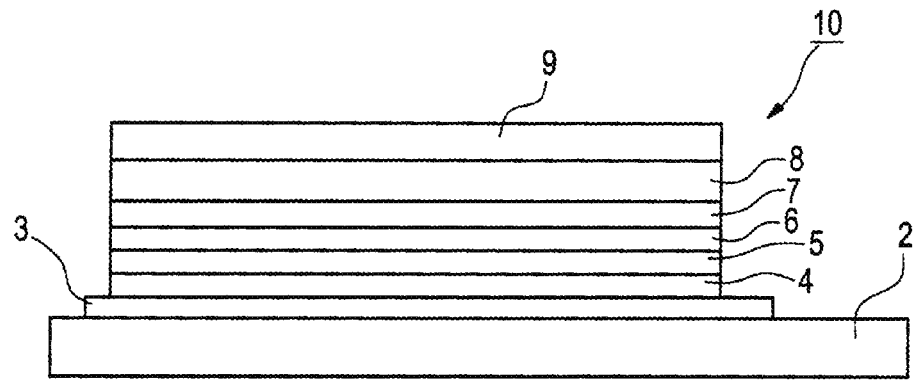
FIG. 1 is a schematic view showing one example of a configuration of an organic electroluminescent element according to the present invention.

Hereinafter, the disclosure of the present invention will be described in detail. The description of the requirements of the configuration as described below is based on representative embodiments and specific examples of the present invention, but the present invention is not limited to these embodiments and specific examples. Incidentally, in the present specification, the numerical range expressed with "to" means a range including the numerical values before and after "to" as the lower limit and the upper limit, respectively.

In the present invention, the hydrogen atom which is used without particular distinction at each occurrence in the description of the respective general formulae also includes isotopes (a deuterium atom and the like), and the atoms additionally constituting the substituent are also intended to include isotopes of the atoms.

[Organic Electroluminescent Element and Material for Organic Electroluminescent Element]

The material for an organic electroluminescent element of the present invention may be represented by the following general formula (1).

The organic electroluminescent element of the present invention may include a substrate, a pair of electrodes including an anode and a cathode, disposed on the substrate, and at least one organic layer including a light emitting layer, disposed between the electrodes, in which the organic layer(s) contains the compound represented by the following general formula (1).

[Chem. 14]

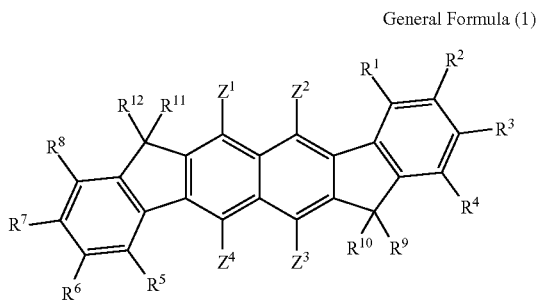

General Formula (1)

(In the general formula (1), $R^1$ to $R^8$ each independently represent a hydrogen atom or a substituent, these may be bonded to each other to form a ring, and at least one of $R^1$ to $R^8$ is a substituent represented by the following general formula (2). $R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8. $Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are respectively bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not respectively bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.)

[Chem. 15]

General Formula (2)

(In the general formula (2), $Ar^1$ and $Ar^2$ each independently represent an alkyl group, an aryl group, or a heteroaryl group and may be bonded to each other to form a ring. $L^1$ represents an arylene group or a heteroarylene group. $Ar^1$ and $Ar^2$, and $L^1$ and $Ar^1$ and/or $L^1$ and $Ar^2$ may be bonded to each other to form a ring. n represents 0 or 1, and when n is 0, $L^1$ represents a single bond.)

<Structure of Material for Organic Electroluminescent Element>

Hereinafter, the structure of the compound represented by the general formula (1) which is the light emitting material for an organic electroluminescent element of the present invention, and other configurations of the organic electroluminescent element of the present invention will be described in detail.

In the general formula (1), at least one of $R^1$ to $R^4$ and at least one of $R^5$ to $R^8$ are each preferably a substituent represented by the general formula (2).

In the general formula (1), $R^1$ to $R^4$ each independently represent a hydrogen atom or a substituent, and at least one of $R^1$ to $R^4$ is a substituent represented by the general formula (2). Preferably, one or two of $R^1$ to $R^4$ are each a substituent, and more preferably, one of $R^1$ to $R^4$ is a substituent. Out of $R^1$ to $R^4$, $R^2$ or $R^3$ is preferably a substituent represented by the general formula (2), and more preferably, $R^3$ is a substituent represented by the general formula (2), from the viewpoint of shortening the light emitting wavelength of an organic electroluminescent element using the compound represented by the general formula (1). Examples of additional substituents represented by the general formula (2), which are represented by $R^1$ to $R^4$, include an alkyl group, an aryl group, a silyl group, a fluorine atom, an alkoxy group, and an aryloxy group, more preferably an alkyl group, particularly preferably an alkyl group having 1 to 3 carbon atoms, and more particularly preferably a methyl group. In the case where $R^1$ to $R^4$ have the additional substituents represented by the general formula (2), it is preferable that $R^2$ have the additional substituent.

$R^1$ to $R^4$ may be bonded to each other to form a ring, but it is preferable that $R^1$ to $R^4$ be not bonded to each other to form a ring.

In the general formula (1), $R^5$ to $R^8$ each independently represent a hydrogen atom or a substituent, and at least one of $R^5$ to $R^8$ is a substituent represented by the general formula (2). Preferably, one or two of $R^5$ to $R^8$ are each a substituent, and more preferably, one of $R^5$ to $R^8$ is a substituent. Out of $R^5$ to $R^8$, $R^6$ or $R^7$ is preferably a substituent represented by the general formula (2), and $R^7$ is more preferably a substituent represented by the general formula (2), from the viewpoint of shortening the light emitting wavelength of an organic electroluminescent element using the compound represented by the general formula (1). Examples of additional substituents represented by the general formula (2), which are represented by $R^5$ to $R^8$, include an alkyl group, an aryl group, a silyl group, a fluorine atom, an alkoxy group, and an aryloxy group, more preferably an alkyl group, particularly preferably an alkyl group having 1 to 3 carbon atoms, and more particularly preferably a methyl group. In the case where $R^5$ to $R^8$ have the additional substituents represented by the general formula (2), it is preferable that $R^6$ have the additional substituent.

$R^5$ to $R^8$ may be bonded to each other to form a ring, but it is preferable that $R^5$ to $R^8$ be not bonded to each other to form a ring.

Among the substituents represented by the general formula (2), $Ar^1$ and $Ar^2$ each independently represent an alkyl group, an aryl group, or a heteroaryl group, and $Ar^1$ and $Ar^2$, and $L^1$ and $Ar^1$ and/or $L^1$ and $Ar^2$ may be bonded to each other to form a ring. $Ar^1$ and $Ar^2$ are each independently preferably an aryl group or a heteroaryl group, more preferably an aryl group, more particularly preferably an aryl group having 6 to 10 carbon atoms, and still more particularly preferably a phenyl group or a 2-naphthyl group.

$Ar^1$ and $Ar^2$ may have an additional substituent, and the additional substituent is preferably an alkyl group, an aryl group, or a fluorine atom, more preferably an alkyl group having 1 to 5 carbon atoms, a phenyl group, or a fluorine atom, and particularly preferably a methyl group. In the case where $Ar^1$ and $Ar^2$ have an additional substituent, the number of the additional substituents per $Ar^1$ and $Ar^2$ is preferably 1 to 3, more preferably 1 or 2, and particularly preferably 1.

Among the substituents represented by the general formula (2), $L^1$ represents an arylene group or a heteroarylene group, preferably an arylene group having 6 to 10 carbon atoms or a heteroarylene group having 6 to 10 ring members, and more preferably a phenylene group, a pyridinyl group, or a pyrimidinyl group.

Among the substituents represented by the general formula (2), n represents 0 or 1, and preferably 0.

In the general formula (1), $R^9$ and $R^{10}$ each independently represent an aryl group or an alkyl group having 1 to 5 carbon atoms. The aryl group represented by $R^9$ and $R^{10}$ is preferably an aryl group having 6 to 10 carbon atoms, more preferably an aryl group having 6 to 10 carbon atoms, having an alkyl group as a substituent, and particularly preferably a phenyl group having an alkyl group as a substituent. $R^9$ and $R^{10}$ are each independently preferably an alkyl group having 1 to 5 carbon atoms, more preferably an alkyl group having 1 to 5 carbon atoms, and particularly preferably an alkyl group having 1 to 3 carbon atoms.

When $R^9$ and $R^{10}$ are each an alkyl group or a substituent having an alkyl chain, the total number of carbon atoms of the alkyl group represented by these groups is from 2 to 8, preferably from 2 to 6, and more preferably from 2 to 4.

In the general formula (1), $R^{11}$ and $R^{12}$ each independently represent an aryl group or an alkyl group having 1 to 5 carbon atoms, and the preferred ranges and the preferred relationship of $R^{11}$ and $R^{12}$ are the same as the preferred ranges and the preferred relationship of $R^9$ and $R^{10}$.

In the general formula (1), $Z^1$ and $Z^2$ may be respectively bonded to each other to form a ring, but they do not form an aromatic ring in any case.

In the case where $Z^1$ and $Z^2$ are respectively bonded to each other to form a ring, $Z^1$ and $Z^2$ each independently represent an alkyl group (provided that $Z^1$ and $Z^2$ are not both alkyl groups in any case), an aryl group, a heteroaryl group, a silyl group, —O—, or —NY— (provided that Y is an alkyl group or an aryl group). In the case where $Z^1$ and $Z^2$ are respectively bonded to each other to form a ring, at least one of $Z^1$ and $Z^2$ is preferably an arylene group (more preferably an arylene group having 6 to 10 carbon atoms, and particularly preferably a phenylene group) or a heteroarylene group from the viewpoint of shortening the light emitting wavelength of the organic electroluminescent element using the compound represented by the general formula (1), and the other is preferably an alkylene group (preferably —$CR^{21}R^{22}$—, and $R^{21}$ and $R^{22}$ each independently represent an alkyl group, and preferably a methyl group), —$SiR^{23}R^{24}$— ($R^{23}$ and $R^{24}$ each independently represent an alkyl group, and preferably a methyl group), —O—, or —NY— (Y is preferably an aryl group, and more preferably a phenyl group). In the case where $Z^1$ and $Z^2$ are respectively bonded to each other to form a ring, $Z^1$ and $Z^2$ may have an additional substituent, but it is preferable that $Z^1$ and $Z^2$ do not have an additional substituent.

On the other hand, in the case where $Z^1$ and $Z^2$ are not respectively bonded to each other to form a ring, $Z^1$ and $Z^2$ each independently represent a hydrogen atom (including a deuterium atom), an alkyl group, an aryl group, a heteroaryl group, a fluorine atom, a silyl group, or a cyano group, preferably a hydrogen atom (including a deuterium atom), an aryl group, a fluorine atom, or a silyl group, and more preferably a hydrogen atom (including a deuterium atom) or an aryl group. Also, in the case where $Z^1$ and $Z^2$ are not respectively bonded to each other to form a ring, at least one of $Z^1$ and $Z^2$ is preferably an aryl group or a heteroaryl group from the viewpoint of shortening the light emitting wavelength of the organic electroluminescent element using the compound represented by the general formula (1), more preferably an aryl group, particularly preferably an aryl group having 6 to 10 carbon atoms, and more particularly preferably a phenyl group. In the case where $Z^1$ and $Z^2$ are not respectively bonded to each other to form a ring, $Z^1$ and $Z^2$ may have an additional substituent, and the substituent on an aryl group is preferably an alkyl group having 1 to 5 carbon atoms, a fluorine atom, or a cyano group, and more preferably a fluorine atom.

In the general formula (1), $Z^3$ and $Z^4$ may be respectively bonded to each other to form a ring, but they do not form an aromatic ring in any case. In the general formula (1), the preferred ranges and the preferred relationship of $Z^3$ and $Z^4$ are the same as the preferred ranges and the preferred relationship of $Z^1$ and $Z^2$.

In the material for an organic electroluminescent element of the present invention, the compound represented by the general formula (1) is preferably a compound represented by the following general formula (3).

[Chem. 16]

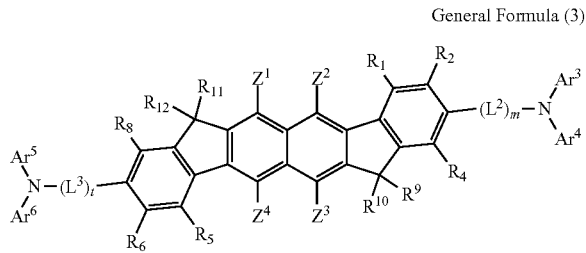

General Formula (3)

In the general formula (3), $R^1$, $R^2$, $R^4$ to $R^6$, and $R^8$ each independently represent a hydrogen atom or a substituent, and these may be bonded to each other to form a ring. The preferred ranges of $R^1$, $R^2$, $R^4$ to $R^6$, and $R^8$ in the general formula (3) are the same as the preferred ranges of $R^1$, $R^2$, $R^4$ to $R^6$, and $R^8$ in the general formula (1).

In the general formula (3), $R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8. The preferred ranges of $R^9$ to $R^{12}$ in the general formula (3) are the same as the preferred ranges of $R^9$ to $R^{12}$ in the general formula (1).

In the general formula (3), $Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring. The preferred ranges of $Ar^3$ and $Ar^4$ in the general formula (3) are the same as the preferred ranges of $Ar^1$ and $Ar^2$ in the general formula (2), and the preferred ranges of $Ar^5$ and $Ar^6$ in the general formula (3) are the same as the preferred ranges of $Ar^1$ and $Ar^2$ in the general formula (2).

In the general formula (3), $L^2$ and $L^3$ each independently represent an arylene group or a heteroarylene group. The preferred ranges of $L^2$ and $L^3$ in the general formula (3) are the same as the preferred ranges of $L^1$ in the general formula (2). $Ar^3$ and $Ar^4$, $L^2$ and $Ar^3$ and/or $L^2$ and $Ar^4$, $Ar^5$ and $Ar^6$, and $L^3$ and $Ar^5$ and/or $L^3$ and $Ar^6$ may be bonded to each other to form a ring.

In the general formula (3), m and t each independently represent 0 or 1. The preferred ranges of m and t in the general formula (3) are the same as the preferred range of n in the general formula (2).

In the general formula (3), $Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group. The preferred ranges of $Z^1$ to $Z^4$ in the general formula (3) are the same as the preferred ranges of $Z^1$ to $Z^4$ in the general formula (1).

In the organic electroluminescent element of the present invention, the compound represented by the general formula (3) is preferably a compound represented by the following general formula (4).

[Chem. 17]

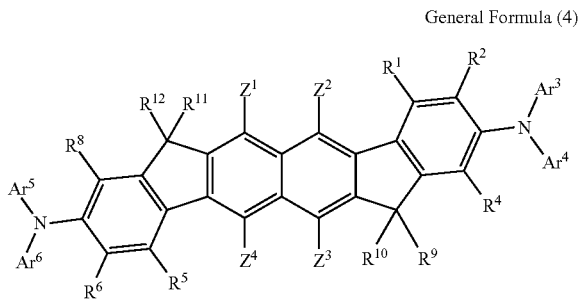

General Formula (4)

In the general formula (4), $R^1$, $R^2$, $R^4$ to $R^6$, and $R^8$ each independently represent a hydrogen atom or a substituent, and these may be bonded to each other to form a ring. The preferred ranges of $R^1$, $R^2$, $R^4$ to $R^6$, and $R^8$ in the general formula (4) are the same as the preferred ranges of $R^1$, $R^2$, $R^4$ to $R^6$, and $R^8$ in the general formula (1).

$R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8. The preferred ranges of $R^9$ to $R^{12}$ in the general formula (4) are the same as the preferred ranges of $R^9$ to $R^{12}$ in the general formula (1).

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring. The preferred ranges of $Ar^3$ and $Ar^4$ in the general formula (4) are the same as the preferred ranges of $Ar^1$ and $Ar^2$ in the general formula (2), and the preferred ranges of $Ar^5$ and $Ar^6$ in the general formula (4) are the same as the preferred ranges of $Ar^1$ and $Ar^2$ in the general formula (2).

$Z^1$ and $Z^2$ and $Z^3$ and $Z^4$ may be respectively bonded to each other to form a ring, but they do not form an aromatic ring in any case. In the case where $Z^1$ and $Z^2$ and $Z^3$ and $Z^4$ are bonded to each other to form a ring, $Z^1$ to $Z^4$ each independently represent an alkyl group (provided that $Z^1$ and $Z^2$ are not both alkyl groups in any case, and $Z^3$ and $Z^4$ are not both alkyl groups in any case), an aryl group, a heteroaryl group, a silyl group, —O—, or —NY— (provided that Y is an alkyl group or an aryl group). In the case where $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group. The preferred ranges of $Z^1$ to $Z^4$ in the general formula (4) are the same as the preferred ranges of $Z^1$ to $Z^4$ in the general formula (1). In the general formula (4), $Z^1$ and $Z^2$ and $Z^3$ and $Z^4$ are not respectively bonded to each other to form a ring, and $Z^1$ to $Z^4$ are each independently more preferably a hydrogen atom (including a deuterium atom), an alkyl group, a fluorine atom, a silyl group, or a cyano group.

In the material for an organic electroluminescent element of the present invention, the compound represented by the general formula (1) is preferably a compound represented by the following general formula (5).

[Chem. 18]

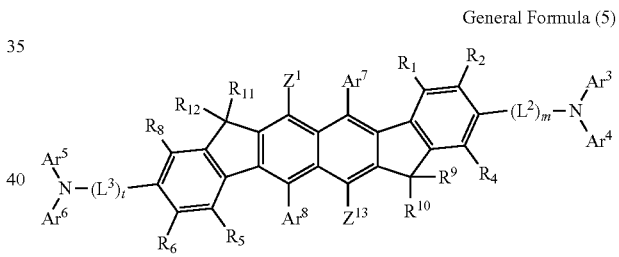

General Formula (5)

In the general formula (5), $R^1$, $R^2$, $R^4$ to $R^6$, and $R^8$ each independently represent a hydrogen atom or a substituent, and these may be bonded to each other to form a ring. The preferred ranges of $R^1$, $R^2$, $R^4$ to $R^6$, and $R^8$ in the general formula (5) are the same as the preferred ranges of $R^1$, $R^2$, $R^4$ to $R^6$, and $R^8$ in the general formula (1).

In the general formula (5), $R^9$ to $R^{12}$ each independently represent an aryl group or an alkyl group having 1 to 5 carbon atoms, when $R^9$ and $R^{10}$ are each an alkyl group or a substituent having an alkyl chain, the total number of carbon atoms of the alkyl group represented by these groups is from 2 to 8, and when $R^{11}$ and $R^{12}$ are each an alkyl group or a substituent having an alkyl chain, the total number of carbon atoms of the alkyl group represented by these groups is from 2 to 8. The preferred ranges of $R^9$ to $R^{12}$ in the general formula (5) are the same as the preferred ranges of $R^9$ to $R^{12}$ in the general formula (1).

In the general formula (5), $Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring. The preferred ranges of $Ar^3$ and $Ar^4$ in the general formula (5) are the same as the preferred ranges of $Ar^1$ and $Ar^2$ in the general formula (2), and the preferred ranges of $Ar^5$ and $Ar^6$ in the general formula (5) are the same as the preferred ranges of $Ar^1$ and $Ar^2$ in the general formula (2).

In the general formula (5), $L^2$ and $L^3$ each independently represent an arylene group or a heteroarylene group. The preferred ranges of $L^2$ and $L^3$ in the general formula (5) are the same as the preferred range of $L^1$ in the general formula (2).

In the general formula (5), m and t each independently represent 0 or 1. The preferred ranges of m and t in the general formula (5) are the same as the preferred range of n in the general formula (2).

In the general formula (5), $Ar^7$ represents an aryl group or a heteroaryl group. $Z^{11}$ and $Ar^7$ may be respectively bonded to each other to form a ring, but they do not form an aromatic ring in any case.

In the case where $Z^{11}$ and $Ar^7$ are bonded to each other to form a ring, $Ar^7$ is preferably an arylene group, more preferably an arylene group having 6 to 10 carbon atoms, and particularly preferably a phenylene group. In the case where $Z^{11}$ and $Ar^7$ are bonded to each other to form a ring, $Z^{11}$ is preferably an alkylene group (preferably —$CR^{21}R^{22}$—, and $R^{21}$ and $R^{22}$ each independently represent an alkyl group, and preferably a methyl group), an arylene group, a heteroarylene group, —$SiR^{23}R^{24}$— ($R^{23}$ and $R^{24}$ each independently represent an alkyl group, and preferably a methyl group), —O—, or —NY— (Y is preferably an aryl group, and more preferably a phenyl group), and more preferably an alkylene group, —$SiR^{23}R^{24}$—, —O—, or —NY—.

In the case where $Z^{11}$ and $Ar^7$ are not respectively bonded to each other to form a ring, $Ar^7$ is preferably an aryl group, more preferably an aryl group having 6 to 20 carbon atoms, more particularly preferably an aryl group having 6 to 10 carbon atoms, and still more particularly preferably a phenyl group. $Ar^7$ may have an additional substituent on an aryl group, and the substituent on an aryl group is preferably an alkyl group having 1 to 5 carbon atoms, a fluorine atom, or a cyano group, and more preferably a fluorine atom. In the case where $Z^{11}$ and $Ar^7$ are not bonded to each other to form a ring, $Z^{11}$ represents a hydrogen atom (including a deuterium atom), an alkyl group, an aryl group, a heteroaryl group, a fluorine atom, a silyl group, or a cyano group, preferably a hydrogen atom (including a deuterium atom), an alkyl group, a fluorine atom, a silyl group, or a cyano group, more preferably a hydrogen atom (including a deuterium atom), a fluorine atom, or a silyl group, and still more preferably a hydrogen atom (including a deuterium atom).

In the general formula (5), $Ar^8$ represents an aryl group or a heteroaryl group. $Z^{12}$ and $Ar^8$ may be respectively bonded to each other to form a ring, but they do not form an aromatic ring in any case.

In the case where $Z^{12}$ and $Ar^8$ are bonded to each other to form a ring, $Ar^8$ is preferably an arylene group, more preferably an arylene group having 6 to 10 carbon atoms, and particularly preferably a phenylene group. In the case where $Z^{12}$ and $Ar^8$ are bonded to each other to form a ring, $Z^{12}$ is preferably an alkylene group (preferably —$CR^{21}R^{22}$—, and $R^{21}$ and $R^{22}$ each independently represent an alkyl group, and preferably a methyl group), an arylene group, a heteroarylene group, —$SiR^{23}R^{24}$— ($R^{23}$ and $R^{24}$ each independently represent an alkyl group, and preferably a methyl group), —O—, or —NY— (Y is preferably an aryl group, and more preferably a phenyl group), and more preferably an alkylene group, —$SiR^{23}R^{24}$—, —O—, or —NY—.

In the case where $Z^{12}$ and $Ar^8$ are not respectively bonded to each other to form a ring, $Ar^8$ is preferably an aryl group, more preferably an aryl group having 6 to 20 carbon atoms, more particularly preferably an aryl group having 6 to 10 carbon atoms, and still more particularly preferably a phenyl group. $Ar^8$ may have an additional substituent on an aryl group, and the substituent on an aryl group is preferably an alkyl group having 1 to 5 carbon atoms, a fluorine atom, or a cyano group, and more preferably a fluorine atom. In the case where $Z^{12}$ and $Ar^8$ are not bonded to each other to form a ring, $Z^{12}$ represents a hydrogen atom (including a deuterium atom), an alkyl group, an aryl group, a heteroaryl group, a fluorine atom, a silyl group, or a cyano group, preferably a hydrogen atom (including a deuterium atom), an alkyl group, a fluorine atom, a silyl group, or a cyano group, more preferably a hydrogen atom (including a deuterium atom), a fluorine atom, or a silyl group, and still more preferably a hydrogen atom (including a deuterium atom).

In the present invention, the compound represented by the general formula (1) is preferably a compound represented by the following general formula (6).

[Chem. 19]

General Formula (6)

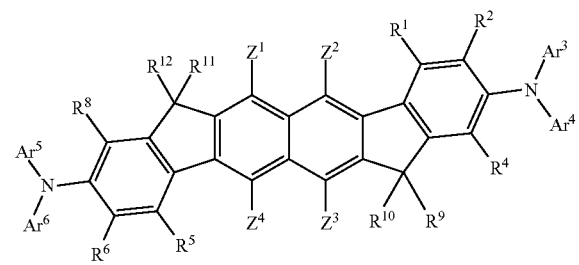

In the general formula (6), the definitions and the preferred ranges of $R^1$, $R^2$, $R^4$ to $R^6$, and $R^8$ are the same as the definitions and the preferred ranges of $R^1$, $R^2$, $R^4$ to $R^6$, and $R^8$ in the general formula (1).

In the general formula (6), the definitions and the preferred ranges of $R^9$ to $R^{12}$ are the same as the definitions and the preferred ranges of $R^9$ to $R^{12}$ in the general formula (1).

In the general formula (6), the definitions and the preferred ranges of $Ar^3$ to $Ar^6$ are the same as the definitions and the preferred ranges of $Ar^3$ to $Ar^6$ in the general formula (5).

In the general formula (6), the definitions and the preferred ranges of $Z^{11}$, $Z^{13}$, $Ar^7$ and $Ar^8$ are the same as the definitions and the preferred ranges of $Z^{11}$, $Z^{13}$, $Ar^7$, and $Ar^8$ in the general formula (5).

In the material for an organic electroluminescent element of the present invention, it is preferable that $Z^{11}$ and $Ar^7$ and $Z^{13}$ and $Ar^8$ in the general formulae (5) and (6) be not respectively bonded to each other to form a ring.

In the material for an organic electroluminescent element of the present invention, $Ar^3$ to $Ar^8$ in the general formulae (3) to (6) each independently preferably represent an aryl group having 6 to 20 carbon atoms, and more preferably an aryl group having 6 to 10 carbon atoms, and the more particularly preferred ranges of $Ar^3$ to $Ar^8$ are the same as described in the description of the general formula (5).

In the material for an organic electroluminescent element of the present invention, in the general formulae (3) to (6), it is preferable that at least two or more of $Ar^3$ to $Ar^8$ be an alkyl group having 1 to 5 carbon atoms, an aryl group having 6 to 12 carbon atoms, a silyl group having 3 to 18 carbon atoms, or an aryl group having a fluorine atom as a substituent, from the viewpoint of inhibition of association, it is more preferable that 2 to 4 groups of $Ar^3$ to $Ar^8$ be an alkyl group having 1 to 5 carbon atoms, or an aryl group having a fluorine atom as a substituent, and it is particularly preferable that $Ar^3$ to $Ar^8$ be an aryl group having a fluorine atom as a substituent.

In the general formulae (5) and (6), $Ar^7$ to $Ar^8$ are preferably (all) an alkyl group having 1 to 5 carbon atoms, an aryl group having 6 to 12 carbon atoms, a silyl group having 3 to 18 carbon atoms, or an aryl group having a fluorine atom as a substituent, and more preferably an aryl group having a fluorine atom as a substituent.

In the material for an organic electroluminescent element of the present invention, at least one of $Ar^3$ to $Ar^6$ in the general formulae (3) to (6) is preferably an alkyl group having 1 to 5 carbon atoms, an aryl group having 6 to 12 carbon atoms, a silyl group having 3 to 18 carbon atoms, or an aryl group having a fluorine atom as a substituent, from the viewpoint of inhibition of association, and more preferably an alkyl group having 1 to 5 carbon atoms or an aryl group having 6 to 12 carbon atoms.

On the other hand, for the material for an organic electroluminescent element of the present invention, in the general formulae (3) to (6), at least one of $Ar^3$ to $Ar^6$ is preferably a substituted or unsubstituted β-naphthyl group or a biphenyl group from the viewpoint of a narrower spectrum, and more preferably a β-naphthyl group.

The maximum light emitting wavelength of the organic electroluminescent element using the compound represented by the general formula (1) is usually less than 455 nm, preferably 400 nm or more and less than 455 nm, more preferably 420 nm or more and less than 455 nm, still more preferably 430 nm or more and less than 455 nm, and most preferably 440 nm or more and less than 455 nm, from the viewpoint of obtaining blue light emission with high color purity.

The molecular weight of the compound represented by the general formula (1) is preferably 1000 or less, more preferably 900 or less, particularly preferably 850 or less, and still more preferably 800 or less. By reducing the molecular weight, a sublimation temperature can be lowered, and thus, it is possible to prevent the thermal decomposition of the compound during the deposition. Further, the energy required for deposition can be suppressed by decreasing the deposition time. Here, since a material having a high sublimation temperature can undergo thermal decomposition during long-term deposition, it is favorable that the sublimation temperature be not too high from the viewpoint of deposition suitability. The sublimation temperature (which means a temperature which leads to reduction by 10% by mass in the present specification) of the compound represented by the general formula (1) is preferably 300° C., more preferably 285° C. or lower, and still more preferably 270° C. or lower.

Specific examples of the compound represented by the general formula (1) are shown below, but it should not be construed that the compound represented by the general formula (1) which can be used in the present invention is limited to the specific examples.

[Chem. 20]

Compound 1

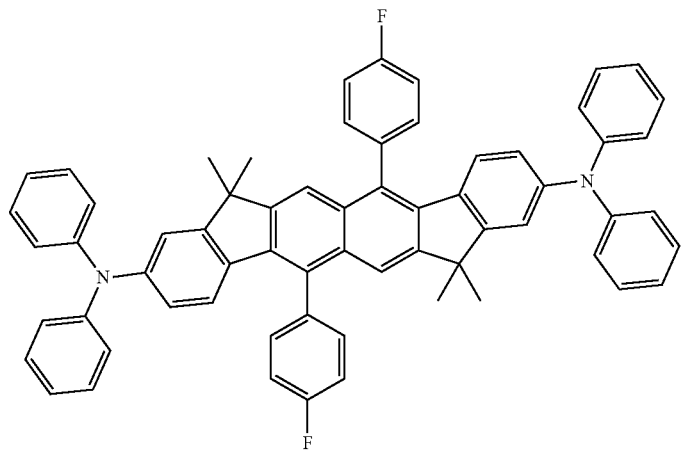

Compound 2
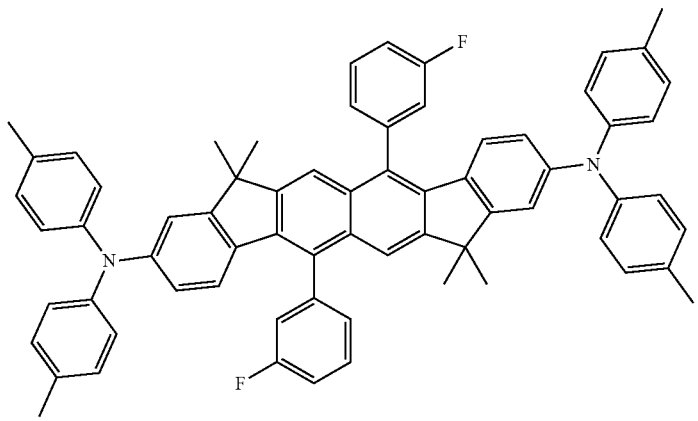
Compound 3
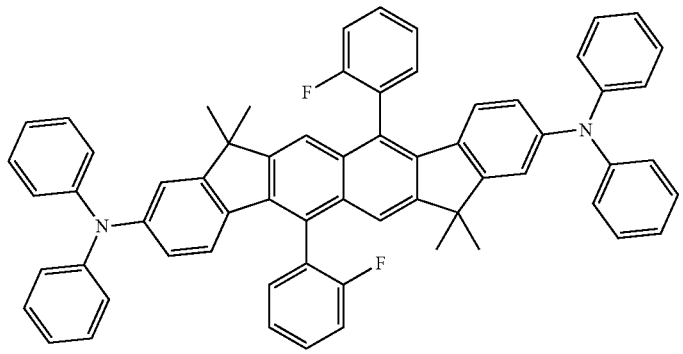
Compound 4
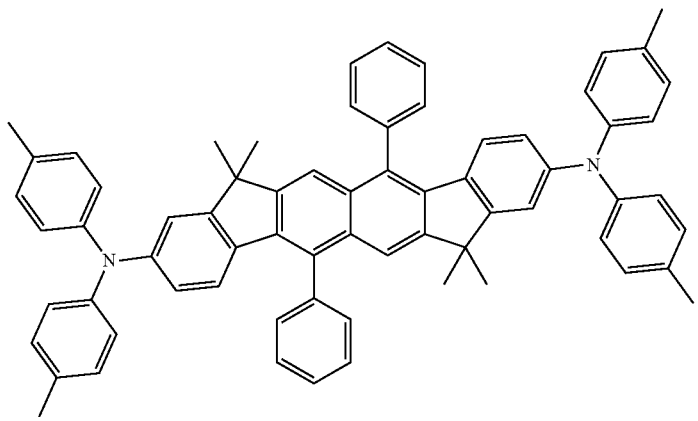
Compound 5
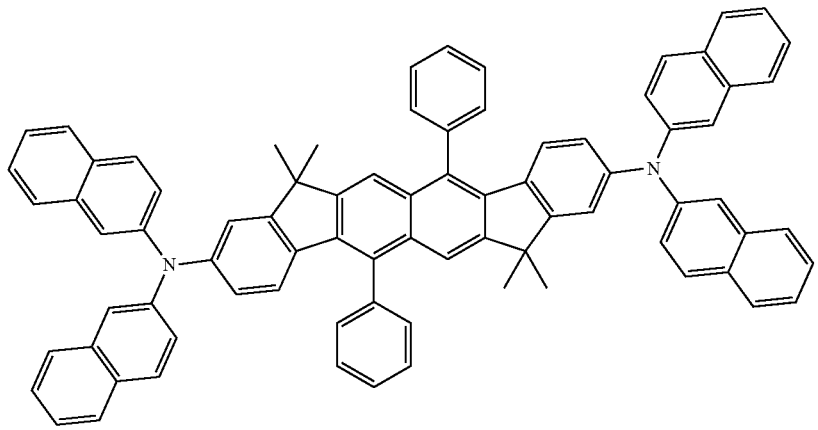

-continued
Compound 6
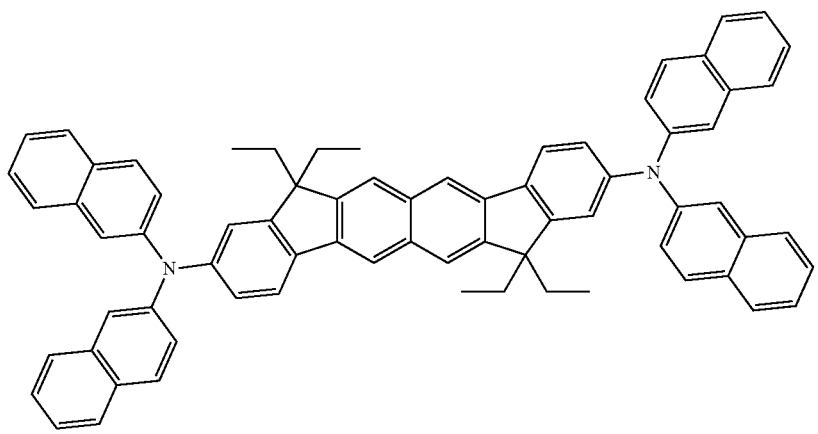
Compound 7
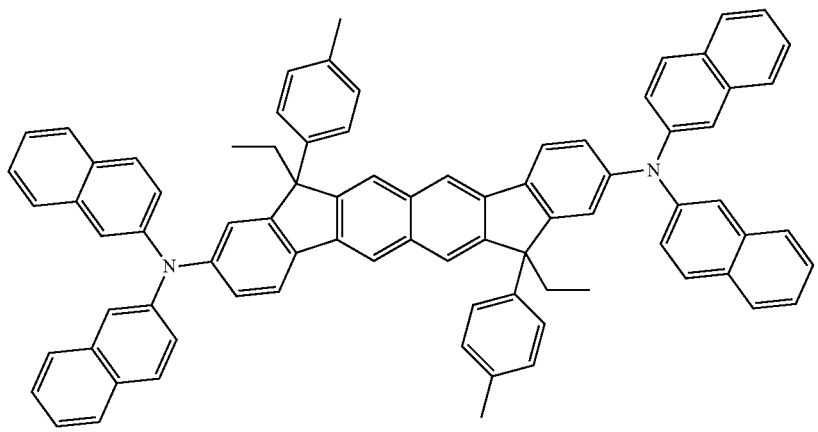
Compound 8
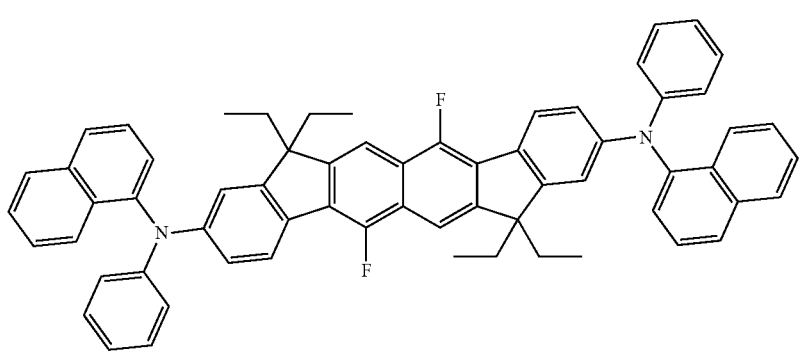

-continued
Compound 9
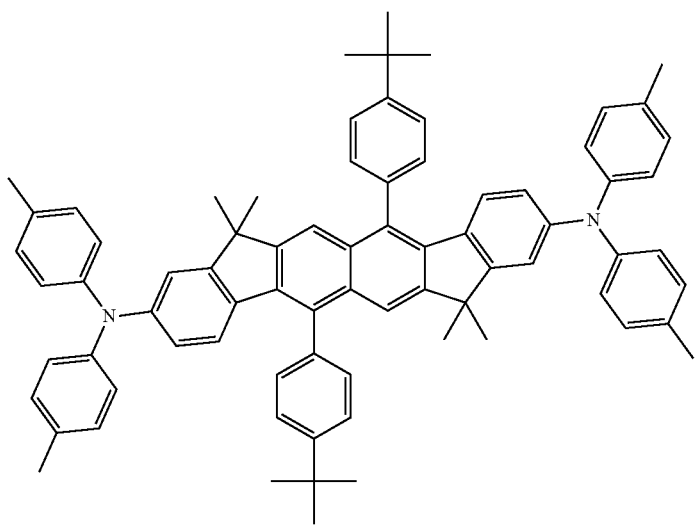
Compound 10
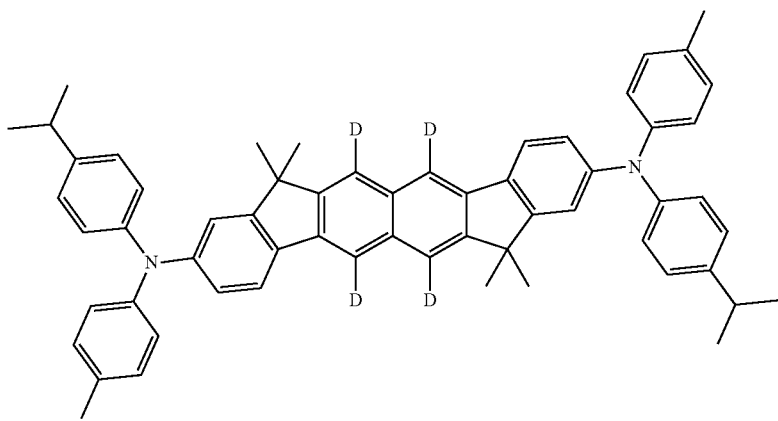
[Chem. 21]
Compound 11
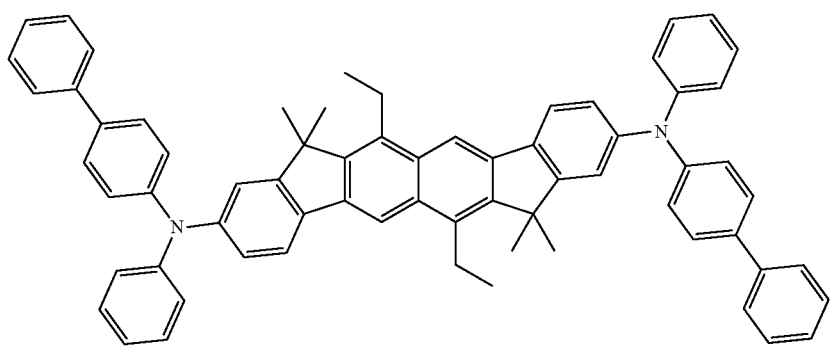

-continued
Compound 12
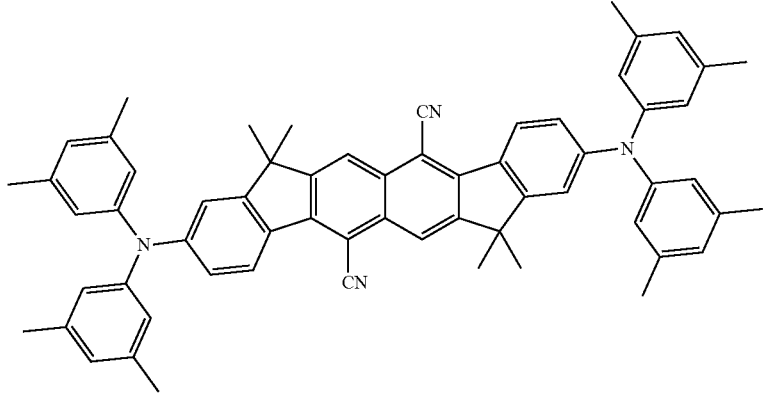
Compound 13
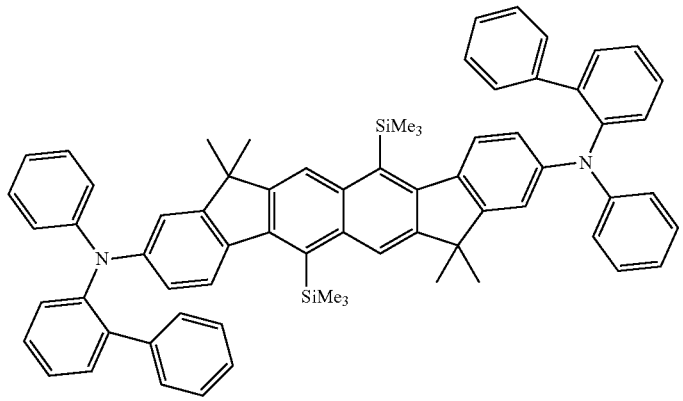
Compound 14
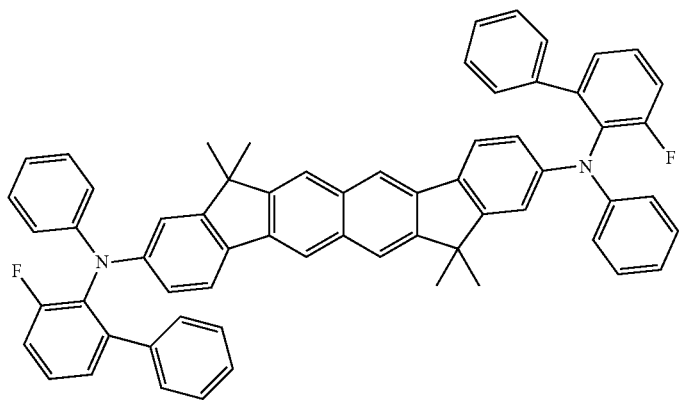
Compound 15
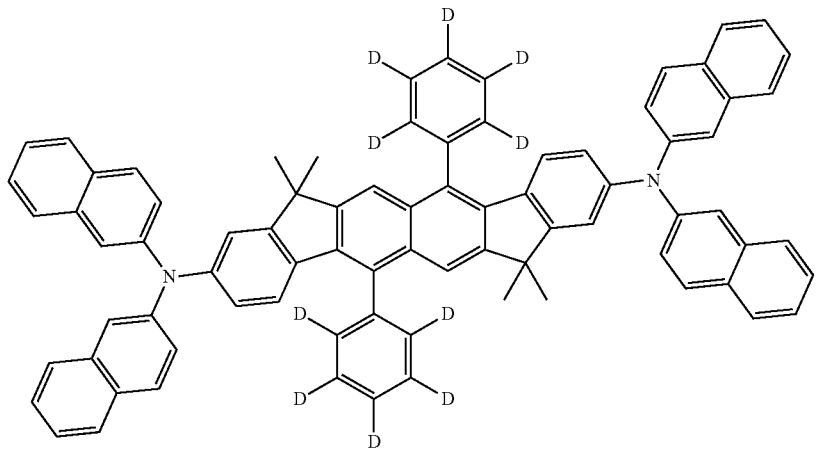

Compound 16
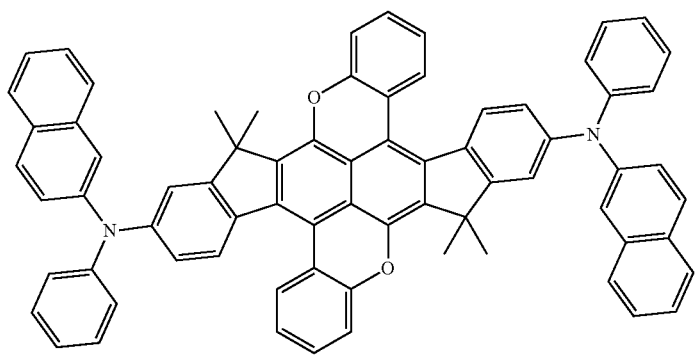
Compound 17
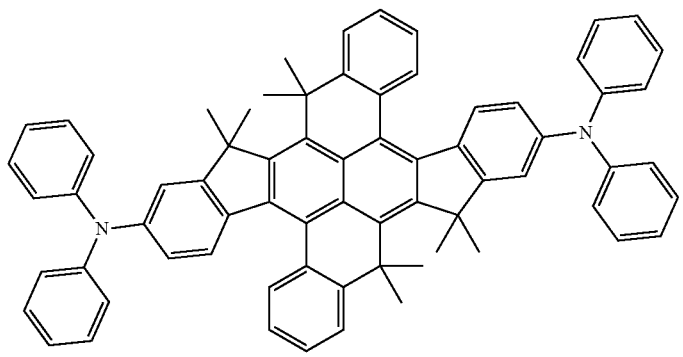
Compound 18
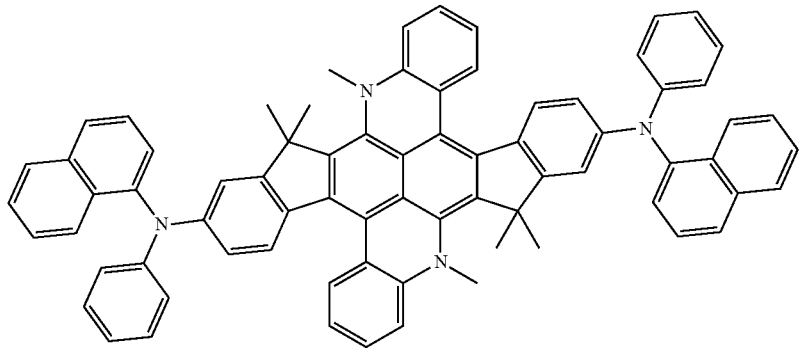
Compound 19
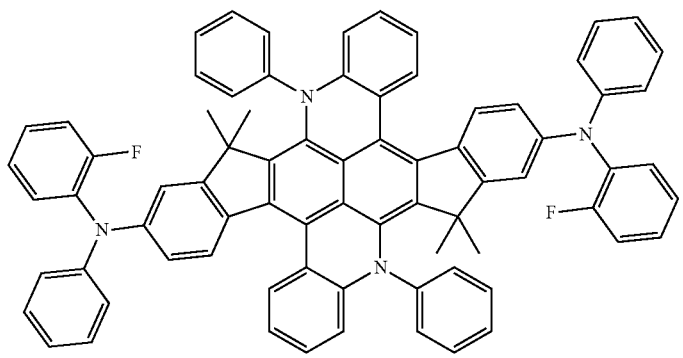

Compound 20
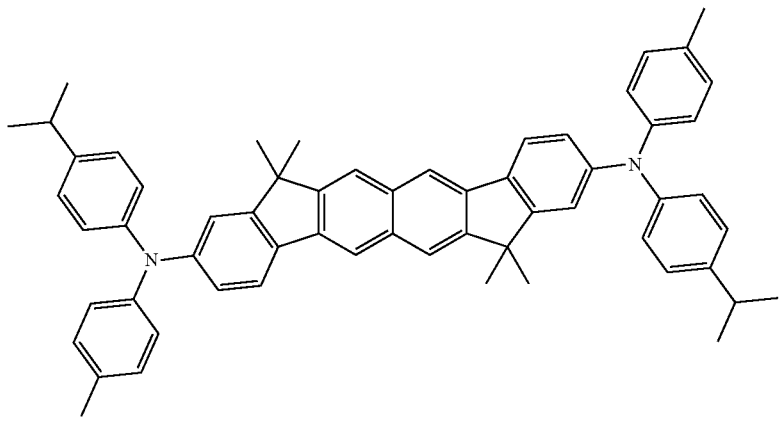
[Chem. 22]
Compound 21
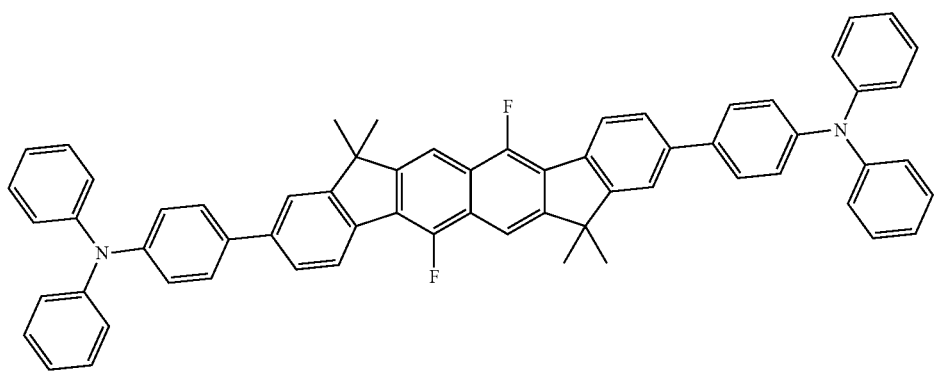
Compound 22
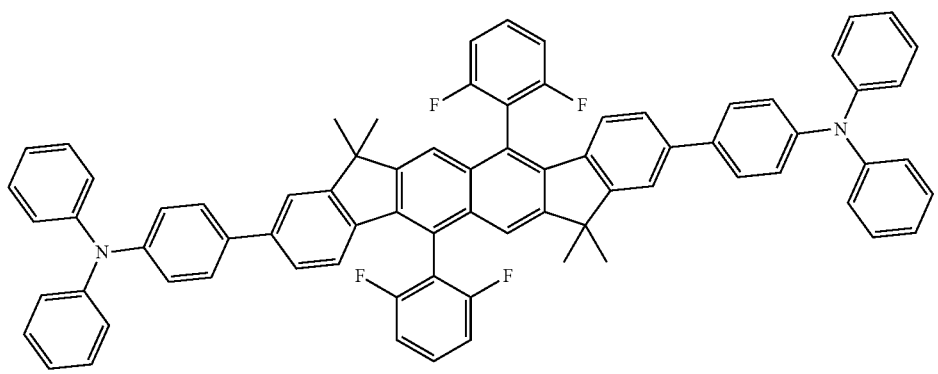
Compound 23
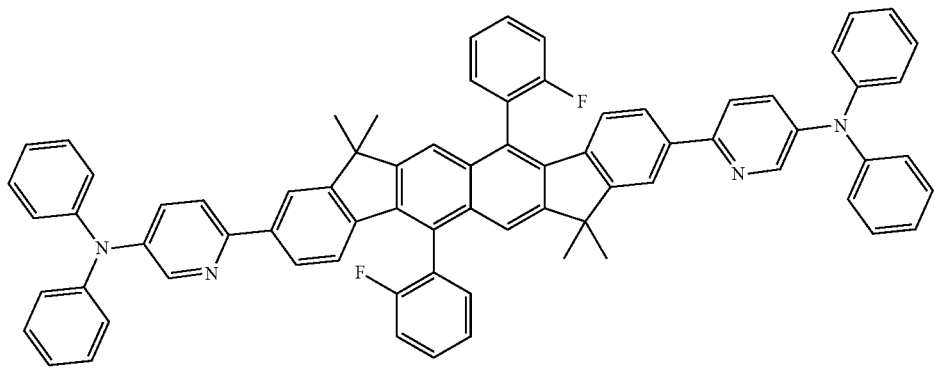

-continued
Compound 24
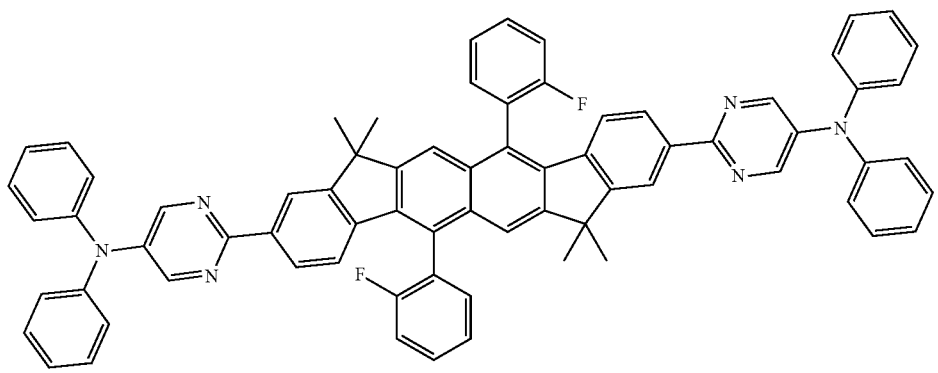
Compound 25
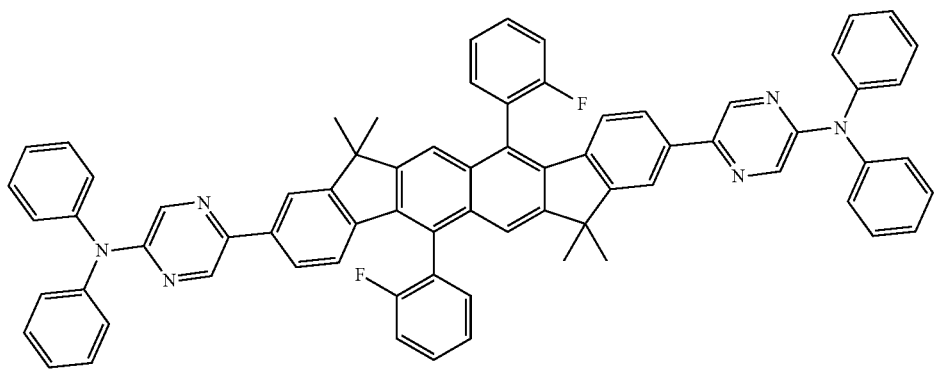
Compound 26
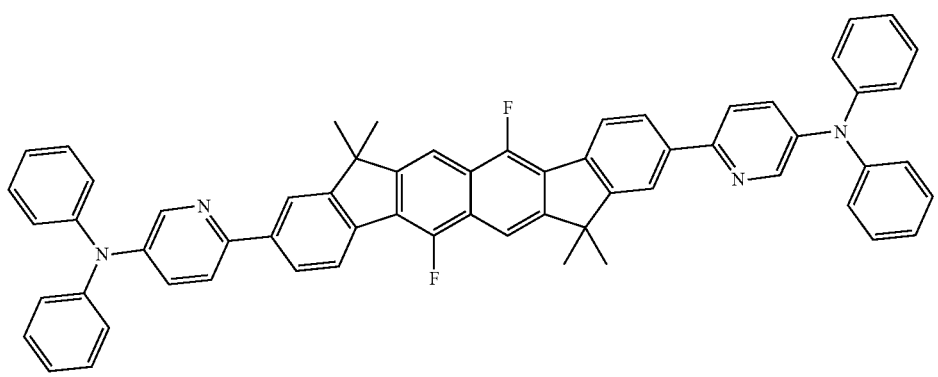
Compound 27
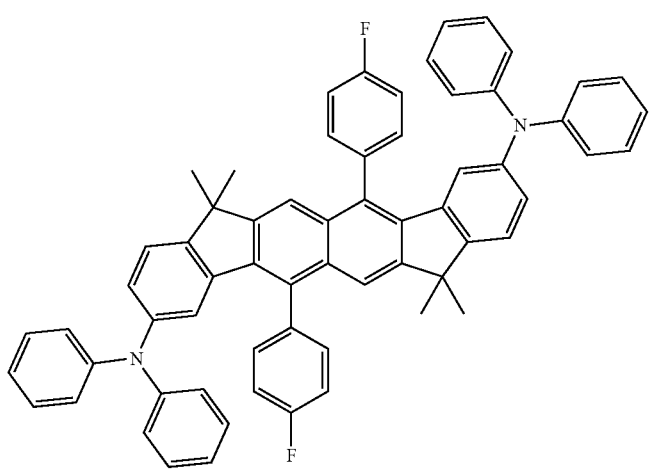

Compound 28
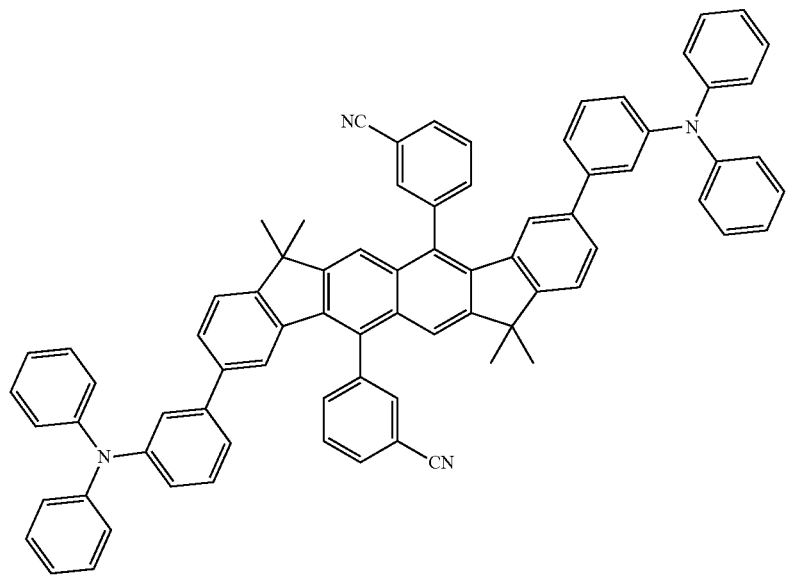
Compound 29
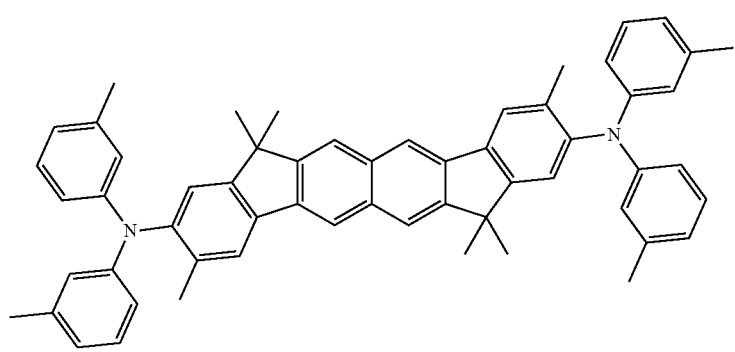
Compound 30
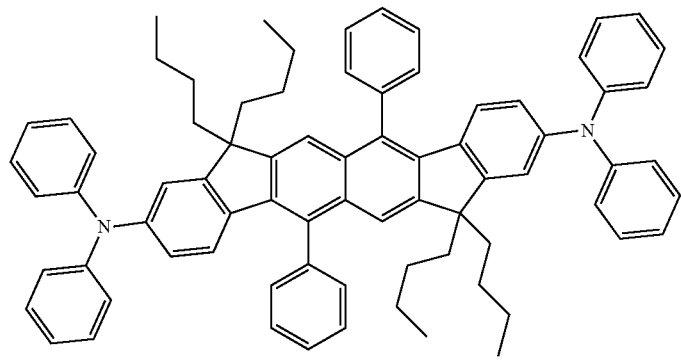

[Chem. 23]
Compound 31
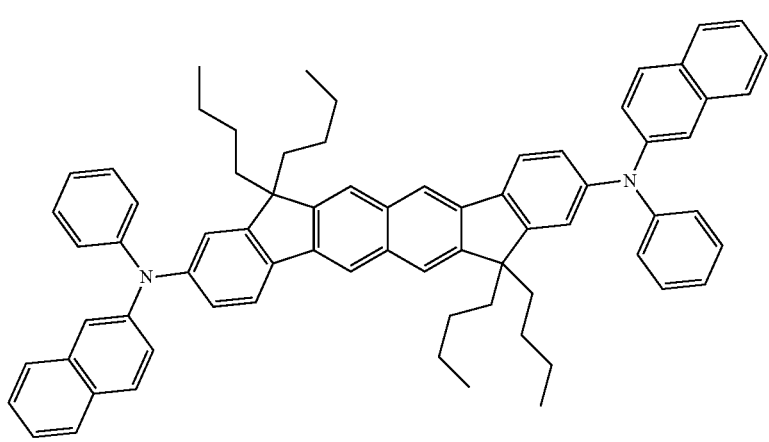
Compound 32
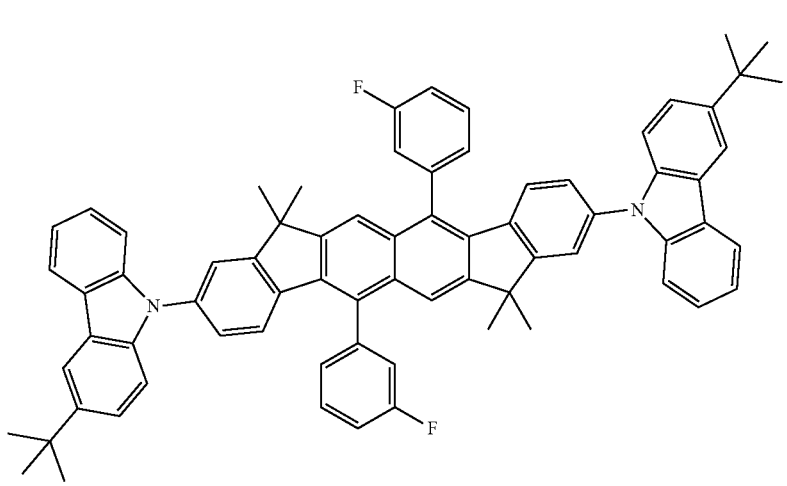
Compound 33
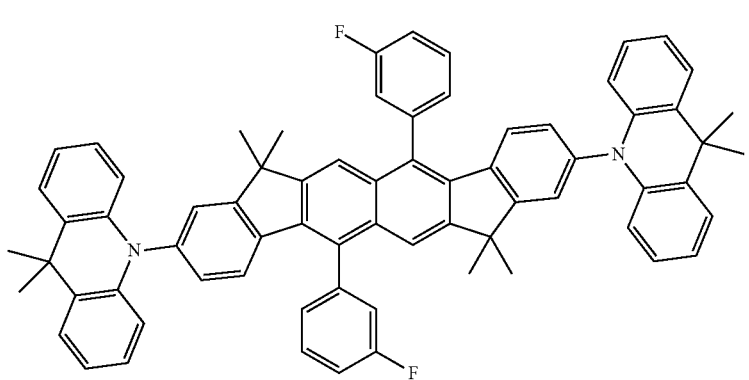

Compound 34
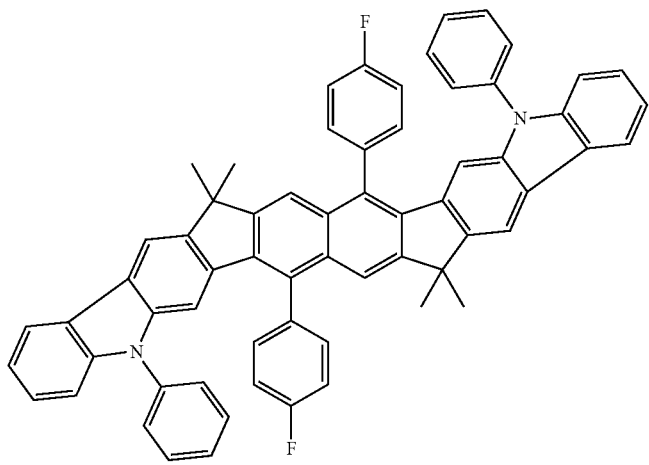
Compound 35
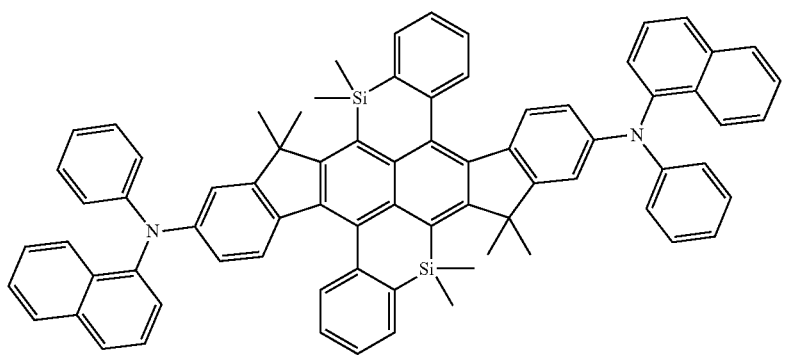
Compound 36
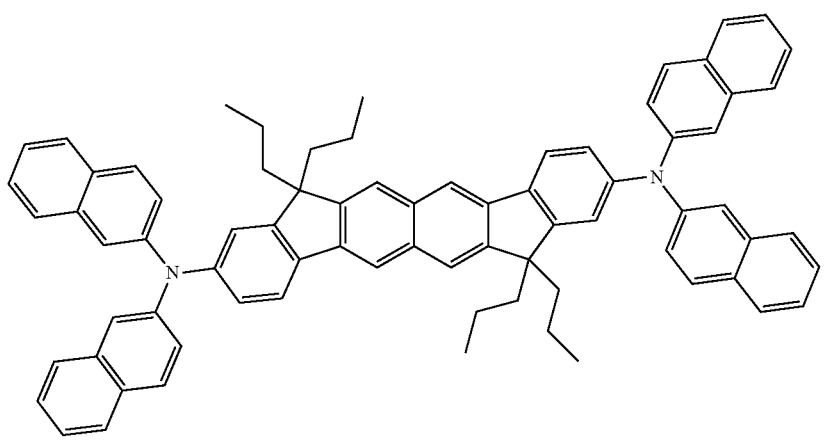

Compound 37
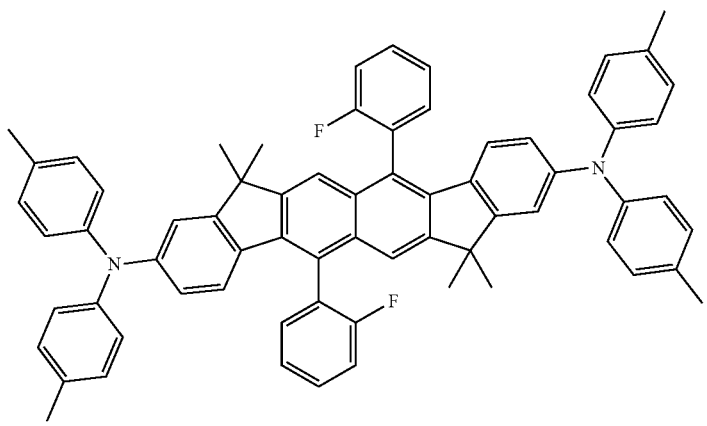
Compound 38
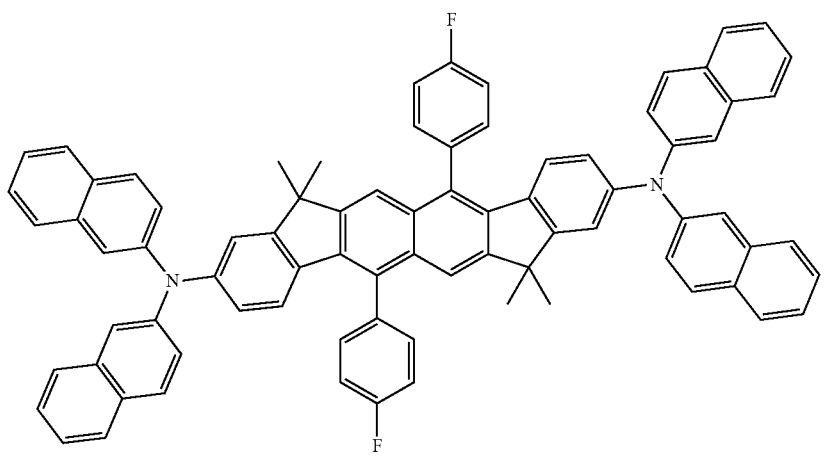
Compound 39
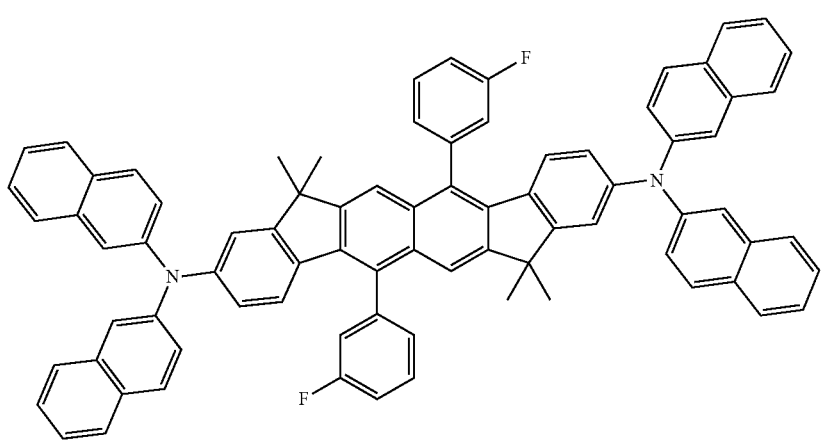

Compound 40
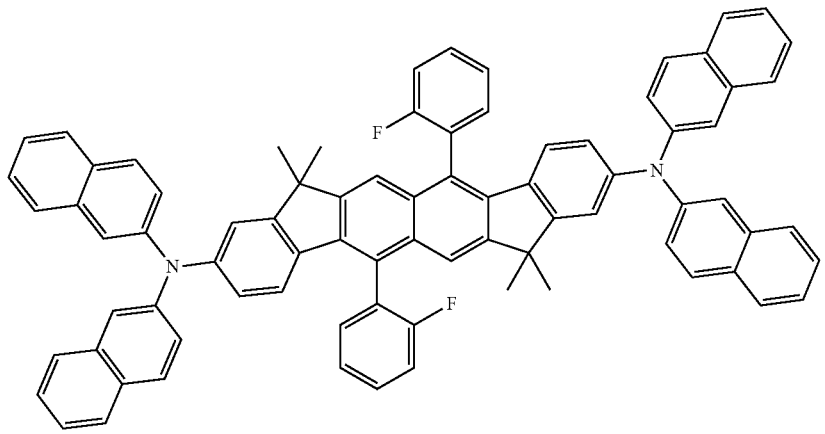
[Chem. 24]
Compound 41
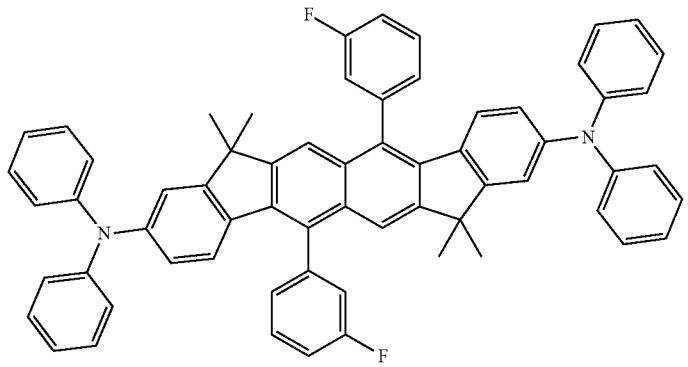
Compound 42
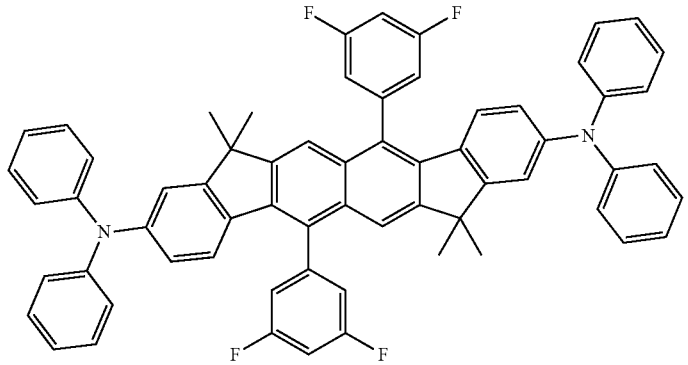
Compound 43
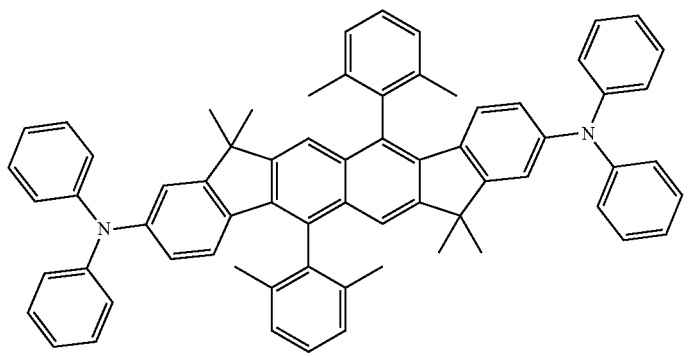

-continued
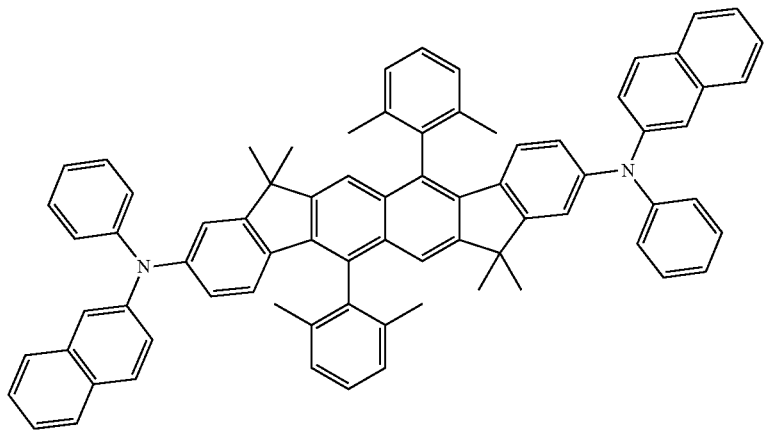
Compound 44
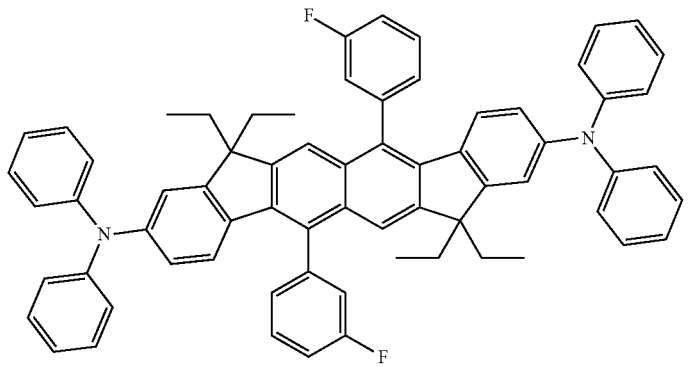
Compound 45
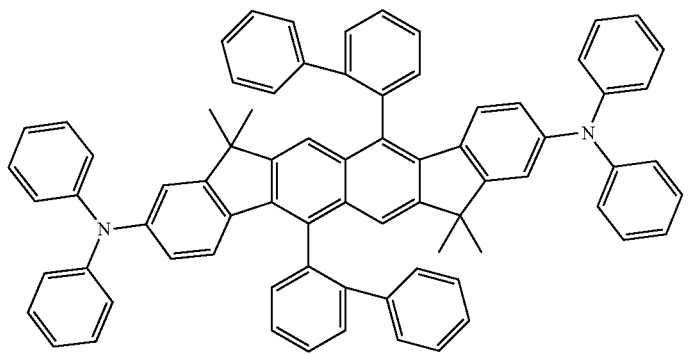
Compound 46
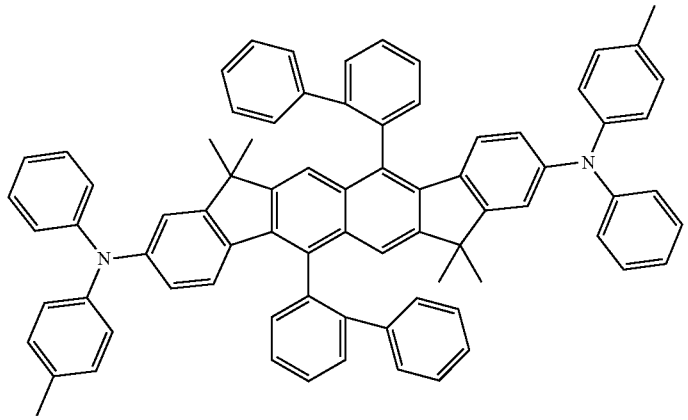
Compound 47

Compound 48
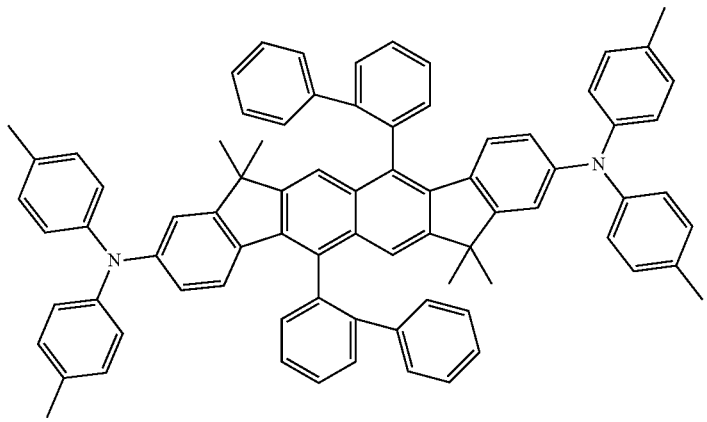
Compound 49
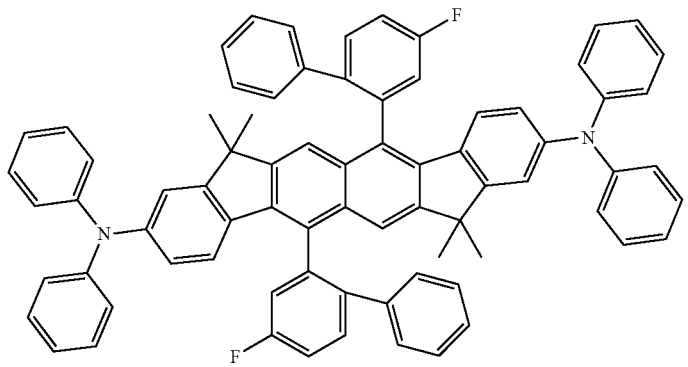
Compound 50
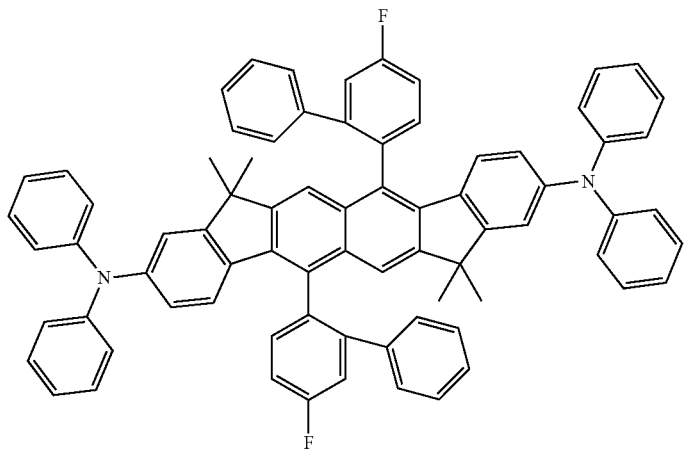
[Chem. 25]
Compound 51
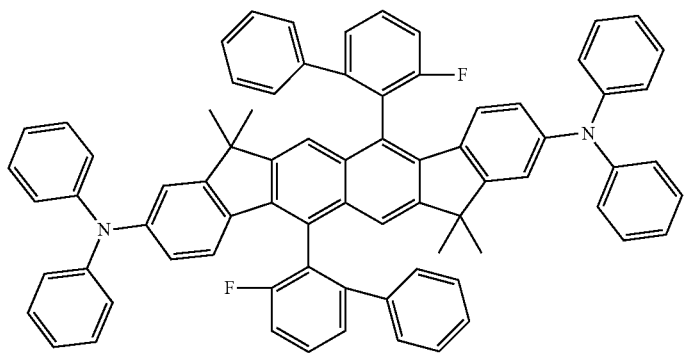

Compound 52
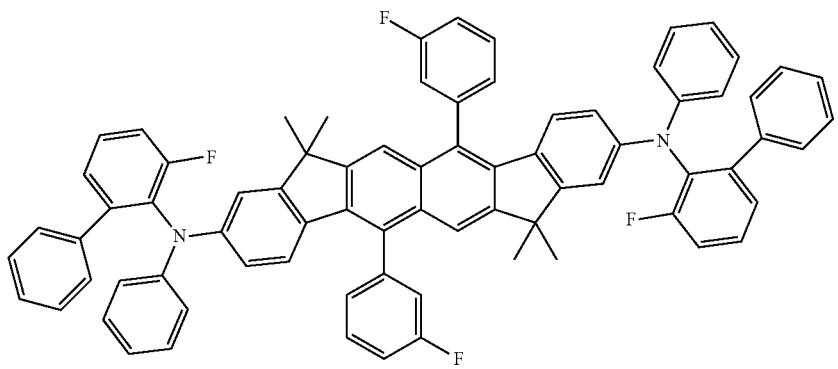
Compound 53
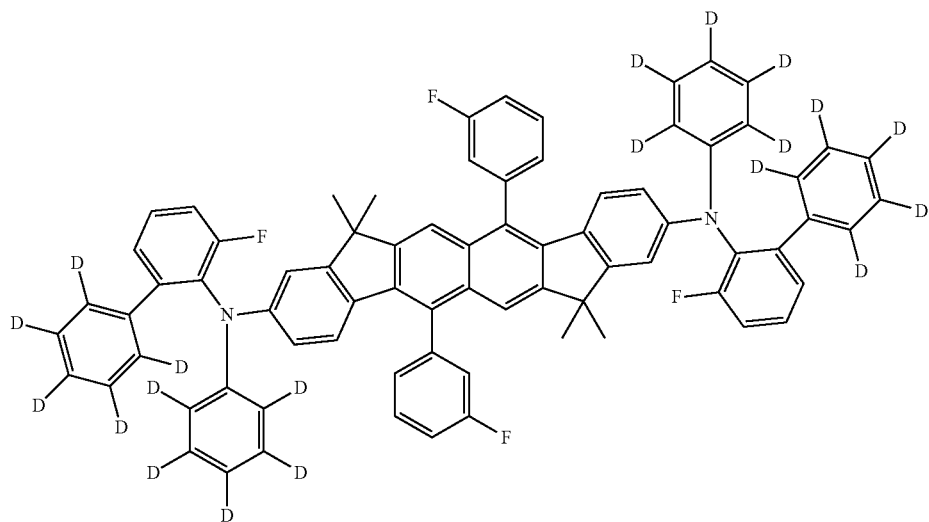
Compound 54
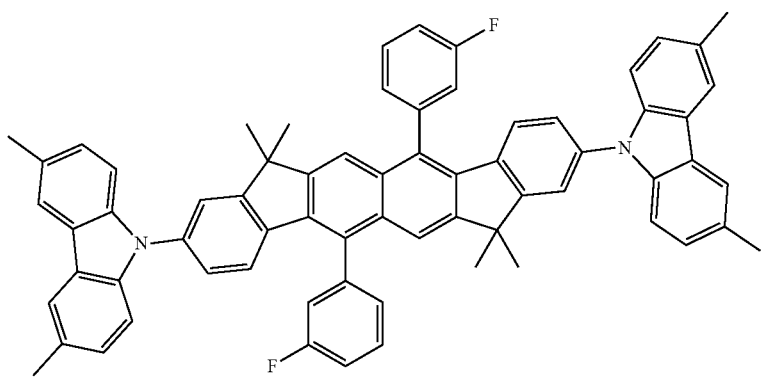
Compound 55
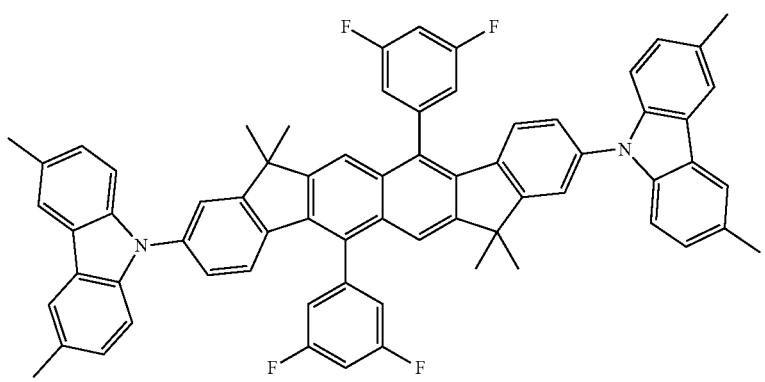

-continued
Compound 56
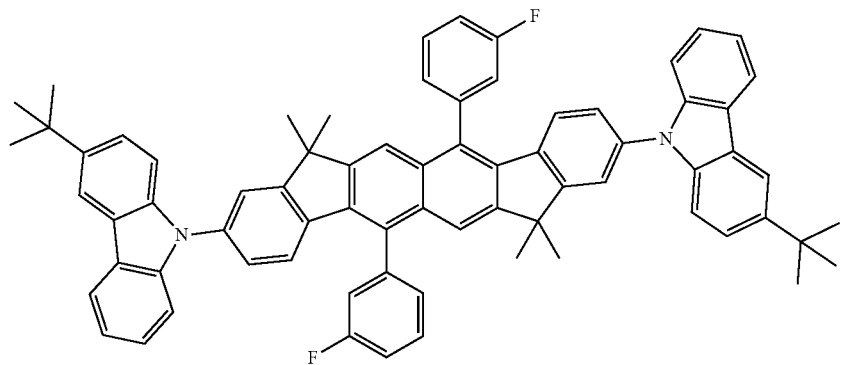
Compound 57
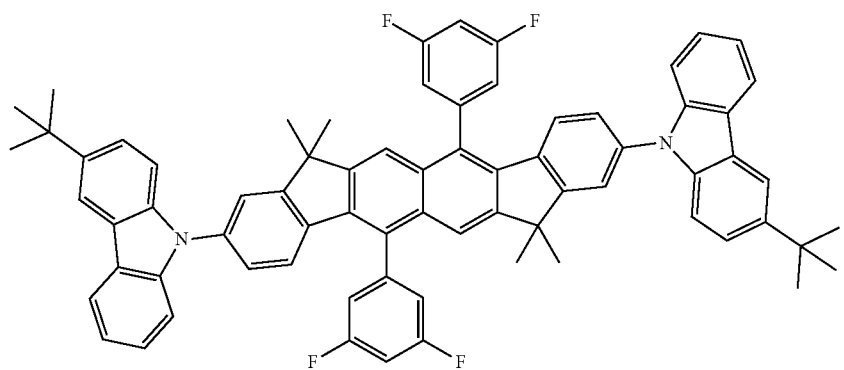
Compound 58
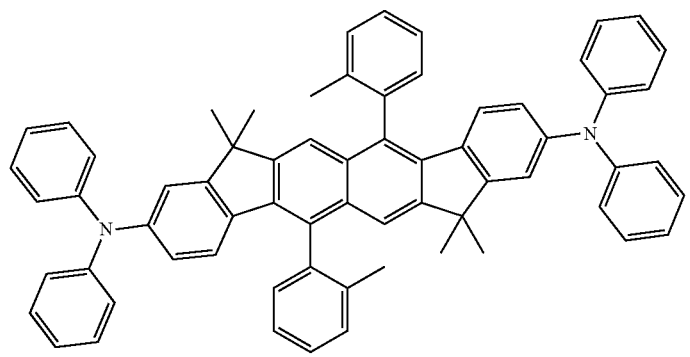
Compound 59
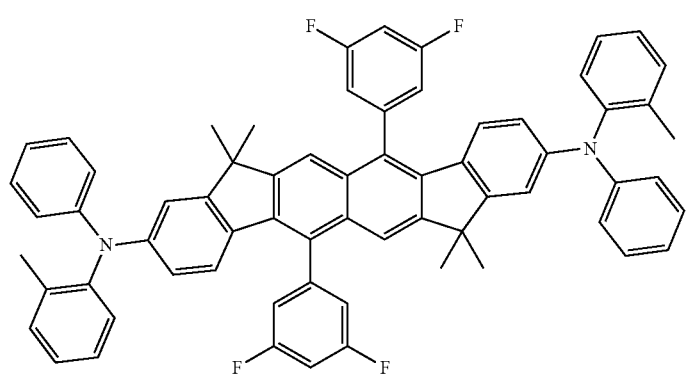

-continued
Compound 60
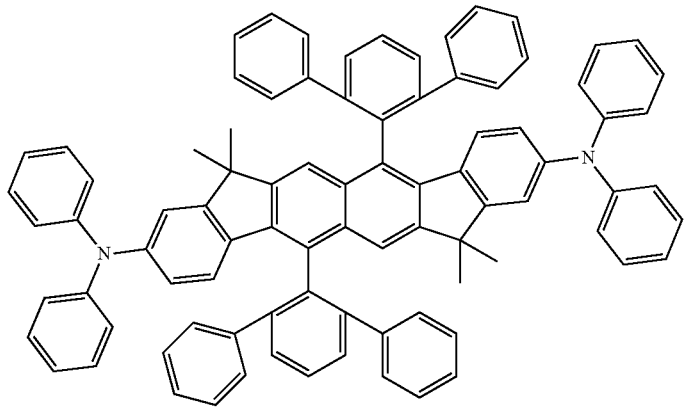
[Chem. 26]
Compound 61
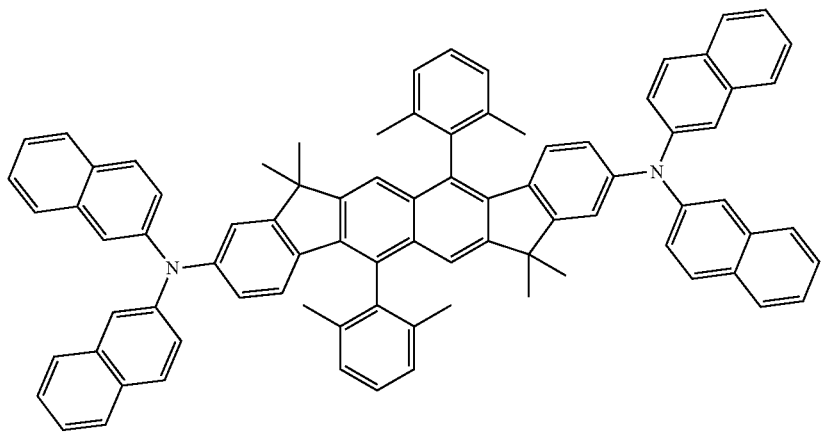
Compound 62
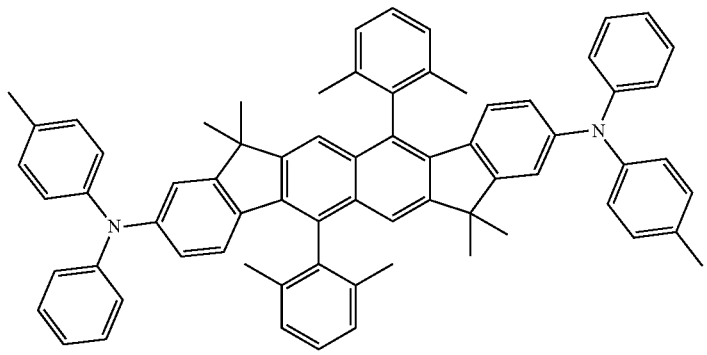

Compound 63
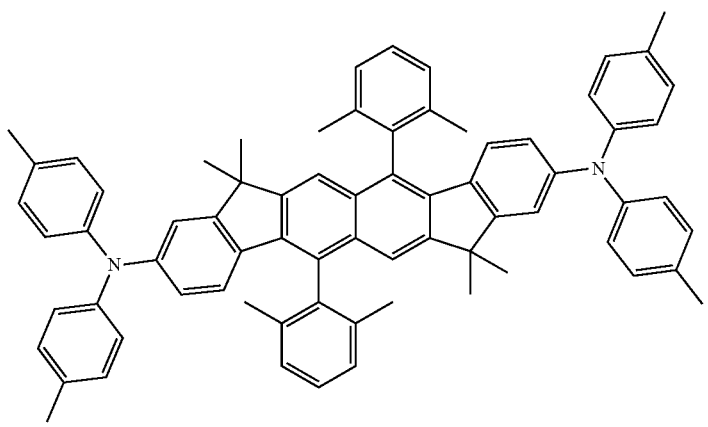
Compound 64
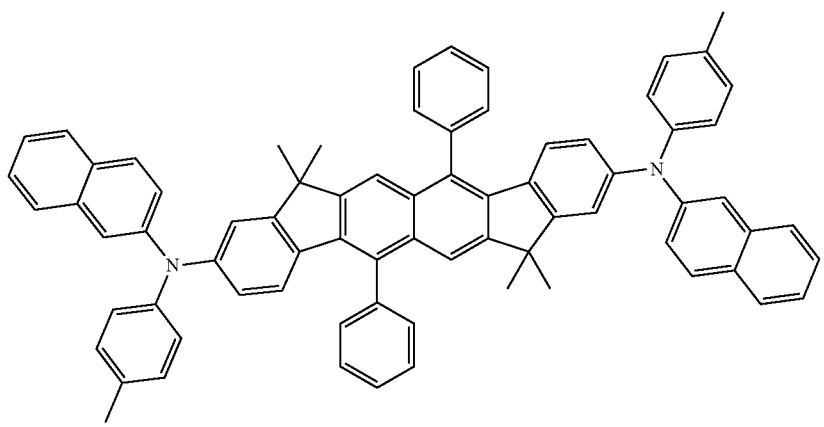
Compound 65
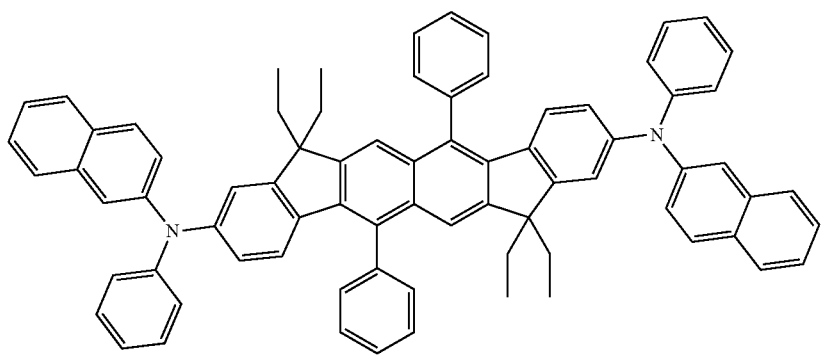
Compound 66
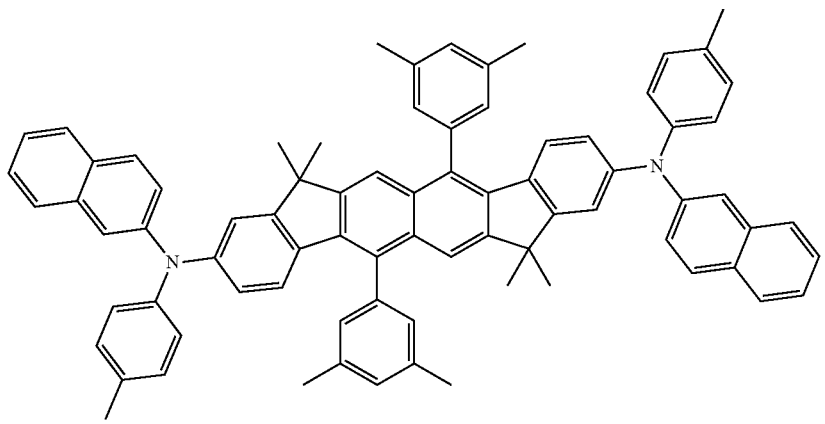

Compound 67
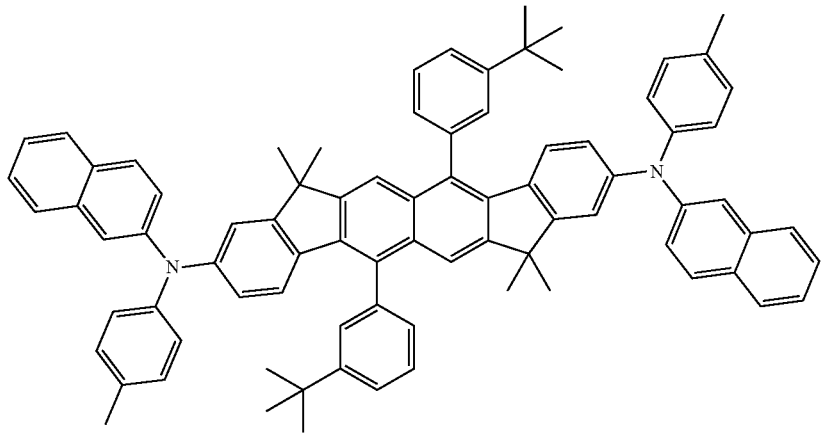
Compound 68
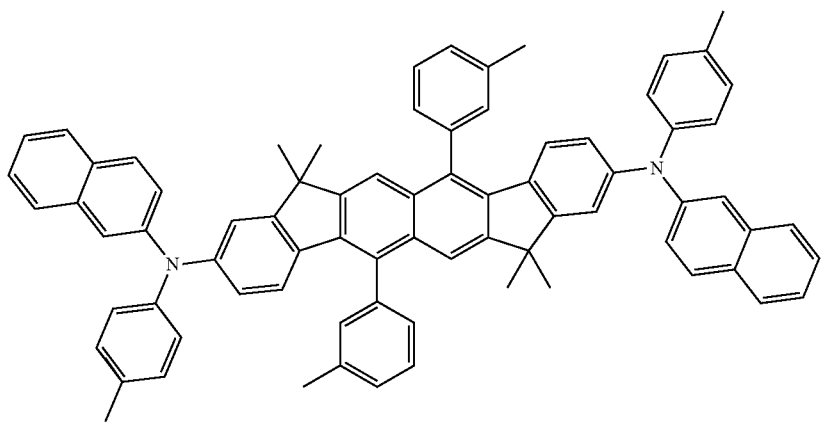
Compound 69
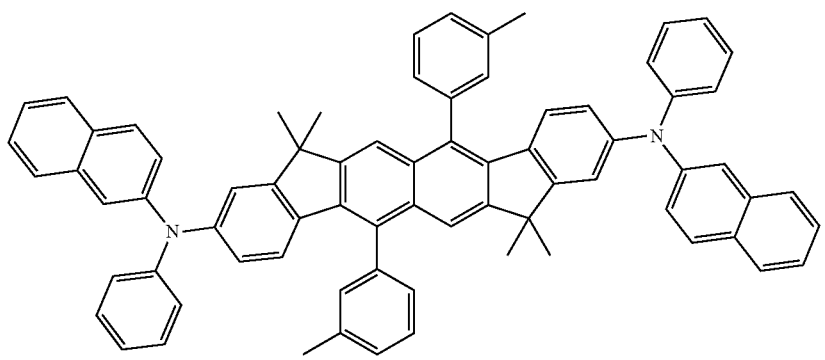
Compound 70
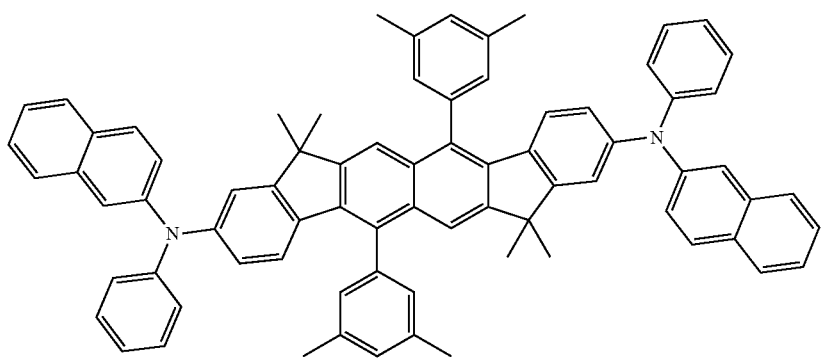

Compound 71
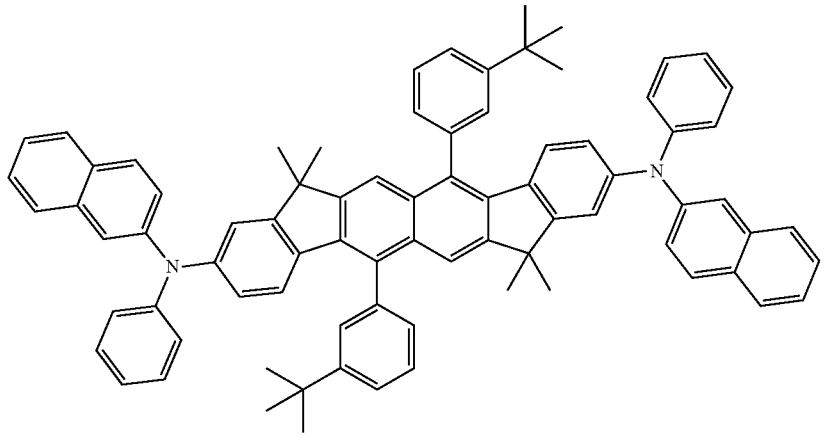
Compound 72
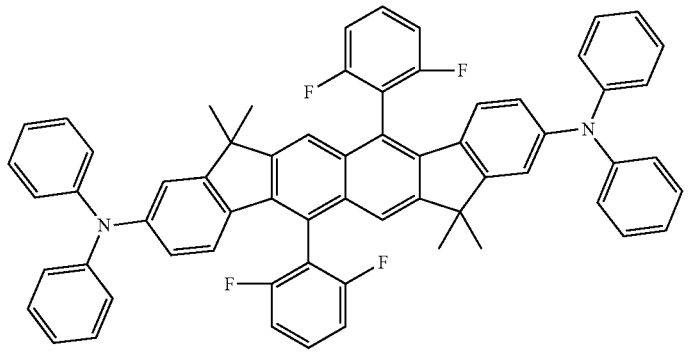
Compound 73
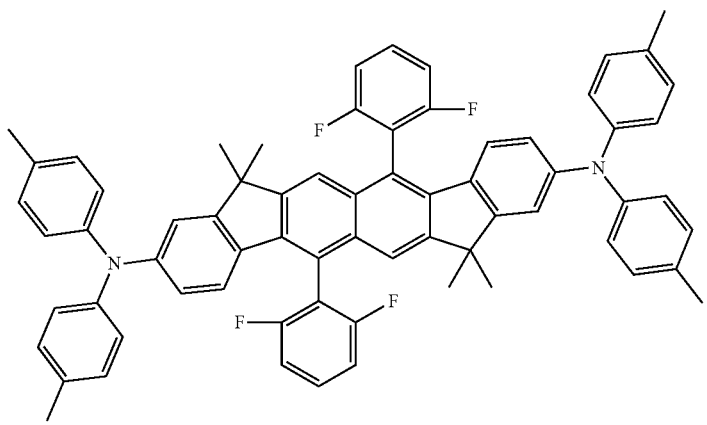

Compound 74
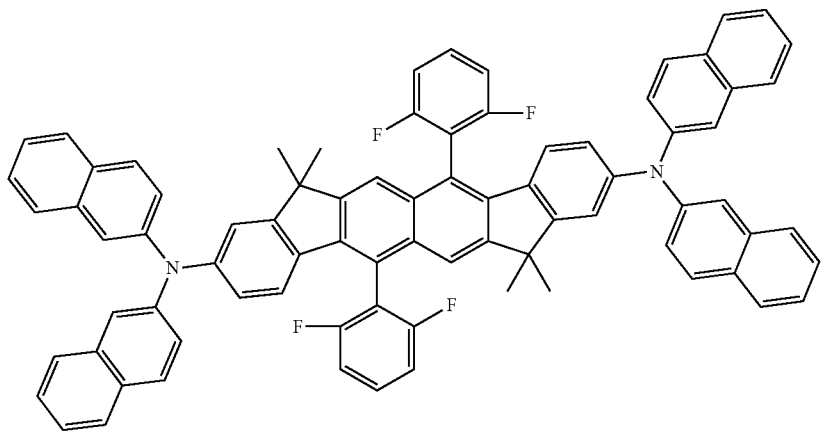
Compound 75
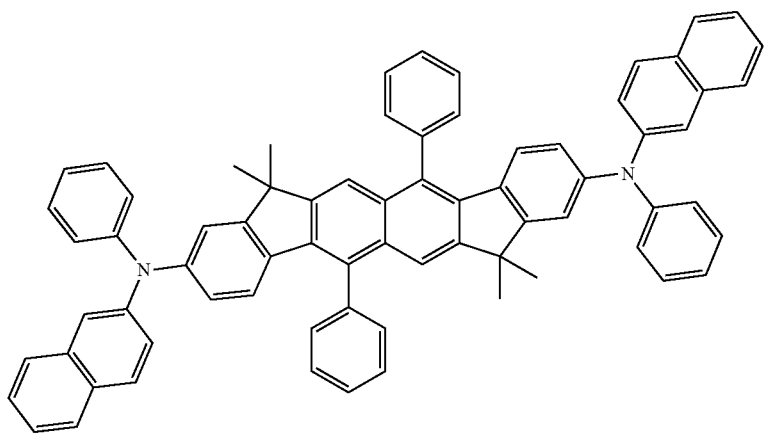
Compound 76
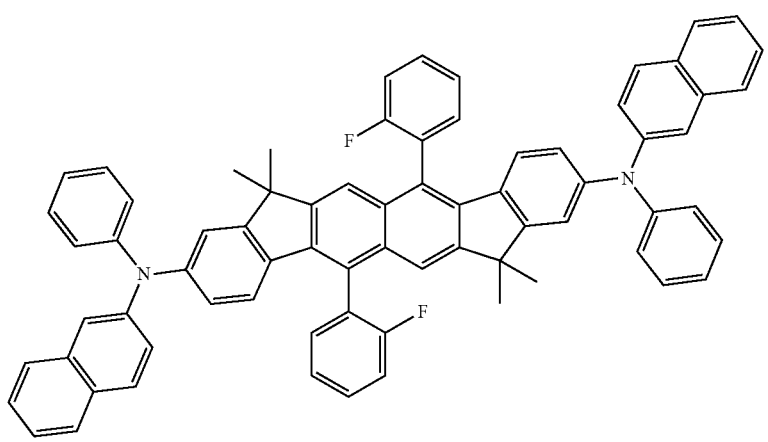

Compound 77
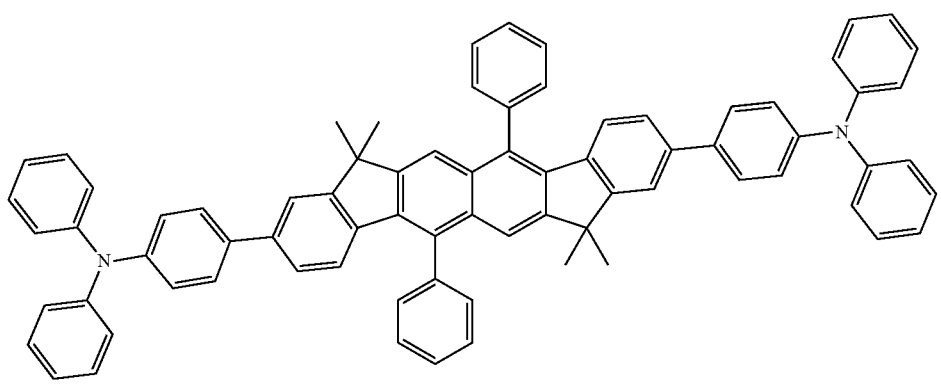
Compound 78
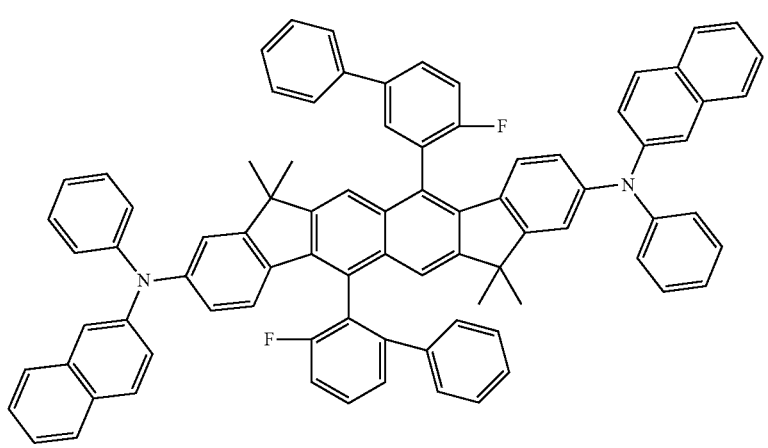
Compound 79
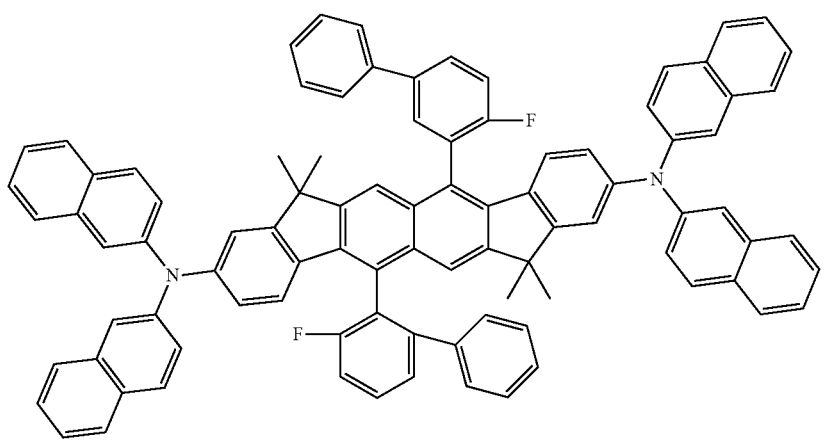

Compound 80
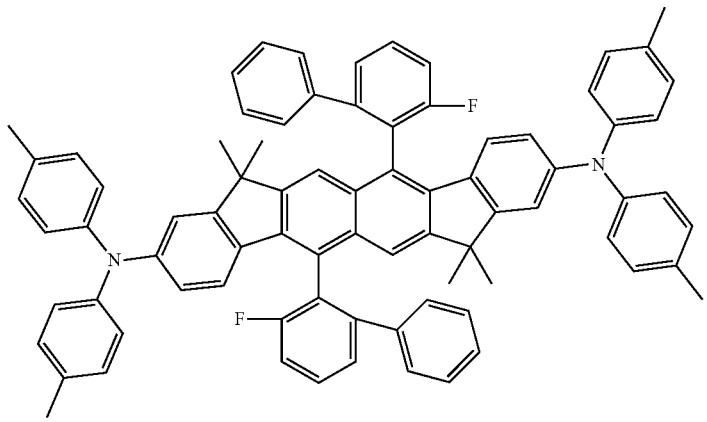
[Chem. 28]
Compound 81
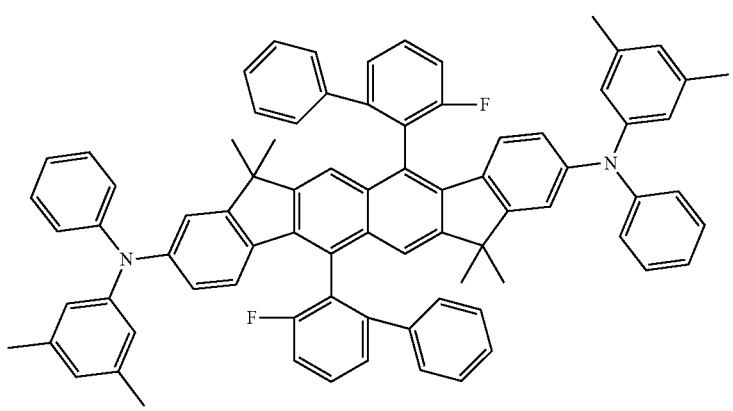
Compound 82
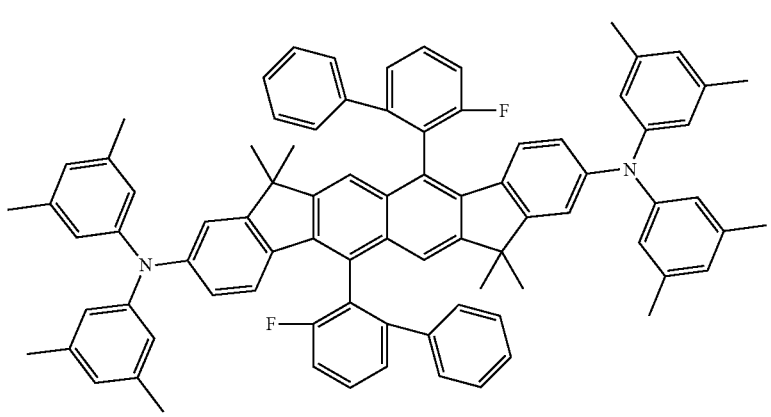

-continued
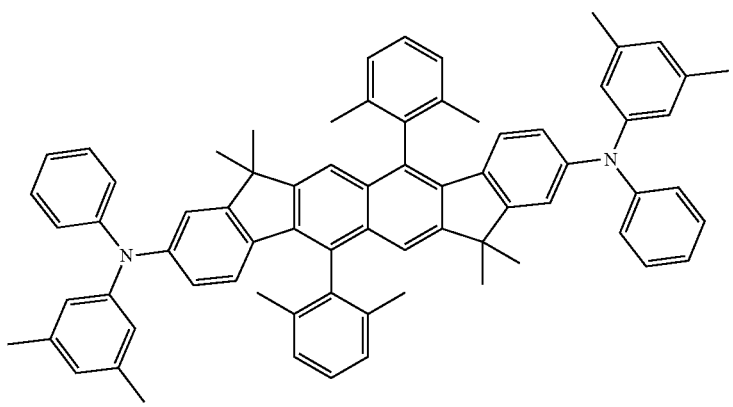
Compound 83
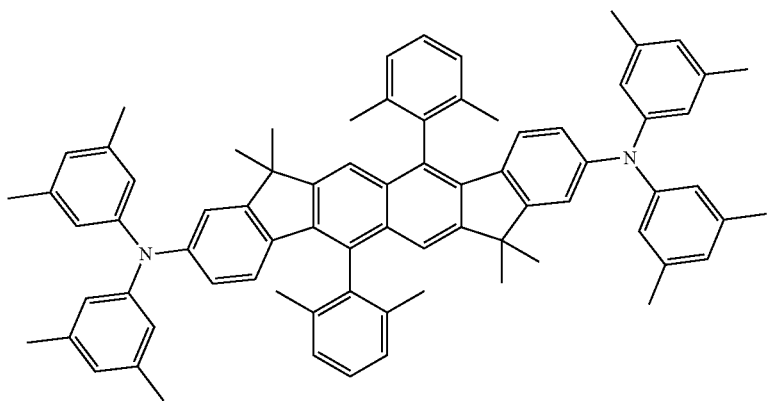
Compound 84
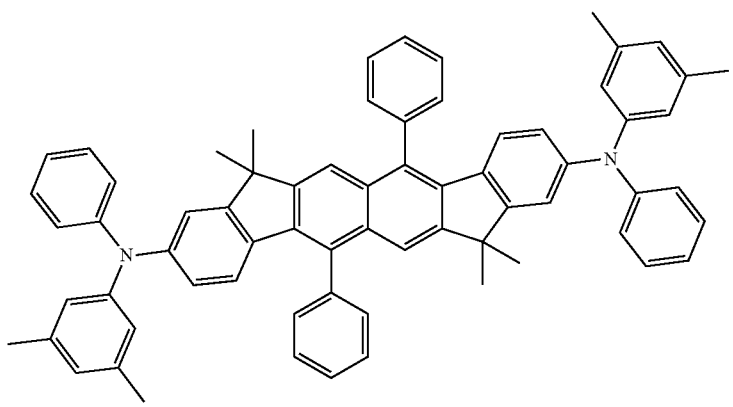
Compound 85
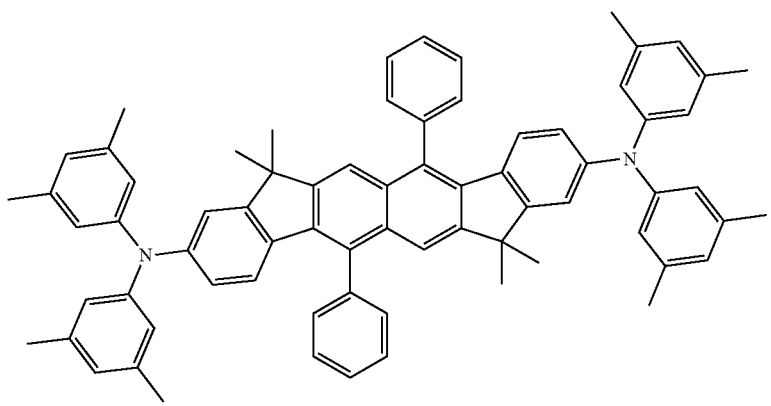
Compound 86

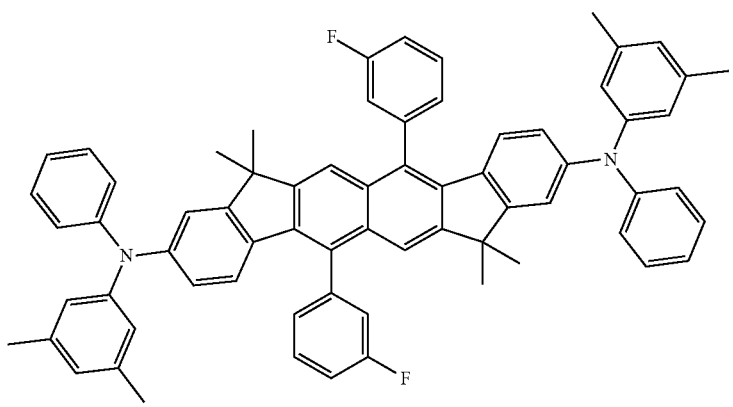
Compound 87
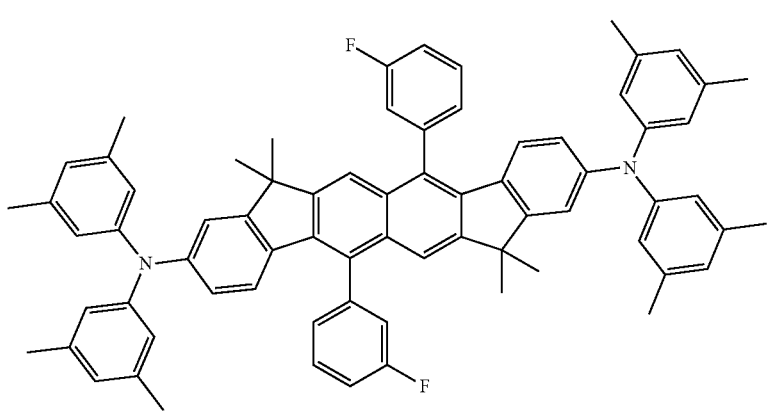
Compound 88
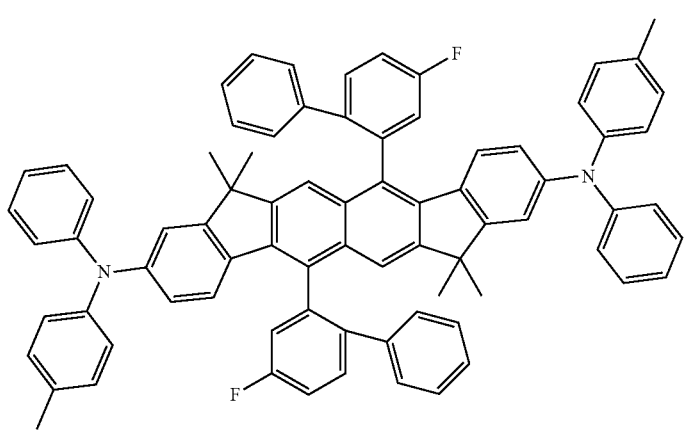
Compound 89

Compound 90
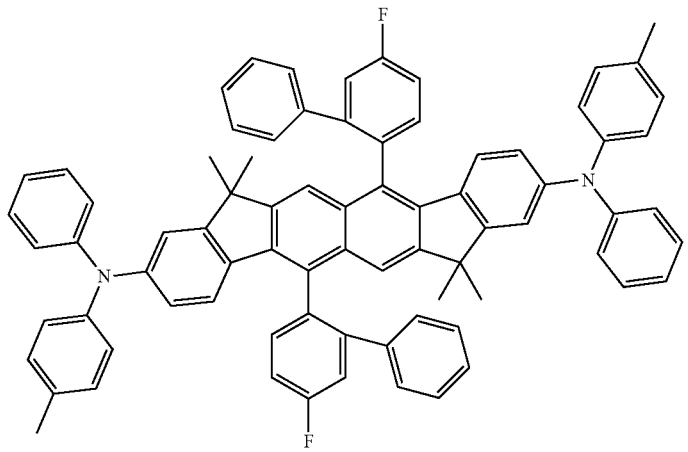
[Chem 29]
Compound 91
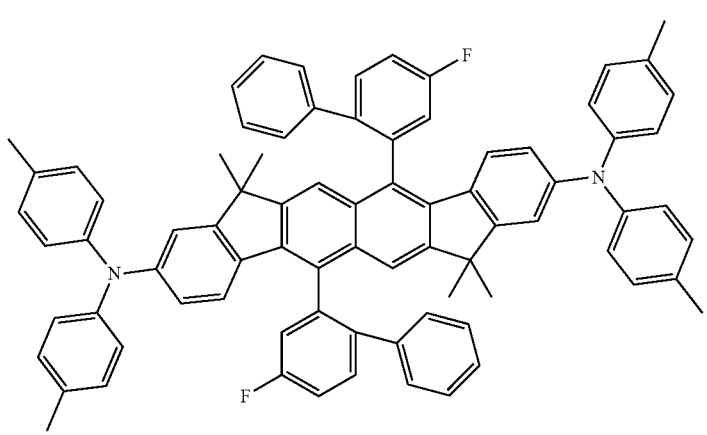
Compound 92
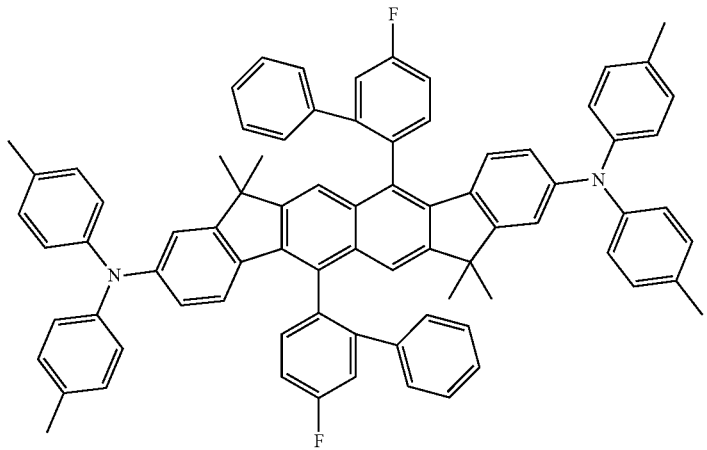

-continued
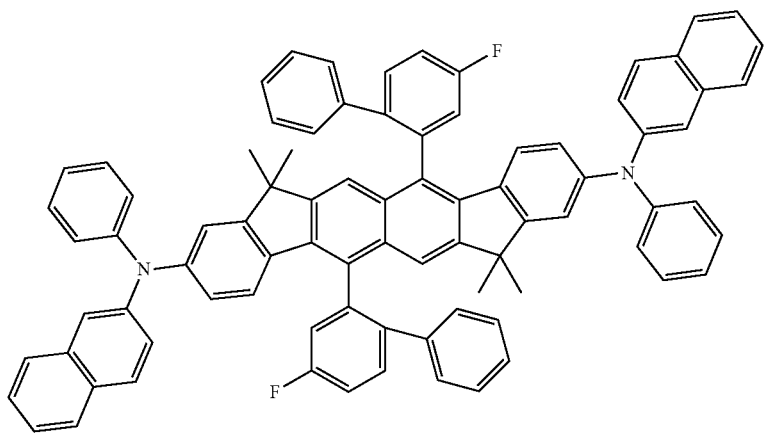
Compound 93
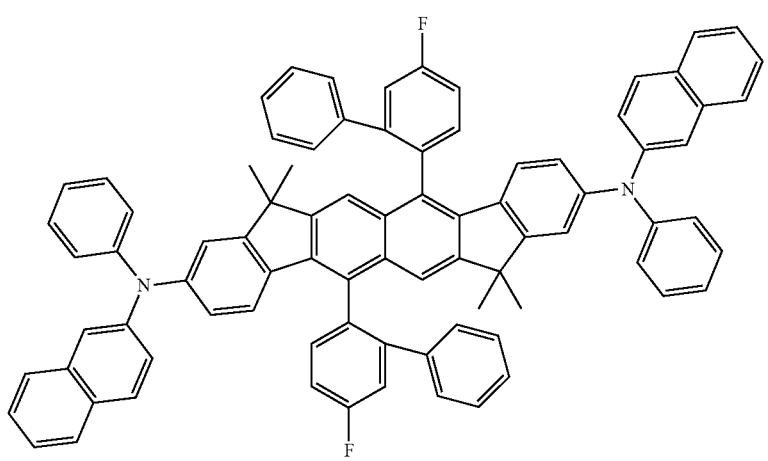
Compound 94
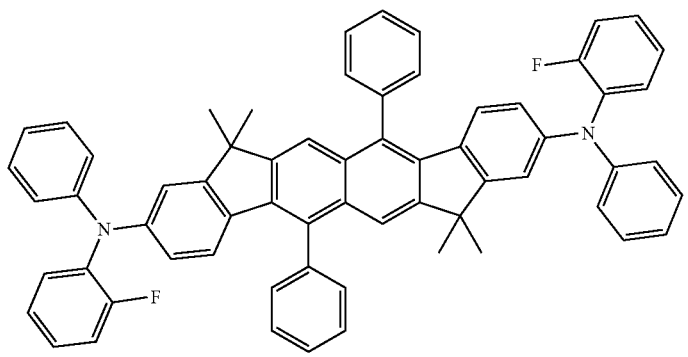
Compound 95
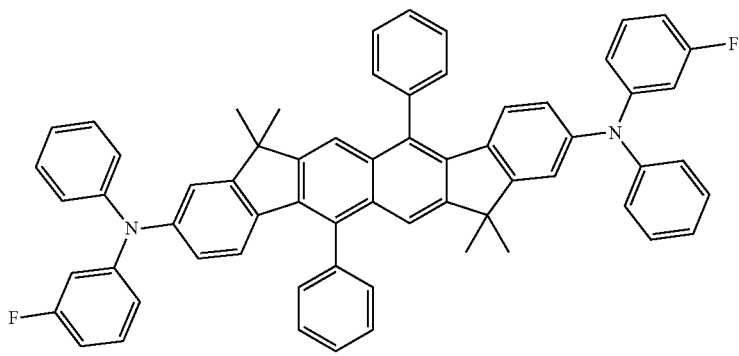
Compound 96

Compound 97
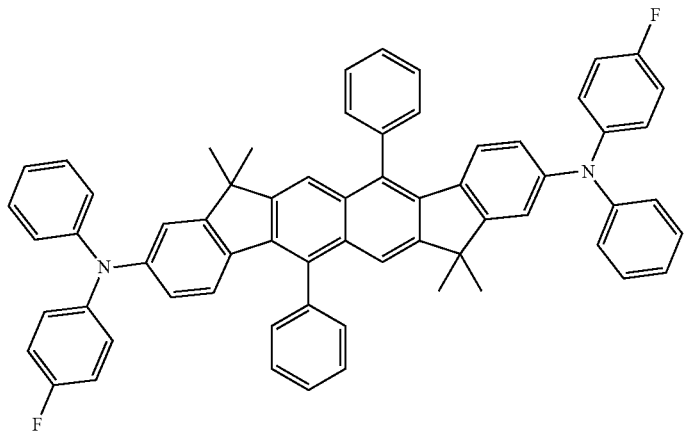
Compound 98
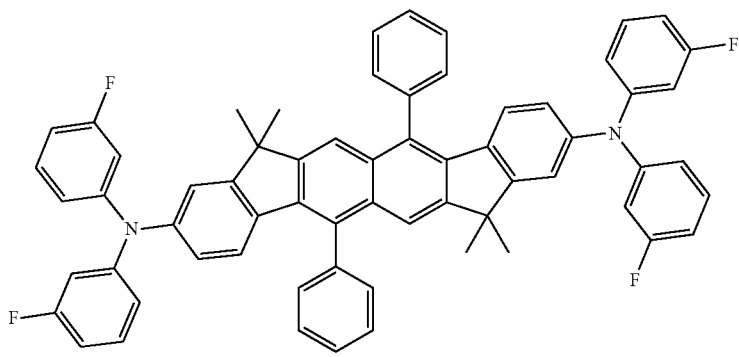
Compound 99
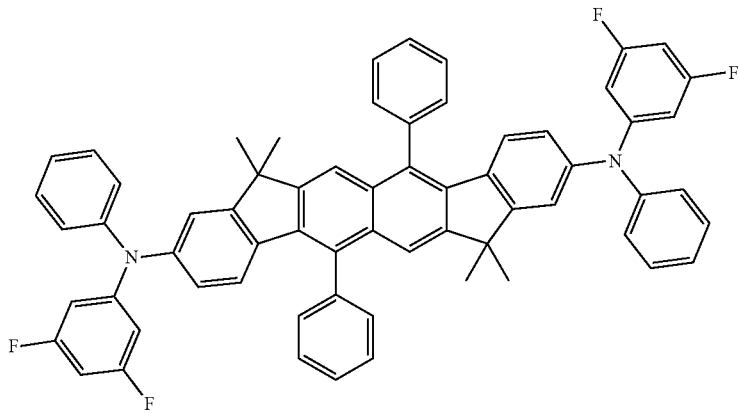
Compound 100
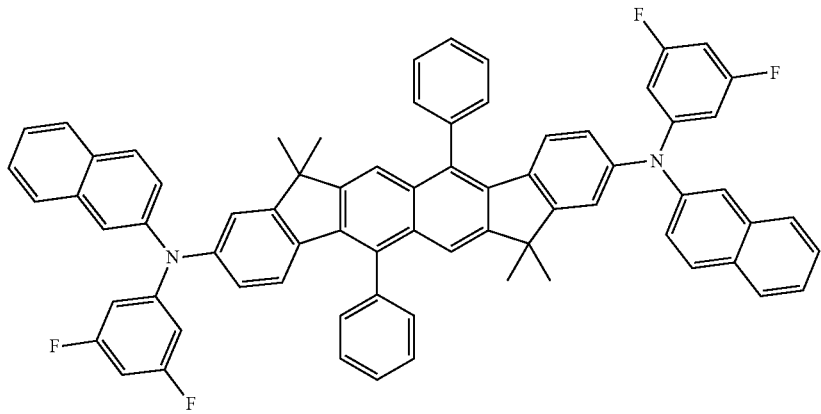

[Chem. 30]
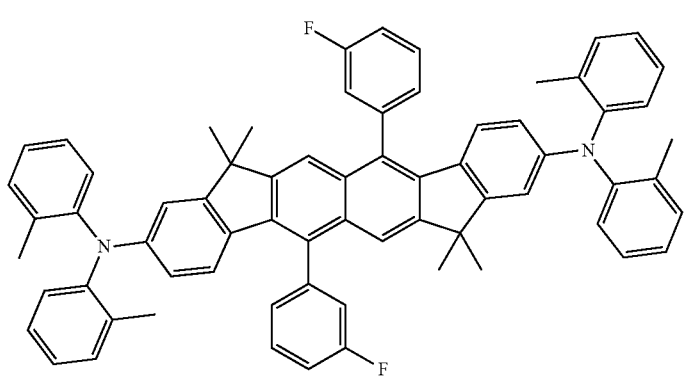
Compound 101
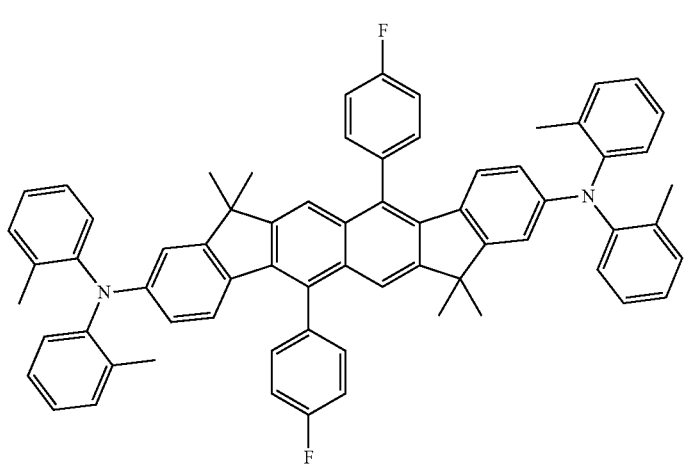
Compound 102
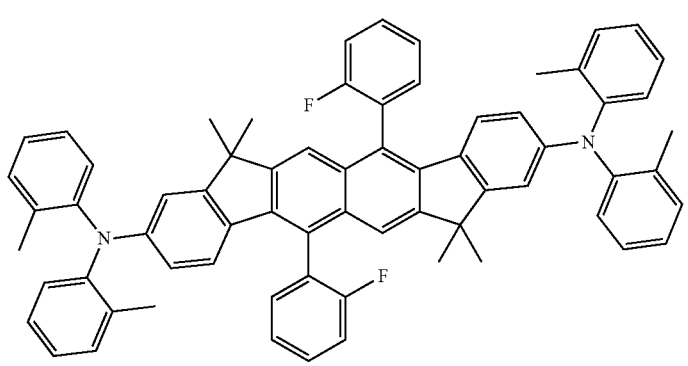
Compound 103
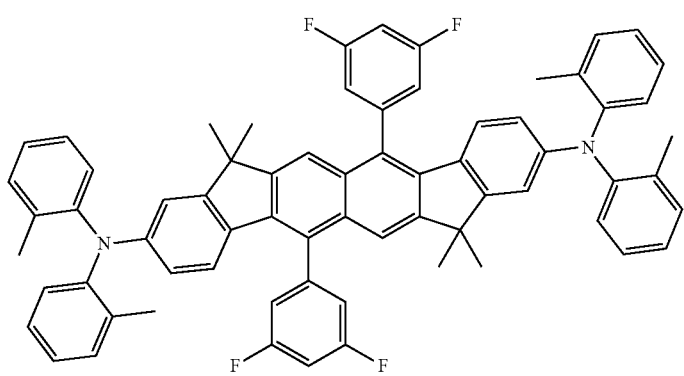
Compound 104

Compound 105
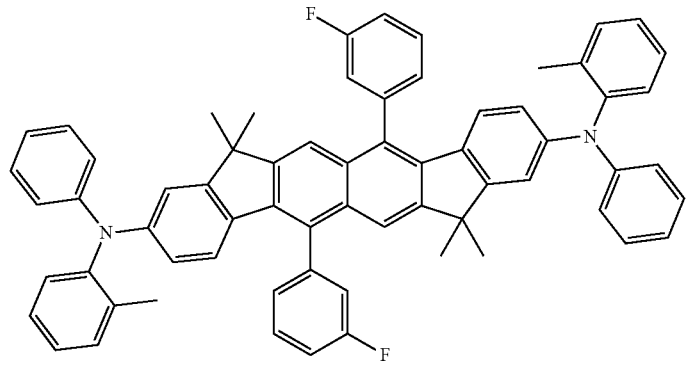
Compound 106
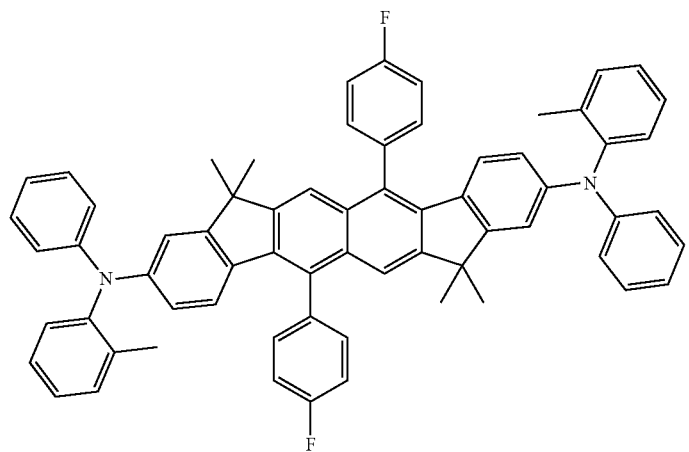
Compound 107
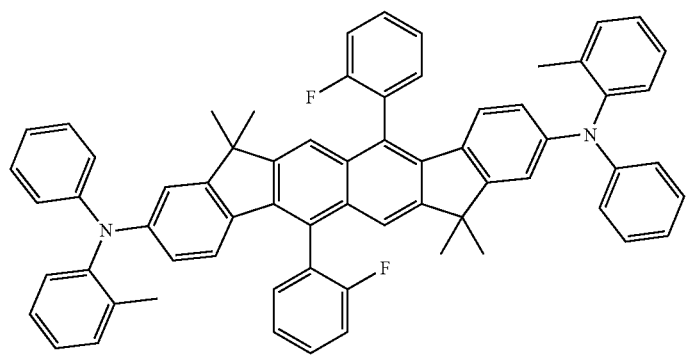
Compound 108
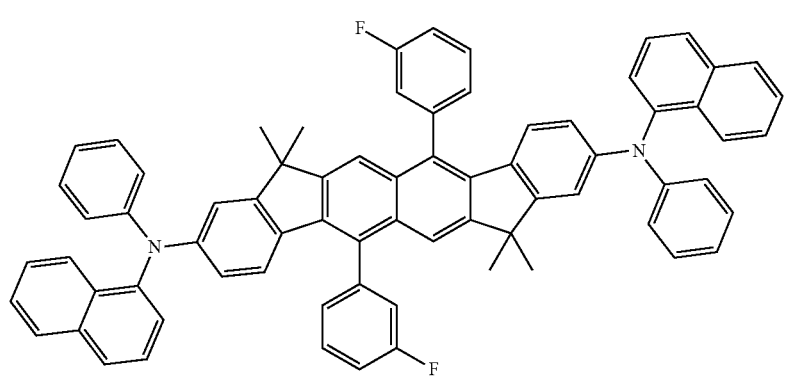

Compound 109
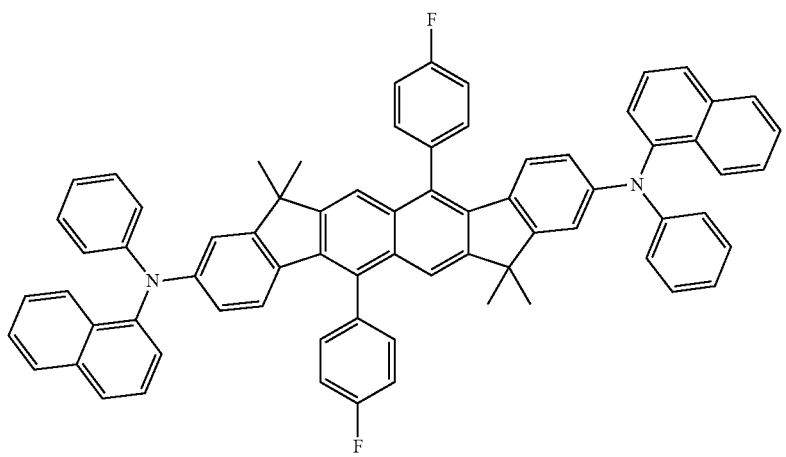
Compound 110
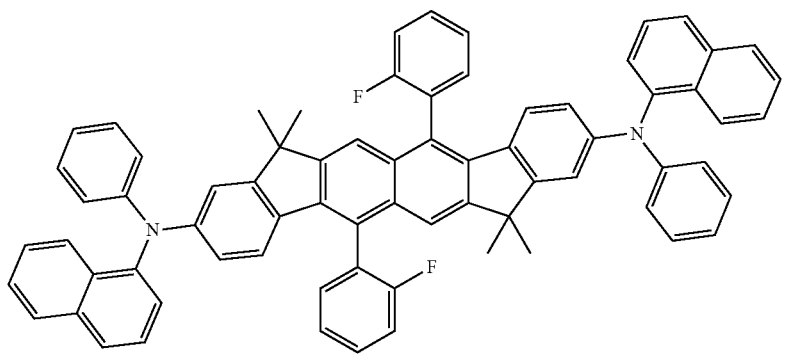
[Chem. 31]
Compound 111
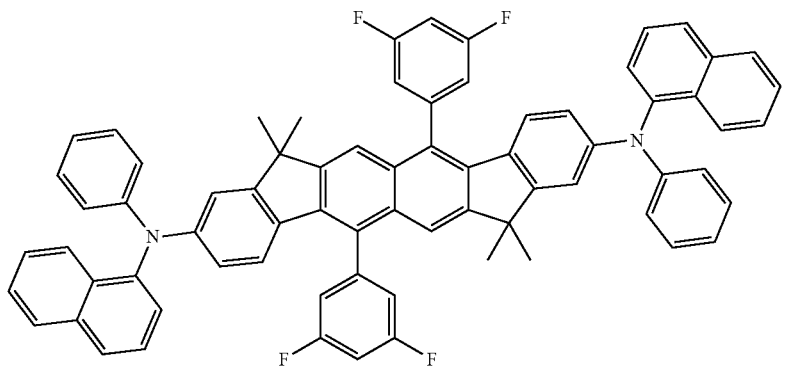
Compound 112
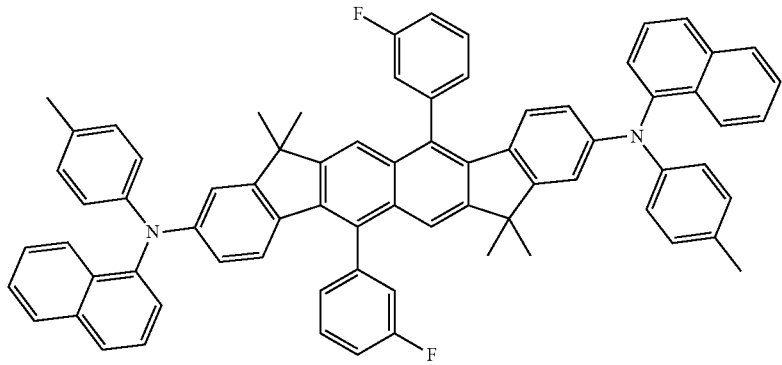

-continued
Compound 113
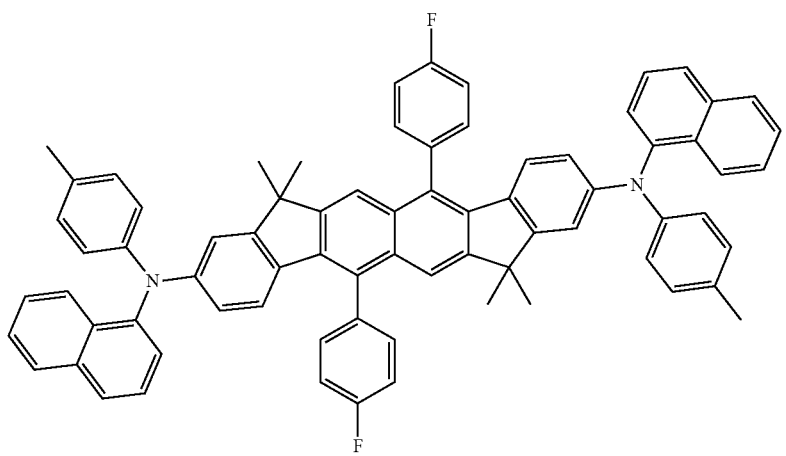
Compound 114
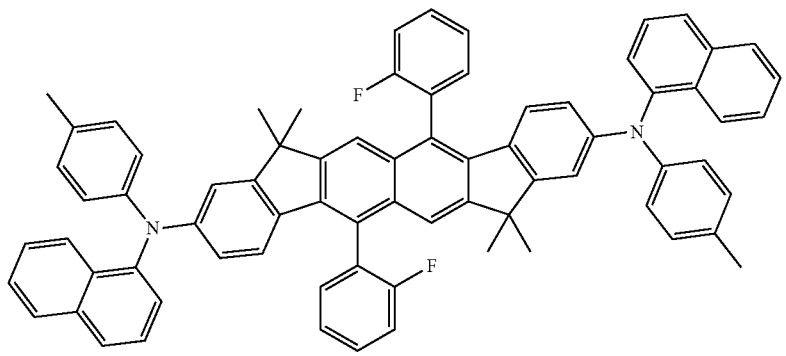
Compound 115
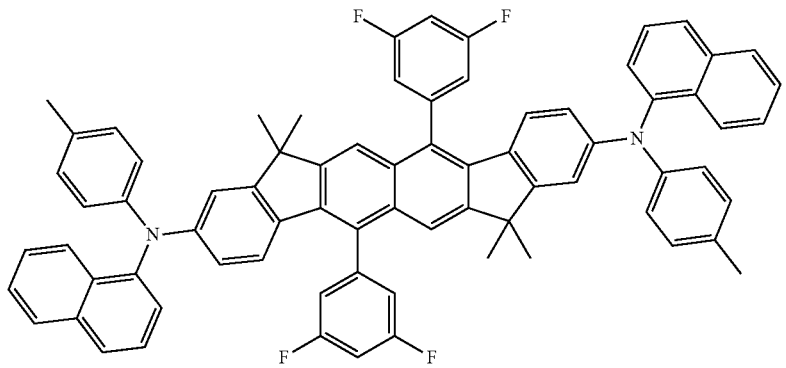
Compound 116
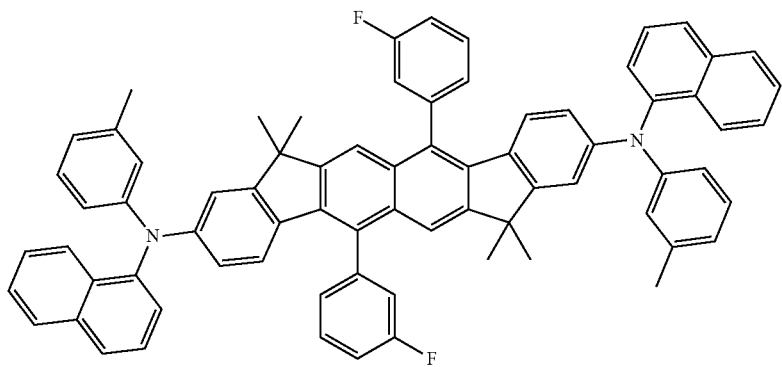

Compound 117
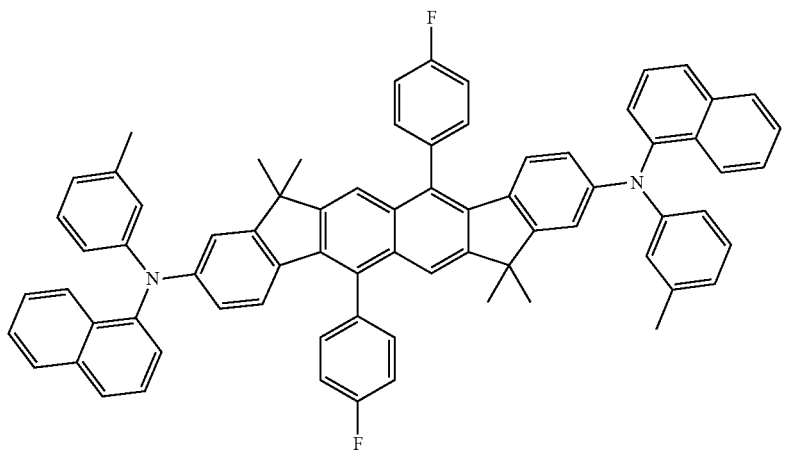
Compound 118
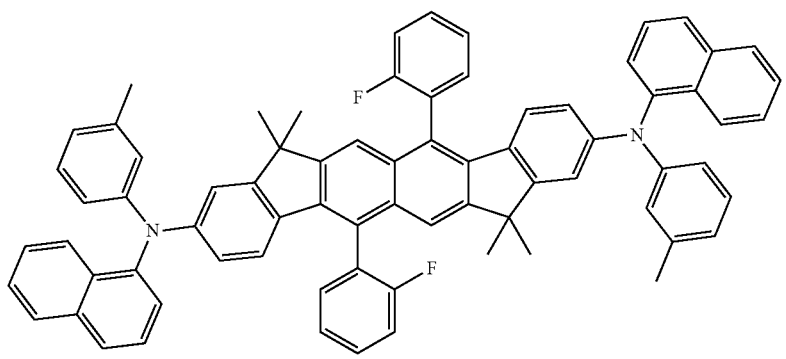
Compound 119
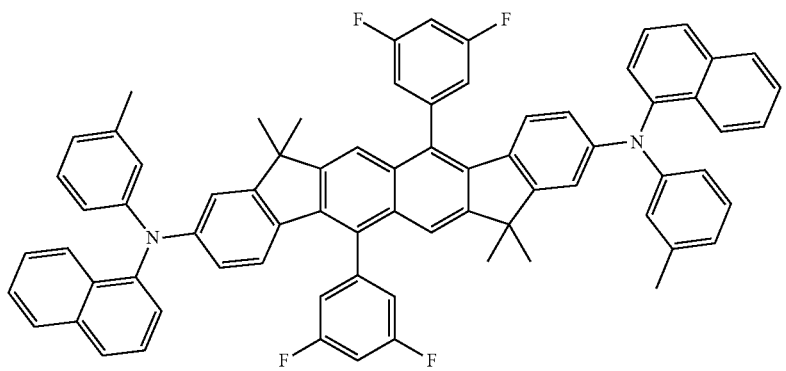
Compound 120
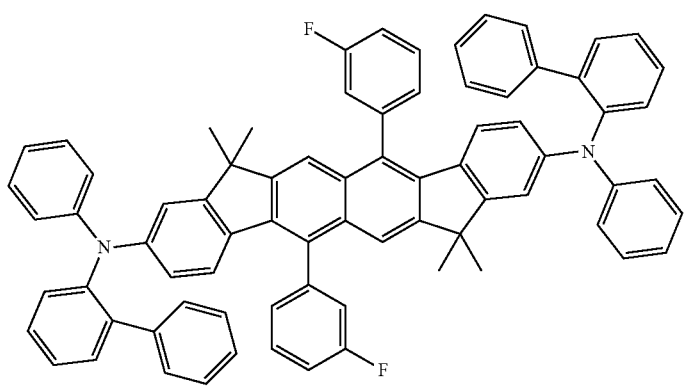

-continued
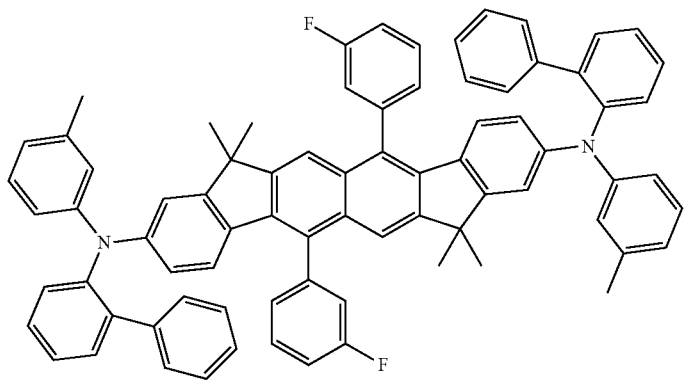
Compound 121
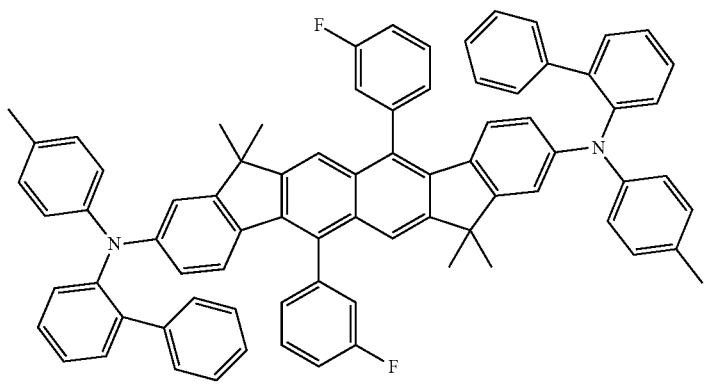
Compound 122
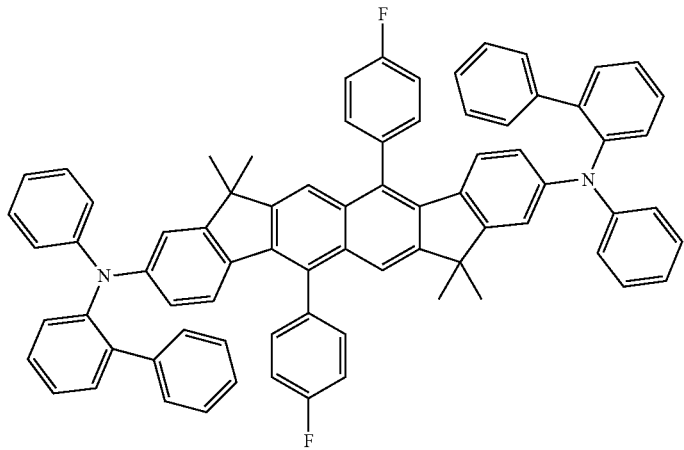
Compound 123

-continued
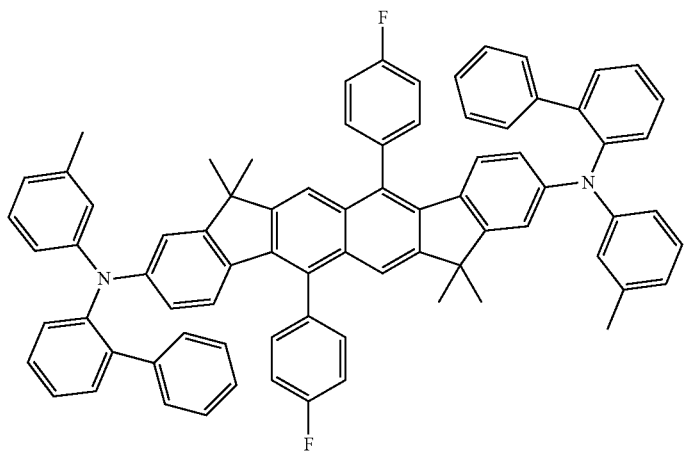
Compound 124
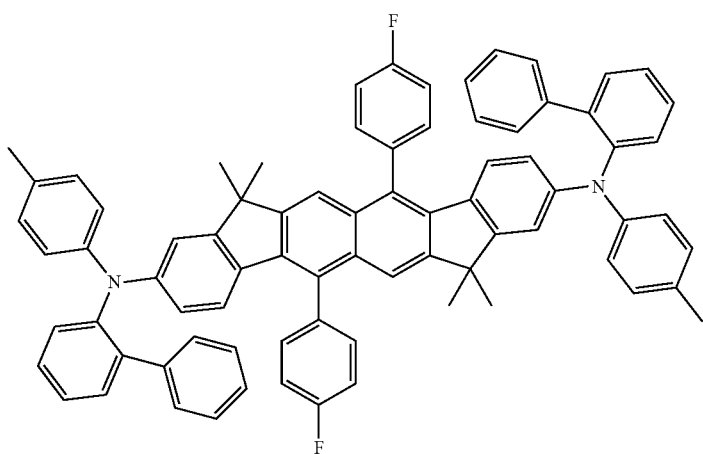
Compound 125
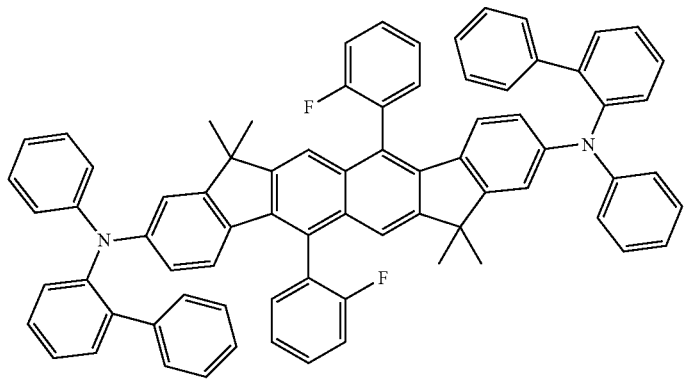
Compound 126

-continued
Compound 127
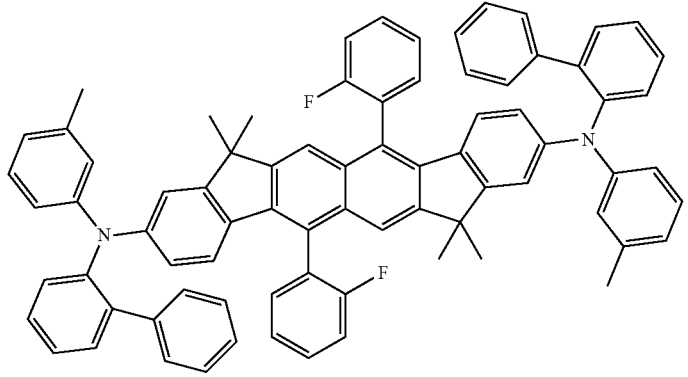
Compound 128
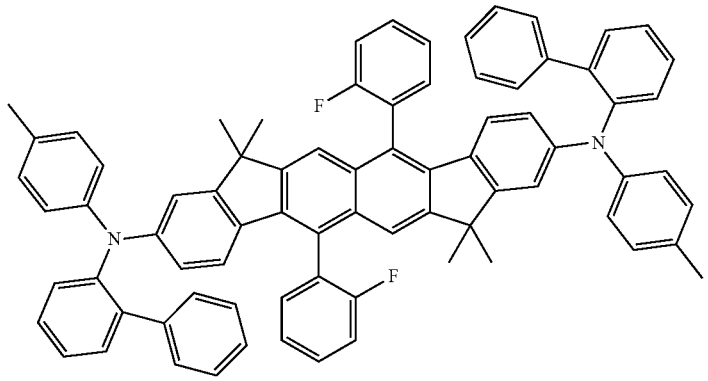
Compound 129
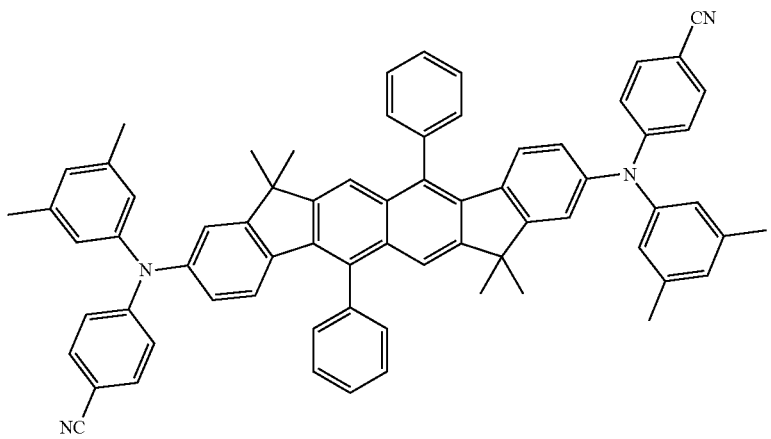
Compound 130
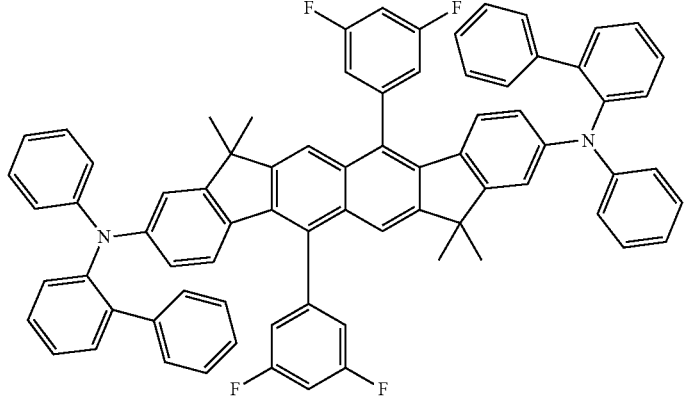

[Chem. 33]
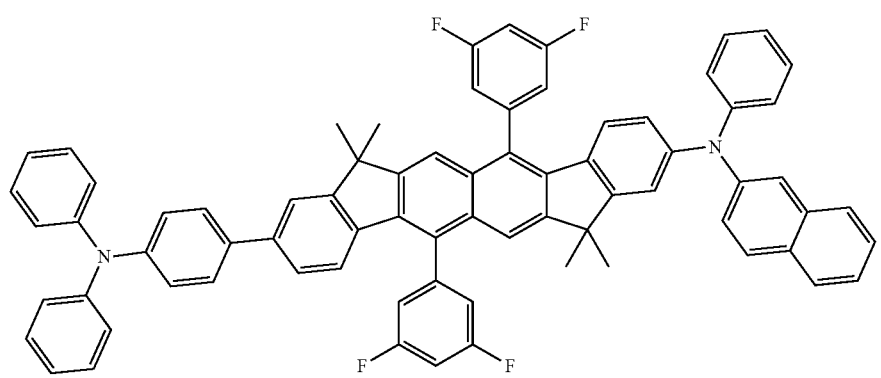
Compound 131
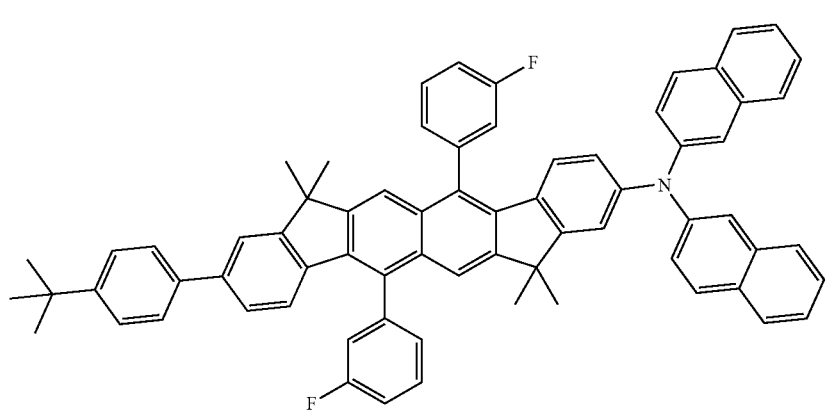
Compound 132
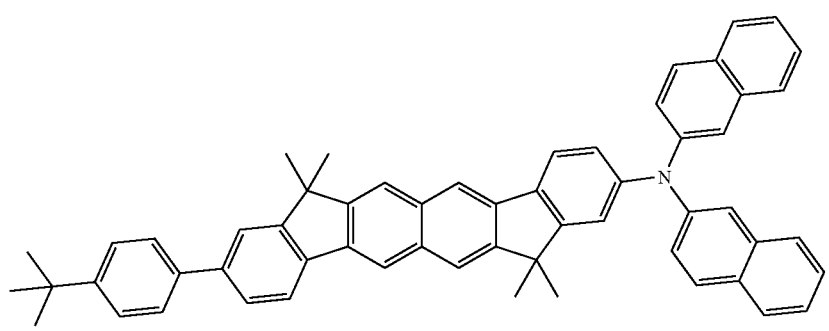
Compound 133
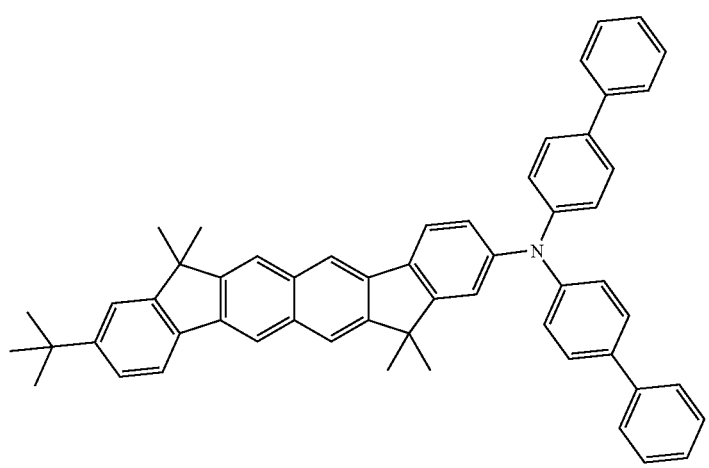
Compound 134

Compound 135
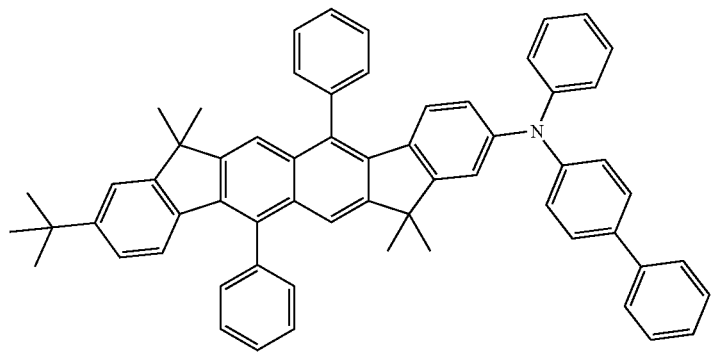
Compound 136
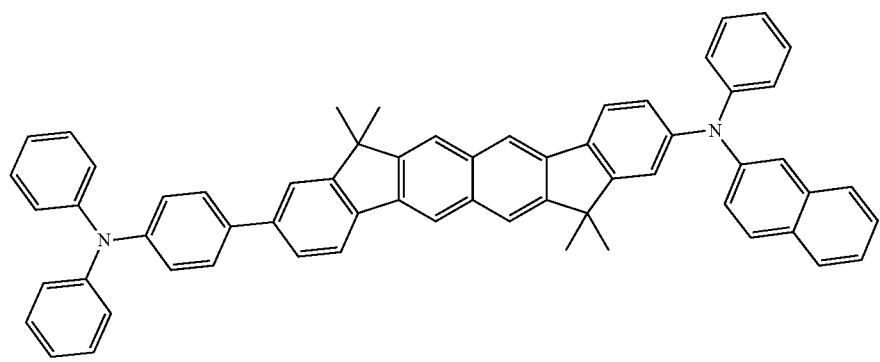
Compound 137
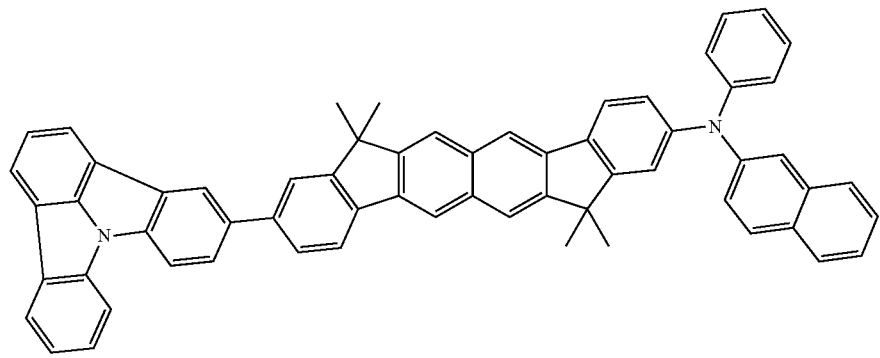
Compound 138
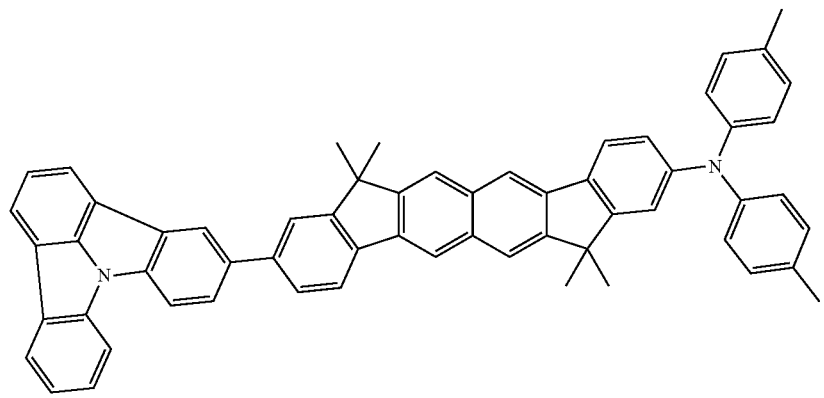

-continued
Compound 139
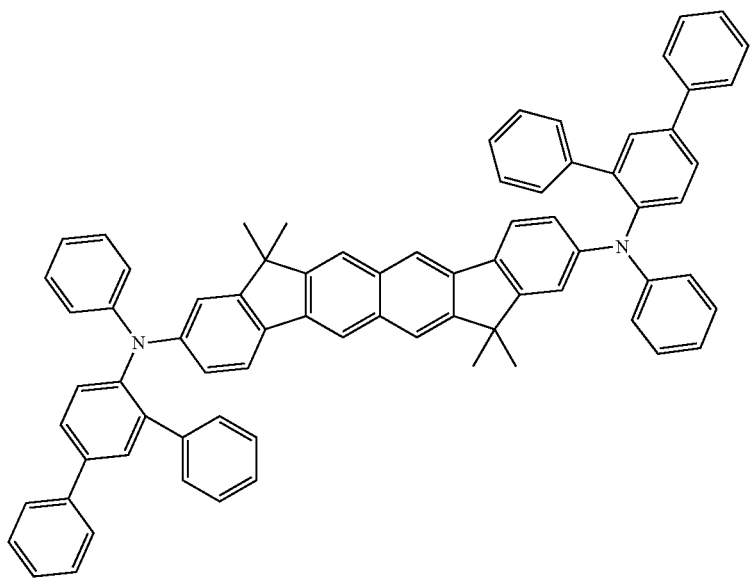
Compound 140
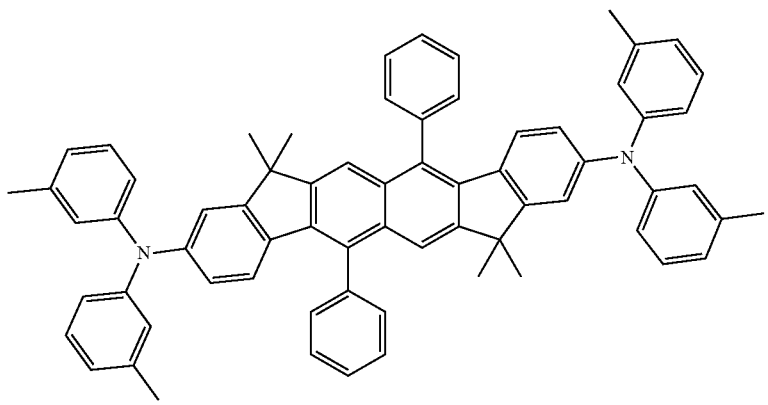
The compound represented by the general formula (1) can be synthesized by the method described in US2005/202279 and WO2011/074231, or a combination of other known reactions. Further, it can also be synthesized by, for example, a combination of the following schemes.
Scheme
[Chem. 34]
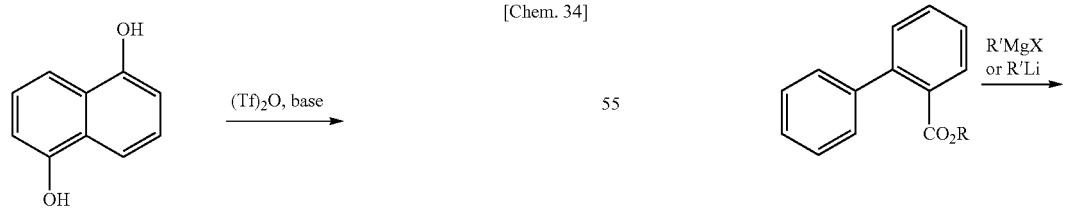
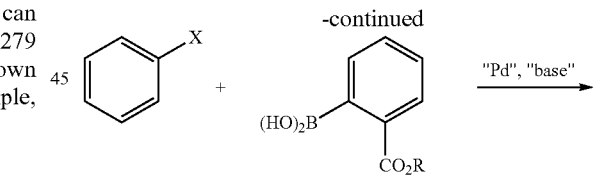
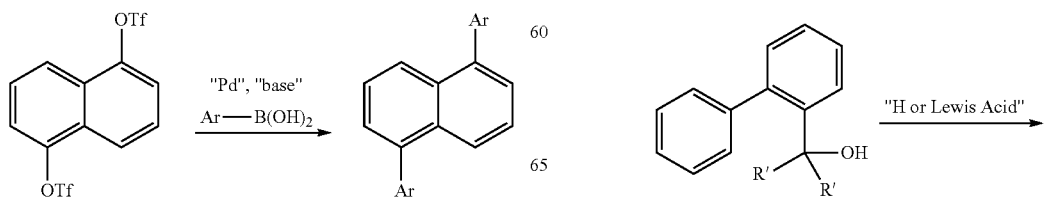

-continued

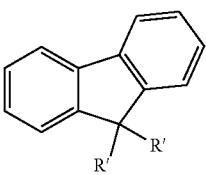

A synthesis intermediate having various substituents can be synthesized by a combination of known reactions. Further, the reaction in each of the steps is as follows. In addition, each of the substituents may be introduced in any step for the intermediate.

[Chem. 35]

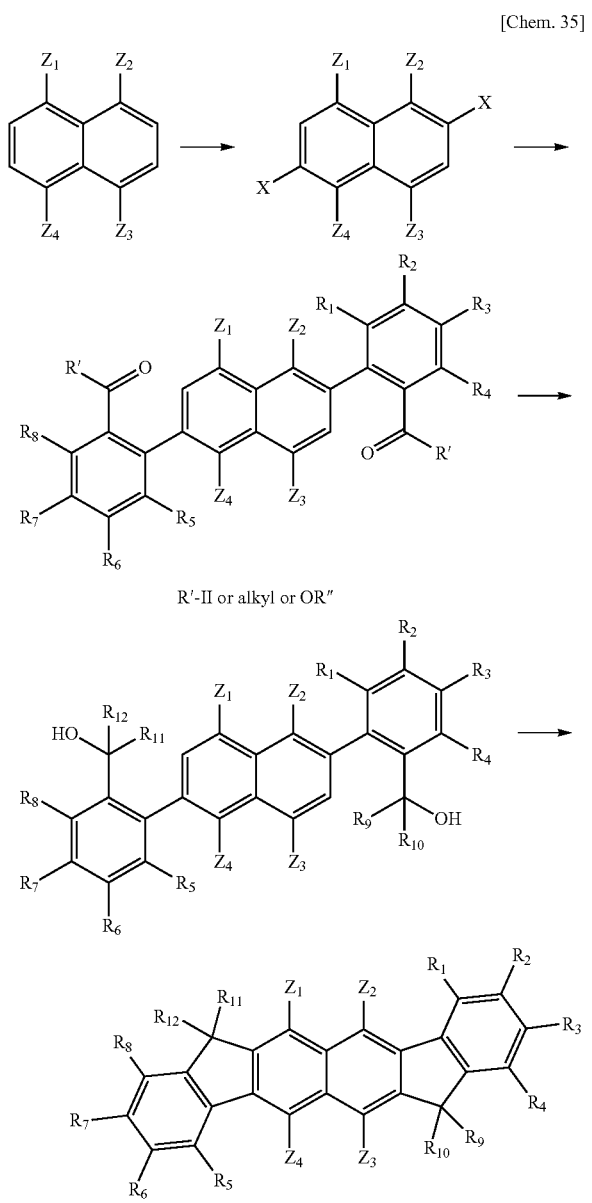

R'-II or alkyl or OR''

After the synthesis, purification is preferably carried out by column chromatography, recrystallization, or the like, and then by sublimation purification. By the sublimation purification, organic impurities can be separated and inorganic salts, residual solvents, or the like can be removed effectively.

The maximum light emitting wavelength of the light emitting material for an organic electroluminescent element, represented by general formula (1), is preferably less than 455 nm, more preferably 400 nm or more and less than 455 nm, particularly preferably 420 nm or more and less than 455 nm, still more preferably 430 nm or more and less than 455 nm, and most preferably 440 nm or more and less than 455 nm.

[Configuration of Organic Electroluminescent Element]

The organic electroluminescent element of the present invention has a substrate, a pair of electrodes including an anode and a cathode, disposed on the substrate, and at least one organic layer including a light emitting layer, disposed between the electrodes, in which the organic layer(s) contains the compound represented by the general formula (1).

The configuration of the organic electroluminescent element of the present invention is not particularly limited. FIG. 1 shows an example of the configuration of the organic electroluminescent element of the present invention. An organic electroluminescent element 10 in FIG. 1 includes organic layers between a pair of electrodes (an anode 3 and a cathode 9) on a substrate 2.

The element configuration, the substrate, the cathode and the anode of the organic electroluminescent element are described in detail, for example, in JP-A-2008-270736, and the detailed descriptions described in the patent publication can be applied to the present invention.

Hereinafter, preferred embodiments of the organic electroluminescent element of the present invention will be described in detail, in the order of a substrate, an electrode, an organic layer, a protective layer, a sealing enclosure, a driving method, the light emitting wavelength, and applications thereof.

<Substrate>

The organic electroluminescent element of the present invention has a substrate.

The substrate used in the present invention is preferably a substrate that does not scatter or attenuate light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be typically one having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

(Cathode)

The cathode may be typically one having a function as an electrode of injecting electrons to an organic layer, and is not particularly limited in its shape, structure, size, or the like. Further, depending on the use and purpose of the light emitting element, the cathode can be suitably selected from the known electrode materials.

<Organic Layer>

The organic electroluminescent element of the present invention includes at least one layer of the organic layer(s) including the light emitting layers disposed between the electrodes, in which the organic layer(s) contains the compound represented by the general formula (1). Above all, for the organic electroluminescent element of the present invention, the light emitting layer preferably contains the compound represented by the general formula (1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the entire surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in order.

(Configuration of Organic Layers)

In the organic electroluminescent element of the present invention, the organic layer includes a light emitting layer.

Furthermore, the organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (1) is preferably contained in the light emitting layer in the organic layer(s) disposed between the electrodes of the organic electroluminescent element.

The compound represented by the general formula (1) may be contained in another organic layer of the organic electroluminescent element of the present invention. Examples of the organic layer other than the light emitting layer, which may contain the compound represented by the general formula (1), include a hole injecting layer, a hole transporting layer, an electron transporting layer, an electron injecting layer, an exciton blocking layer, and a charge blocking layer (a hole blocking layer, an electron blocking layer, or the like), preferably any one of an exciton blocking layer, a charge blocking layer, an electron transporting layer, and an electron injecting layer, and more preferably an exciton blocking layer, a charge blocking layer, or an electron transporting layer.

The compound represented by the general formula (1) is contained in the amount of preferably 0.1% by mass to 100% by mass, more preferably 0.1% by mass to 50% by mass, still more preferably 0.5% by mass to 20% by mass, and more particularly preferably 0.5% by mass to 10% by mass, with respect to the total mass of the light emitting layer.

(Method for Forming Organic Layers)

Each of the organic layers in the organic electroluminescent element of the present invention can be suitably formed by any of dry type film forming methods such as a deposition method and a sputtering method, and wet type film forming methods (solution coating methods) such as a transfer method, a printing method, a spin coating method, and a bar coating method.

For the light emitting layer disposed between the pair of electrodes in the organic electroluminescent element of the present invention, the light emitting layer is preferably formed by a vacuum deposition process or a wet type process, and the light emitting layer is more preferably formed by deposition of a composition containing the compound represented by the general formula (1) in at least one layer.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of one kind or two or more kinds thereof. The host material is preferably a charge transporting material. The host material may be made of one kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. Each of the layers may include the same light emitting material or host material, and may also include different materials from each other over layers. In the case where a plurality of light emitting layers are present, each of the light emitting layers may emit light in different luminous colors from each other.

The thickness of the light emitting layer is not particularly limited, but it is usually preferably from 2 nm to 300 nm, and above all, from the viewpoint of external quantum efficiency, it is more preferably from 5 nm to 100 nm, and still more preferably from 10 nm to 50 nm.

In the organic electroluminescent element of the present invention, the light emitting layer contains the compound represented by the general formula (1), and the compound represented by the general formula (1) is used as the light emitting material of the light emitting layer. The host material used in the light emitting layer is not particularly limited. Here, in the present specification, the host material is a compound which usually plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element.

(Light Emitting Material)

In the organic electroluminescent element of the present invention, the compound represented by the general formula (1) is preferably used as the light emitting material, but in this case, a combination of the compound with light emitting materials different from the compound represented by the general formula (1) can be used. Further, in the organic electroluminescent element of the present invention, in the case where the compound represented by the general formula (1) is used as a host material of the light emitting layer or in the case where the compound represented by the general formula (1) is used in an organic layer other than the light emitting layer, a light emitting material different from the compound represented by the general formula (1) is used in the light emitting layer.

The light emitting material which can be used in the present invention may be any one of a phosphorescent light emitting material, a fluorescent light emitting material, and the like. Further, the light emitting layer in the present invention may contain two or more kinds of light emitting materials in order to improve the color purity or widen the light emitting wavelength region.

The fluorescent light emitting material and the phosphorescent light emitting material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, and the detailed descriptions in these publications can be applied to the present invention.

Examples of the phosphorescent light emitting material which can be used in the present invention include phosphorescent light emitting compounds described in patent documents, for example, U.S. Pat. Nos. 6,303,238 and 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, and Ir complexes, Pt complexes, and Re complexes are particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, chromaticity, or the like, Ir complexes and Pt complexes are particularly preferred, and Ir complexes are the most preferred.

The kind of the fluorescent light emitting material which can be used in the present invention is not particularly limited, but examples thereof include those other than the compound represented by the general formula (1), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in paragraph No. [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of one kind or two or more kinds. The host material is preferably a charge transporting material. The host material may be made of one kind or two or more kinds. Examples thereof include a configuration in which an electron transporting host material and a hole transporting host material are mixed. Further, the light emitting layer may contain a material which does not have charge transporting properties and which does not emit light.

In addition, the light emitting layer may be made of a single layer or multiple layers of two or more layers. Each of the layers may include the same light emitting materials or host materials, and may also include different materials from each other over layers. In the case where a plurality of light emitting layers are present, each of the light emitting layers may emit light in different luminous colors from each other.

(Host Material)

The host material is a compound that usually plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less with respect to the total amount of light emitting in the entirety of the element.

Examples of the host material which can be used in the organic electroluminescent element of the present invention include the following compounds:

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, a variety of metal complexes typified by metal complexes of phthalocyanine and 8-quinolinol derivatives and metal complexes having metal phthalocyanine, benzoxazole, or benzothiazole as a ligand thereof, and derivatives thereof (which may have a substituent or a fused ring). In addition, the compounds described in paragraph No. [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in paragraph Nos. [0033] to [0064] of WO 2010/134350 are particularly preferred, and examples thereof include Compounds H-1, H-2, and H-4 as to be described later.

The light emitting element of the present invention preferably contains a compound represented by the following general formula (An-1) as a host material.

[Chem. 36]

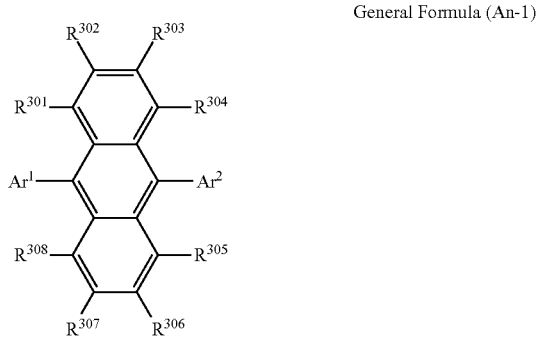

General Formula (An-1)

In the general formula (An-1), $Ar^1$ and $Ar^2$ each independently represent an aryl group or a heteroaryl group, and $R^{301}$ to $R^{308}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be bonded to each other to form a ring.

In the general formula (An-1), the aryl group represented by $Ar^1$ and $Ar^2$ is preferably an aryl group having 6 to 36 carbon atoms, more preferably an aryl group having 6 to 18 carbon atoms, particularly preferably an aryl group having 6 to 14 carbon atoms, and more particularly preferably a phenyl group or a naphthyl group.

The heteroaryl group represented by $Ar^1$ and $Ar^2$ is preferably a heteroaryl group having 5 to 20 ring members, and more preferably a heteroaryl group having 5 to 13 ring members. The heteroatom contained in the heteroaryl group represented by $Ar^1$ and $Ar^2$ is preferably a nitrogen atom, an oxygen atom, or a sulfur atom, and more preferably a nitrogen atom. The number of heteroatoms contained in the heteroaryl group represented by $Ar^1$ and $Ar^2$ is preferably from 1 to 3, more preferably 1 or 2, and particularly preferably 1. The heteroaryl group represented by $Ar^1$ and $Ar^2$ is particularly preferably a pyridyl group, a carbazolyl group, a dibenzofuryl group, or a dibenzothiophenyl group.

$Ar^1$ and $Ar^2$ are each preferably a phenyl group, a naphthyl group, a pyridyl group, a carbazolyl group, a dibenzofuryl group, a dibenzothiophenyl group, or a group formed by a combination thereof. Above all, $Ar^1$ and $Ar^2$ are each more preferably a phenyl group or a naphthyl group, and at least one of $Ar^1$ and $Ar^2$ is particularly preferably a substituted or unsubstituted phenyl group.

$Ar^1$ and $Ar^2$ may have an additional substituent, and examples of the substituent include an aryl group, a heteroaryl group, a fluorine atom, an alkyl group (preferably having 1 to 4 carbon atoms), an alkenyl group, a silyl group, and a cyano group.

In the general formula (An-1), examples of the substituents represented by $R^{301}$ to $R^{308}$ include an aryl group, a heteroaryl group, a fluorine atom, an alkyl group, a silyl group, a cyano group, and a group formed by a combination thereof, preferably a phenyl group, a naphthyl group, a pyridyl group, a carbazolyl group, a dibenzofuryl group, a dibenzothiophenyl group, a fluorine atom, an alkyl group, a silyl group, a cyano group, and a group formed by a combination thereof, and more preferably a phenyl group, a naphthyl group, an alkyl group having 1 to 5 carbon atoms (particularly preferably a tert-butyl group).

In the general formula (An-1), $R^{301}$ to $R^{308}$ may have an additional substituent, and examples of the substituent include an aryl group, a heteroaryl group, and an alkyl group, preferably an aryl group and a heteroaryl group, and more preferably an aryl group having 6 to 18 carbon atoms.

In the general formula (An-1), the number of the substituents contained in $R^{301}$ to $R^{308}$ is preferably from 0 to 4, more preferably 0 or 2, particularly preferably 0 or 1, and more particularly preferably 0.

In the general formula (An-1), the positions of the substituents contained in $R^{301}$ to $R^{308}$ are preferably $R^{302}$, $R^{303}$, $R^{306}$ or $R^{307}$, and more preferably either of $R^{302}$ and $R^{303}$ or either of $R^{306}$ and $R^{307}$.

In the general formula (An-1), $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be bonded to each other to form a ring, but are preferably not bonded to each other to form a ring.

The compound represented by the general formula (An-1) is preferably a compound represented by the following general formula (An-2).

[Chem. 37]

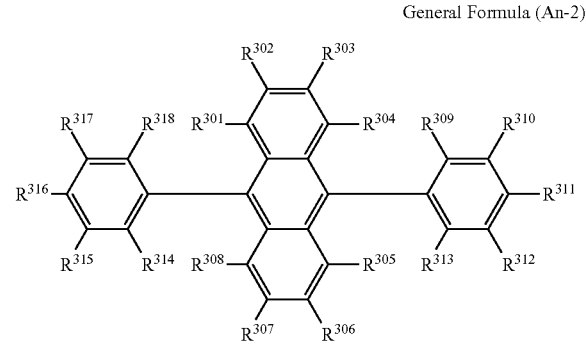

General Formula (An-2)

In the general formula (An-2), $R^{301}$ to $R^{318}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{313}$ and $R^{314}$, $R^{314}$ and $R^{315}$, $R^{315}$ and $R^{316}$, $R^{316}$ and $R^{317}$, and $R^{317}$ and $R^{318}$ may be bonded to each other to form a ring.

The preferred ranges of $R^{301}$ to $R^{308}$ in the general formula (An-2) are the same as the preferred ranges of $R^{301}$ to $R^{308}$ in the general formula (An-1).

Examples of the substituents represented by $R^{309}$ to $R^{318}$ in the general formula (An-2) include an aryl group, a heteroaryl group, a fluorine atom, an alkyl group, a silyl group, a cyano group, and a group formed by a combination thereof, an aryl group having 6 to 18 carbon atoms, a heteroaryl group having 5 to 20 ring members, a fluorine atom, an alkyl group, alkenyl group, a silyl group, a cyano group, and a group formed by a combination thereof, more preferably a phenyl group, a naphthyl group, a pyridyl group, a carbazolyl group, a dibenzofuryl group, a dibenzothiophenyl group, a fluorine atom, an alkyl group, alkenyl group, a silyl group, a cyano group, and a group formed by a combination thereof, and particularly preferably a phenyl group, a naphthyl group, and a carbazolyl group.

In the general formula (An-1), $R^{309}$ to $R^{318}$ may have an additional substituent, examples of the substituent include an aryl group, an alkyl group, and a fluorine atom, and the substituents may be bonded to each other to form a ring.

In the general formula (An-1), the number of substituents contained in $R^{309}$ to $R^{318}$ is preferably 0 to 4, more preferably 0 or 2, particularly preferably 0 or 1, and more particularly preferably 0.

In the general formula (An-1), the positions of the substituents contained in $R^{309}$ to $R^{318}$ are not particularly limited, but in the case of having the substituents, the substituents are preferably contained in at least one of $R^{311}$ and $R^{316}$.

In the general formula (An-1), $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may be bonded to each other to form a ring, and the ring thus formed is preferably a 5- or 6-membered ring, and more preferably a 5-membered ring.

Specific examples of the compound represented by the general formula (An-1) are shown below, but it should not be construed that the compound represented by the general formula (An-1) which can be used in the present invention is limited to the specific examples.

[Chem. 38]

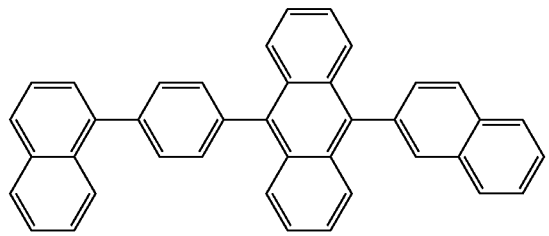

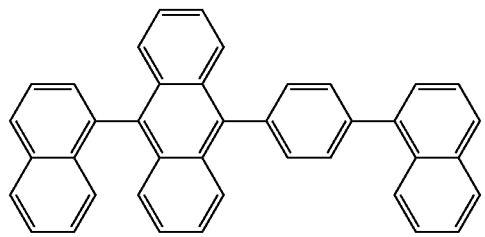

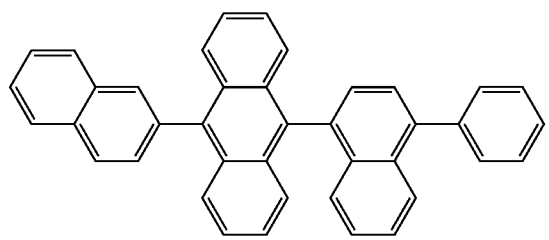

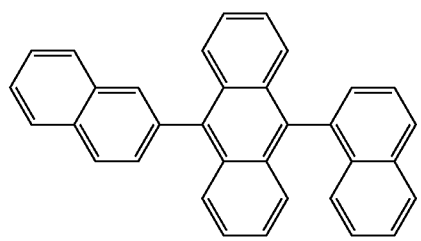

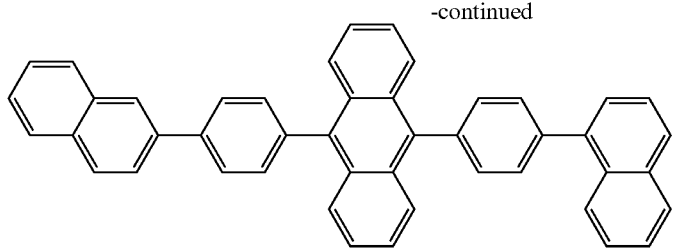
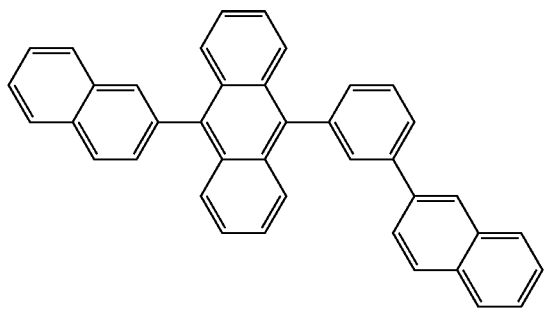
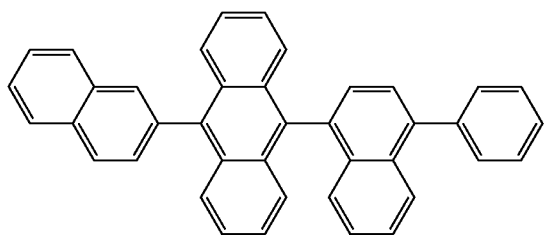
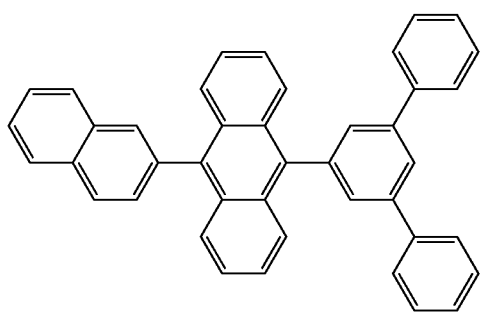
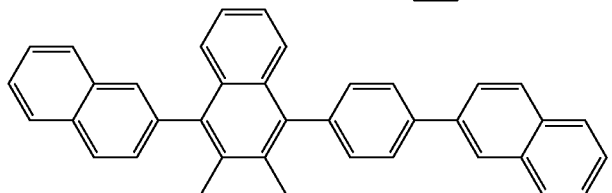
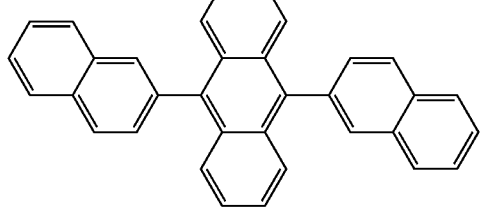

-continued
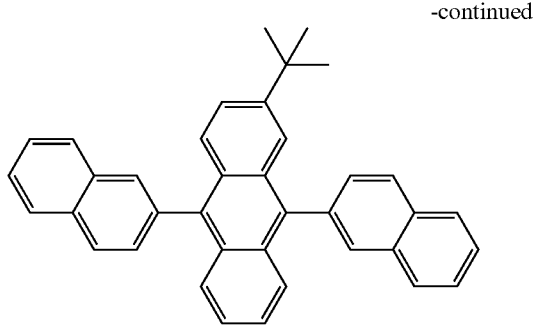
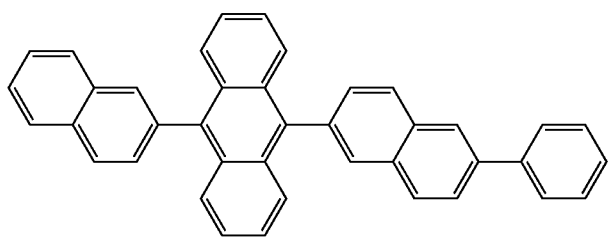
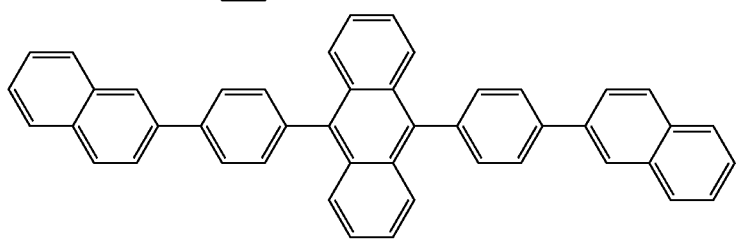
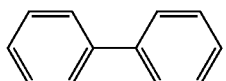
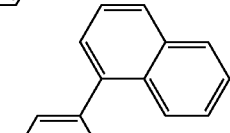
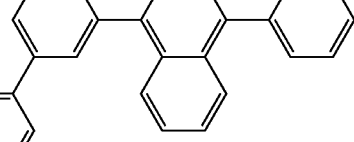
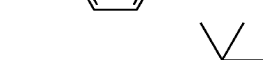
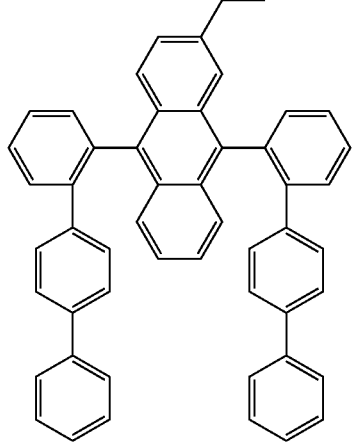

-continued
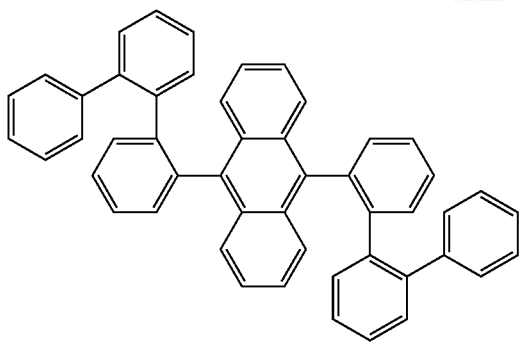
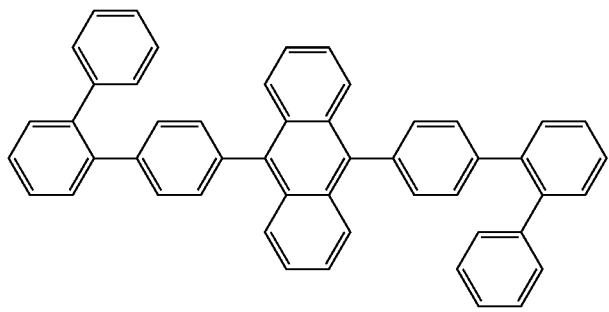
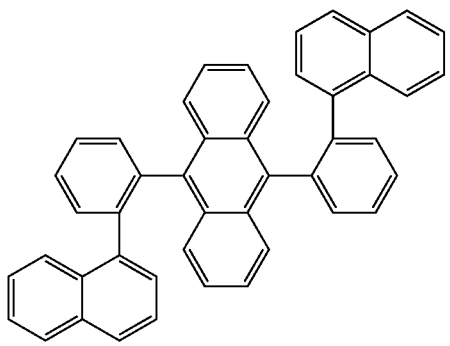
[Chem. 39]
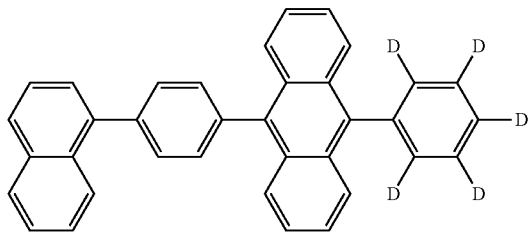
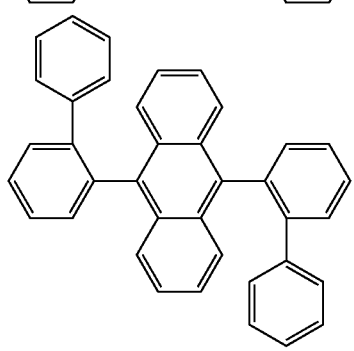

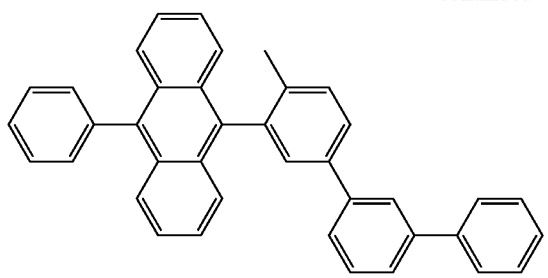
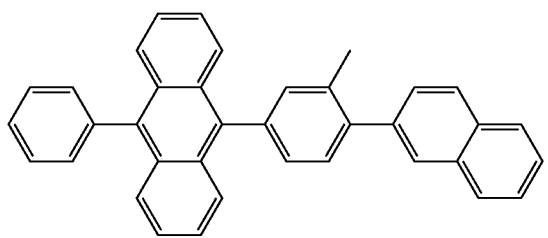
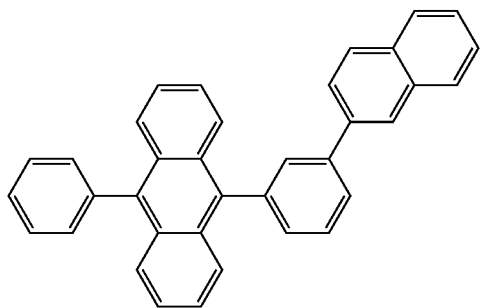
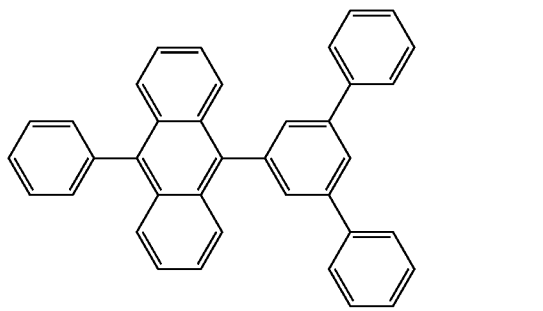
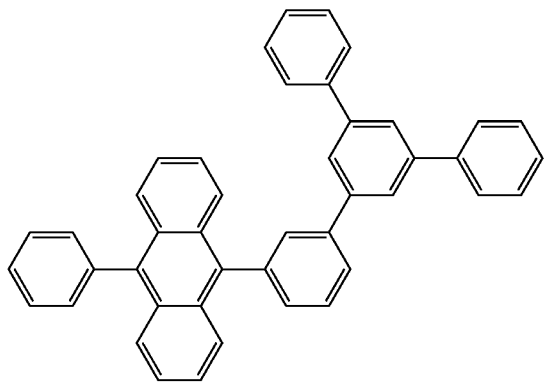

-continued
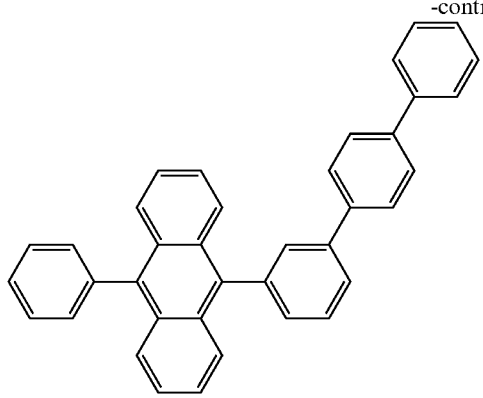
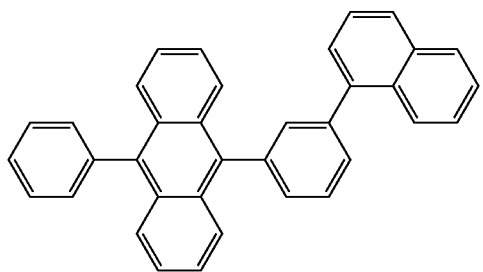
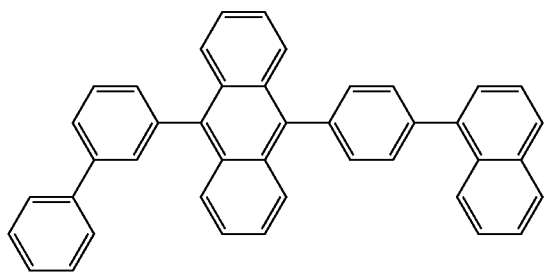
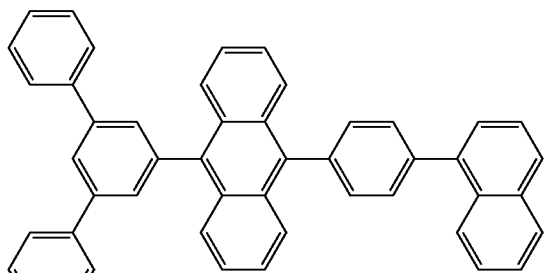
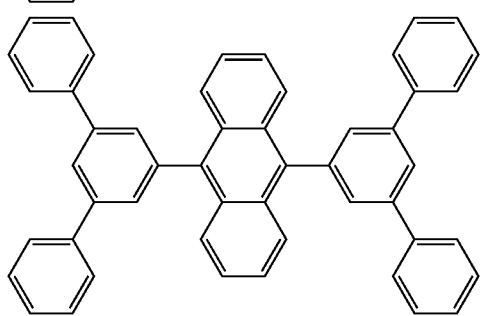

-continued
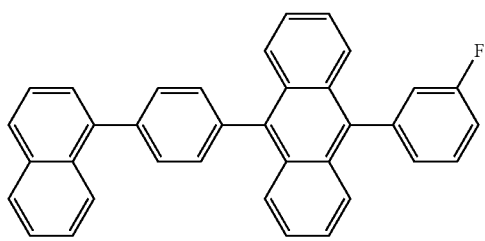
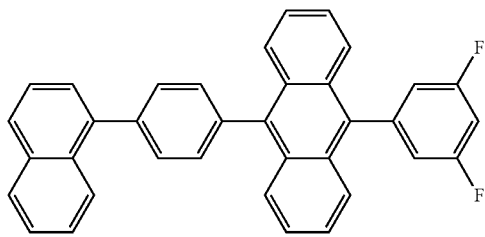
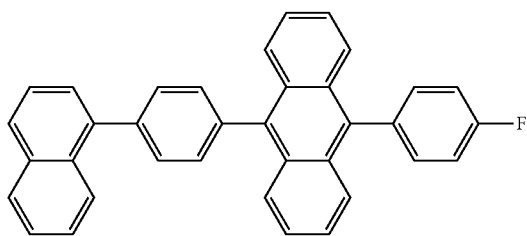
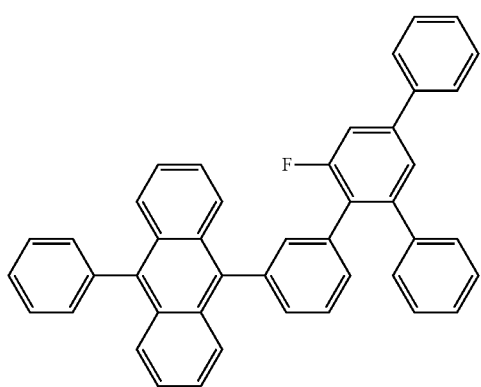
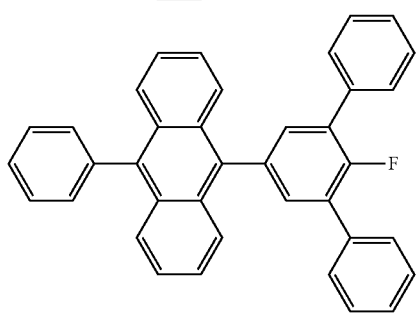
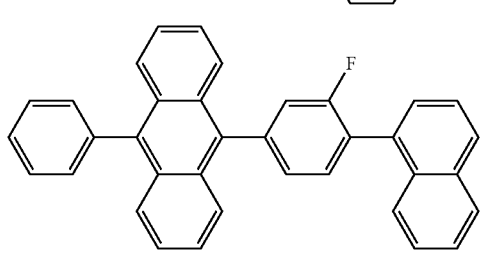

-continued
[Chem. 40]
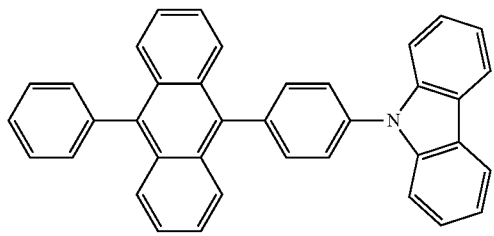
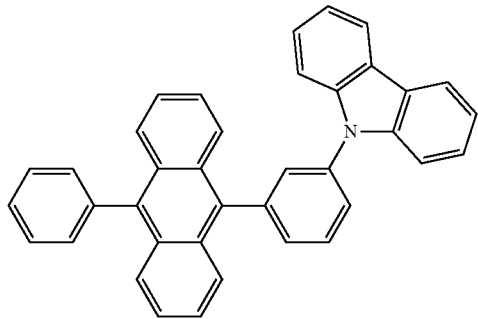
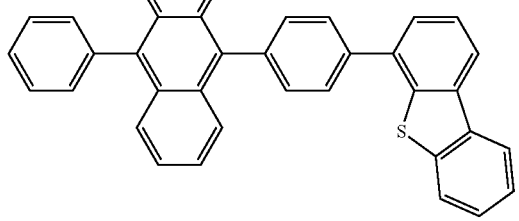
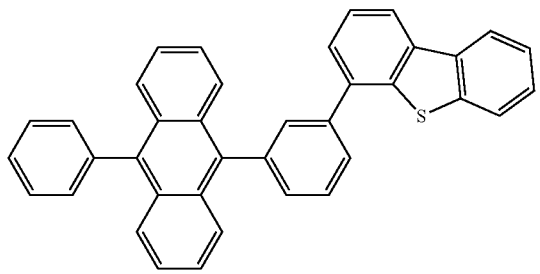
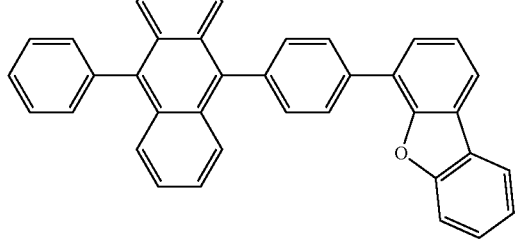
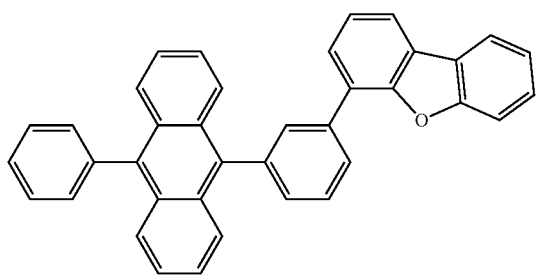

-continued
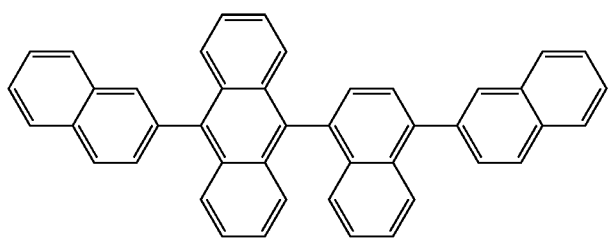
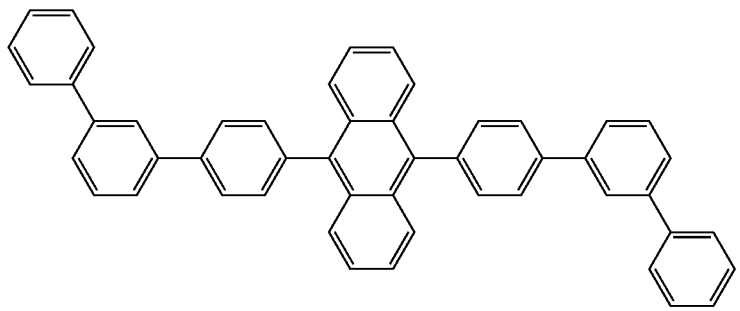
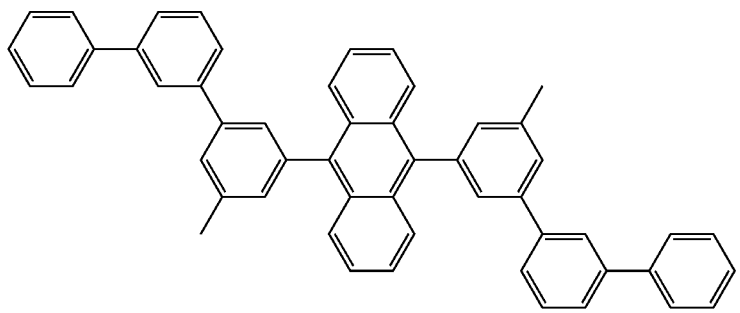
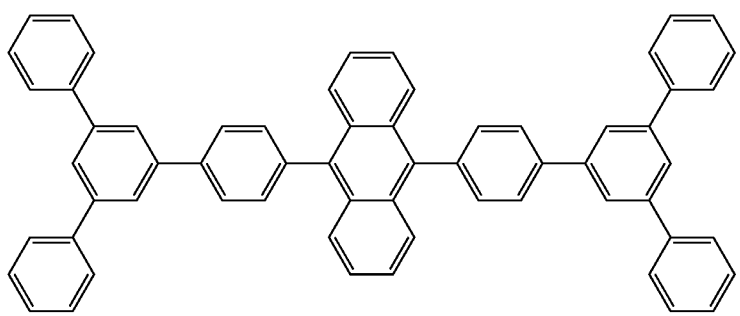
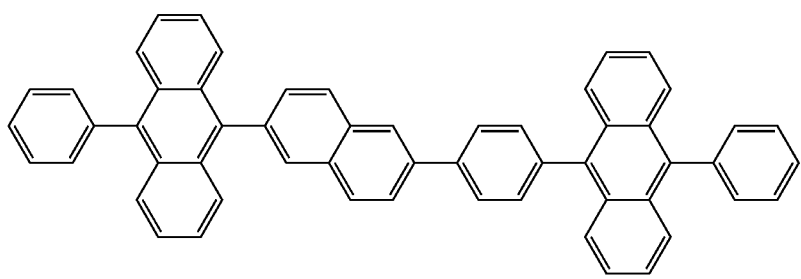

-continued
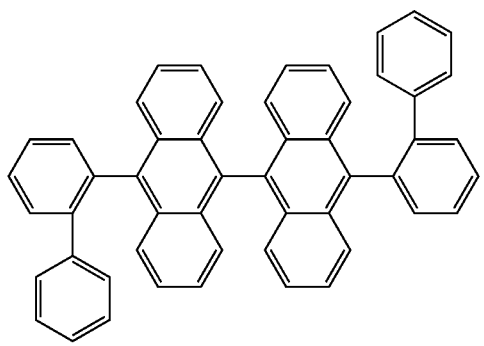
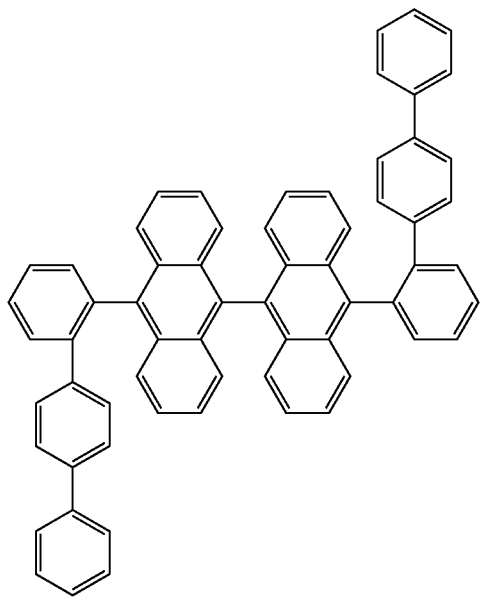
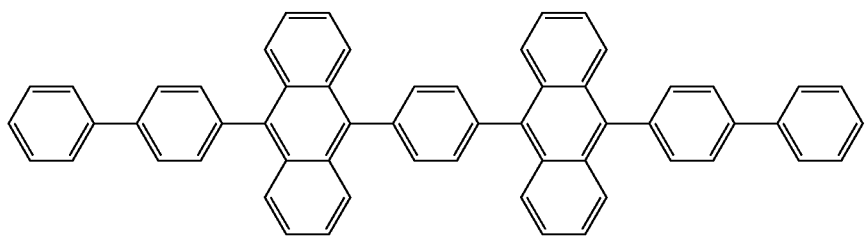
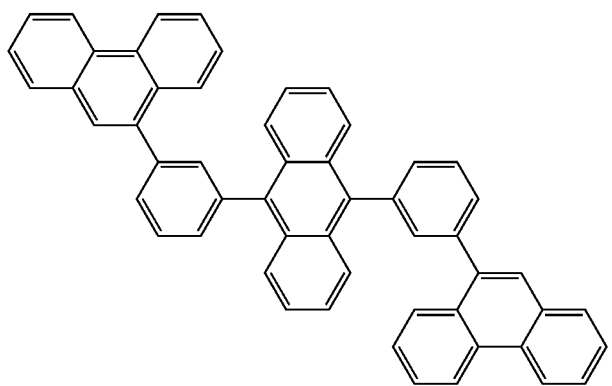

-continued
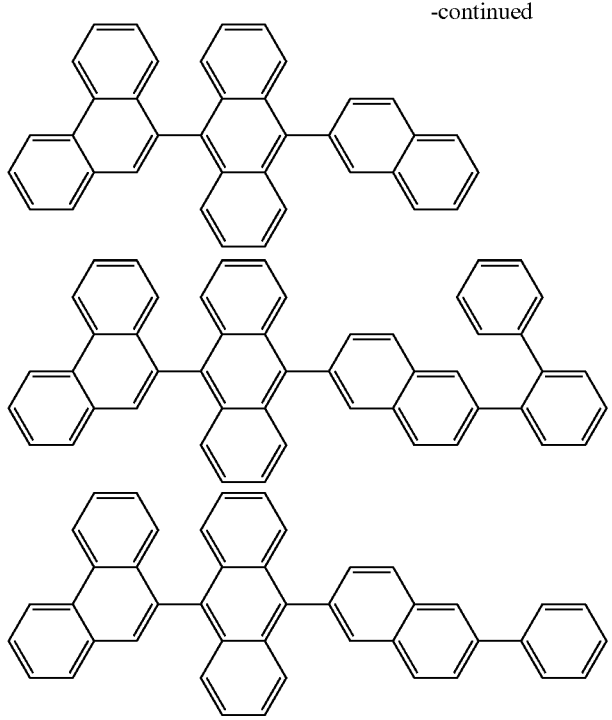
[Chem. 41]
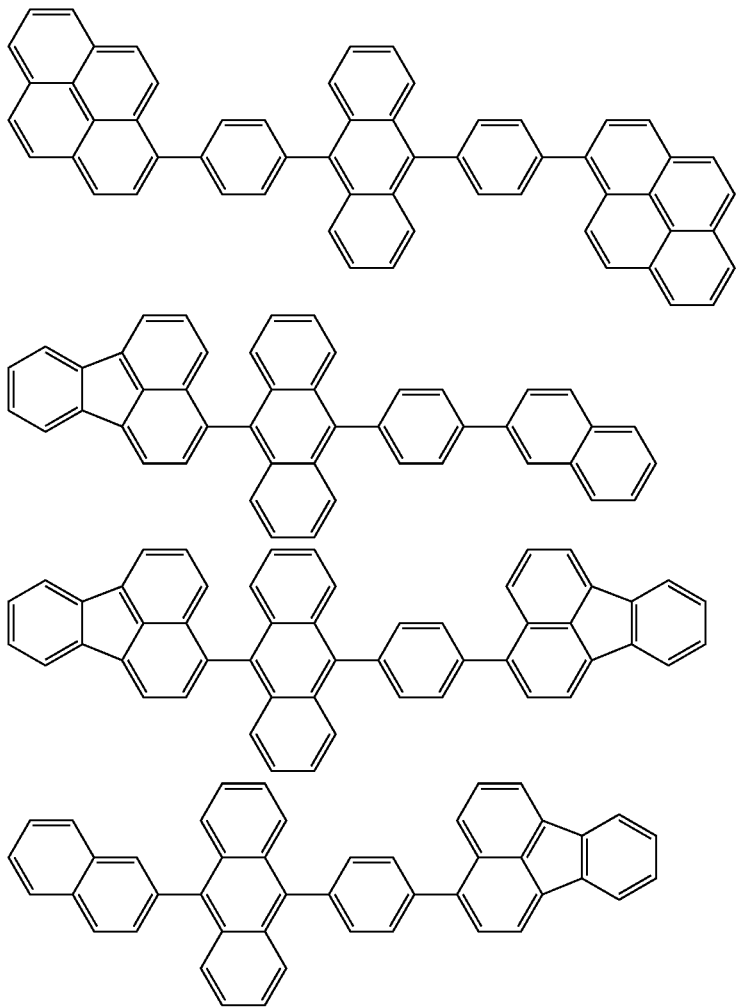

-continued
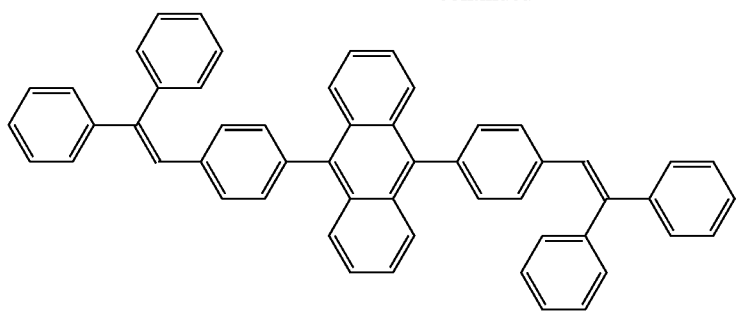
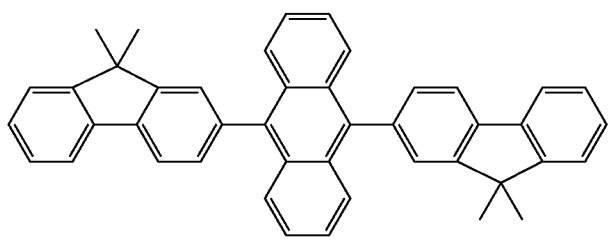
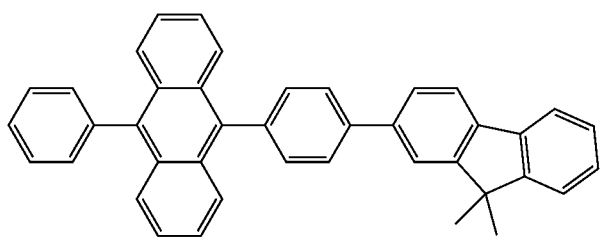
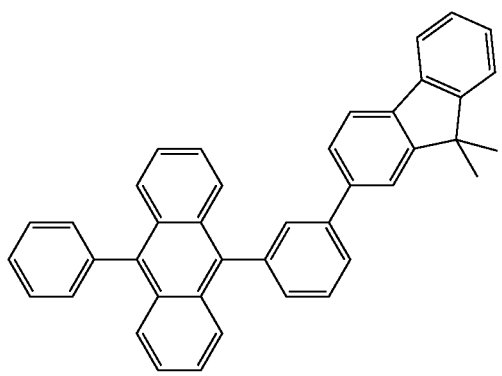
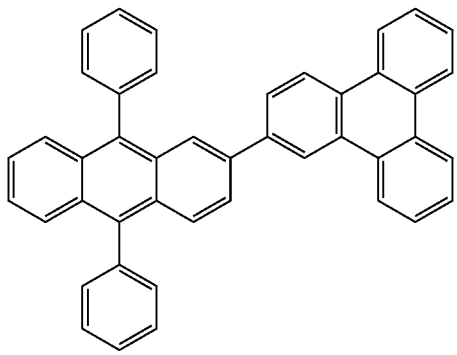

-continued
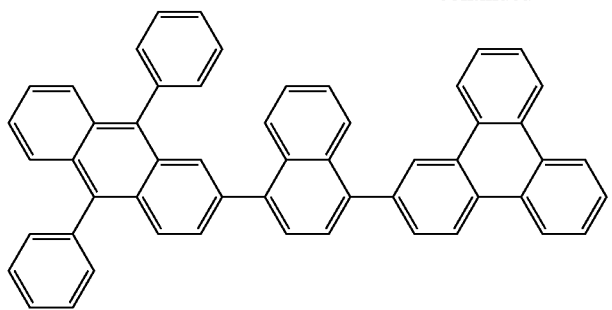
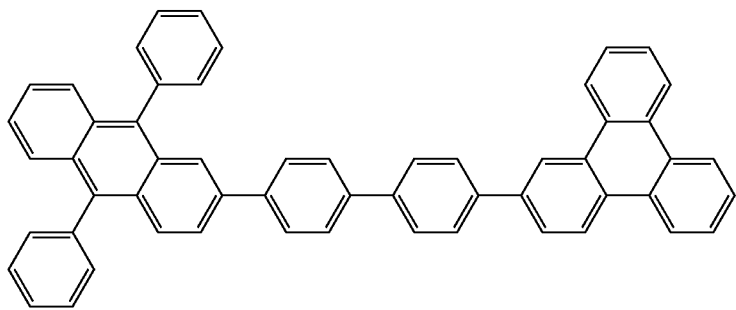
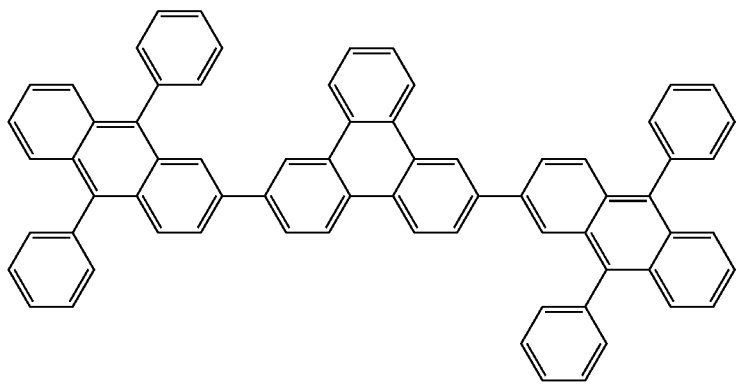
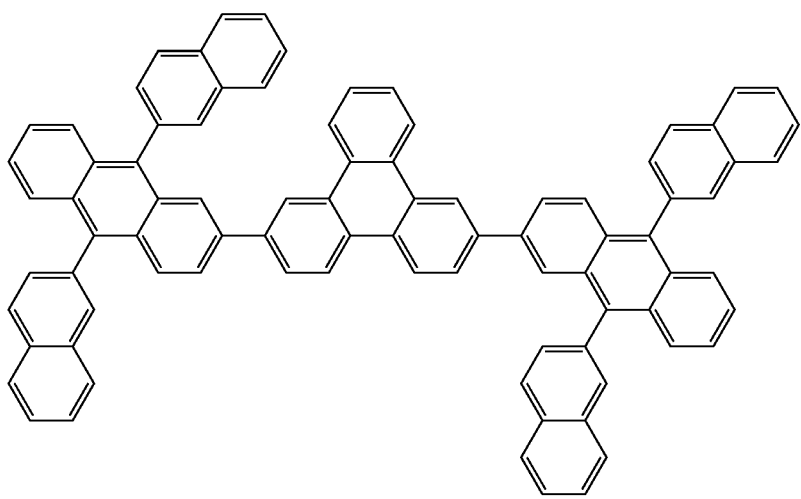

-continued
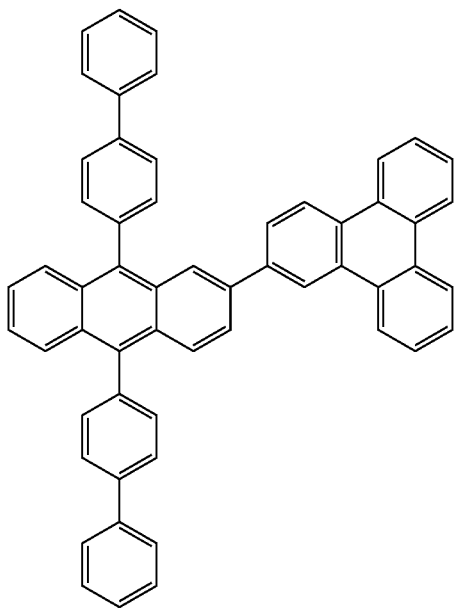
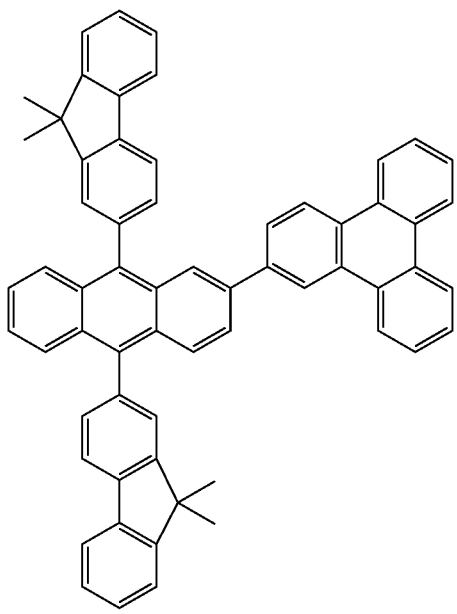
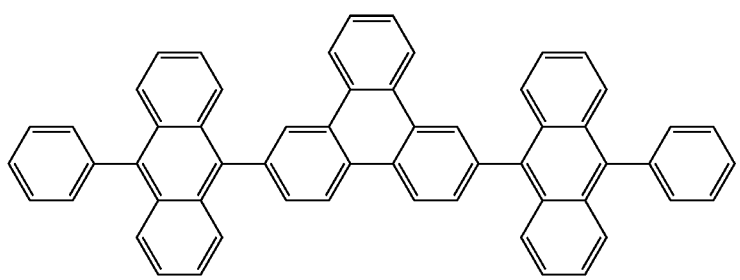

-continued

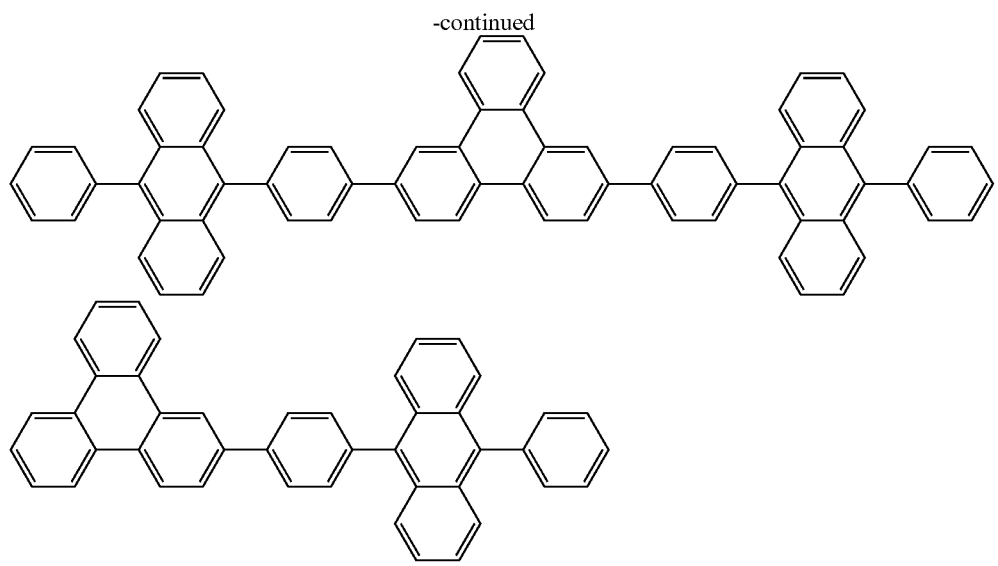

The host material that can be used in the light emitting layer in the organic electroluminescent element of the present invention may be a host material having hole transporting properties or a host material having electron transporting properties.

In the light emitting layer, the singlet minimum excited energy ($S_1$ energy) in the film state of the host material is preferably higher than the $S_1$ energy of the light emitting material from the viewpoints of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the $S_1$ of the light emitting material. Further, even in the case where $S_1$ of the host material is higher than the $S_1$ of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Moreover, the content of the host compound in the light emitting layer in the organic electroluminescent element of the present invention is not particularly limited, but from the viewpoint of luminous efficiency and driving voltage, it is preferably from 15% by mass to 98% by mass, and more preferably from 80% by mass to 99% by mass, with respect to the total mass of the compounds forming the light emitting layer. When the light emitting layer includes a plurality of kinds of host compounds containing the compound represented by the general formula (1), the content of the compound represented by the general formula (1) is preferably from 50% by mass to 99% by mass, with respect to the total host compounds.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, and Anode/hole injecting layer/hole transporting layer/blocking layer/light emitting layer/blocking layer/electron transporting layer/electron injecting layer/cathode.

The organic electroluminescent element of the present invention preferably includes at least one (A) organic layer which is preferably disposed between the anode and the light emitting layer. Examples of the (A) organic layer which is preferably disposed between the anode and the light emitting layer include an hole injecting layer, a hole transporting layer, and an electron blocking layer from the anode side.

The organic electroluminescent element of the present invention preferably includes at least one (B) organic layer which is preferably disposed between the cathode and the light emitting layer. Examples of the (B) organic layer which is preferably disposed between the cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer(s) preferably includes at least one compound of the compounds represented by the following general formulae (Sa-1), (Sb-1), and (Sc-1).

[Chem. 42]

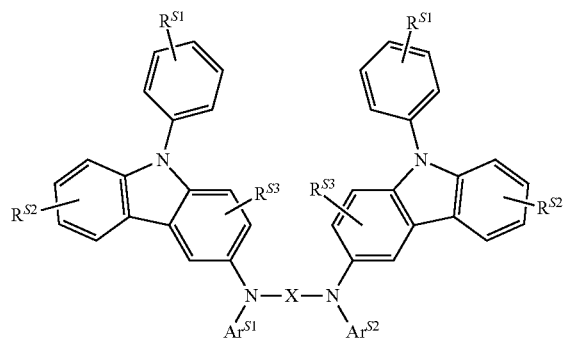

General Formula (Sa-1)

(In the formula, X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, a substituted or unsubstituted heterocyclic group having 2 to 30 carbon atoms, or a group formed by a combination thereof. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 43]

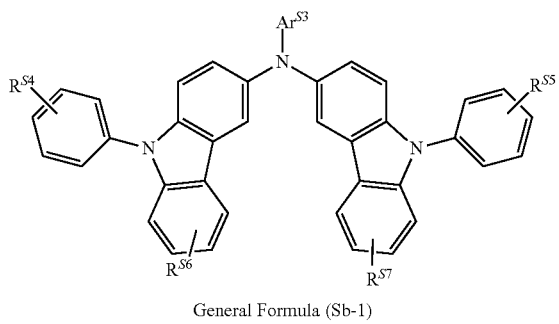

General Formula (Sb-1)

(In the formula, $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 44]

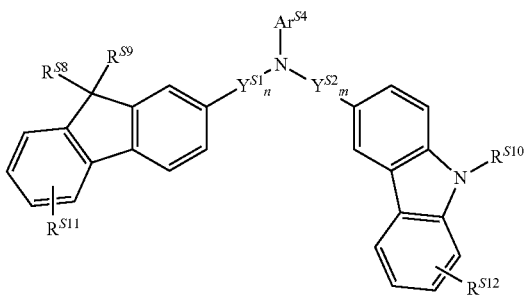

General Formula (Sc-1)

(In the formula, $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, a substituted or unsubstituted heterocyclic group having 2 to 30 carbon atoms, or a group formed by a combination thereof. X is preferably a substituted or unsubstituted arylene group having 6 to 30 carbon atoms, more preferably a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$, and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ $Y^{S2}$ represent a substituted or unsubstituted alkylene having 1 to 30 carbon atoms, or a substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

[Chem. 45]

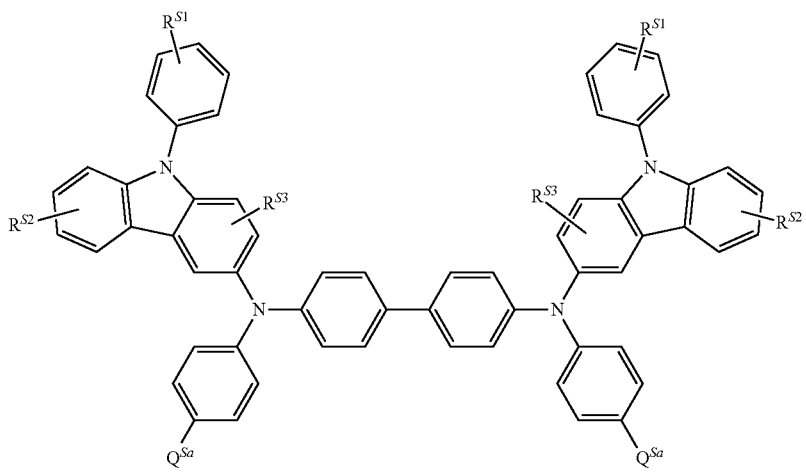

General Formula (Sa-2)

(In the formula, $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$s each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. $Q^{Sa}$s each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

[Chem. 46]

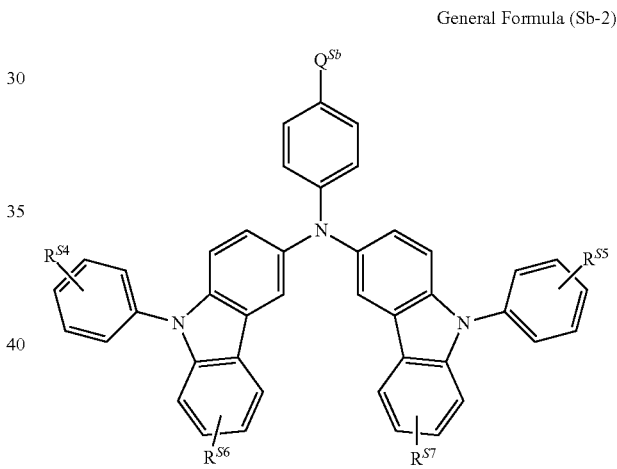

General Formula (Sb-2)

(In the formula, $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxyl group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$, and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

[Chem. 47]

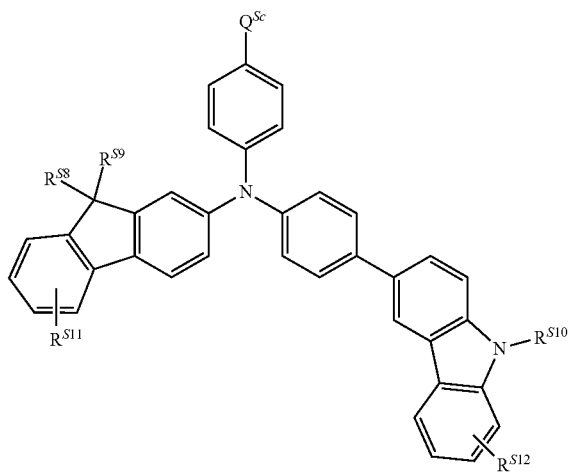

General Formula (Sc-2)

(In the formula, $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxyl group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$, and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 48]

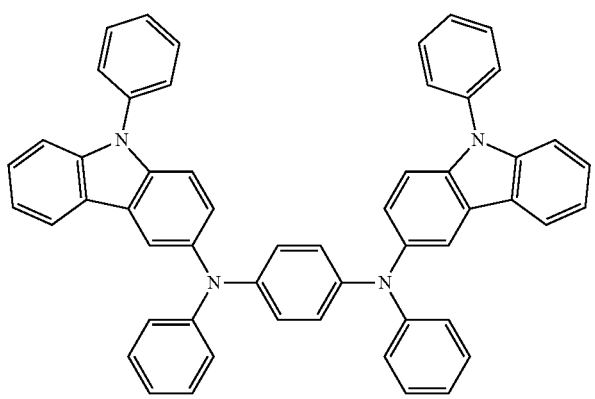

1

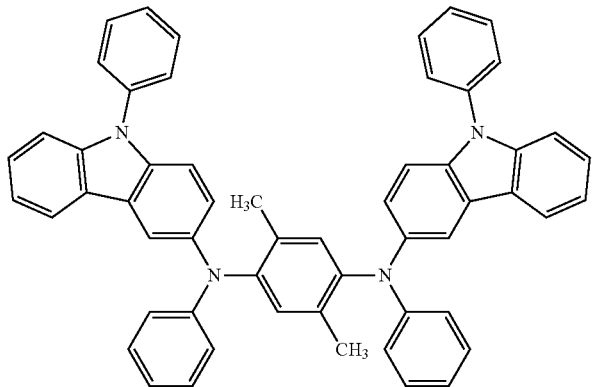
2
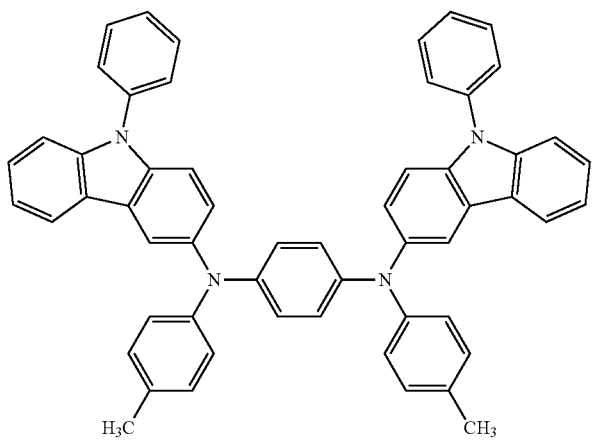
3
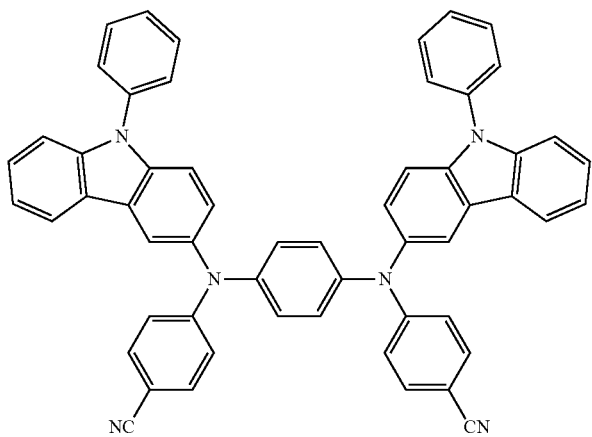
4

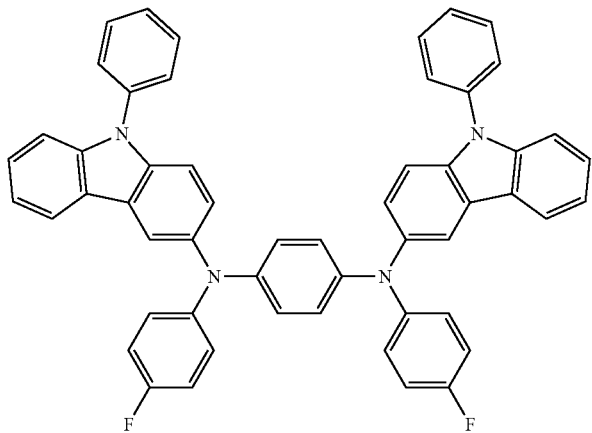
5
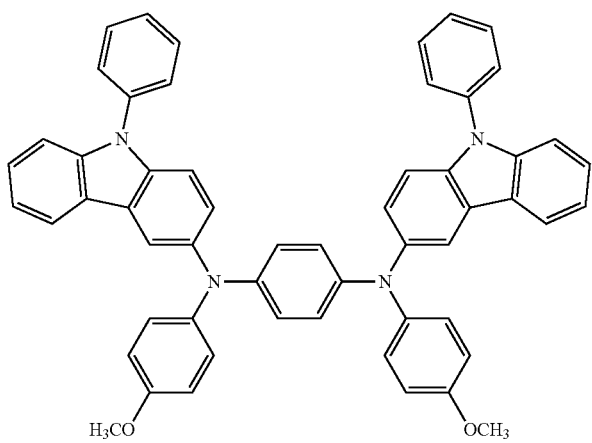
6
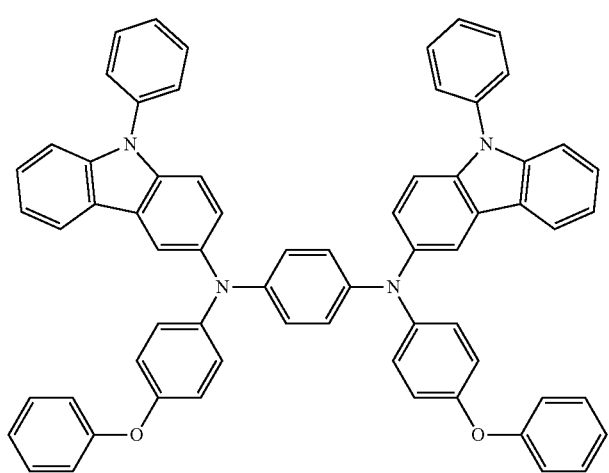
7

-continued
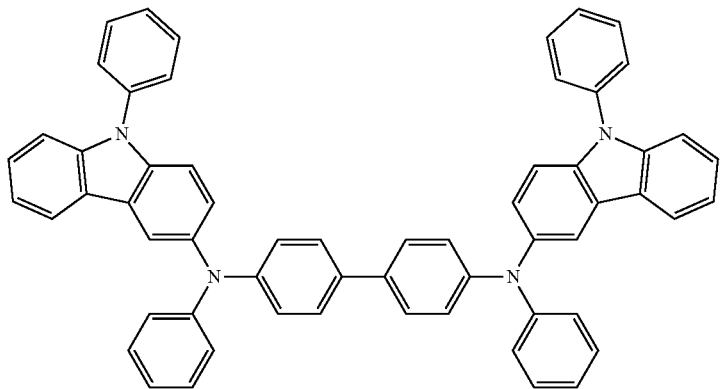
8
[Chem. 49]
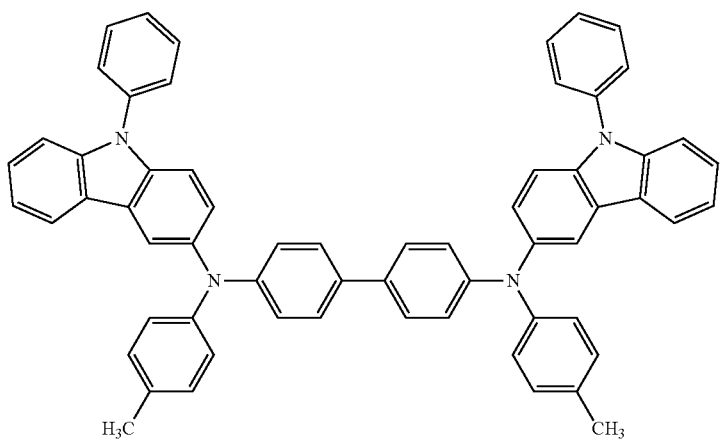
9
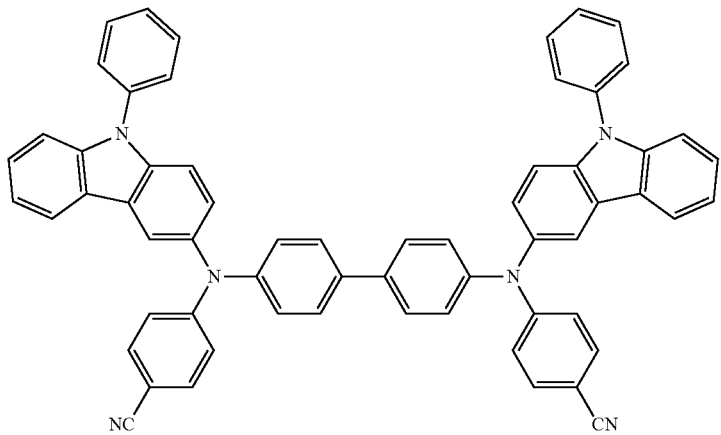
10

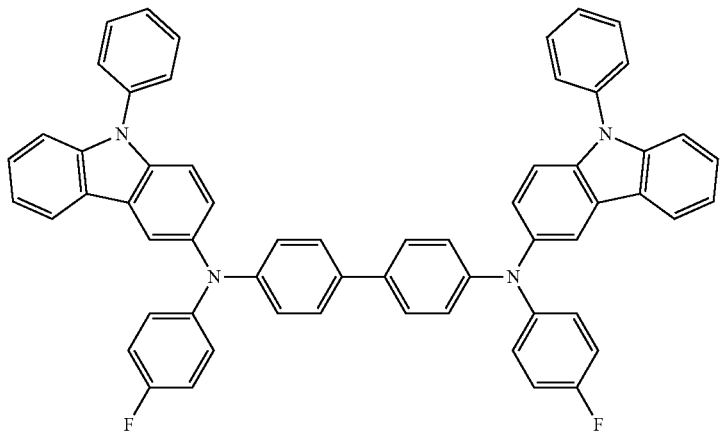
11
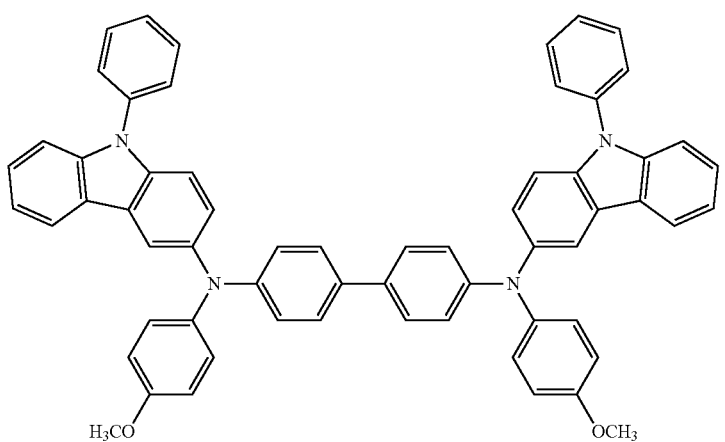
12
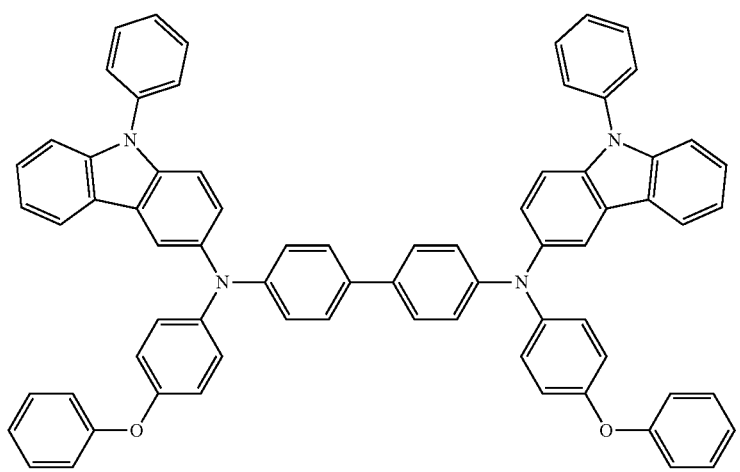
13

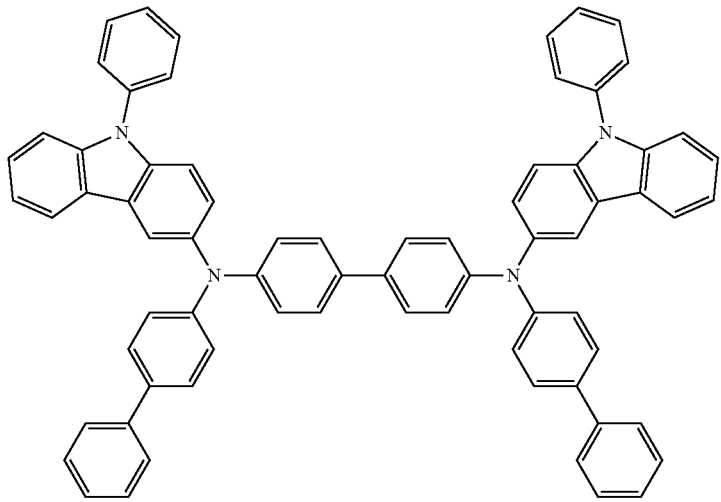
14
[Chem. 50]
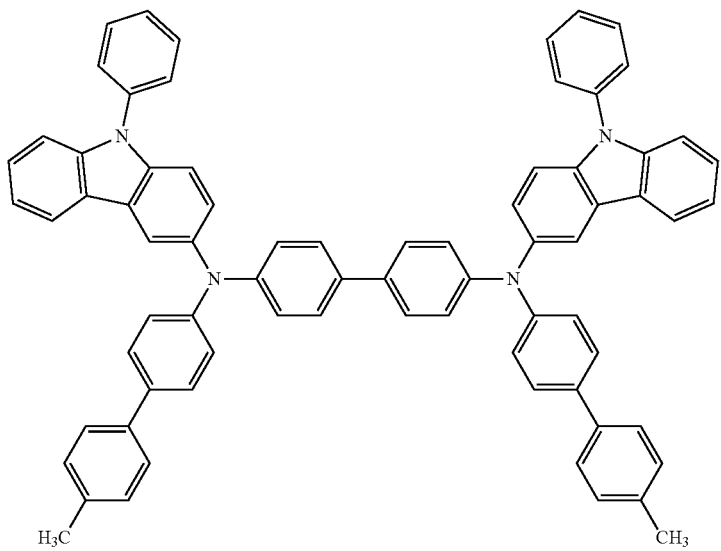
15
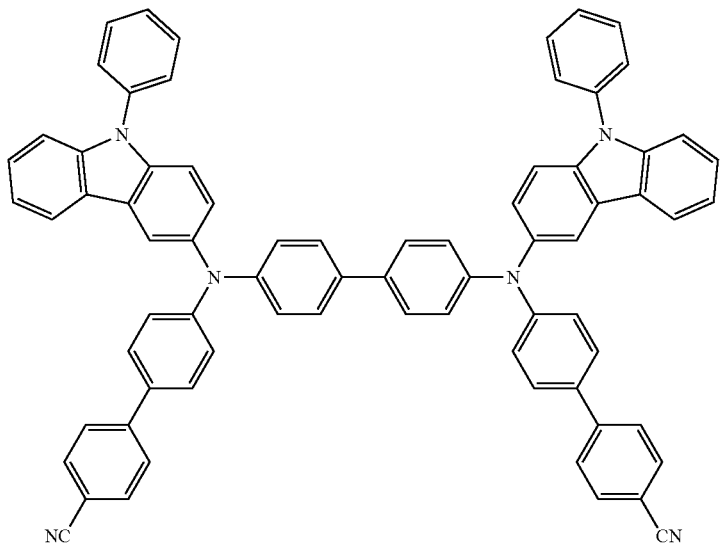
16

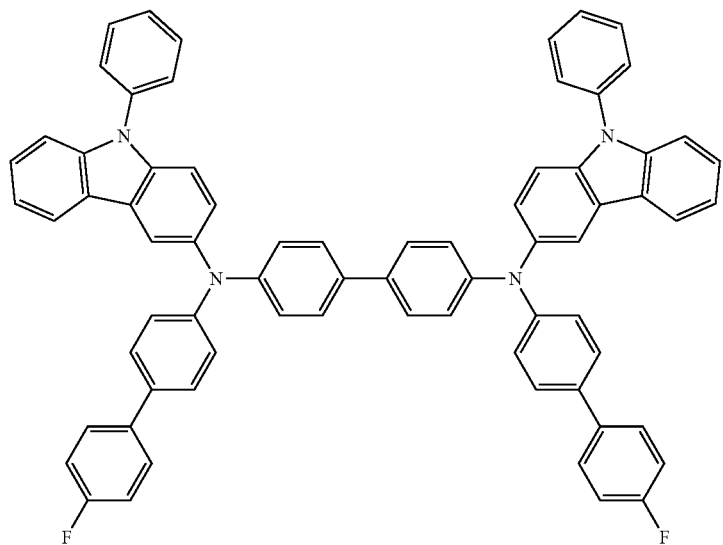
17
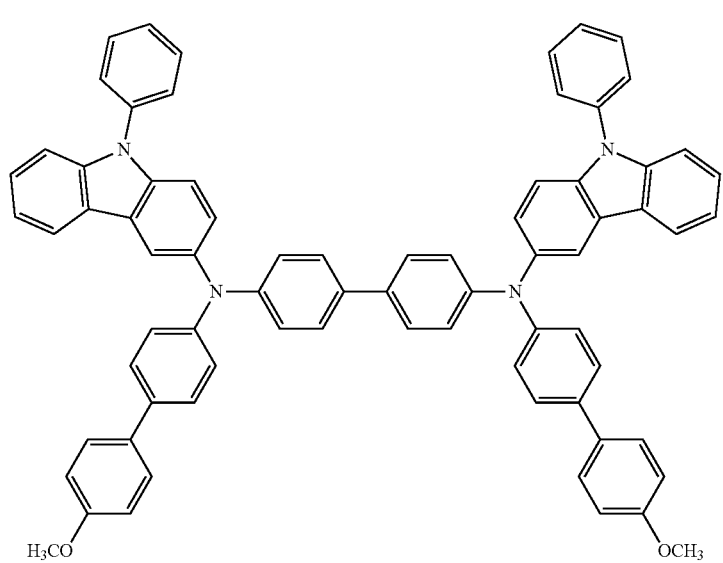
18
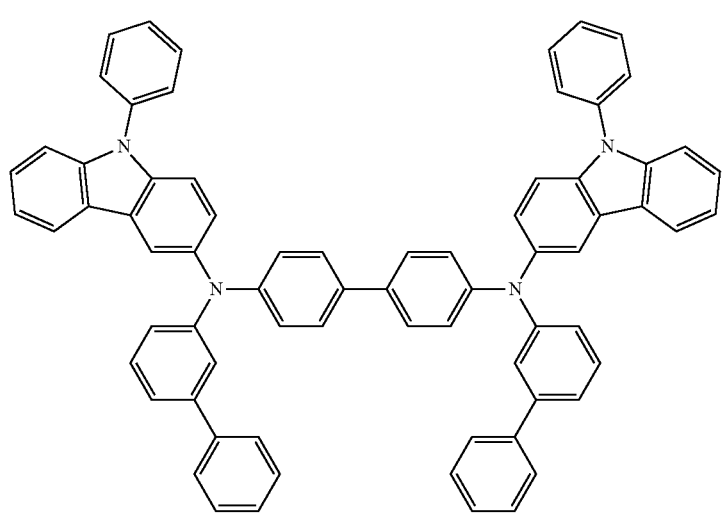
19

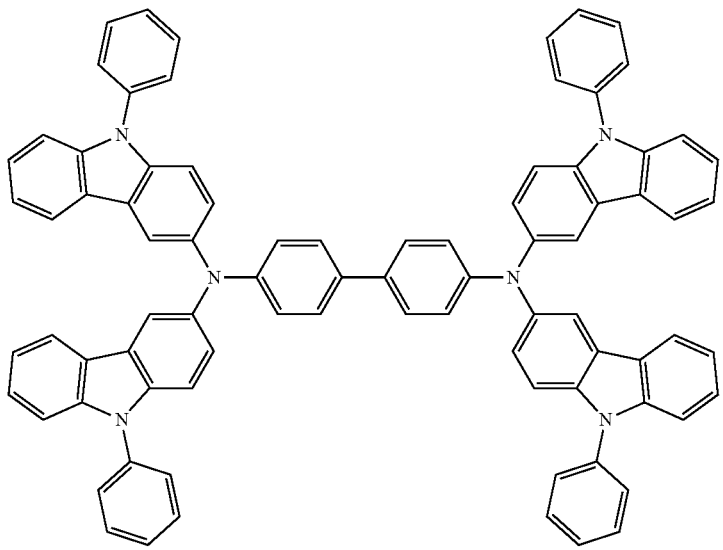
20
[Chem. 51]
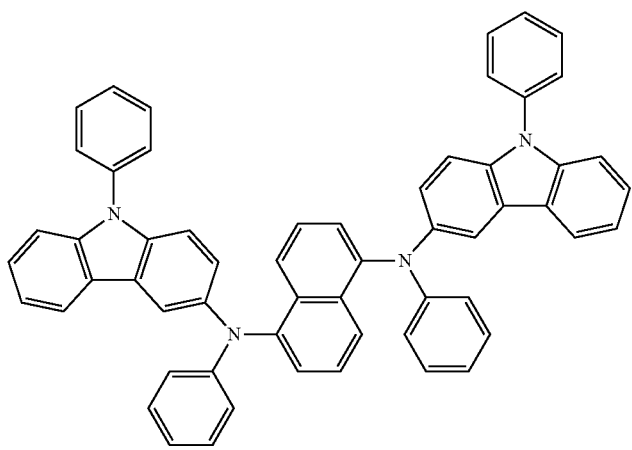
21
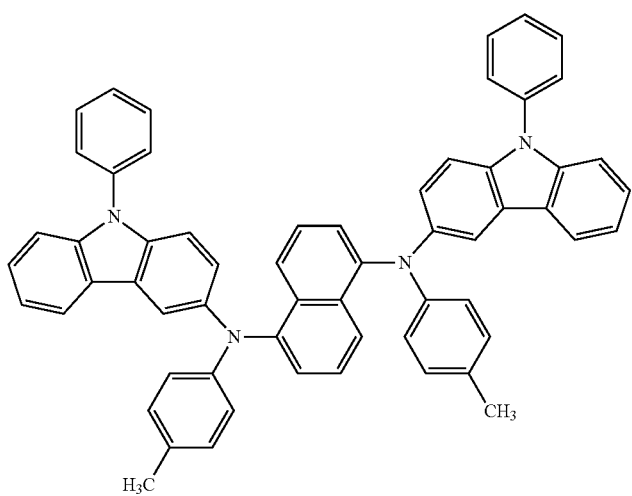
22

-continued
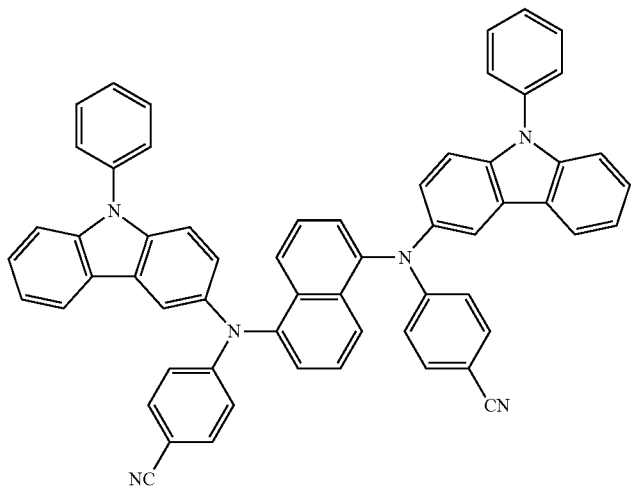
23
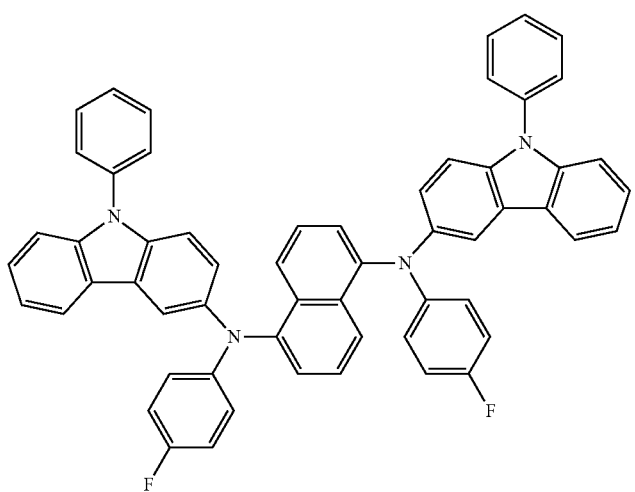
24
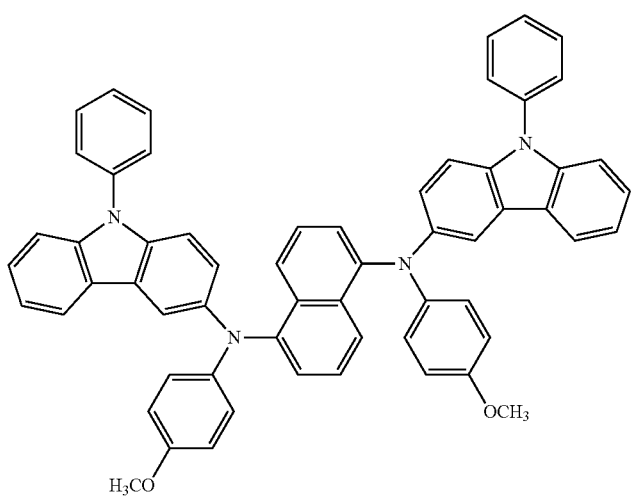
25

-continued
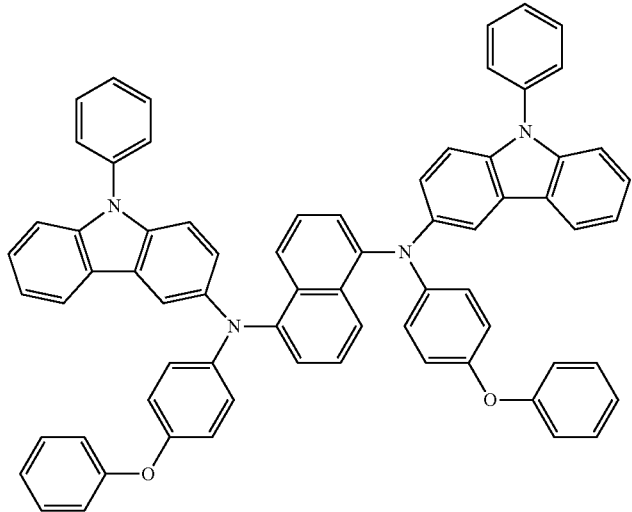
26
[Chem. 52]
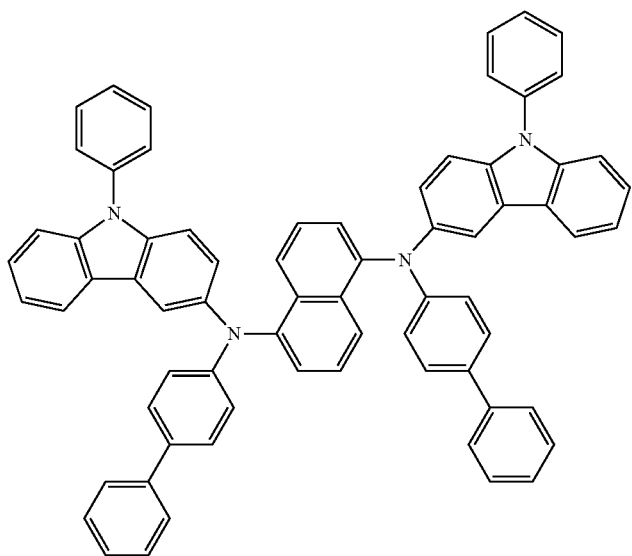
27
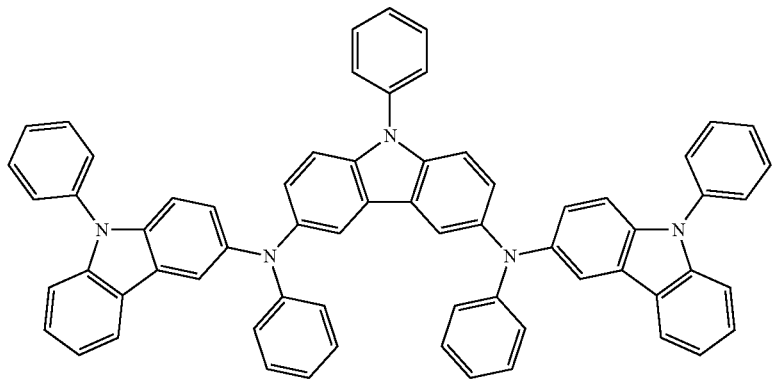
28

29
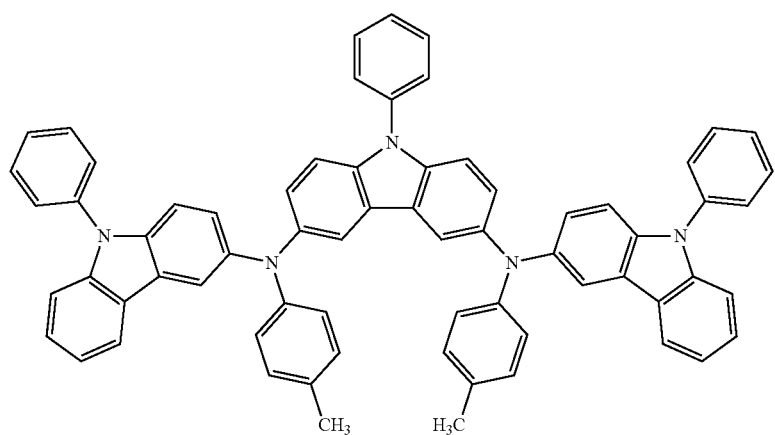
30
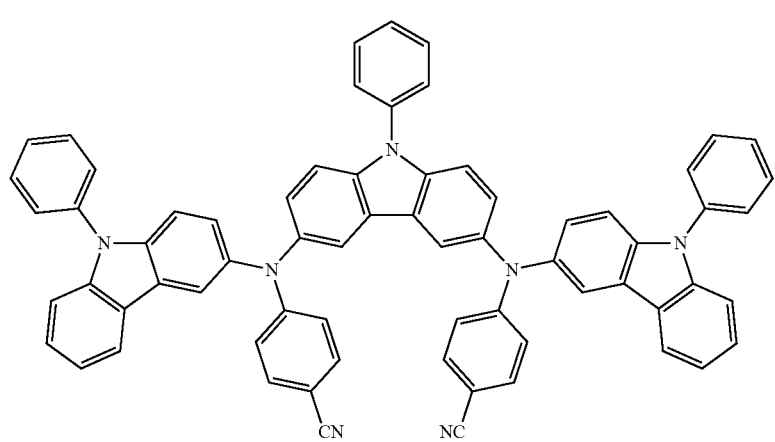
31
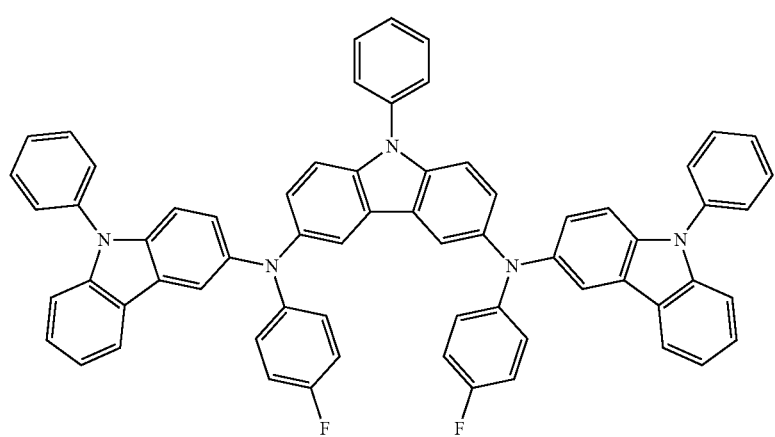

-continued
32
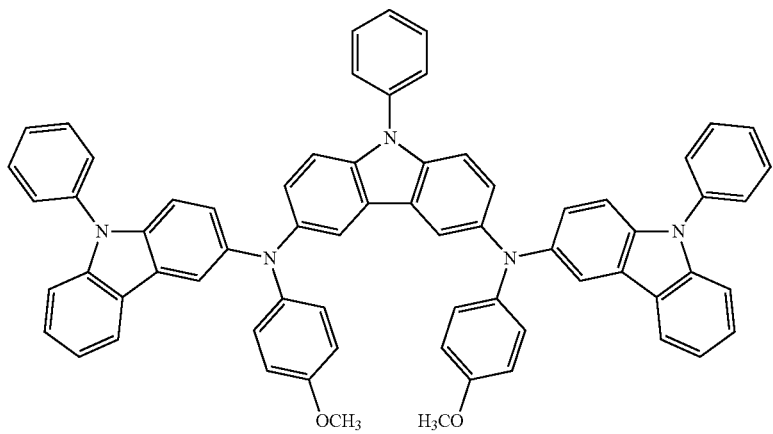
[Chem. 53]
33
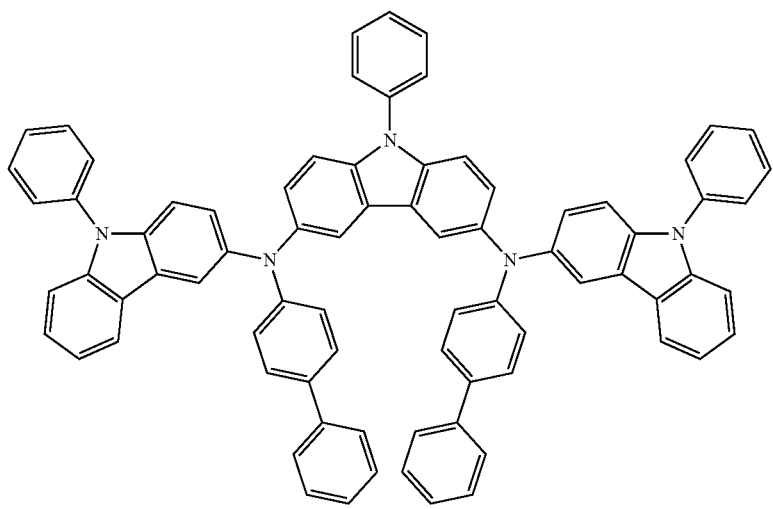
34
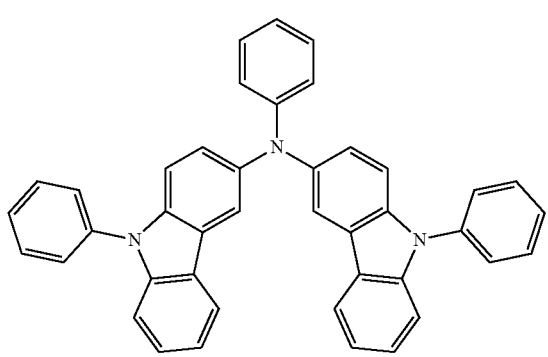

-continued
35
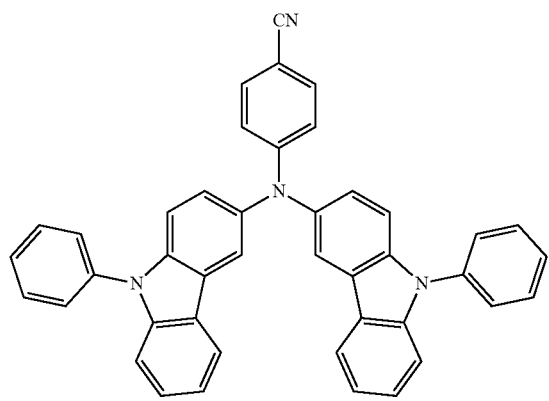
36
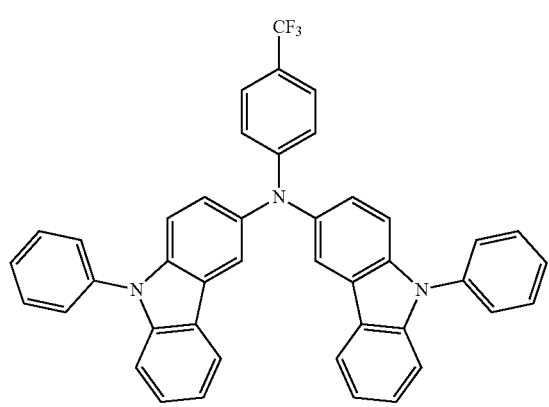
37
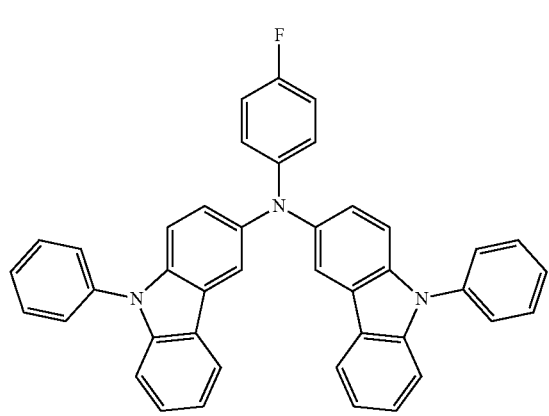
38
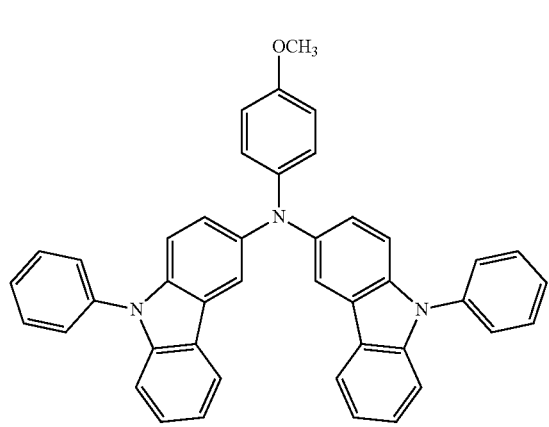

-continued
[Chem. 54]
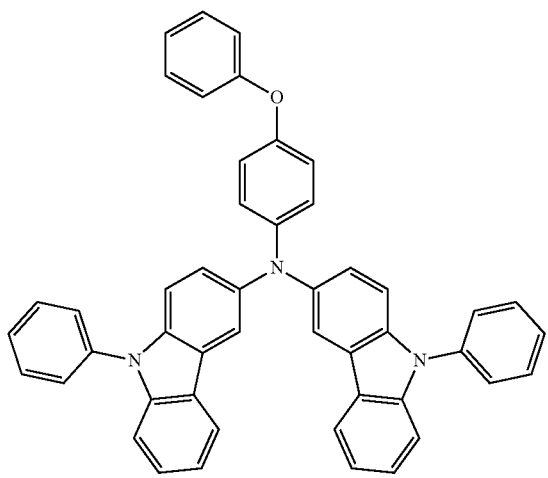
39
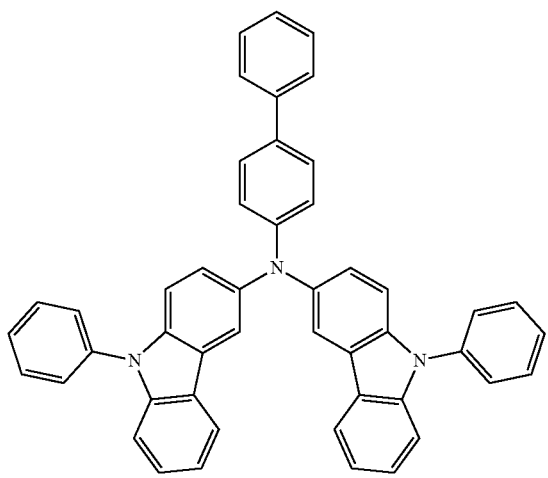
40
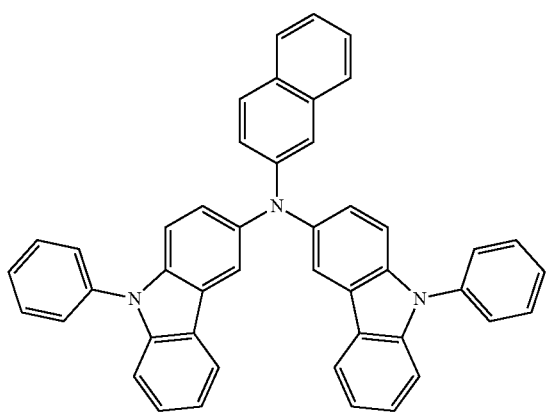
41

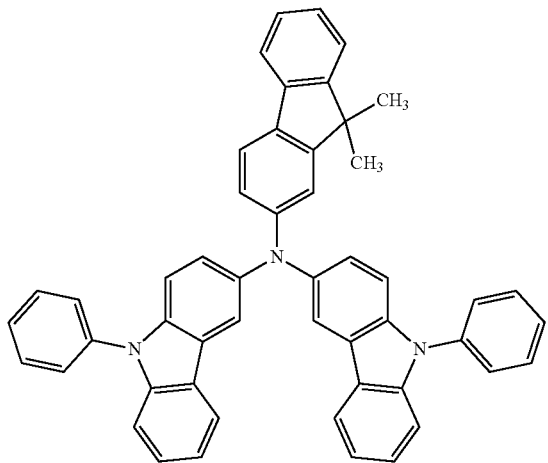
42
[Chem. 55]
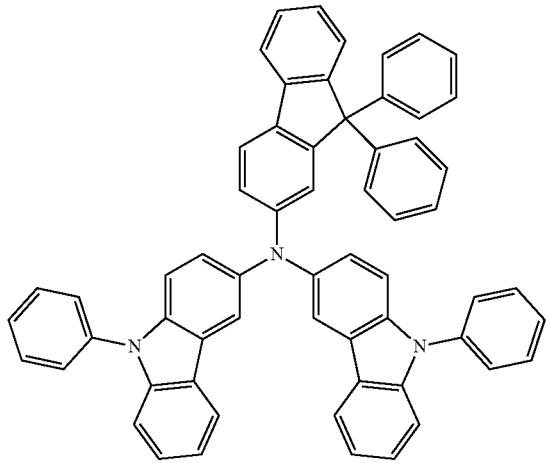
43
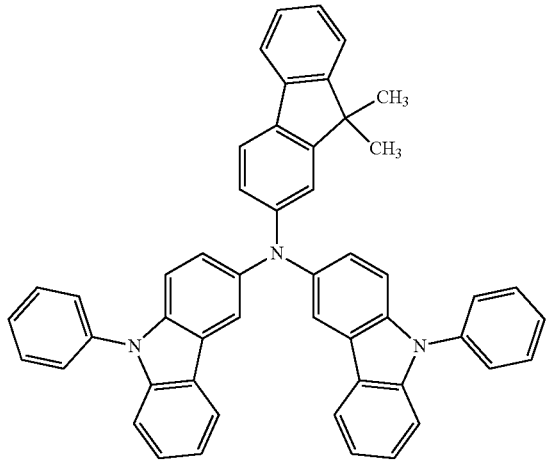
44

45
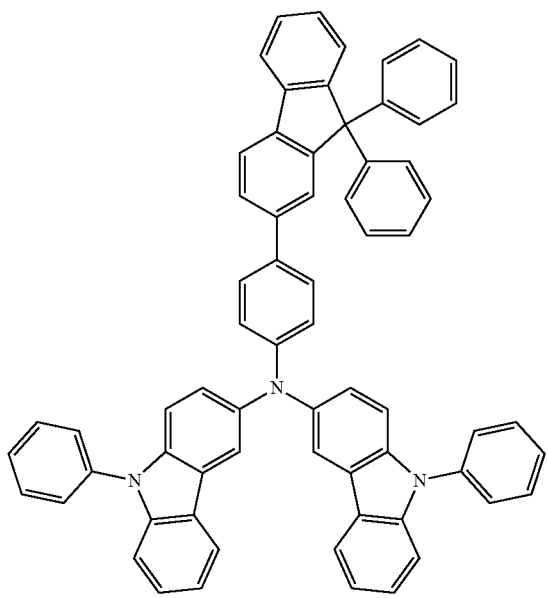
46
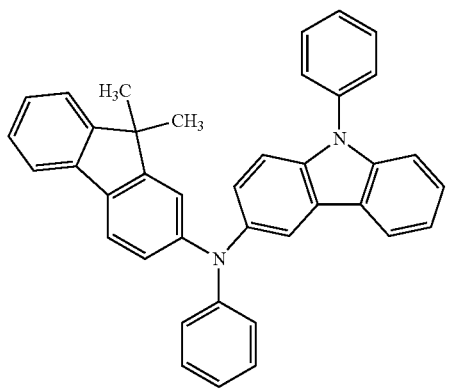
[Chem. 56]
47
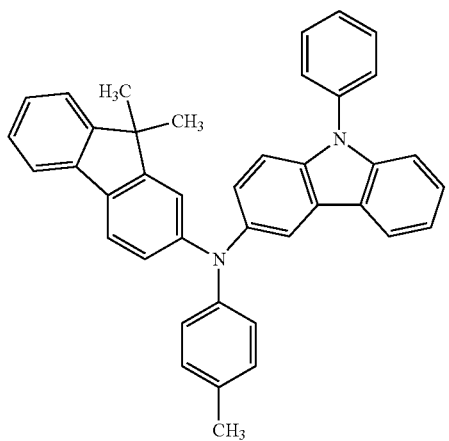

48
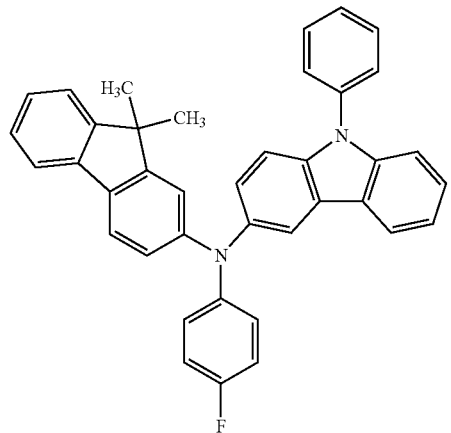
49
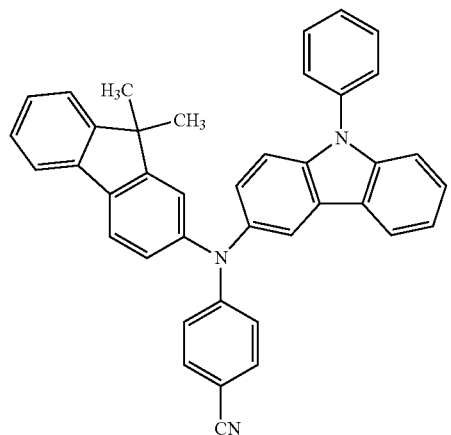
50
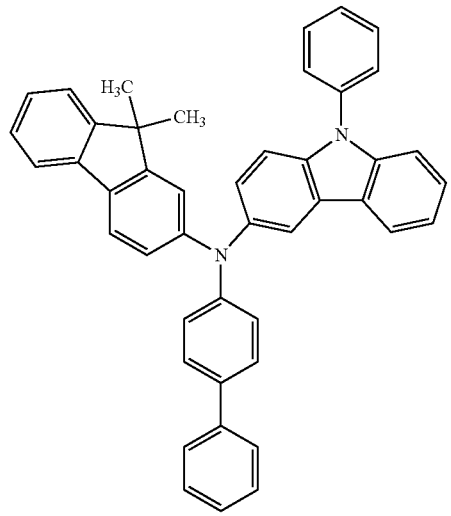

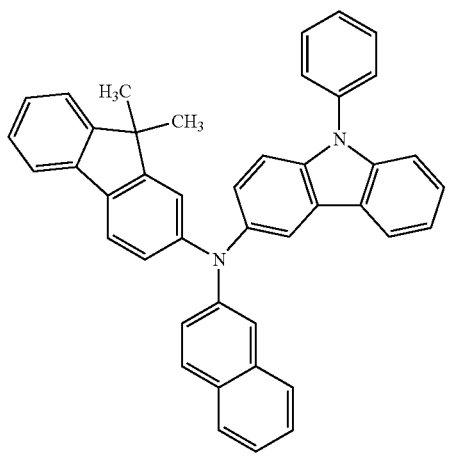
51
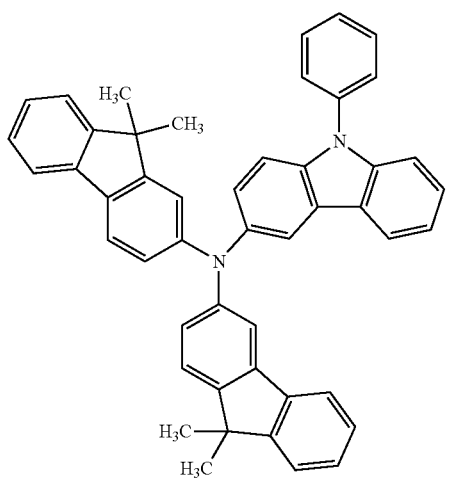
52
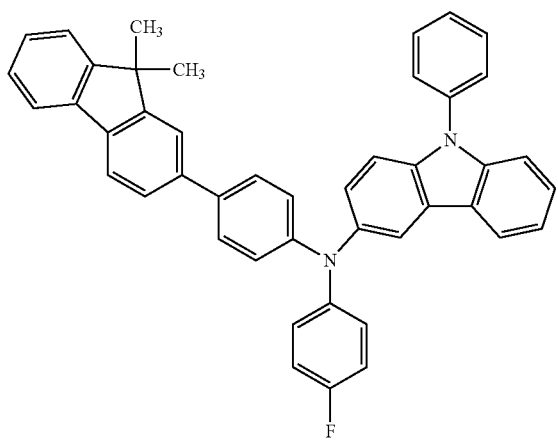
53

-continued
54
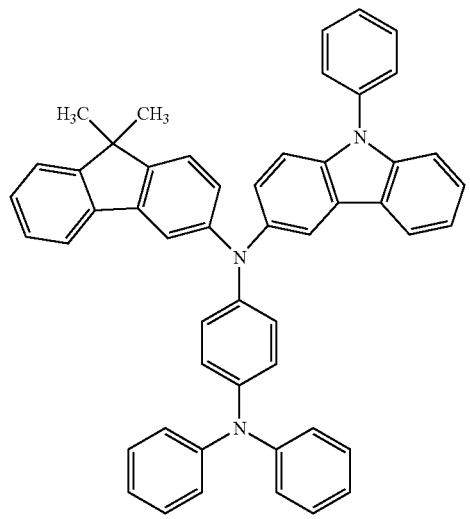
55
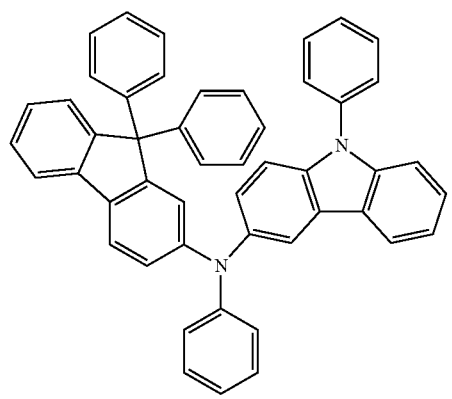
[Chem. 57]
56
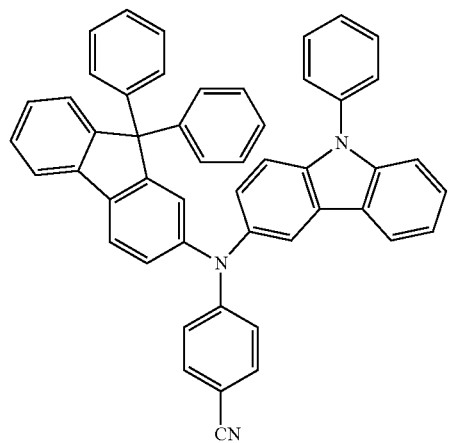

57
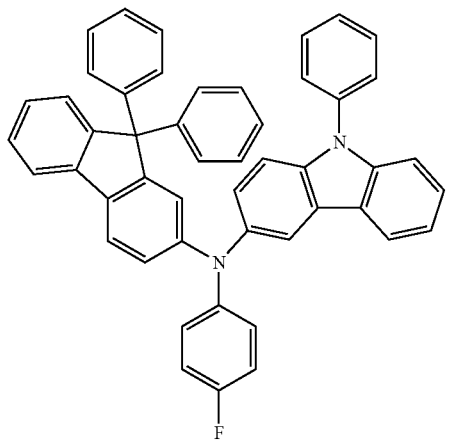
58
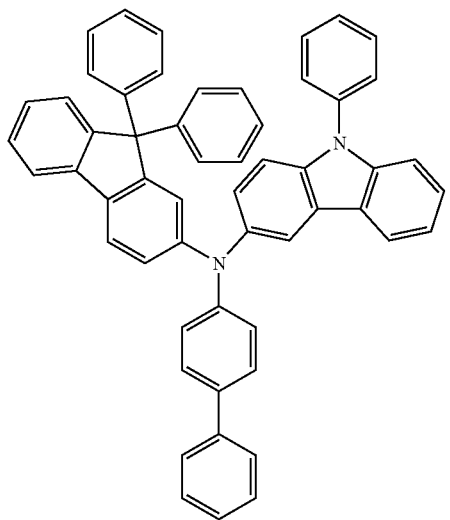
59
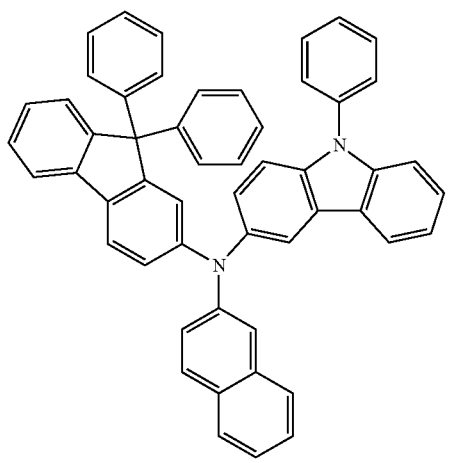

-continued
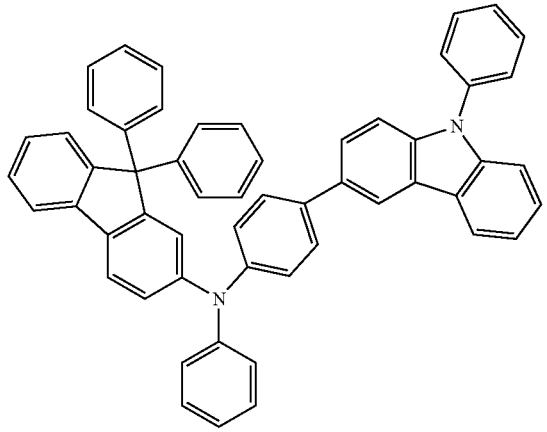
60
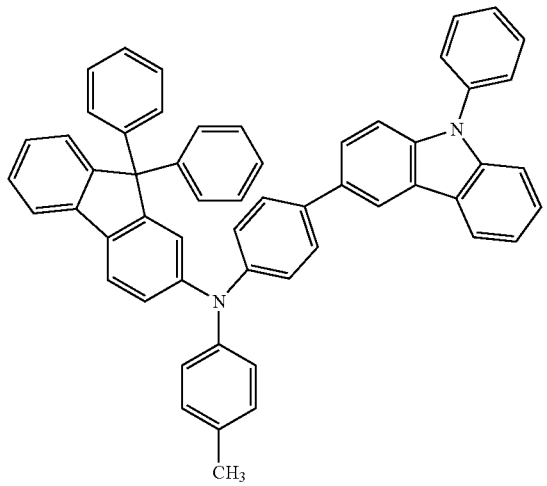
61
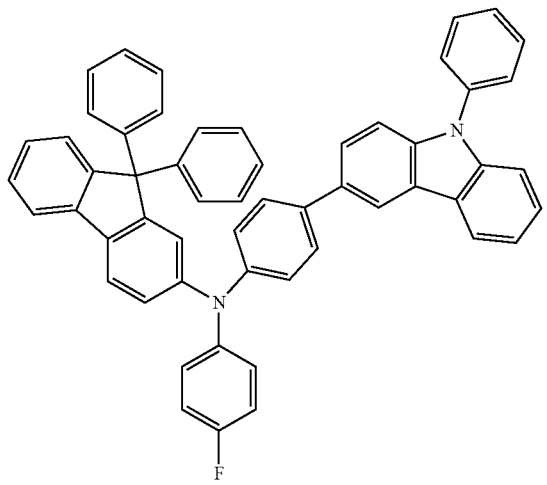
62

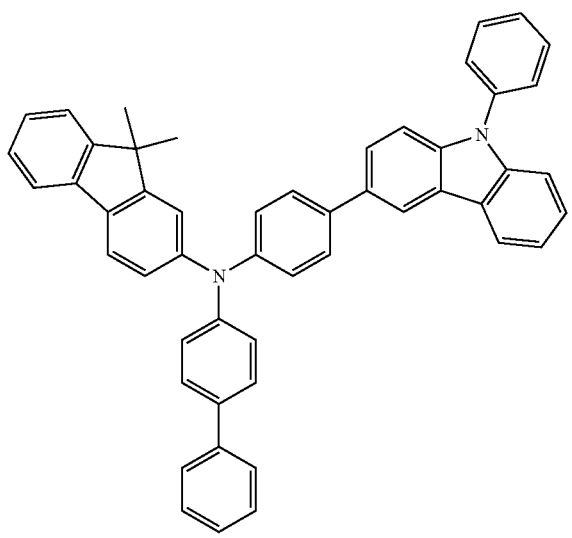

63

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably contained in the organic layer between the light emitting layer and the anode, and above all, it is more preferably contained in the layer on the anode side adjacent to the light emitting layer, and it is particularly preferably a hole transporting material contained in the hole transporting layer.

The compound represented by the general formula (Sa-1), (Sb-1), or (Sc-1) is contained in the amount of preferably from 70% by mass to 100% by mass, and more preferably from 85% by mass to 100% by mass, with respect to the total mass of the organic layer added.

[Compound Represented by General Formula (M-3)]

The organic electroluminescent element of the present invention is a material which is particularly preferably used in the (A) organic layer preferably disposed between the anode and the light emitting layer, and examples thereof include at least one kind of compound represented by the following general formula (M-3).

The compound represented by the general formula (M-3) is more preferably contained in the organic layer adjacent to the light emitting layer, between the light emitting layer and the anode, but is not limited in its uses and may be further contained in any layer in the organic layers. A layer into which the compound represented by the general formula (M-3) is introduced may contain any one or a plurality of a light emitting layer, a hole injecting layer, a hole transporting layer, an electron transporting layer, an electron injecting layer, and a charge blocking layer.

The organic layer adjacent to the light emitting layer between the light emitting layer and the anode, in which the compound represented by the general formula (M-3) is contained, is more preferably an electron blocking layer or a hole transporting layer.

[Chem. 58]

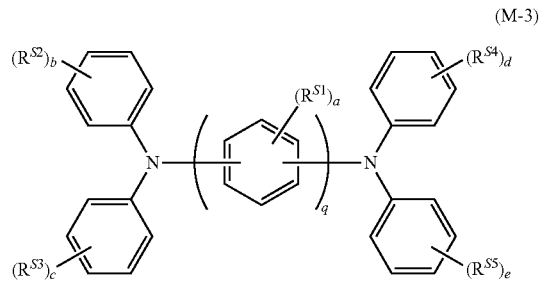

(M-3)

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —CO$_2$R, —C(O)R, —NR$_2$, —NO$_2$, —OR, a halogen atom, an aryl group, or a heteroaryl group, and may further have a substituent Z. Rs each independently represent a hydrogen atom, an alkyl group, a perhaloalkyl group, an alkenyl group, an alkynyl group, a heteroalkyl group, an aryl group, or a heteroaryl group. When a plurality of $R^{S1}$ to $R^{S5}$ are present, those groups may be bonded to each other to form a ring, and may further have a substituent Z.

a represents an integer of 0 to 4, and when a plurality of $R^{S1}$s are present, the $R^{S1}$s may be the same as or different from one another, and may be bonded to each other to form a ring. b to e each independently represent an integer of 0 to 5, and when a plurality of groups are present for each $R^{S2}$ to $R^{S5}$, the groups may be the same as or different from one another, and any two thereof may be bonded to each other to form a ring.

q is an integer of 1 to 5, and when q is 2 or more, a plurality of $R^{S1}$s may be the same as or different from one another and may be bonded to each other to form a ring.

The alkyl group may have a substituent and may be saturated or unsaturated, and examples of the group that may be substituted include the substituent Zs as described above. The alkyl group represented by $R^{S1}$ to $R^{S5}$ is preferably an alkyl group having a total carbon number of 1 to 8, and more preferably an alkyl group having a total carbon number of 1 to 6, and examples thereof include a methyl group, an ethyl group, an i-propyl group, a cyclohexyl group, and a t-butyl group.

The cycloalkyl group may have a substituent and may be saturated or unsaturated, and examples of the group that may be substituted include the substituent Zs as described above. The cycloalkyl group represented by $R^{S1}$ to $R^{S5}$ is preferably a cycloalkyl group having 4 to 7 ring members, and more preferably a cycloalkyl group having a total carbon number of 5 or 6, and examples thereof include a cyclopenthyl group and a cyclohexyl group.

The alkenyl group represented by $R^{S1}$ to $R^{S5}$ preferably has 2 to 30 carbon atoms, more preferably has 2 to 20 carbon atoms, and particularly preferably has 2 to 10 carbon atoms, and examples thereof include vinyl, allyl, 1-propenyl, 1-isopropenyl, 1-butenyl, 2-butenyl, and 3-pentenyl.

The alkynyl group represented by $R^{S1}$ to $R^{S5}$ preferably has 2 to 30 carbon atoms, more preferably has 2 to 20 carbon atoms, and particularly preferably has 2 to 10 carbon atoms, and examples thereof include ethynyl, propargyl, 1-propynyl, and 3-pentynyl.

The perfluoroalkyl group represented by $R^{S1}$ to $R^{S5}$ includes a group obtained by substituting all the hydrogen atoms in the above-mentioned alkyl group with fluorine atoms.

The aryl group represented by $R^{S1}$ to $R^{S5}$ is preferably a substituted or unsubstituted aryl group having 6 to 30 carbon atoms, and examples thereof include a phenyl group, a tolyl group, a biphenyl group, and a terphenyl group.

The heteroaryl group represented by $R^{S1}$ to $R^{S5}$ is preferably a heteroaryl group having 5 to 8 carbon atoms, and more preferably a substituted or unsubstituted 5- or 6-membered heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferred examples thereof include a pyridyl group, a pyrimidinyl group, an imidazolyl group, and a thienyl group, and more preferred examples thereof include a pyridyl group and a pyrimidinyl group.

$R^{S1}$ to $R^{S5}$ are each preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and still more preferably a hydrogen atom, an alkyl group, or an aryl group. The substituent Z is preferably an alkyl group, an alkoxy group, a fluoro group, a cyano group, or a dialkylamino group, and more preferably a hydrogen atom or an alkyl group.

Any two of $R^{S1}$ to $R^{S5}$ may be bonded to each other to form a fused 4- to 7-membered ring, the fused 4- to 7-membered ring is cycloalkyl, aryl, or heteroaryl, and the fused 4- to 7-membered ring may further have a substituent Z. The definitions and the preferred ranges of the formed cycloalkyl, aryl and heteroaryl are the same as those of the cycloalkyl group, the aryl group, and the heteroaryl group defined in $R^{S1}$ to $R^{S5}$.

In the case where the compound represented by the general formula (M-3) is used in a hole transporting layer, the compound represented by the general formula (M-3) is preferably contained in an amount of 50% by mass to 100% by mass, more preferably contained in an amount of 80% by mass to 100% by mass, and particularly preferably contained in an amount of 95% by mass to 100% by mass.

In addition, in the case where the compound represented by the general formula (M-3) is used in a plurality of organic layers, the compound is preferably contained in each layer within the above range.

The thickness of the hole transporting layer containing the compound represented by the general formula (M-3) is preferably from 1 nm to 500 nm, more preferably from 3 nm to 200 nm, and still more preferably from 5 nm to 100 nm. In addition, the hole transporting layer is preferably provided to be adjacent to the light emitting layer.

Specific examples of the compound represented by the general formula (M-3) are shown below, but the present invention is not limited thereto.

[Chem. 59]

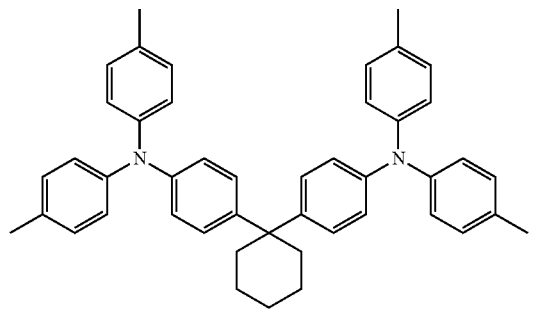
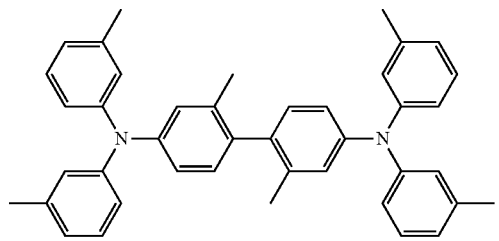

-continued
191
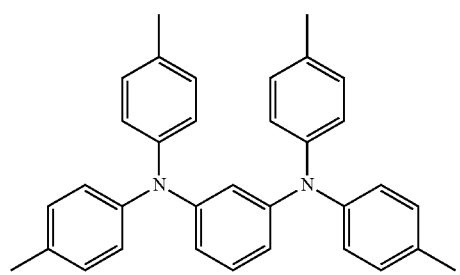
192
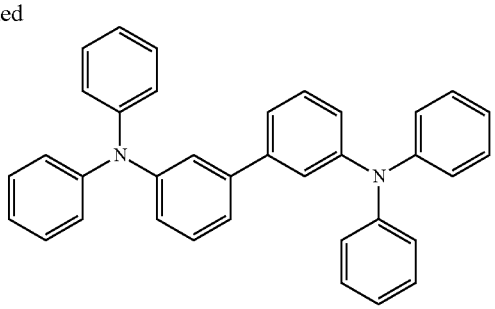
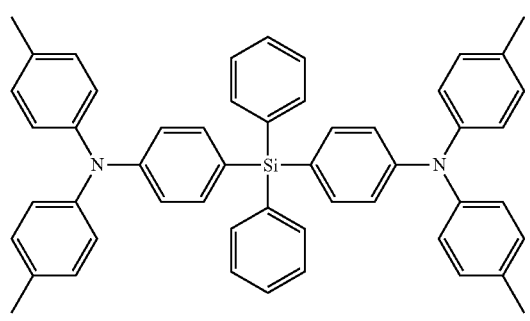
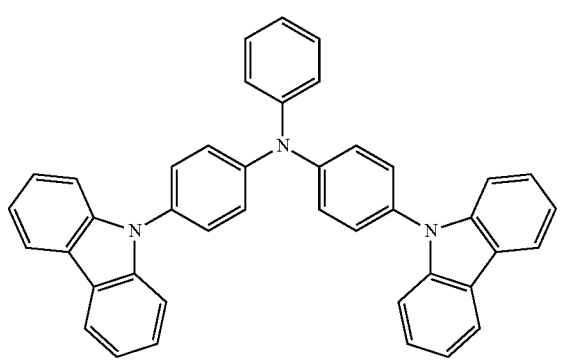
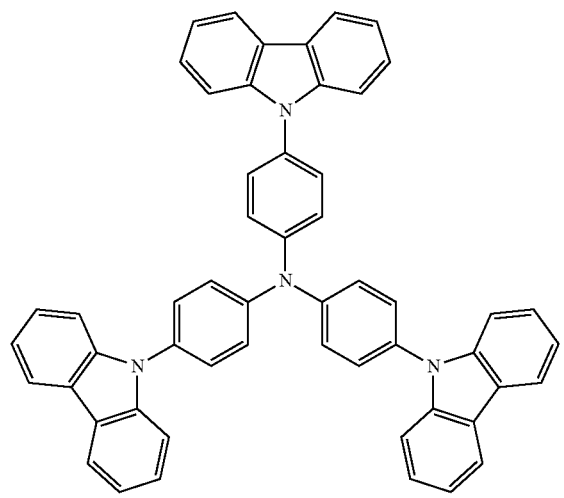
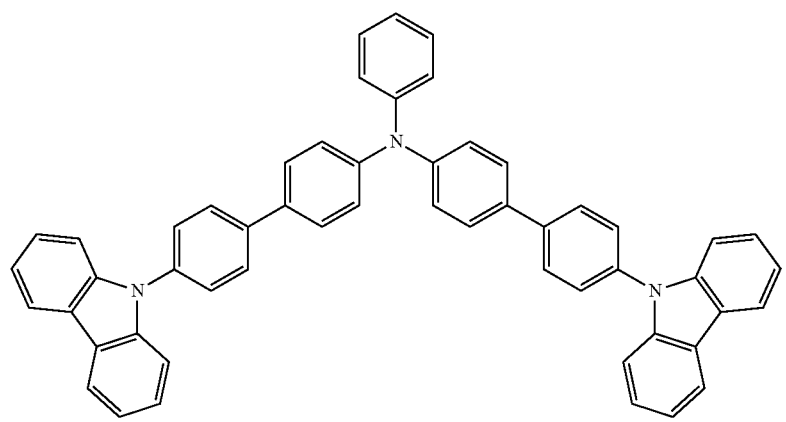

-continued
193
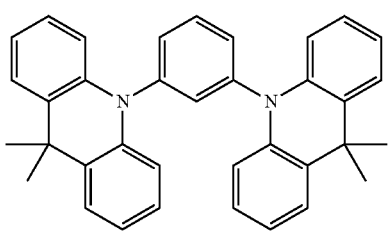
194
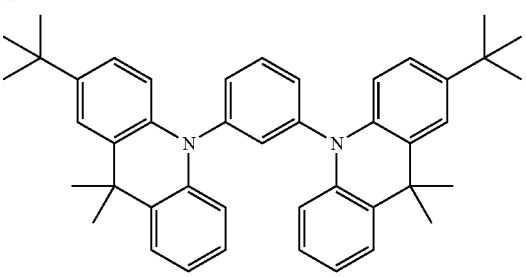
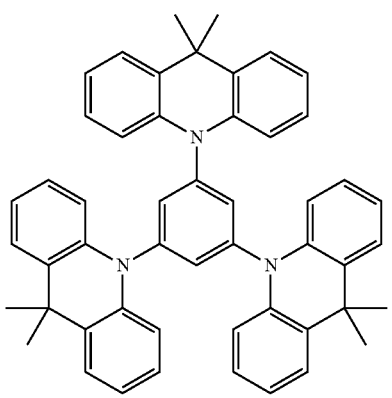
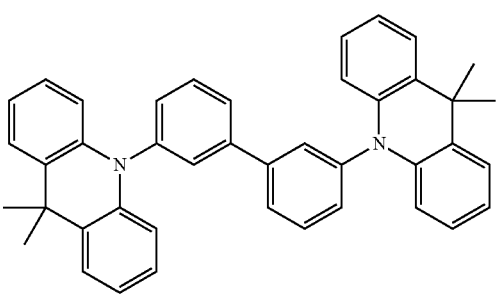
[Chem. 60]
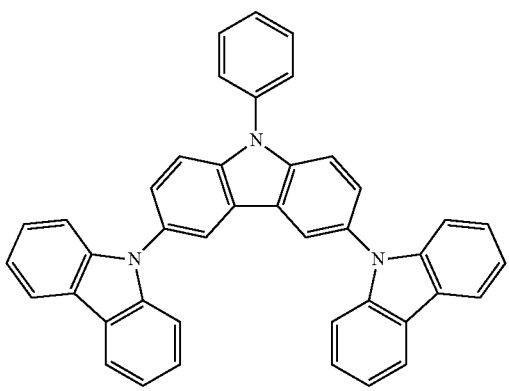
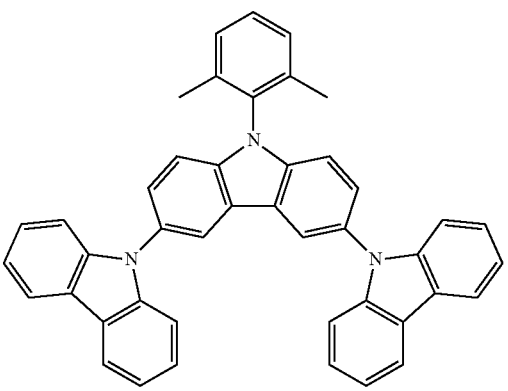
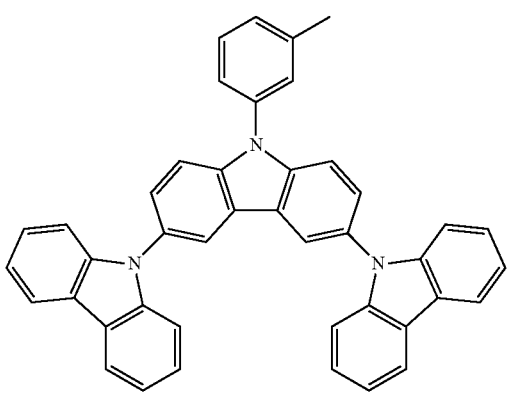
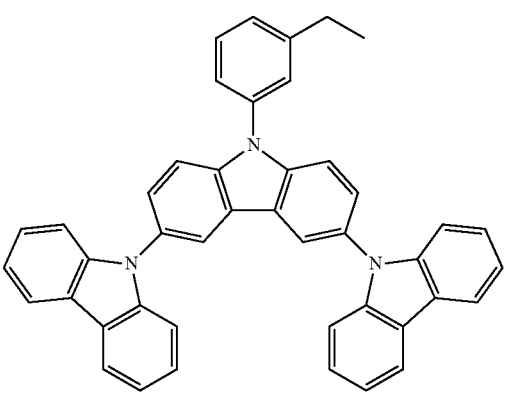

-continued
195
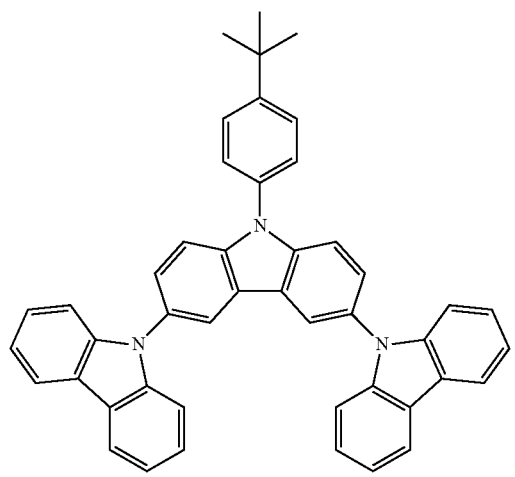
196
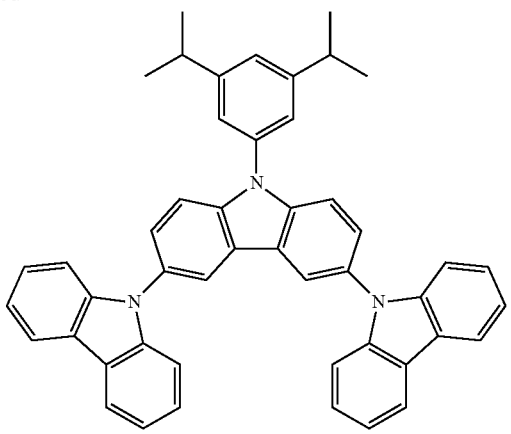
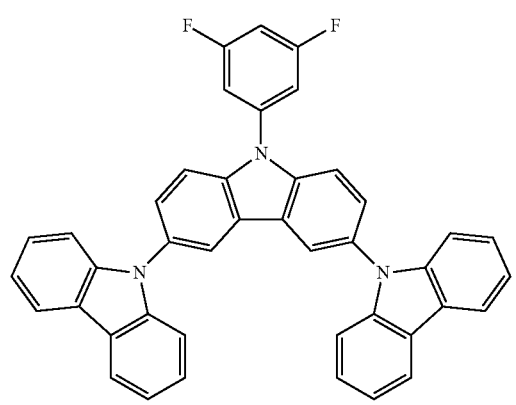
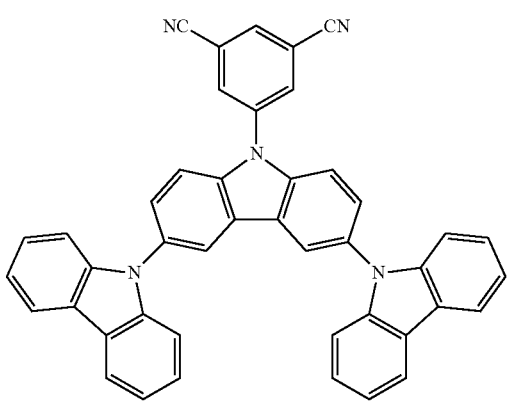
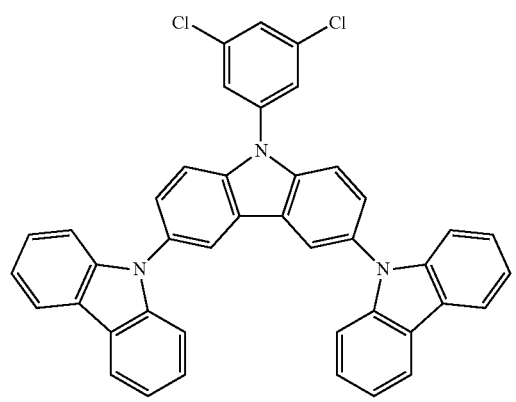
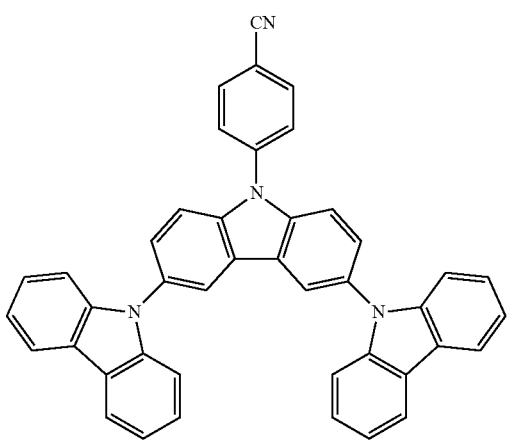

-continued
197
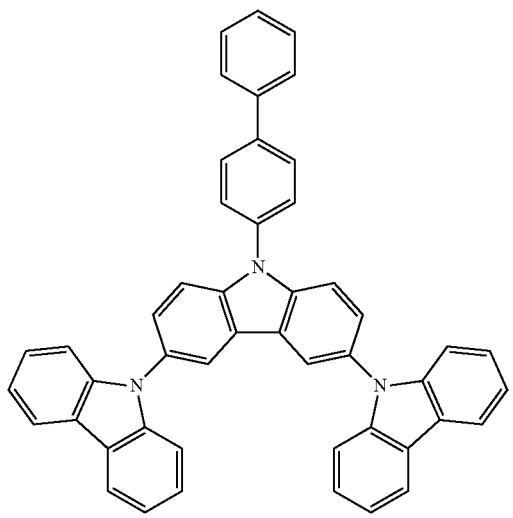
198
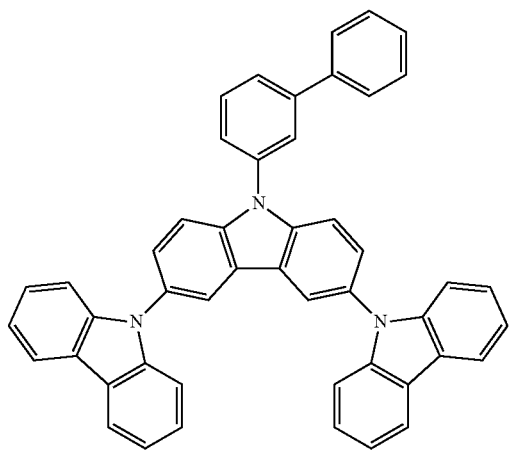
[Chem. 61]
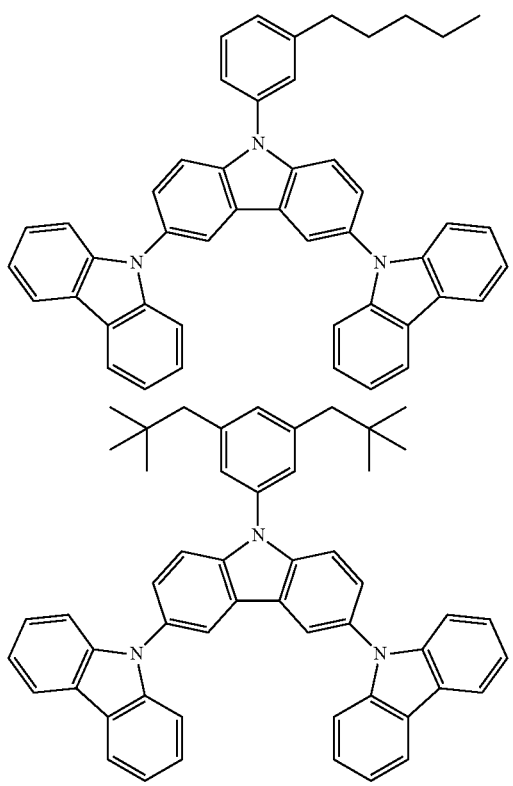
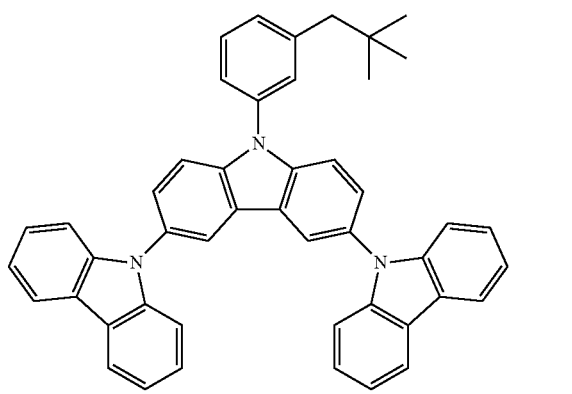
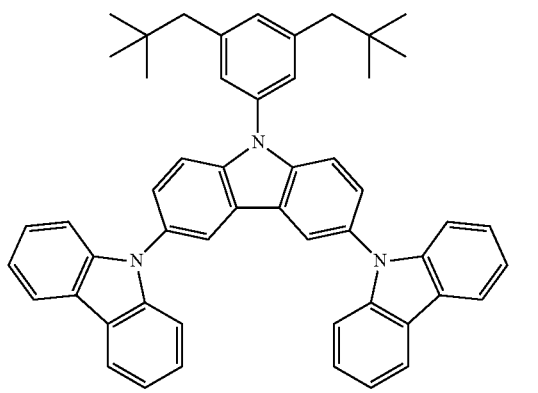
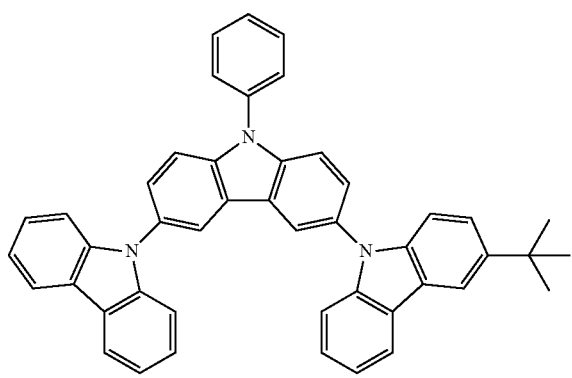
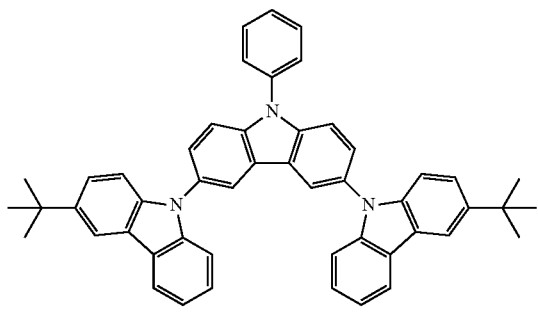
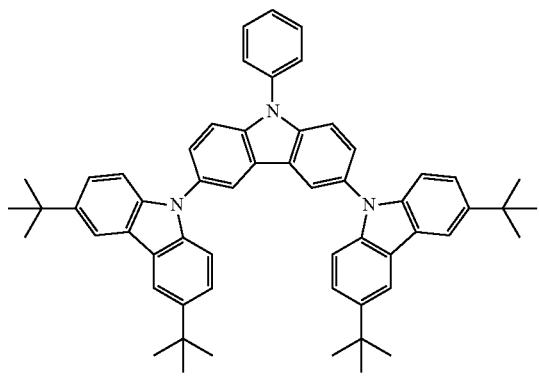

199 200
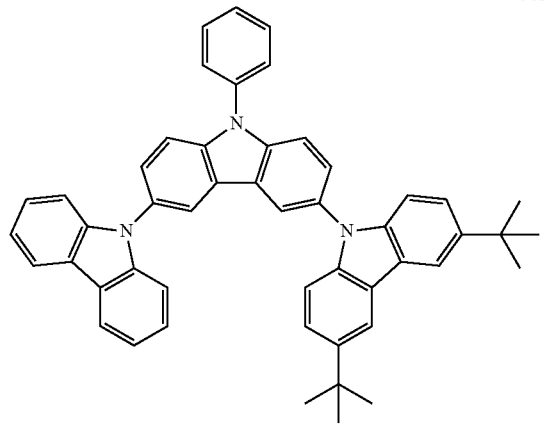
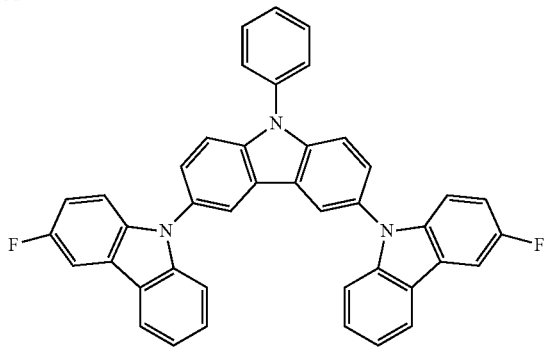
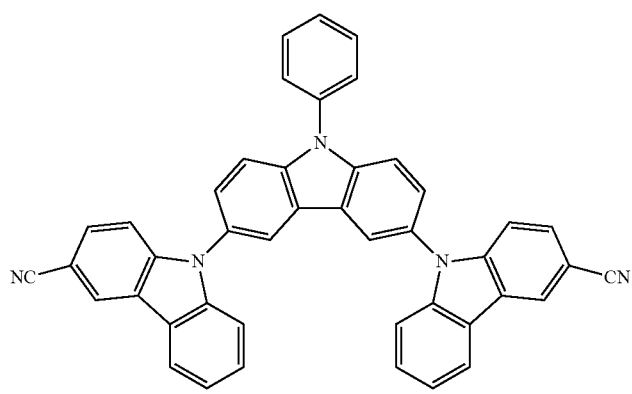
[Chem. 62]
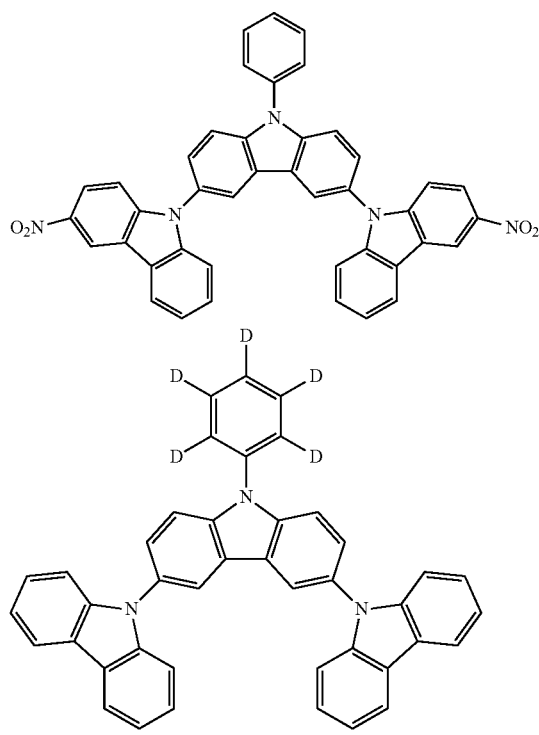
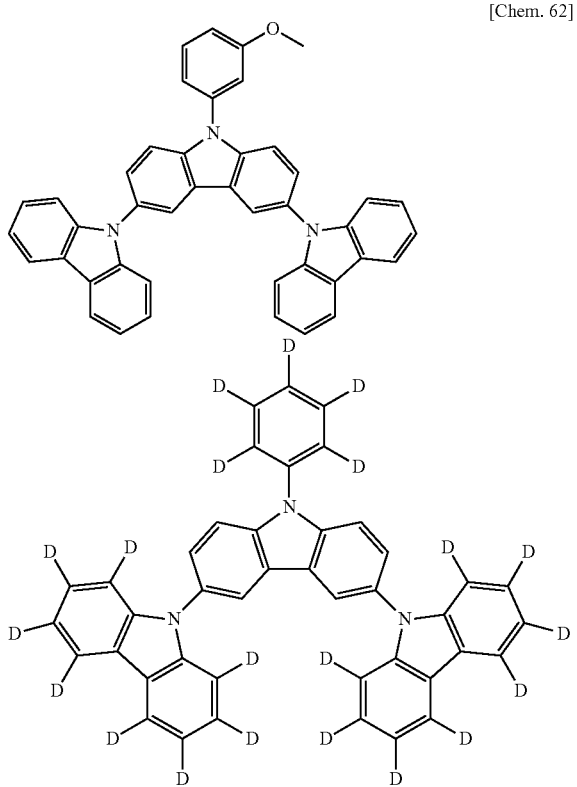

201 202
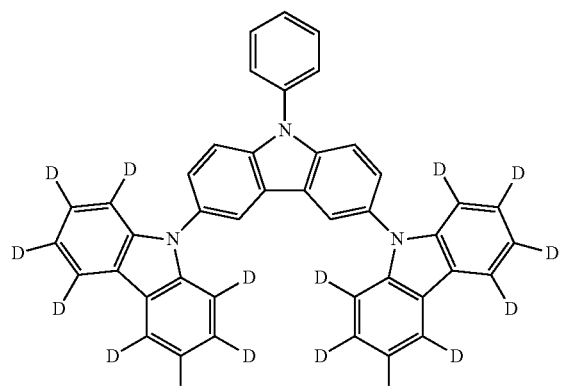
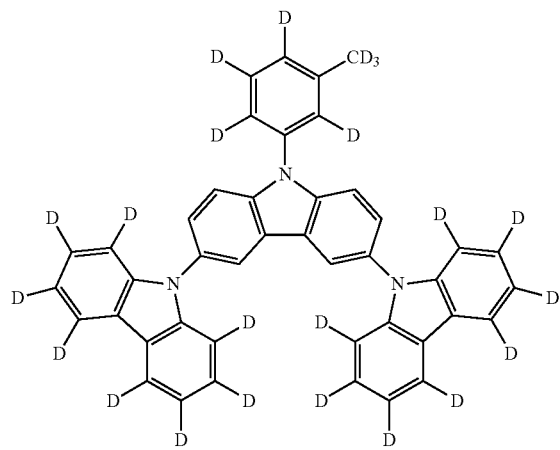
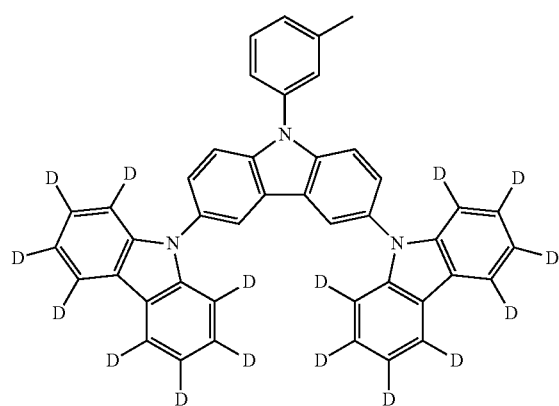
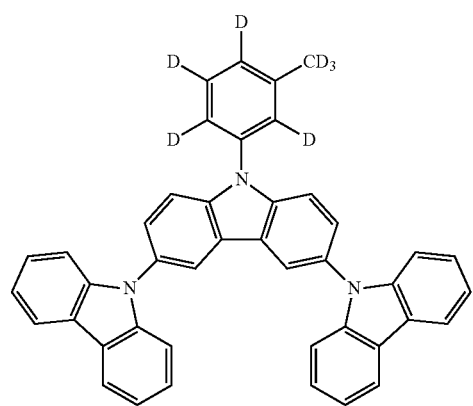
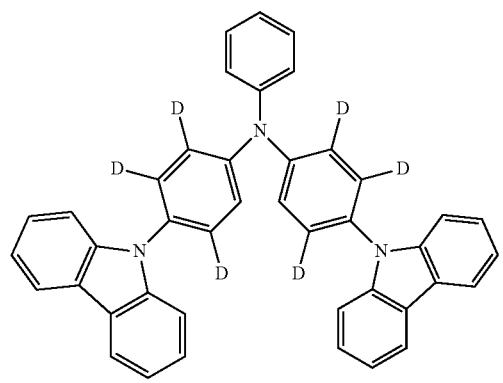
[Chem. 63]
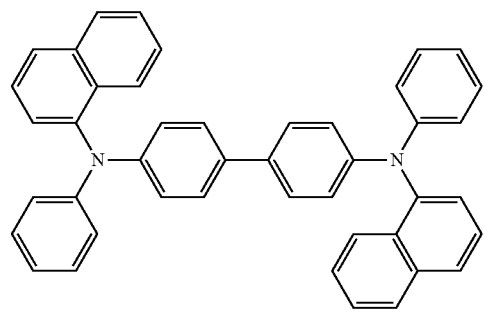

203
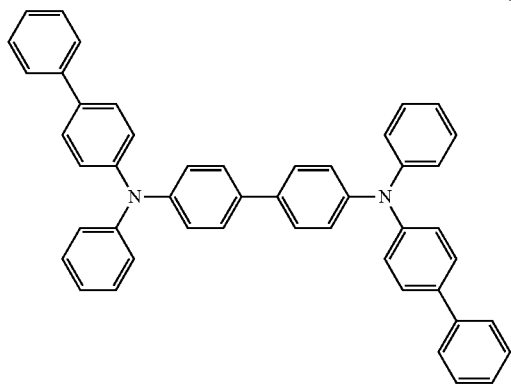
204
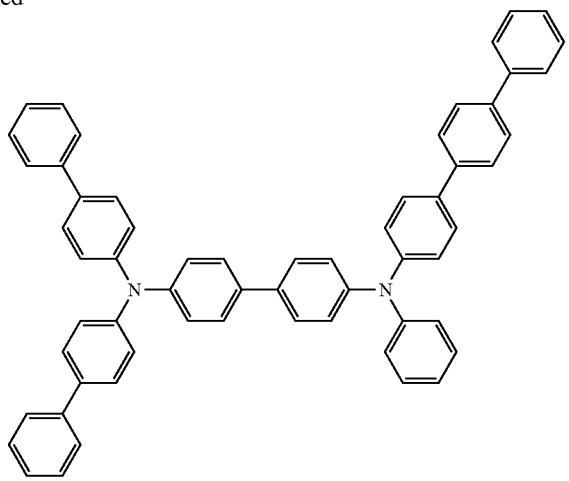
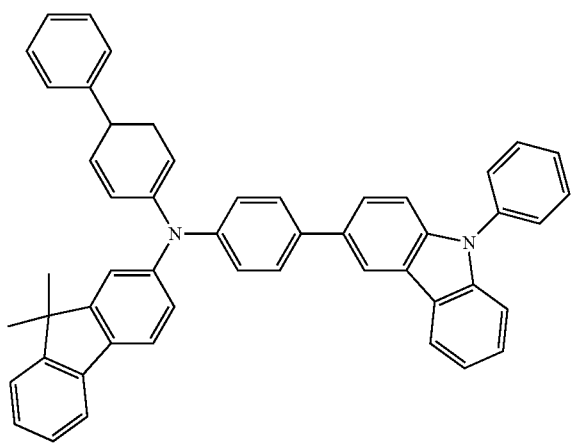
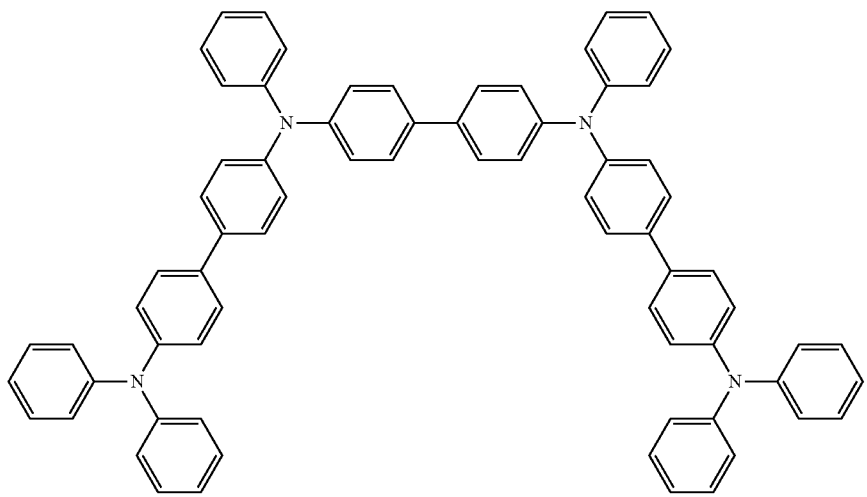

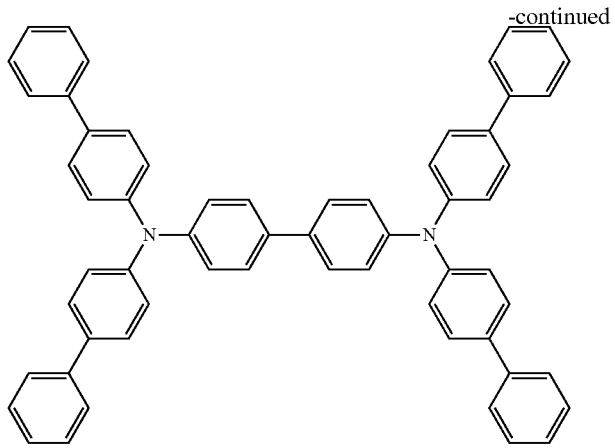

In addition, with respect to the hole injecting layer and the hole transporting layer, the detailed descriptions in paragraph Nos. [0165] to [0167] of JP-A-2008-270736 can be applied to the present invention. Further, the detailed descriptions in paragraph Nos. [0250] to [0339] of JP-A-2011-71452 can be applied to the hole injecting layer and the hole transporting layer of the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include TCNQ compounds such as tetracyanoquinodimethane (TCNQ) and tetrafluorotetracyanoquinodimethane ($F_4$-TCNQ), hexaazatriphenylene compounds such as hexacyanohexaazatriphenylene (HAT-CN), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be applied.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one kind or two or more kinds of the above-described materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is higher than the $S_1$ of the light emitting material preferably by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof; organic silane derivatives typified by silole; and hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one kind or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (1) can be used.

Examples of organic compounds constituting the hole blocking layer, other than the compound represented by the general formula (1), include aluminum complexes such as aluminum (III) bis(2-methyl-8-quinolinato)-4-phenylphenolate (abbreviated as BAlq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one kind or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is higher than the $S_1$ of the light emitting material preferably by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (1), a compound represented by the following general formula (P-1), and a compound represented by the following general formula (O-1).

Hereinafter, the compound represented by the general formula (O-1) and the compound represented by the general formula (P-1) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 64]

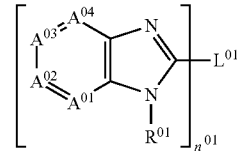

General Formula (O-1)

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferred examples thereof include an alkyl group and an aryl group, and still more preferred examples thereof include an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^4$, or $A^{O1}$ be a nitrogen atom and $A^{O2}$ to $A^{O4}$ be C—$R^4$; it is more preferable that $A^{O1}$ be a nitrogen atom, and $A^{O2}$ to $A^{O4}$ be C—$R^4$; it is still more preferable that $A^{O1}$ be a nitrogen atom, $A^{O2}$ to $A^{O4}$ be C—$R^4$, and $R^4$s be all hydrogen atoms.

$R^4$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. Further, a plurality of $R^4$s may be the same as or different from each other. $R^4$ is preferably a hydrogen atom or an alkyl group, and more preferably a hydrogen atom.

$L^{O1}$ represents any of divalent to hexavalent linking groups including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the Substituent Group A as described above, and in a case of having the substituent, the substituent is preferably an alkyl group, an aryl group, or a cyano group. Specific examples of $L^{O1}$ include the following.

[Chem. 65]

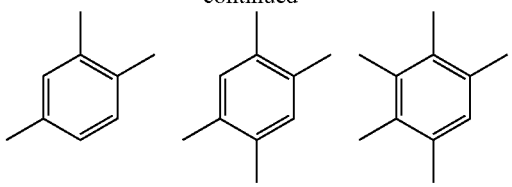

-continued

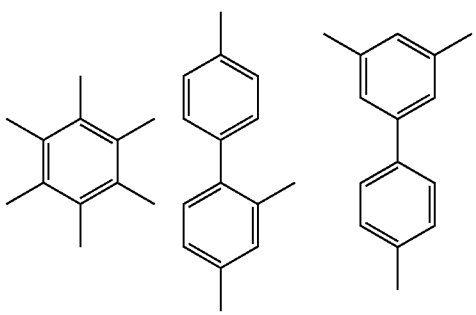

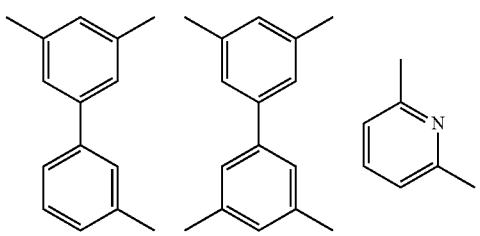

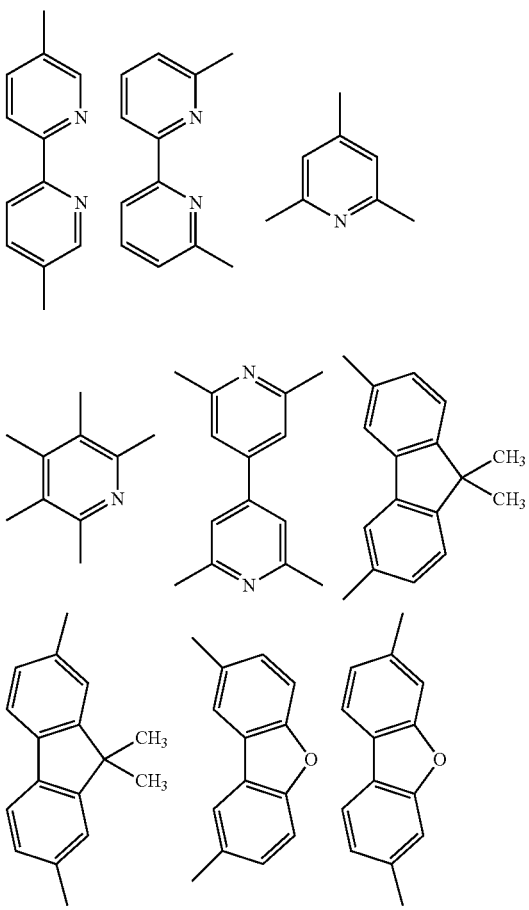

-continued

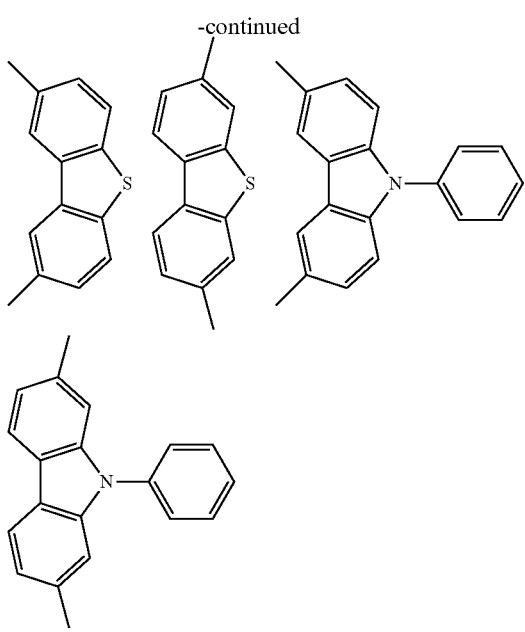

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 66]

OM-1

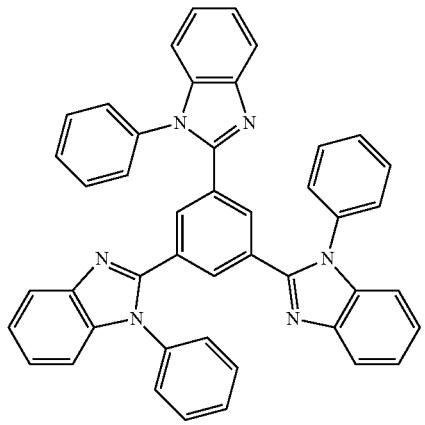

OM-2

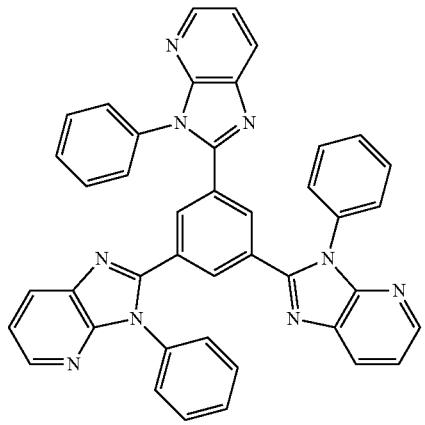

OM-3

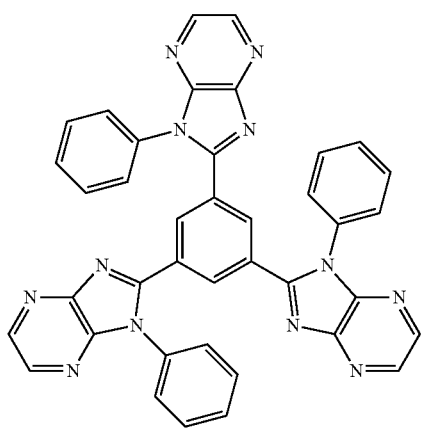

OM-4

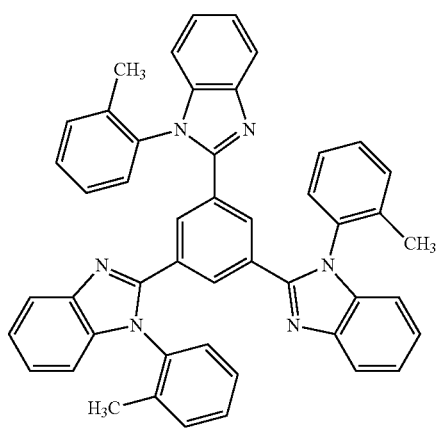

-continued
OM-5
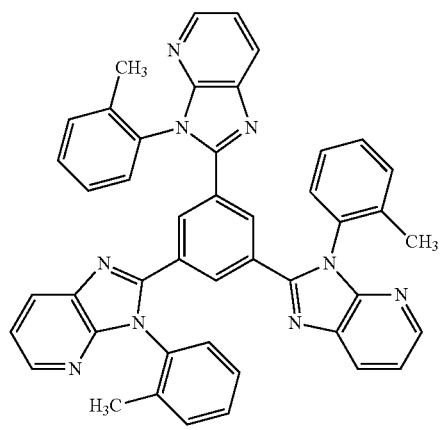
OM-6
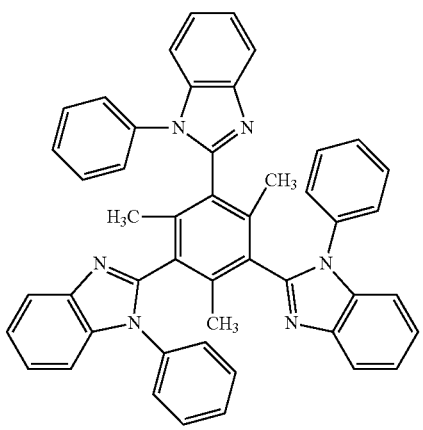
OM-7
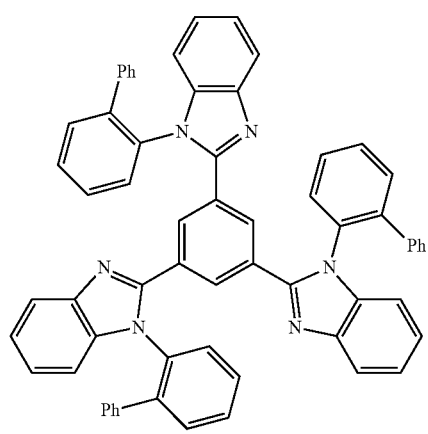
OM-8
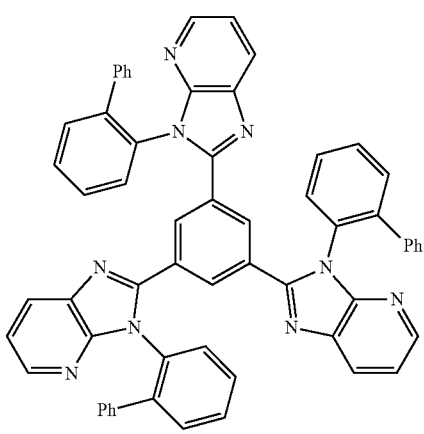
OM-9
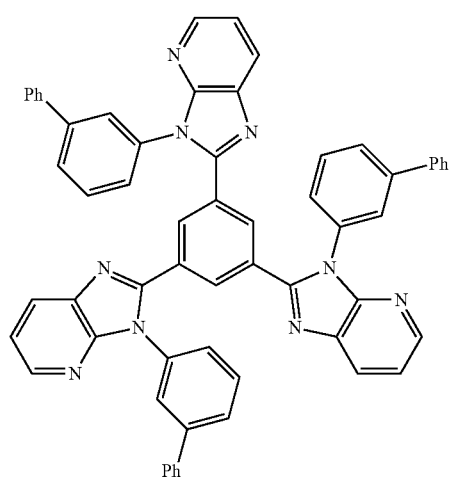

[Chem. 67]
OM-10
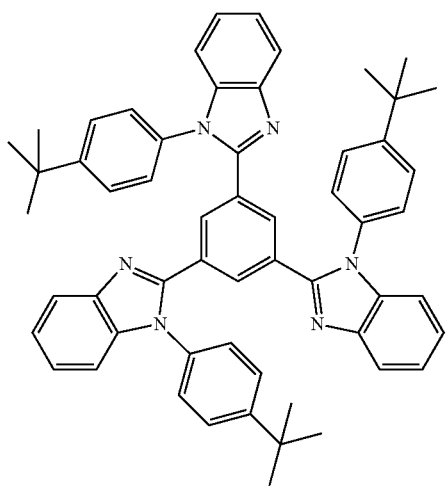
OM-11
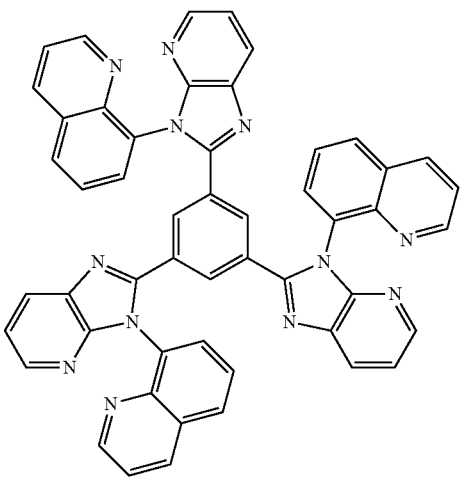
OM-12
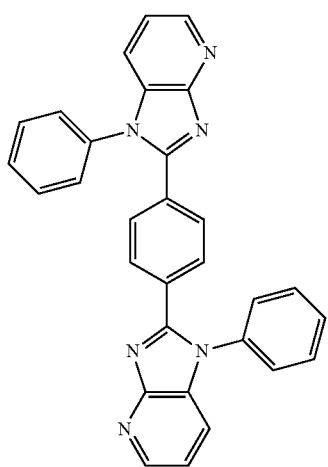
OM-13
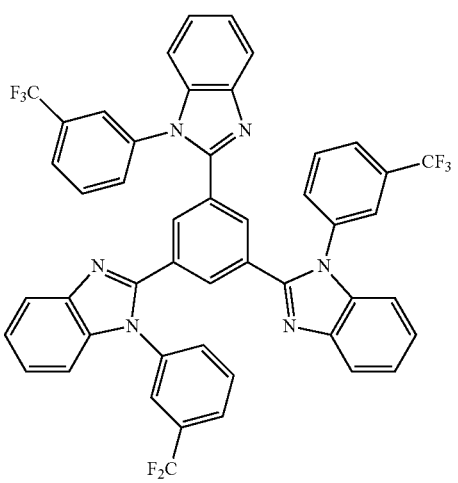
OM-14
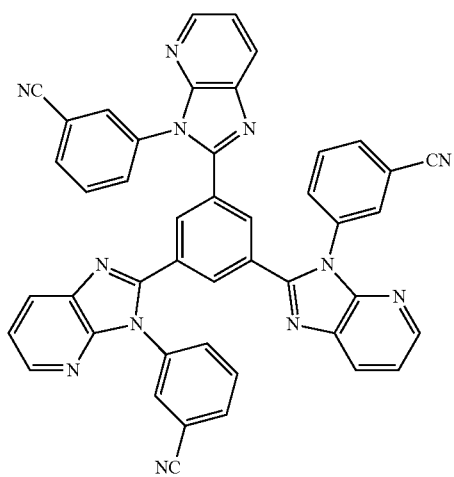
OM-15
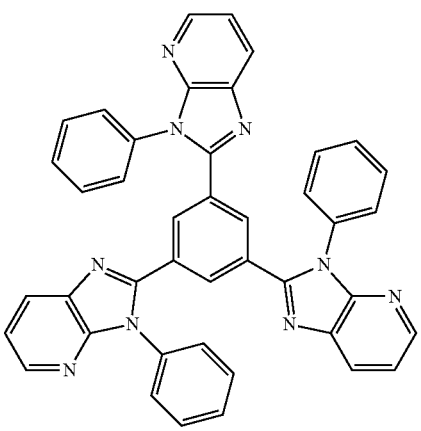

-continued
OM-16
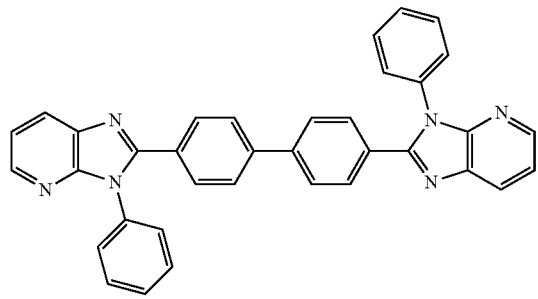
OM-17
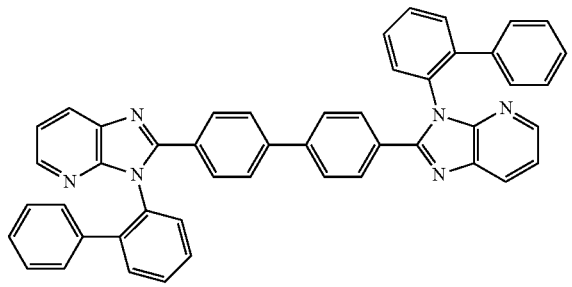
OM-18
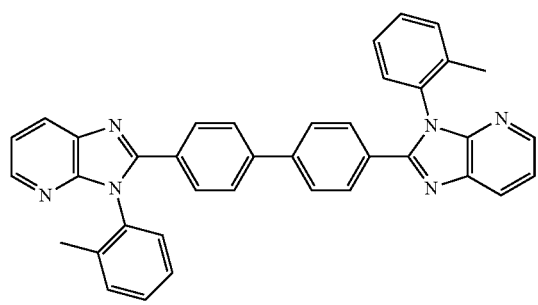
OM-19
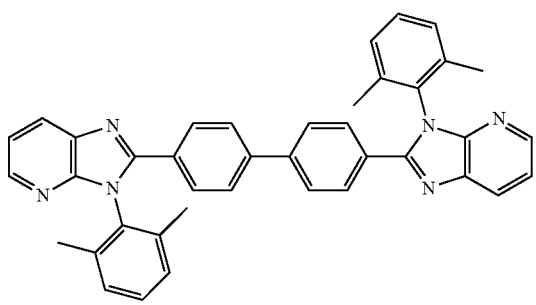
OM-20
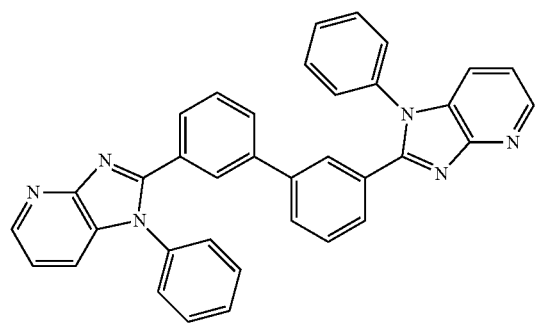
OM-21
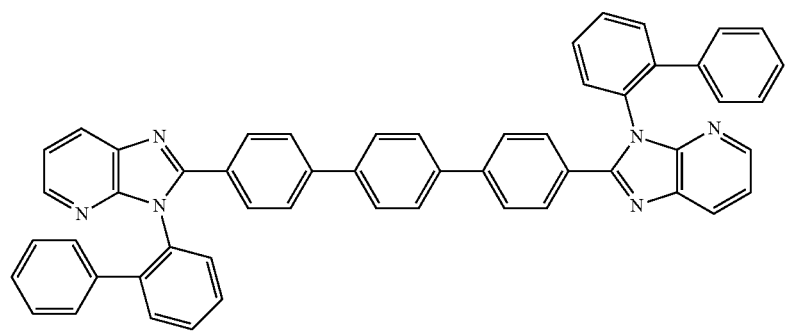
OM-22
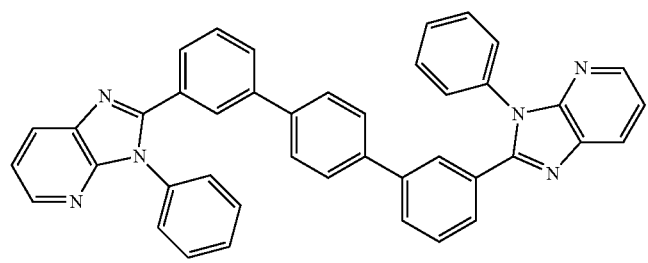

-continued

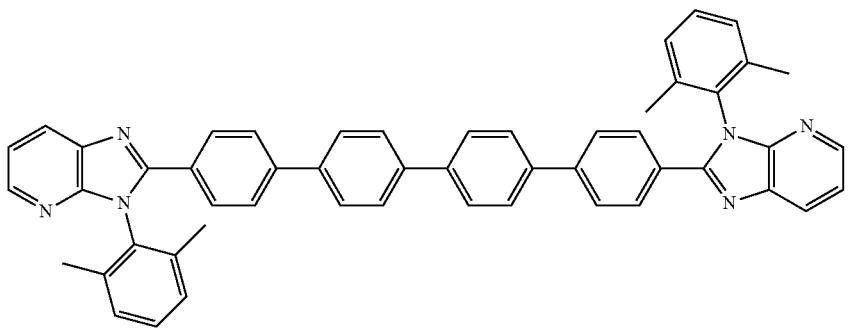

OM-23

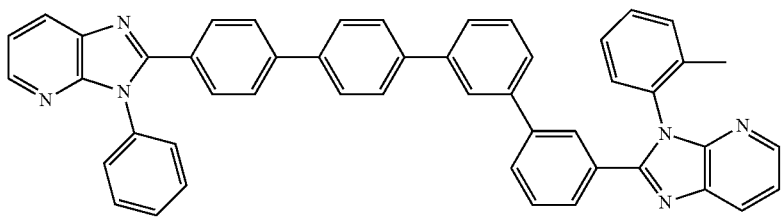

OM-24

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably contained in the organic layer between the light emitting layer and the cathode, however, it is more preferably contained in the layer on the cathode side adjacent to the light emitting layer.

The compound represented by the general formula (O-1) is contained in the amount of preferably from 70% by mass to 100% by mass, and more preferably from 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one kind of compounds represented by the following general formula (P), from the viewpoint of efficiency or the driving voltage of an element. Hereinafter, the general formula (P) will be described.

[Chem. 68]

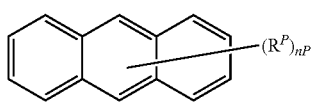

General Formula (P)

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. nP represents an integer of 1 to 10, and in the case where there are a plurality of $R^P$s, these may be the same as or different from each other. At least one of $R^P$s is a substituent represented by the following general formulae (P-1) to (P-5).

[Chem. 69]

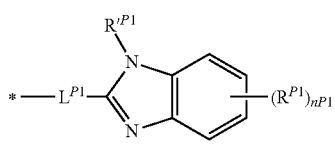

General Formula (P-1)

General Formula (P-2)

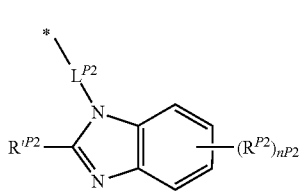

General Formula (P-3)

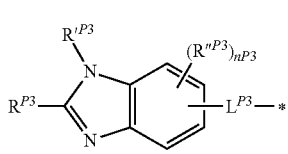

General Formula (P-4)

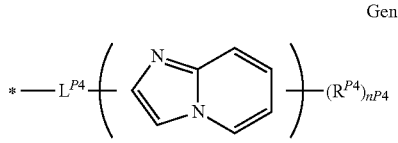

General Formula (P-5)

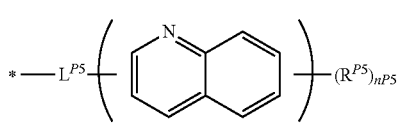

The general formula (P-4) is more preferably the following general formula (P-4').

[Chem. 70]

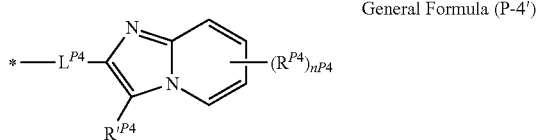

General Formula (P-4')

The general formula (P-5) is more preferably the following general formula (P-5').

[Chem. 71]

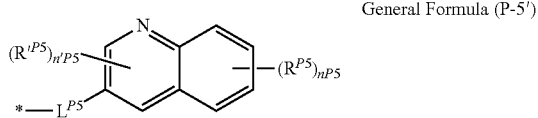

General Formula (P-5')

(In the general formulae (P-1) to (P-5), $R^{P1}$ to $R^{P5}$, $R^{\prime P1}$ to $R^{\prime P3}$, $R^{\prime P5}$, and $R^{\prime\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. $n^{P1}$, $n^{P2}$, $n^{P4}$, and $n^{P5}$ each represent an integer of 0 to 4, $n^{P3}$ and $n^{\prime P5}$ each represent an integer of 0 to 2, and in the case where there are a plurality of $R^{P1}$ to $R^{P5}$, $R^{\prime P1}$ to $R^{\prime P3}$, $R^{\prime P5}$, and $R^{\prime\prime P3}$, these may be the same as or different from each other. $L^{P1}$ to $L^{P5}$ represent any one of divalent linking groups consisting of a single bond, an aryl ring, or a heteroaryl ring. * represents a binding position with an anthracene ring of the general formula (P).)

A preferred substituent other than the substituents represented by (P-1) to (P-5) as $R^P$ is an aryl group, a more preferred substituent is any one of a phenyl group, a biphenyl group, a terphenyl group, and a naphthyl group, and still a more preferred substituent is a naphthyl group.

$R^{P1}$ to $R^{P5}$, $R^{\prime P1}$ to $R^{\prime P3}$, $R^{\prime P5}$, and $R^{\prime\prime P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P5}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 72]

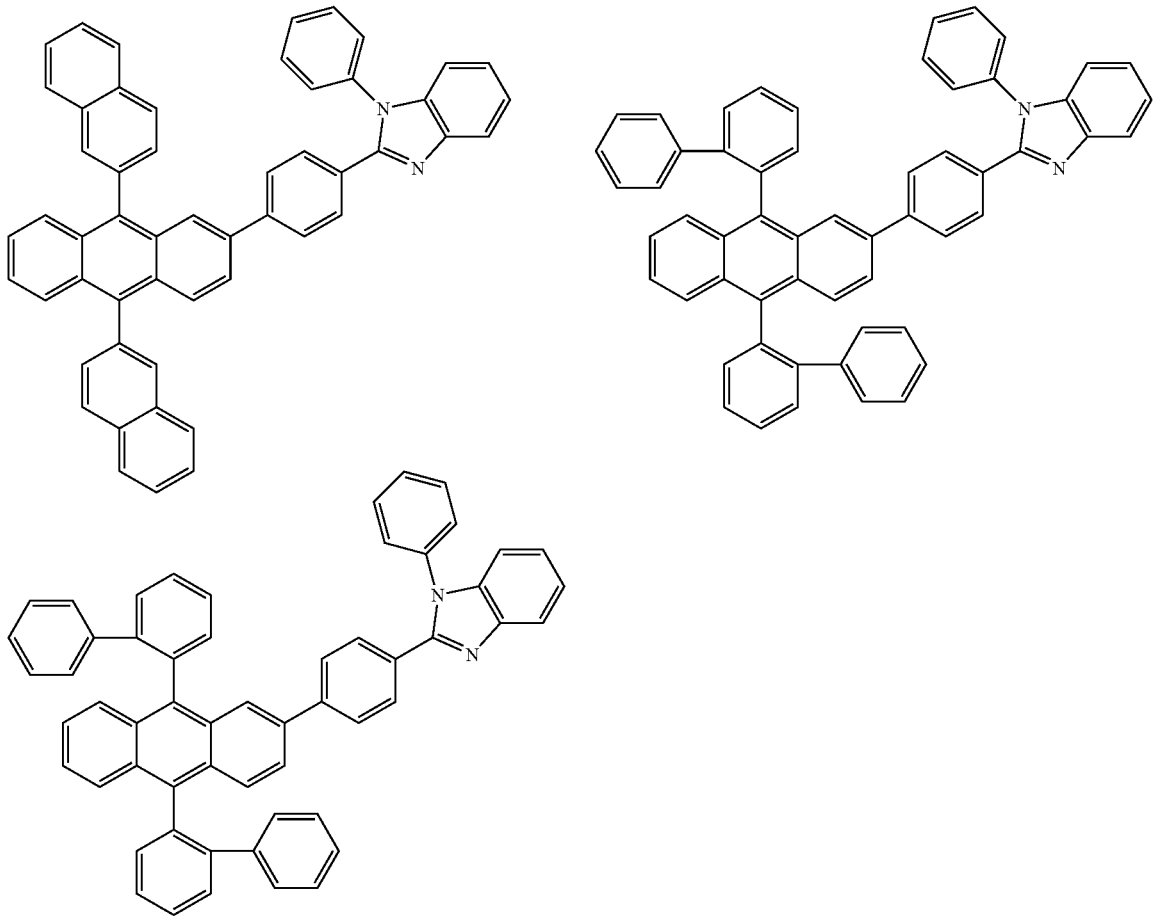

-continued
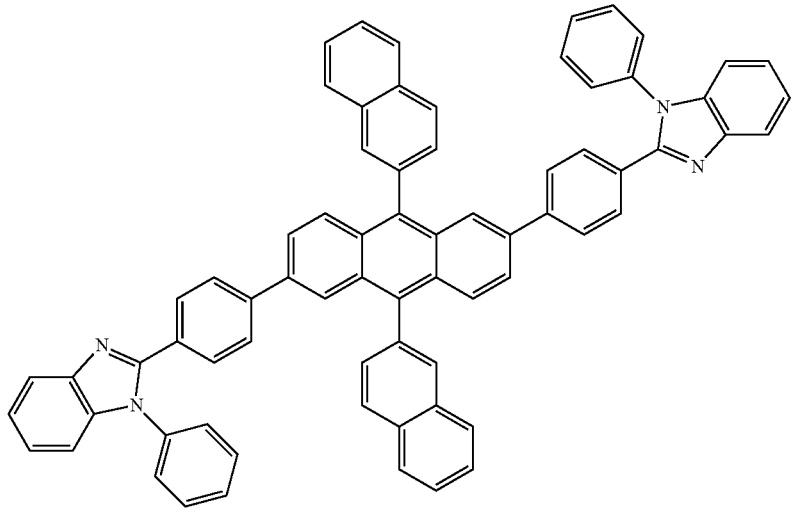
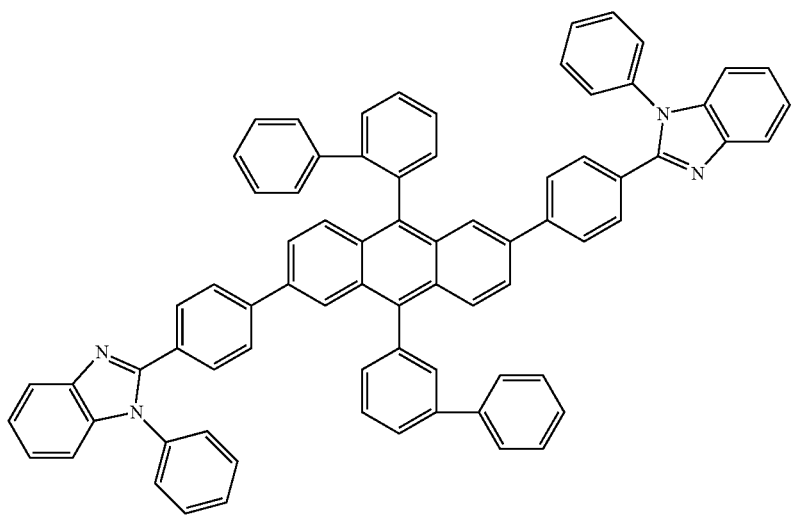
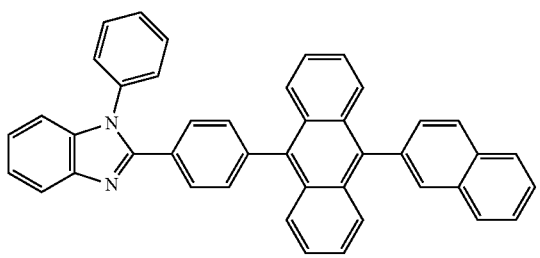
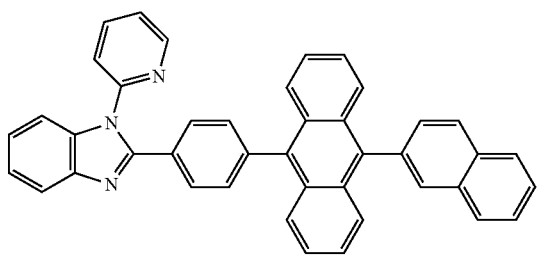
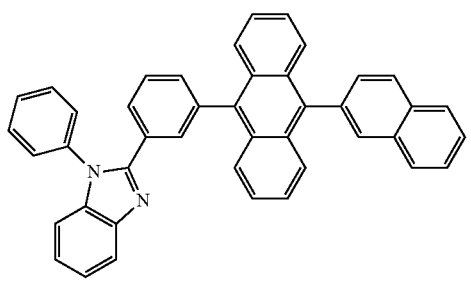

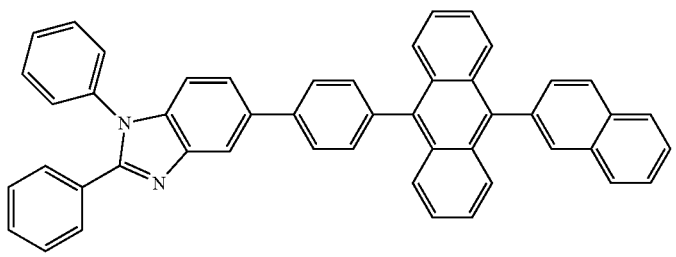
[Chem. 73]
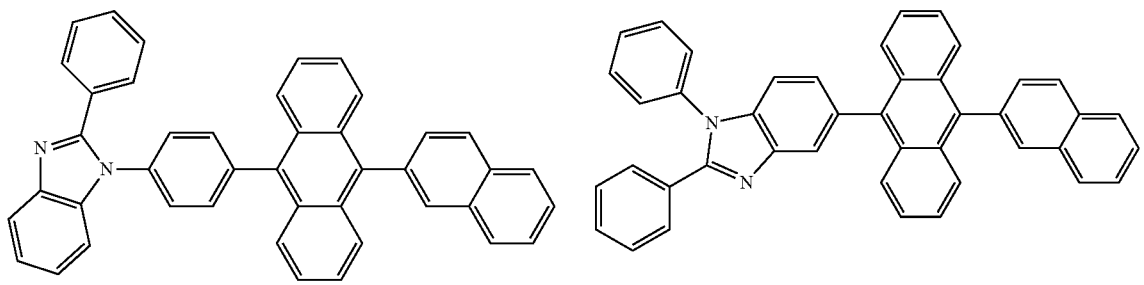
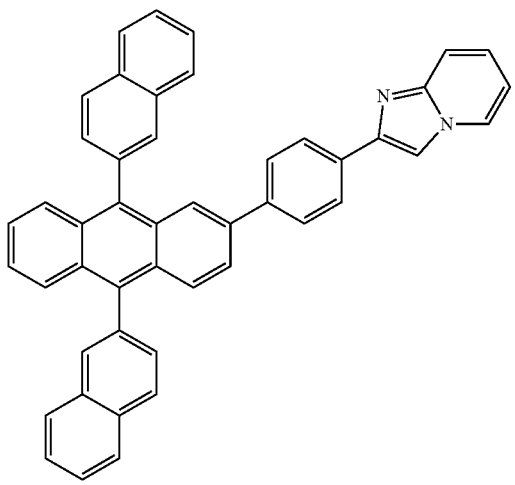
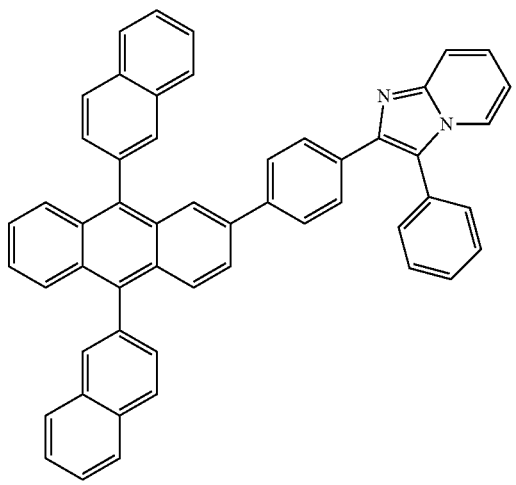
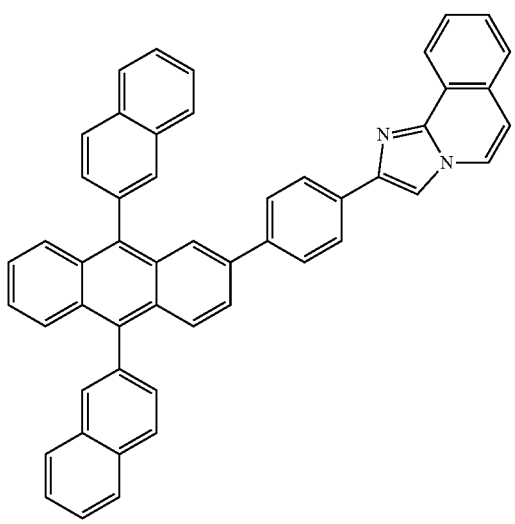
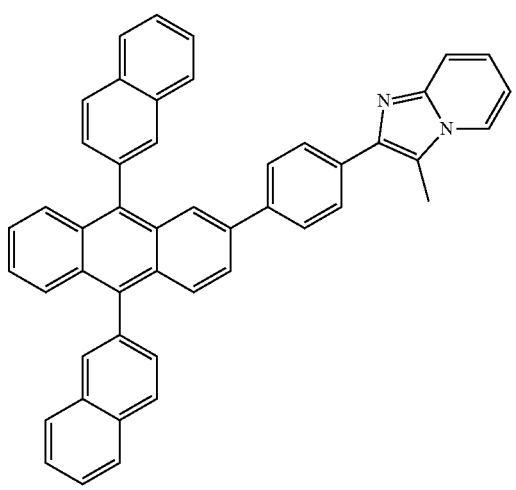

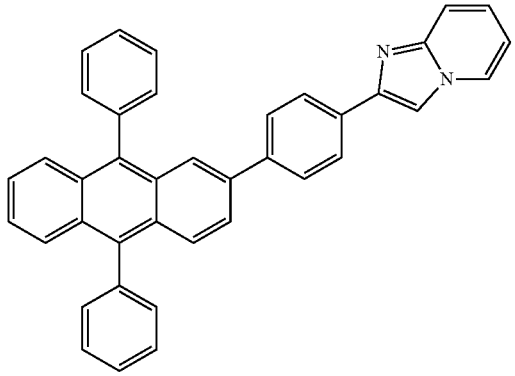
[Chem. 74]
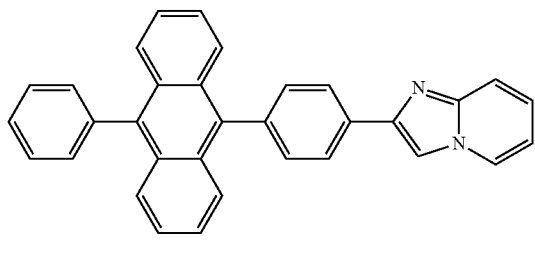
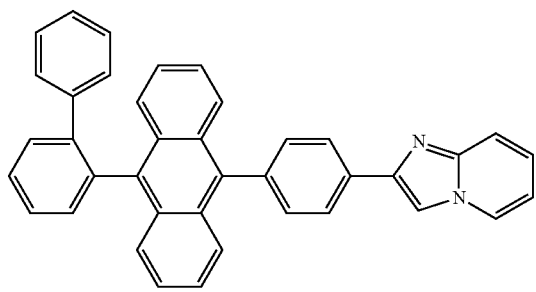
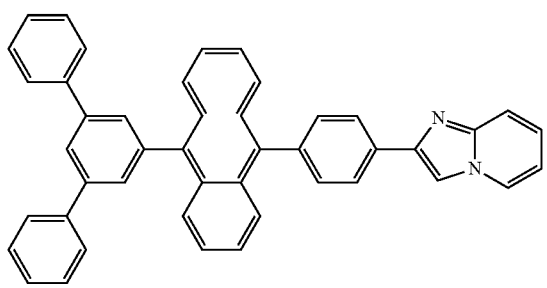
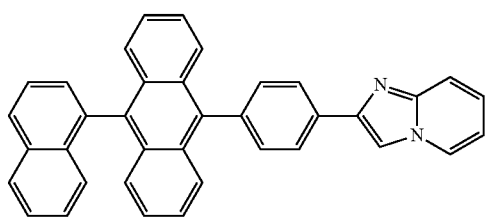
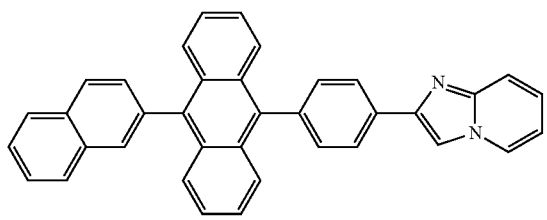
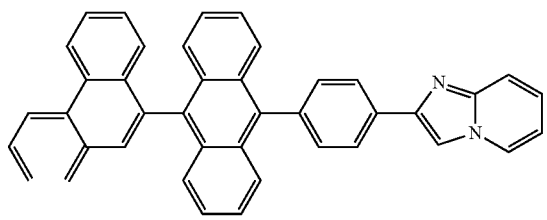
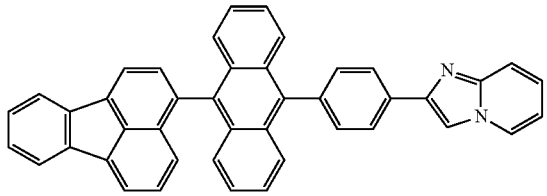
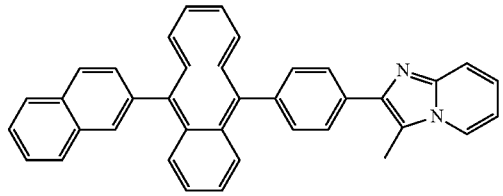
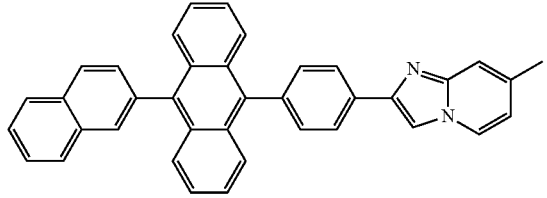
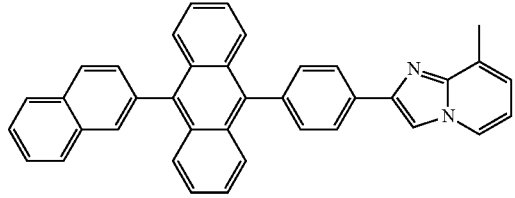

-continued
| 229 | 230 |
|---|---|
| 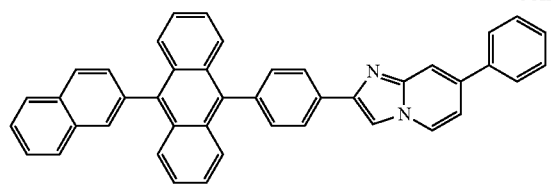 | 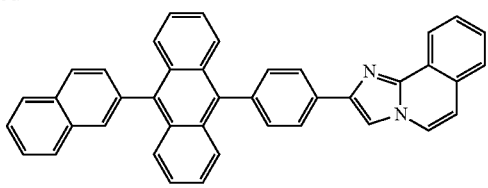 |
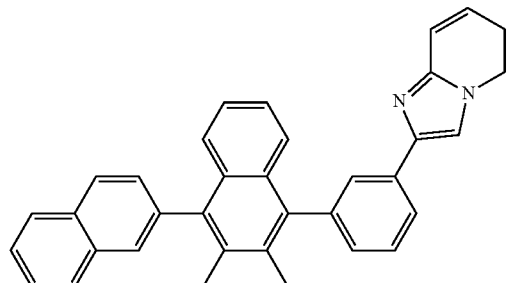
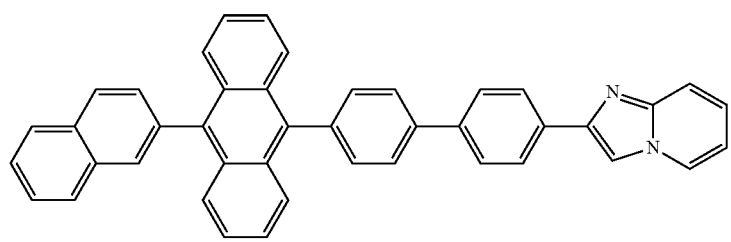
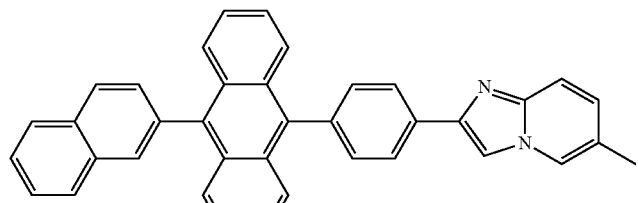
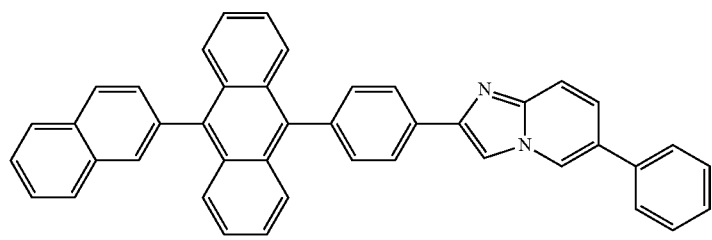
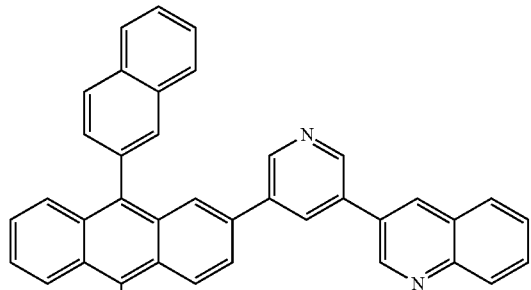  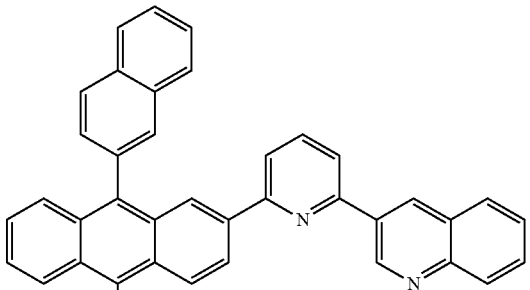
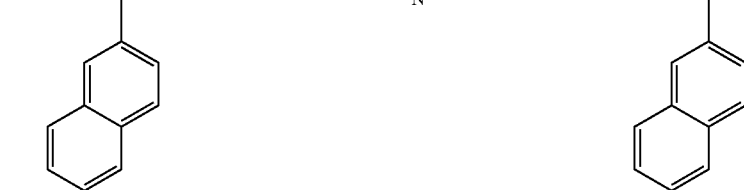

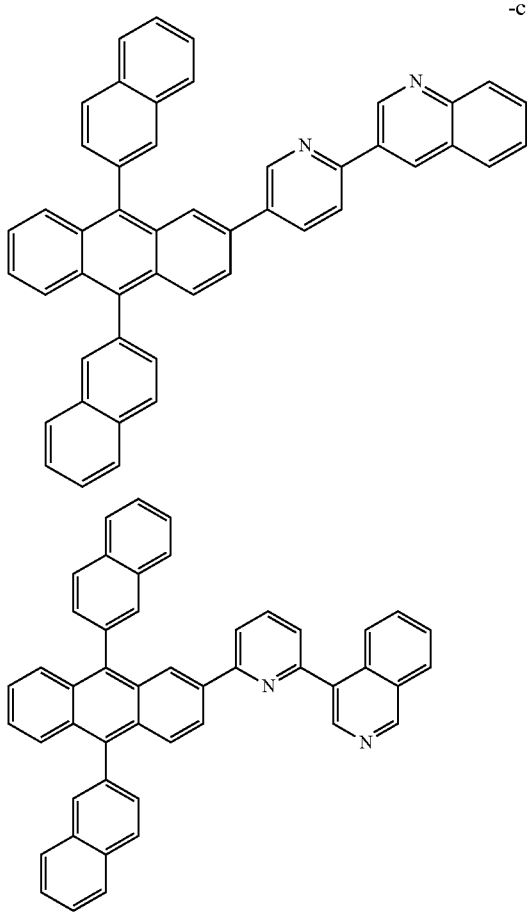
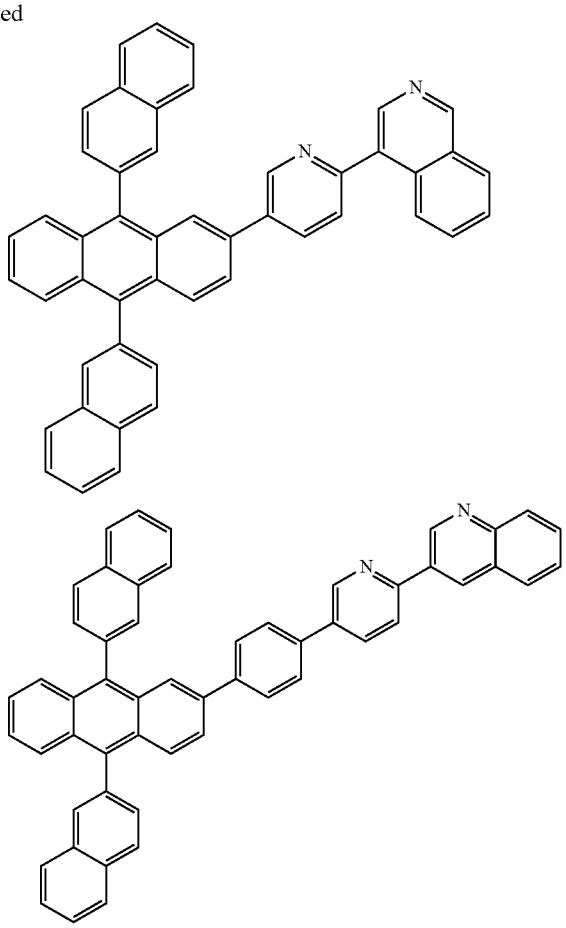

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably contained in the organic layer between the light emitting layer and the cathode, and more preferably contained in the layer adjacent to the cathode.

The compound represented by the general formula (P) is contained in the amount of preferably from 70% by mass to 100% by mass, and more preferably from 85% by mass to 100% by mass, with respect to the total mass of the organic layer added.

Preferred examples of the material other than the material used in the electron injecting layer or the electron transporting layer in the organic electroluminescent element of the present invention include silole compounds described in JP-A-9-194487 or the like, phosphineoxide compounds described in JP-A-2006-73581 or the like, nitrogen-containing aromatic 6-membered ring hetero compounds described in JP-A-2005-276801, JP-A-2006-225320, WO 2005/085387, or the like, compounds having nitrogen-containing aromatic 6-membered hetero structures and carbazole structures, described in WO 2003/080760, WO 2005/085387, or the like, and aromatic hydrocarbon compounds described in US2009/0009065, WO 2010/134350, JP-T-2010-535806, or the like (naphthalene compounds, anthracene compounds, triphenylene compounds, phenanthrene compounds, pyrene compounds, fluoranthene compounds, and the like).

<Protective Layer>

In the present invention, the entirety of the organic electroluminescent element may be protected by a protective layer.

For the protective layer, the detailed descriptions in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in each of the publications of JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of from 300 cd/m² to 400 cd/m² obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by a light extraction efficiency. The light extraction efficiency in usual organic EL elements is about 20%, but by adjusting the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is not limited, but is preferably used for blue or white light emission. Above all, in the organic electroluminescent element of the present invention, the compound represented by the general formula (1) is preferably used as a fluorescent light emitting material to emit light, and particularly preferably to emit blue light.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
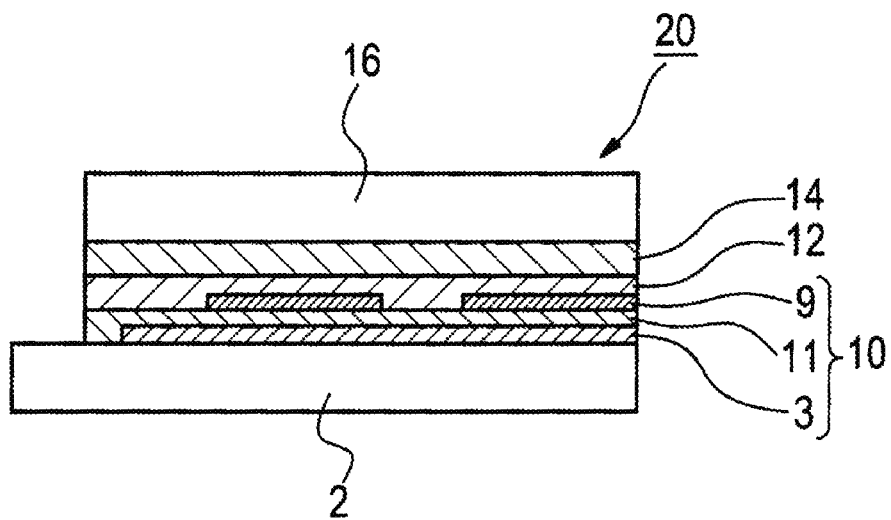
FIG. 2 is a schematic view showing one example of a light emitting device according to the present invention.

FIG. 2 is a cross-sectional view schematically showing one example of the light emitting device of the present invention. A light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and the sealing enclosure 16 is further provided via an adhesive layer 14 on the protective layer 12. Incidentally, a part of each of the electrodes 3 and 9, a diaphragm, an insulating layer, and the like are omitted.

Here, a photocurable adhesive such as an epoxy resin, or a thermosetting adhesive can be used for the adhesive layer 14, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
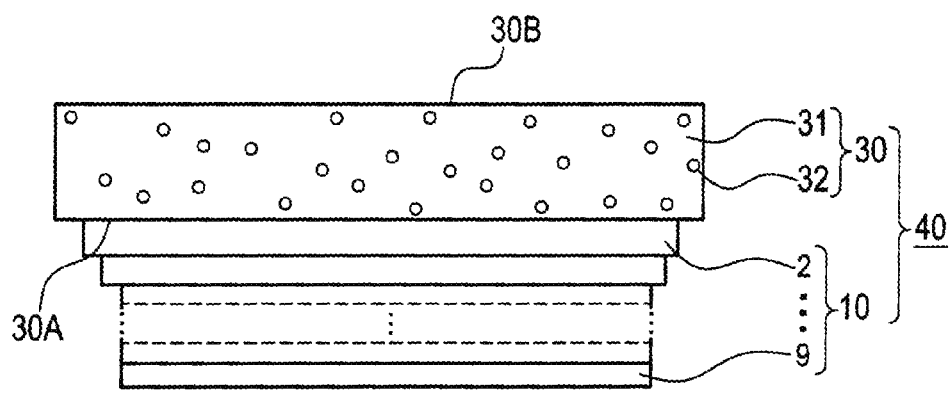
FIG. 3 is a schematic view showing one example of an illumination device according to the present invention.

FIG. 3 is a cross-sectional view schematically showing one example of the illumination device of the present invention. An illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on a light incident surface 30A of the scattering member 30, the incident light is scattered by the light scattering member 30 and the scattered light is output as illuminating light from a light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

Hereinafter, the characteristic features of the present invention are described in more detail with reference to the following Examples and Comparative Examples. The materials, use amounts, ratios, treatment details, treatment procedures, and the like shown in the following Examples can be appropriately modified in so far as the gist of the present invention is not deviated. Accordingly, it should not be construed that the scope of the present invention is limited to the specific examples shown below.

Example 1

<Synthesis of Material for Organic Electroluminescent Element Represented by General Formula (1)>

The compound represented by the general formula (1) can be synthesized by the method described in US2005/202279 or WO2011/074231, or a combination of other known reactions. Representative examples of the specific synthesis procedure of the compound represented by the general formula (1) will be described below.

(Synthesis Example 1) Synthesis of Compound 1
[Chem. 75]
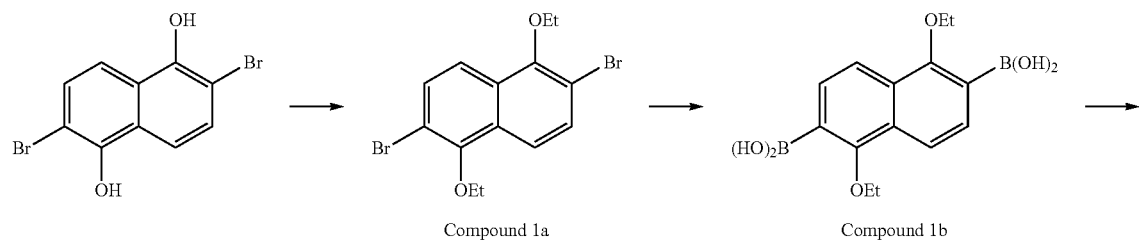
Compound 1a    Compound 1b
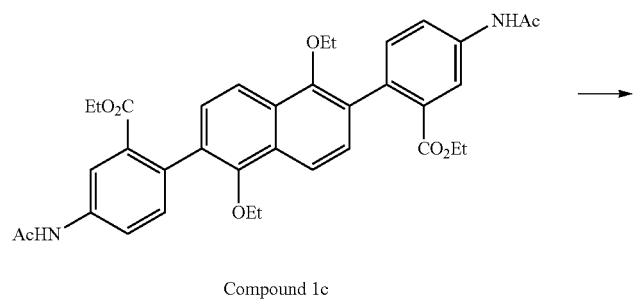
Compound 1c
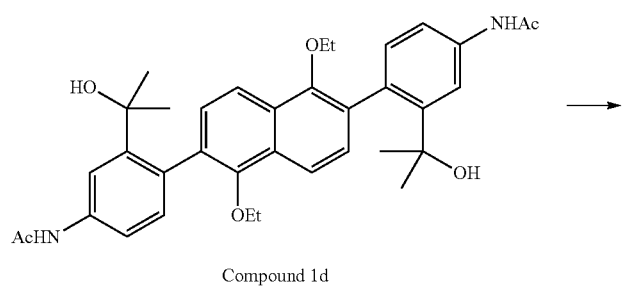
Compound 1d
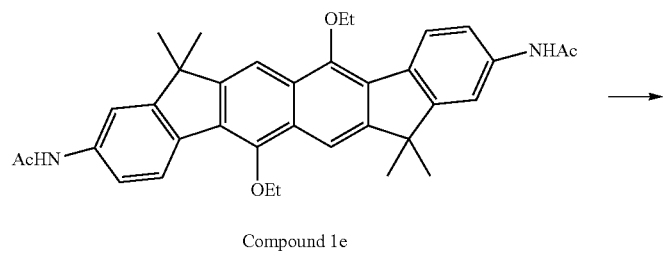
Compound 1e
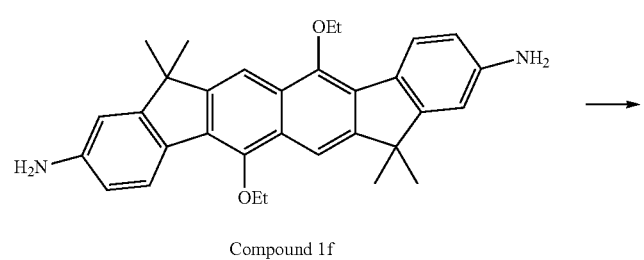
Compound 1f -continued
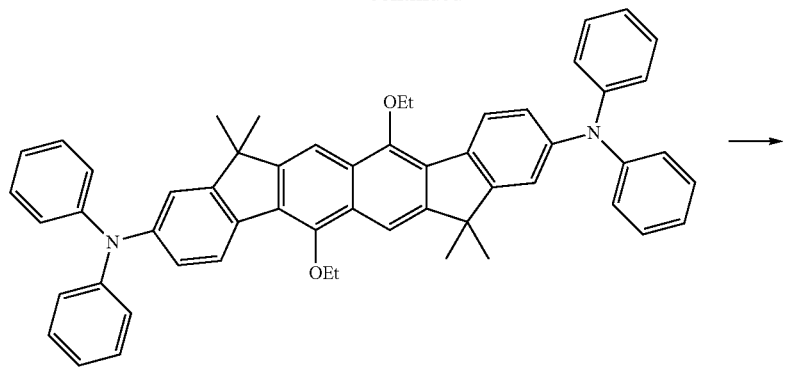
Compound 1g
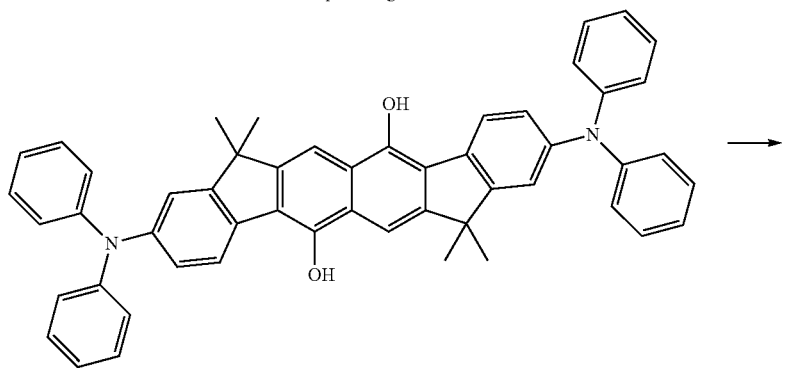
Compound 1h
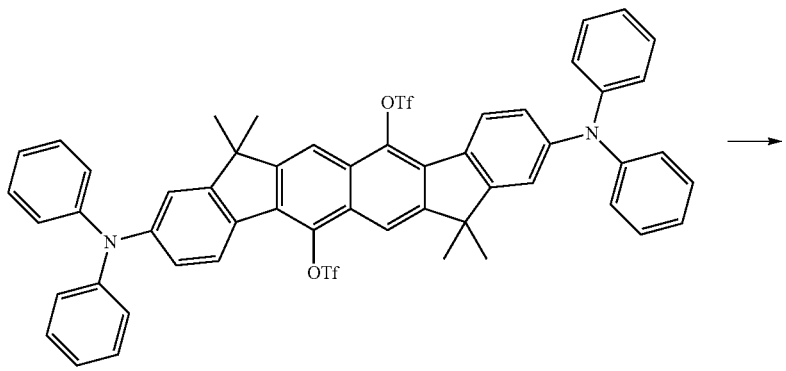
Compound 1i
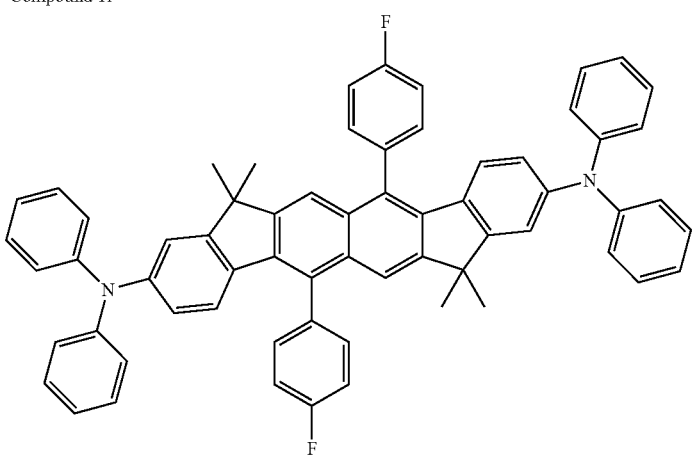
Compound 1

Synthesis of Compound 1a

To 2,6-dibromo-1,5-dihydroxynaphthalene (20 g) (manufactured by Tokyo Chemical Industry Co., Ltd.), potassium carbonate (35 g), and DMAc (400 ml) was added iodoethane (15 ml), followed by stirring at 80° C. for 2 hours under a nitrogen atmosphere. The reaction liquid was filtered and the filtrate was poured into a 1 N hydrochloric acid solution. The obtained crude crystal was recrystallized from toluene/ethanol to obtain a compound 1a (13 g).

Synthesis of Compound 1b

To a solution of the compound 1a (13 g) in THF was added dropwise 44 ml of nBuLi/hexane at −78° C., followed by stirring for 1 hour. To the reaction liquid was added dropwise B(OMe)$_3$ (22 g), followed by stirring for 2 hours, and then the reaction liquid was warmed to room temperature. The reaction liquid was poured into a 1 N hydrochloric acid solution and ethyl acetate was added thereto to carry out a liquid separation operation. Furthermore, the organic layer was washed with brine, dried over magnesium sulfate, and then concentrated under reduced pressure. The concentrated residue was washed with methanol to obtain a compound 1b (6.9 g).

Synthesis of Compound 1c

To the compound 1b (6.5 g), ethyl-5-acetamido-2-bromobenzoate (14.7 g), and potassium carbonate (11.8 g) in toluene/water (50 ml/25 ml) was added 5% by mole Pd(PPh$_3$)$_4$, followed by stirring at 100° C. for 5 hours under a nitrogen atmosphere. The reaction liquid was poured into ethyl acetate/diluted hydrochloric acid (mixing ratio: ethyl acetate/diluted hydrochloric acid=1/1), and the organic layer was washed with brine, dried over magnesium sulfate, and then concentrated under reduced pressure. The concentrated residue was purified by silica gel column chromatography to obtain a compound 1c (10.1 g).

Synthesis of Compound 1d

A solution of the compound 1c (10.0 g) in THF (50 ml) was allowed to undergo a reaction with 8 equivalents of a methyl Grignard reagent at 0° C., followed by stirring at 80° C. for 3 hours. To the reaction liquid was added ethanol, thereby decomposing the excessive Grignard reagent, and then the mixture was poured into ethyl acetate/brine. The organic layer was washed with brine, dried over magnesium sulfate, and then concentrated under reduced pressure. The concentrated residue was purified by silica gel column chromatography to obtain a compound 1d (8.4 g).

Synthesis of Compound 1e

A solution (80 ml) of the compound 1d (8.0 g) in dichloromethane/methanesulfonic acid=1/1 was stirred for 2 hours under ice-cooling. The reaction liquid was poured into ice water, followed by neutralization with an aqueous sodium hydroxide solution. Ethyl acetate was added thereto, and the organic layer was extracted, washed with saturated brine, and then dried over magnesium sulfate. After concentrated under reduced pressure, the concentrated residue was purified by silica gel column chromatography to obtain a compound 1e (6.2 g).

Synthesis of Compound 1f 100 ml of a solution of the compound 1e (6.0 g) and a saturated aqueous potassium hydroxide solution (4 ml) in ethylene glycol/triglyme=1/1 was stirred at 120° C. for 5 hours. The reaction liquid was cooled and the precipitated crude crystal was collected by filtration. The obtained crude crystal was recrystallized from toluene/methanol to obtain a compound 1f (4.8 g).

Synthesis of Compound 1g

To a solution (50 ml) of the compound 1f (4.5 g), tBuONa (1.8 g), and iodobenzene (manufactured by Wako Pure Chemical Industries, Ltd.) (5.8 g) in xylene were added Pd$_2$(dba)$_3$ (0.86 g) and a 10% by mass tri-tertiary butylphosphine/hexane solution (3.8 ml) under a nitrogen atmosphere, followed by stirring at 100° C. for 9 hours. The reaction liquid was poured into ethyl acetate/brine, and the organic layer was washed with brine, dried over magnesium sulfate, and then concentrated under reduced pressure. The concentrated residue was purified by silica gel column chromatography to obtain a compound 1g (5.1 g).

Synthesis of Compound 1h

To a solution (100 ml) of the compound 1g (5.0 g) in dichloromethane was added BBr$_3$ (3.8 g) at 0° C., followed by stirring for 30 minutes. The mixture was warmed to room temperature and then stirred for 1 hour. The reaction liquid was poured into ice water, ethyl acetate was added thereto, and the organic layer was extracted, washed with saturated brine, and then dried over magnesium sulfate. The residue was concentrated under reduced pressure and the concentrated residue was purified by silica gel column chromatography to obtain a compound 1h (4.5 g).

Synthesis of Compound 1i

To a solution (50 ml) of the compound 1h (4.5 g) in pyridine was added dropwise trifluoromethanesulfonic anhydride (4.2 g) at 0° C., followed by stirring at room temperature for 3 hours. Water was added thereto and the precipitated crystal was collected by filtration to obtain a compound 1i (5.7 g). Further, in the reaction scheme, Tf represents a trifluoromethanesulfonyl group (trifuryl group).

Synthesis of Compound 1

The compound 1i (5.5 g), p-fluorophenylboric acid (1.7 g), tris(dibenzylideneacetone) dipalladium (Pd$_2$(dba)$_3$) (0.51 g), 2-dicyclohexylphosphino-2',6'-dimethoxybiphenyl (SPhos) (0.91 g), and potassium phosphate (11.8 g) were mixed, and 100 ml of toluene/50 ml of water was added thereto, followed by heating and refluxing for 8 hours under a nitrogen atmosphere. The temperature of the reaction liquid was returned to room temperature, ethyl acetate and pure water were then added thereto, and the organic layer was extracted. The organic layer was dried over sodium sulfate, concentrated under reduced pressure, and purified by silica gel column chromatography to obtain a compound 1 (3.5 g).

Further, identification of the obtained compound was carried out by elemental analysis, and NMR and MASS spectra.

$^1$H-NMR (CDCl$_3$) δ: 1.38 (12H, s), 6.22 (2H, d), 6.67 (2H, d), 6.95-7.30 (28H, m), 7.4 (2H, s), 7.5-7.6 (2H, m)

(Synthesis of Other Compounds)

The compounds 1 to 5, 7, 9, 13 to 15, 20, 22, 23, 27, 30, 31, 36, 41 to 43, 46, 49, 53, 55, 70, 71, 75, 78, 83, 87, 100, 101, 104, 108, 114, 116, 120, 121, and 129 used in Examples were also synthesized by a method similar to that for the compound 1.

<Evaluation of Physical Properties of Materials>

(Test Example 1) Evaluation of Chromaticity

The following host material H-5 and each of light emitting materials described in Table 1 below were deposited on a 25 mm×25 mm×0.7 mm quartz glass substrate by a vacuum deposition method in a mass ratio (99:1), thereby forming a thin film having a film thickness of 50 nm. The obtained film was irradiated with UV rays of 350 nm to emit light. The luminous spectrum at a time of light emission was measured using a fluorescent spectrophotometer (FP-6300, manufactured by JASCO Corporation) and the chromaticity (x, y) was determined. Based on the y values at that time, the chromaticity was evaluated as the following 4 grades.

A $0.03 \leq y \leq 0.08$
B $0.025 \leq y < 0.03$, $0.08 < y \leq 0.10$
C $0.02 \leq y < 0.025$, $0.10 < y \leq 0.12$
D $y < 0.02$, $0.12 < y$

[Chem. 76]

Host Compound H-5

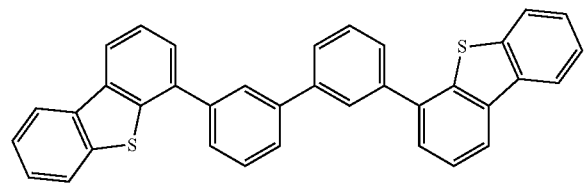

(Test Example 2) Evaluation of Association Forming Property

The luminous spectrum of a thin film obtained from the host material H-5 and each of light emitting materials described in Table 1 below in a mass ratio of 95:5 was measured and the chromaticity (x, y) was determined. A difference in chromaticity was calculated from the y value at that time and the y value of the chromaticity (x, y) in the luminous spectrum obtained in Test Example 1, and evaluated as the following 4 grades.

A Difference in chromaticity $\leq 0.02$
B $0.02 <$ Difference in chromaticity $\leq 0.05$
C $0.05 <$ Difference in chromaticity $\leq 0.10$
D $0.10 <$ Difference in chromaticity (Test Example 3) Evaluation of Orientation Properties The host material and the light emitting material shown in Table 1 below were deposited on a 25 mm×25 mm×0.7 mm quartz glass substrate by a vacuum deposition method in a mass ratio (95:5), thereby forming a film. The degree of orientation of the light emitting material was calculated as a horizontal orientation order parameter S by analysis with a polarized ATR-IR method and evaluated as the following 4 grades.

A $0.8 \leq S$
B $0.7 \leq S < 0.8$
C $0.5 \leq S < 0.7$
D $S < 0.5$

The comparative compounds 1 to 4 used as the comparative light emitting materials in Table 1 below have the following structures.

[Chem. 77]

Comparative compound 1

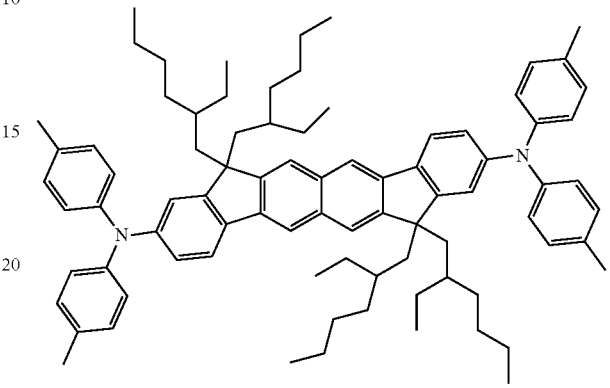

Compound described in US2005/202279

Comparative compound 2

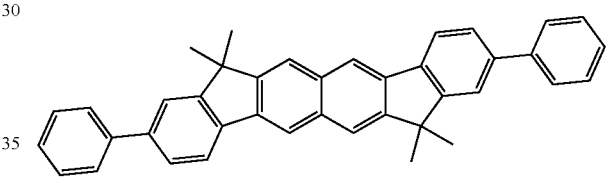

Compound described in US2002/132134

Comparative compound 3

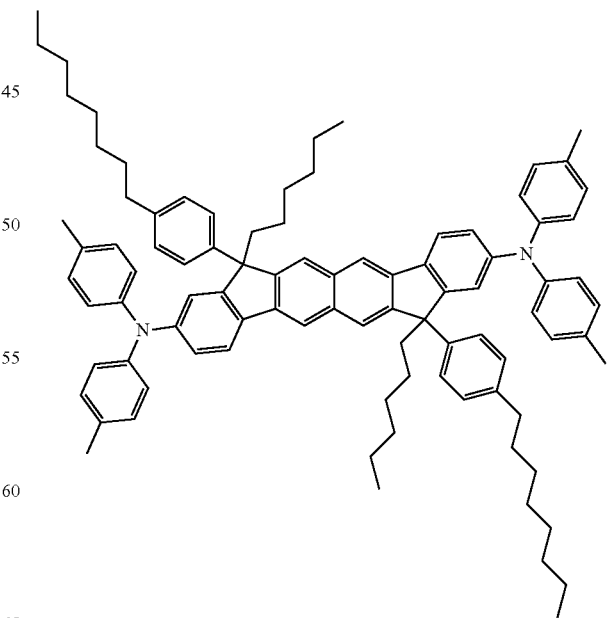

Compound described in US2005/202279

-continued

Comparative compound 4

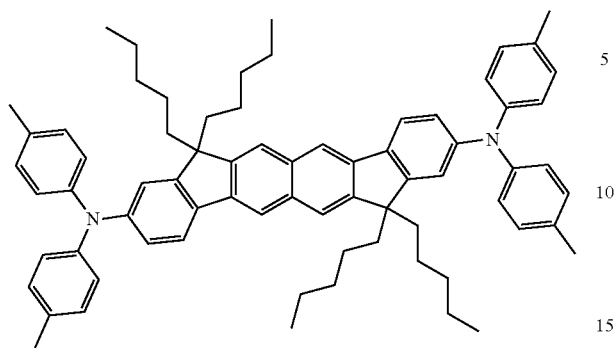

TABLE 1

| Light emitting material | Total number of carbon atoms in alkyl chain of substituent in fluorene-bridged site $(C(R^9) + C(R^{10})$ or $C(R^{11}) + C(R^{12}))$ | Alkyl chain length in $R^9$ to $R^{12}$ | Chromaticity | Inhibition of association (difference in chromaticity) | Degree of orientation S (horizontal orientation order parameter S) | Note |
|---|---|---|---|---|---|---|
| Compound 1 | 2 | 1 | A | C | B | The present invention |
| Compound 2 | 2 | 1 | B | A | A | The present invention |
| Compound 3 | 2 | 1 | A | A | B | The present invention |
| Compound 4 | 2 | 1 | B | C | A | The present invention |
| Compound 5 | 2 | 1 | B | C | B | The present invention |
| Compound 7 | 3 | 2 | B | A | C | The present invention |
| Compound 9 | 2 | 1 | B | B | C | The present invention |
| Compound 13 | 2 | 1 | B | A | C | The present invention |
| Compound 14 | 2 | 1 | B | A | B | The present invention |
| Compound 15 | 2 | 1 | B | C | B | The present invention |
| Compound 20 | 3 | 2 | C | B | B | The present invention |
| Compound 22 | 2 | 1 | C | A | A | The present invention |
| Compound 23 | 2 | 1 | C | B | A | The present invention |
| Compound 27 | 2 | 1 | C | A | C | The present invention |
| Compound 30 | 8 | 4 | B | A | C | The present invention |
| Compound 31 | 8 | 4 | B | B | C | The present invention |
| Compound 36 | 6 | 3 | C | B | B | The present invention |
| Compound 41 | 2 | 1 | A | A | A | The present invention |
| Compound 42 | 2 | 1 | B | A | B | The present invention |
| Compound 43 | 2 | 1 | A | A | B | The present invention |
| Compound 46 | 2 | 1 | A | A | C | The present invention |
| Compound 49 | 2 | 1 | A | A | C | The present invention |
| Compound 53 | 2 | 1 | A | A | A | The present invention |
| Compound 55 | 2 | 1 | A | B | B | The present invention |
| Compound 70 | 2 | 1 | B | C | B | The present invention |
| Compound 71 | 2 | 1 | B | B | B | The present invention |
| Compound 75 | 2 | 1 | A | C | B | The present invention |
| Compound 78 | 2 | 1 | A | A | C | The present invention |
| Compound 83 | 2 | 1 | A | A | B | The present invention |
| Compound 87 | 2 | 1 | A | A | A | The present invention |
| Compound 100 | 2 | 1 | B | C | B | The present invention |
| Compound 101 | 2 | 1 | A | A | B | The present invention |
| Compound 104 | 2 | 1 | A | A | B | The present invention |
| Compound 108 | 2 | 1 | A | A | A | The present invention |
| Compound 114 | 2 | 1 | A | A | B | The present invention |
| Compound 116 | 2 | 1 | A | A | A | The present invention |
| Compound 120 | 2 | 1 | A | A | B | The present invention |
| Compound 121 | 2 | 1 | A | A | B | The present invention |
| Compound 129 | 2 | 1 | B | B | B | The present invention |
| Comparative compound 1 | 16 | 8 | C | B | D | Comparative Example |
| Comparative compound 2 | 2 | 1 | D | D | C | Comparative Example |
| Comparative compound 3 | 14 | 8 | C | B | D | Comparative Example |
| Comparative compound 4 | 10 | 5 | C | C | D | Comparative Example |

In Table 1 above, a reference to the "total number of carbon atoms in an alkyl chain of a substituent in a fluorene-bridged site" represents a smaller number of $C(R^9)+C(R^{10})$ or $C(R^{11})+C(R^{12})$ when the numbers of carbon atoms of skeletons represented by the following general formula (1') of each light emitting material, that is, the alkyl chains in the substituents corresponding to the substituents $R^9$ to $R^{12}$ in the general formula (1) are denoted as $C(R^9)$ to $C(R^{12})$, respectively. Further, the "alkyl chain length" represents the chain length of a skeleton represented by the following general formula (1') of each light emitting material, that is, the longest alkyl group in the substituents corresponding to the substituents $R^9$ to $R^{12}$ in the general formula (1).

<Fabrication and Evaluation of Organic Electroluminescent Elements>

The materials used for the fabrication of organic electroluminescent elements were all subjected to sublimation purification and it was confirmed that the purity (absorption intensity area ratio at 254 nm) was 99.9% or more by using high performance liquid chromatography (TSKgel ODS-100Z, manufactured by Tosoh Corporation).

The structures of the materials other than the light emitting materials used for the fabrication of the organic electroluminescent element in each of Examples and Comparative Examples are shown below.

[Chem. 78]

General Formula (1')

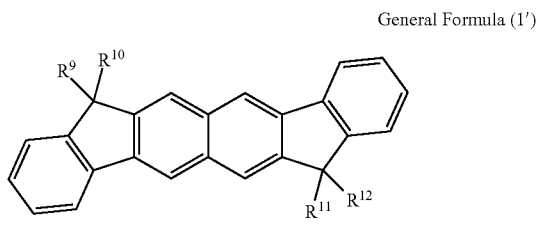

[Chem. 79]

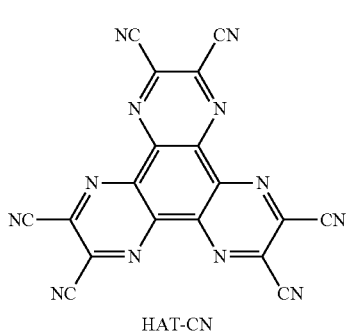

HAT-CN

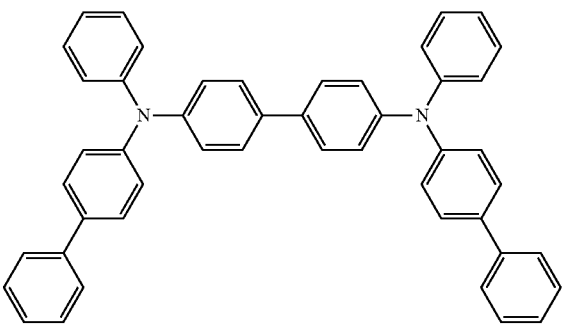

HT-1

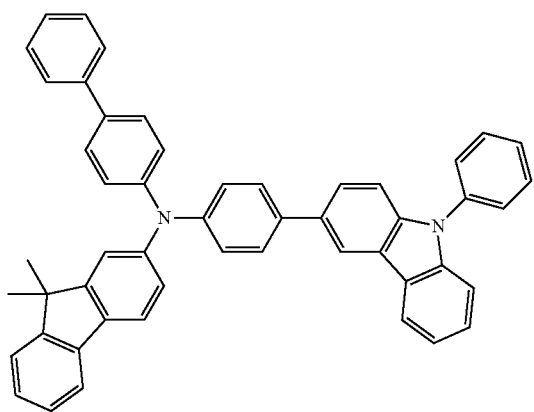

HT-2

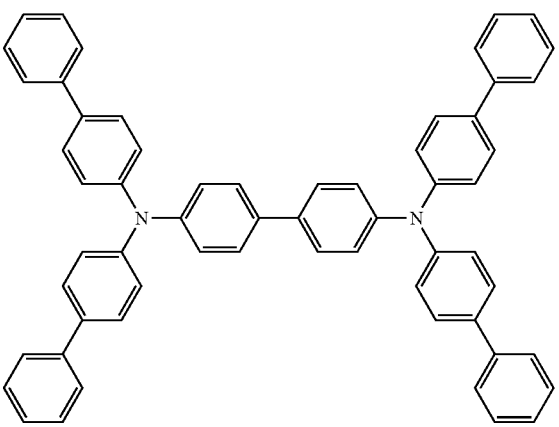

HT-3

-continued
HT-4
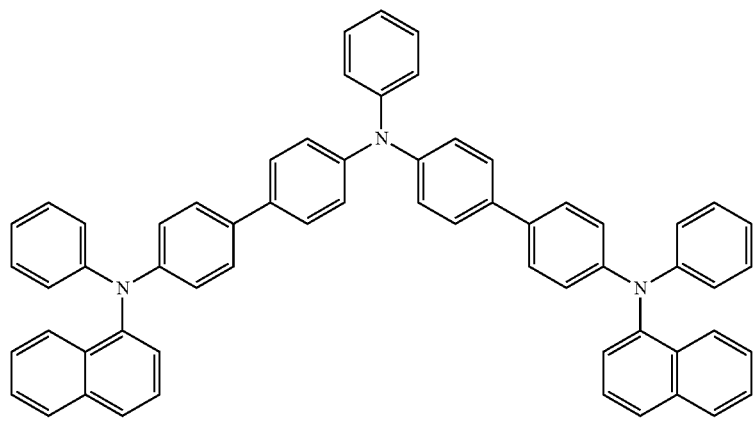
H-1
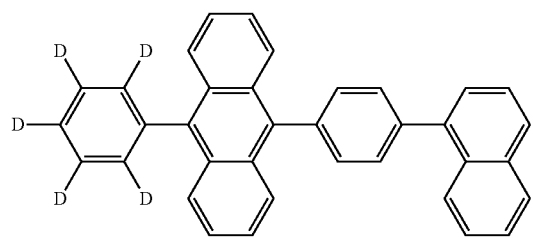
H-2
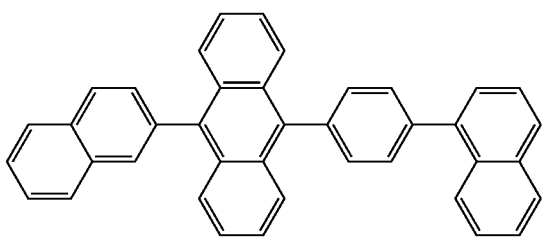
H-3
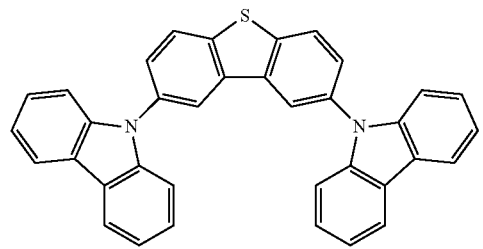
H-4
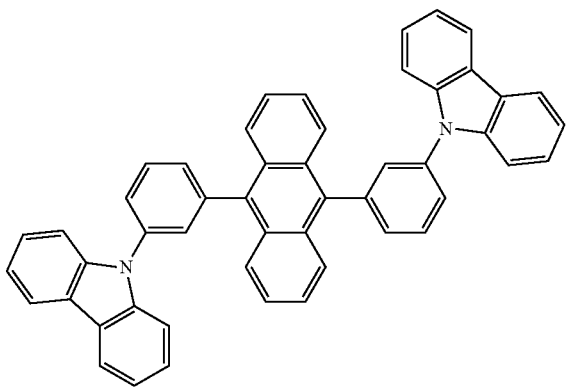
ET-1
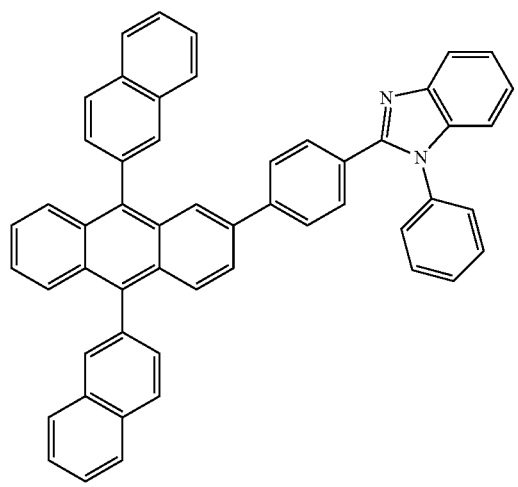
ET-2
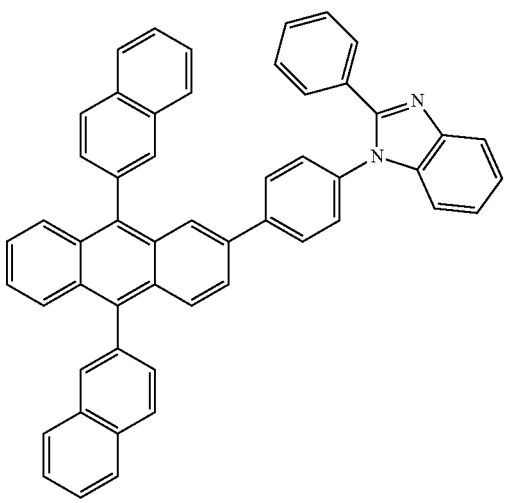

-continued

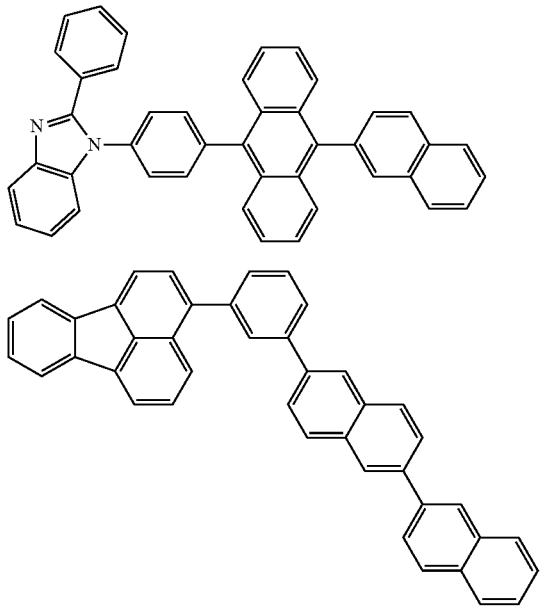

ET-3

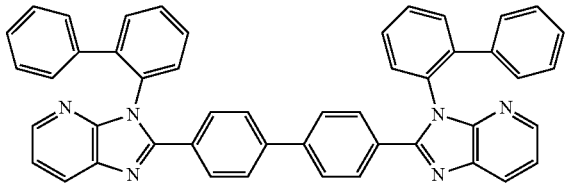

ET-4

ET-5

Example 2

A 0.5 mm-thick and 2.5 cm square glass substrate (manufactured by Geomatec Co., Ltd., surface resistance: 10Ω/☐) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method. Furthermore, the deposition rates in Examples and Comparative Examples below are 0.1 nm/sec unless otherwise indicated. The deposition rates were measured using a quartz crystal oscillator. Further, the thickness of each of the layers below was measured using the quartz crystal oscillator.

First layer: HAT-CN, Film thickness of 10 nm

Second layer: HT-2, Film thickness of 60 nm

Third layer: H-1 and the light emitting material described in Table 2 below (mass ratio=97:3), Film thickness of 30 nm Fourth layer: ET-1:Liq=1:1, Film thickness of 20 nm 1 nm of lithium fluoride and 100 nm of metallic aluminum were deposited in this order thereon, thereby forming a cathode. At this time, a patterned mask (mask having a light emitting area of 2 mm×2 mm) was placed on the layer of lithium fluoride, and the metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba, Ltd.), thereby obtaining organic electroluminescent elements 1-1 to 1-39, and comparative organic electroluminescent elements 1-1 to 1-4, each having a light emitting area in a 2 mm×2 mm square. Light emission due to the light emitting material was observed in each of the elements. For each of the obtained organic electroluminescent elements, the following tests were carried out.

(a) External Quantum Efficiency

Light was emitted by applying a direct current voltage to each of the elements by using a source measure unit 2400 manufactured by Keithley Instruments Inc., and the luminance was measured using a luminance meter (BM-8 manufactured by Topcon Corporation). The luminous spectrum and the light emitting wavelength were measured using a spectrum analyzer (PMA-11 manufactured by Hamamatsu Photonics K. K.). Based on these values, the external quantum efficiency (η) at a luminance in the vicinity of 1000 cd/m$^2$ was calculated by using a luminance conversion method, and is expressed as a relative value, taking the value of an organic electroluminescent element using the comparative compound 1 as 1.0. Larger numeral values are preferable because larger numeral values indicate better efficiency.

(b) Chromaticity

From the luminous spectrum at a time of light emission by applying a direct current voltage to each of the organic electroluminescent elements to give a luminance of 1000 cd/m$^2$, the chromaticity (x, y) was determined. From the y values at that time, the chromaticity was evaluated as the following 3 grades.

A $0.03 \leq y \leq 0.08$

B $0.025 \leq y < 0.03$, $0.08 < y \leq 0.10$

C $0.02 \leq y < 0.025$, $0.10 < y \leq 0.12$

D $y < 0.02$, $0.12 < y$ (c) Chromaticity after Deterioration by Driving

When light was continuously emitted by applying a direct current voltage to each of the organic electroluminescent elements to give a luminance of 1000 cd/m$^2$, and the luminance decreased to 500 cd/m$^2$, the chromaticity (x', y') was determined from a luminous spectrum. From Δy (=|y'−Δy|) which indicates a change in y values before and after the deterioration by driving, the change in the chromaticity before and after the deterioration by driving was evaluated as the following 3 grades.

B $\Delta y \leq 0.01$

C $0.01 < \Delta y \leq 0.02$

D $0.02 < \Delta y$

TABLE 2

| Element No. | Light emitting material | Relative external quantum efficiency | Chromaticity | Chromaticity after Deterioration by Driving | Note |
|---|---|---|---|---|---|
| Element 1-1 | Compound 1 | 1.4 | B | C | The present invention |
| Element 1-2 | Compound 2 | 1.5 | B | B | The present invention |
| Element 1-3 | Compound 3 | 1.4 | A | B | The present invention |
| Element 1-4 | Compound 4 | 1.5 | C | C | The present invention |
| Element 1-5 | Compound 5 | 1.4 | C | C | The present invention |
| Element 1-6 | Compound 7 | 1.2 | B | B | The present invention |
| Element 1-7 | Compound 9 | 1.3 | B | C | The present invention |
| Element 1-8 | Compound 13 | 1.2 | B | B | The present invention |
| Element 1-9 | Compound 14 | 1.4 | B | B | The present invention |
| Element 1-10 | Compound 15 | 1.3 | C | C | The present invention |
| Element 1-11 | Compound 20 | 1.4 | C | C | The present invention |
| Element 1-12 | Compound 22 | 1.5 | C | B | The present invention |
| Element 1-13 | Compound 23 | 1.5 | C | B | The present invention |
| Element 1-14 | Compound 27 | 1.2 | C | B | The present invention |
| Element 1-15 | Compound 30 | 1.1 | B | C | The present invention |
| Element 1-16 | Compound 31 | 1.1 | B | C | The present invention |
| Element 1-17 | Compound 36 | 1.3 | C | C | The present invention |
| Element 1-18 | Compound 41 | 1.5 | A | B | The present invention |
| Element 1-19 | Compound 42 | 1.4 | B | B | The present invention |
| Element 1-20 | Compound 43 | 1.4 | A | B | The present invention |
| Element 1-21 | Compound 46 | 1.1 | A | B | The present invention |
| Element 1-22 | Compound 49 | 1.1 | A | B | The present invention |
| Element 1-23 | Compound 53 | 1.5 | A | B | The present invention |
| Element 1-24 | Compound 55 | 1.4 | A | B | The present invention |
| Element 1-25 | Compound 70 | 1.4 | C | C | The present invention |
| Element 1-26 | Compound 71 | 1.4 | B | B | The present invention |
| Element 1-27 | Compound 75 | 1.4 | B | B | The present invention |
| Element 1-28 | Compound 78 | 1.2 | A | B | The present invention |
| Element 1-29 | Compound 83 | 1.4 | A | B | The present invention |
| Element 1-30 | Compound 87 | 1.5 | A | B | The present invention |
| Element 1-31 | Compound 100 | 1.4 | C | B | The present invention |
| Element 1-32 | Compound 101 | 1.4 | A | B | The present invention |
| Element 1-33 | Compound 104 | 1.4 | A | B | The present invention |
| Element 1-34 | Compound 108 | 1.5 | A | B | The present invention |
| Element 1-35 | Compound 114 | 1.4 | A | B | The present invention |
| Element 1-36 | Compound 116 | 1.5 | A | B | The present invention |
| Element 1-37 | Compound 120 | 1.4 | A | B | The present invention |
| Element 1-38 | Compound 121 | 1.4 | A | B | The present invention |
| Element 1-39 | Compound 129 | 1.4 | B | B | The present invention |
| Comparative element 1-1 | Comparative compound 1 | 1.0 | C | D | Comparative Example |
| Comparative element 1-2 | Comparative compound 2 | 0.3 | D | D | Comparative Example |
| Comparative element 1-3 | Comparative compound 3 | 0.7 | C | C | Comparative Example |
| Comparative element 1-4 | Comparative compound 4 | 1.1 | C | D | Comparative Example |

Example 3

An organic electroluminescent element was fabricated in the same manner as in Example 2, except that the layer configurations were changed as follows, and evaluations were carried out in the same manner as in Example 2. The results are shown in Table 3 below. Further, the external quantum efficiency in Table 3 below is shown as a relative value, taking the external quantum efficiency of an organic electroluminescent element using the comparative compound 1 as 1.0.

First layer: HT-4: Film thickness of 50 nm
Second layer: HT-3: Film thickness of 45 nm
Third layer: H-2 and the light emitting material described in Table 3 below (mass ratio=95:5): Film thickness of 25 nm
Fourth layer: ET-5: Film thickness of 5 nm
Fifth layer: ET-3: Film thickness of 20 nm

TABLE 3

| Element No. | Light emitting material | Relative external quantum efficiency | Chromaticity | Chromaticity after Deterioration by Driving | Note |
|---|---|---|---|---|---|
| Element 2-1 | Compound 1 | 1.5 | B | C | The present invention |
| Element 2-2 | Compound 2 | 1.6 | B | B | The present invention |
| Element 2-3 | Compound 3 | 1.4 | A | B | The present invention |
| Element 2-4 | Compound 4 | 1.4 | C | C | The present invention |
| Element 2-5 | Compound 5 | 1.5 | C | C | The present invention |
| Element 2-6 | Compound 7 | 1.2 | B | B | The present invention |
| Element 2-7 | Compound 9 | 1.4 | B | C | The present invention |
| Element 2-8 | Compound 13 | 1.2 | C | B | The present invention |
| Element 2-9 | Compound 14 | 1.4 | B | B | The present invention |
| Element 2-10 | Compound 15 | 1.3 | C | C | The present invention |

TABLE 3-continued

| Element No. | Light emitting material | Relative external quantum efficiency | Chromaticity | Chromaticity after Deterioration by Driving | Note |
|---|---|---|---|---|---|
| Element 2-11 | Compound 20 | 1.5 | C | C | The present invention |
| Element 2-12 | Compound 22 | 1.3 | C | B | The present invention |
| Element 2-13 | Compound 23 | 1.4 | C | B | The present invention |
| Element 2-14 | Compound 27 | 1.3 | C | B | The present invention |
| Element 2-15 | Compound 30 | 1.2 | B | C | The present invention |
| Element 2-16 | Compound 31 | 1.2 | B | C | The present invention |
| Element 2-17 | Compound 36 | 1.3 | C | C | The present invention |
| Element 2-18 | Compound 41 | 1.6 | A | B | The present invention |
| Element 2-19 | Compound 42 | 1.4 | B | B | The present invention |
| Element 2-20 | Compound 43 | 1.5 | A | B | The present invention |
| Element 2-21 | Compound 46 | 1.2 | A | B | The present invention |
| Element 2-22 | Compound 49 | 1.2 | A | B | The present invention |
| Element 2-23 | Compound 53 | 1.6 | A | B | The present invention |
| Element 2-24 | Compound 55 | 1.5 | A | B | The present invention |
| Element 2-25 | Compound 70 | 1.4 | C | C | The present invention |
| Element 2-26 | Compound 71 | 1.3 | B | B | The present invention |
| Element 2-27 | Compound 75 | 1.3 | B | B | The present invention |
| Element 2-28 | Compound 78 | 1.3 | A | B | The present invention |
| Element 2-29 | Compound 83 | 1.5 | A | B | The present invention |
| Element 2-30 | Compound 87 | 1.6 | A | B | The present invention |
| Element 2-31 | Compound 100 | 1.3 | C | B | The present invention |
| Element 2-32 | Compound 101 | 1.5 | A | B | The present invention |
| Element 2-33 | Compound 104 | 1.5 | A | B | The present invention |
| Element 2-34 | Compound 108 | 1.6 | A | B | The present invention |
| Element 2-35 | Compound 114 | 1.5 | A | B | The present invention |
| Element 2-36 | Compound 116 | 1.6 | A | B | The present invention |
| Element 2-37 | Compound 120 | 1.5 | A | B | The present invention |
| Element 2-38 | Compound 121 | 1.5 | A | B | The present invention |
| Element 2-39 | Compound 129 | 1.4 | B | B | The present invention |
| Comparative element 2-1 | Comparative compound 1 | 1.0 | C | D | Comparative Example |
| Comparative element 2-2 | Comparative compound 2 | 0.4 | D | D | Comparative Example |
| Comparative element 2-3 | Comparative compound 3 | 0.7 | C | C | Comparative Example |
| Comparative element 2-4 | Comparative compound 4 | 0.9 | C | D | Comparative Example |

Example 4

An organic electroluminescent element was fabricated in the same manner as in Example 2, except that the layer configurations were changed as follows, and evaluations were carried out in the same manner as in Example 2. The results are shown in Table 4 below. Further, the external quantum efficiency in Table 4 below is shown as a relative value, taking the external quantum efficiency of an organic electroluminescent element using the comparative compound 1 as 1.0.

First layer: HAT-CN: Film thickness of 10 nm
Second layer: HT-2: Film thickness of 30 nm
Third layer: H-1 and the light emitting material described in Table 4 below (mass ratio=97:3): Film thickness of 30 nm
Fourth layer: ET-4: Film thickness of 30 nm

TABLE 4

| Element No. | Light emitting material | Relative external quantum efficiency | Chromaticity | Chromaticity after Deterioration by Driving | Note |
|---|---|---|---|---|---|
| Element 3-1 | Compound 1 | 1.3 | A | C | The present invention |
| Element 3-2 | Compound 2 | 1.4 | B | B | The present invention |
| Element 3-3 | Compound 3 | 1.4 | A | B | The present invention |
| Element 3-4 | Compound 4 | 1.4 | B | C | The present invention |
| Element 3-5 | Compound 5 | 1.4 | B | C | The present invention |
| Element 3-6 | Compound 7 | 1.2 | B | B | The present invention |
| Element 3-7 | Compound 9 | 1.3 | B | C | The present invention |
| Element 3-8 | Compound 13 | 1.3 | B | B | The present invention |
| Element 3-9 | Compound 14 | 1.4 | B | B | The present invention |
| Element 3-10 | Compound 15 | 1.2 | B | C | The present invention |
| Element 3-11 | Compound 20 | 1.3 | C | C | The present invention |
| Element 3-12 | Compound 22 | 1.4 | C | B | The present invention |
| Element 3-13 | Compound 23 | 1.4 | C | B | The present invention |
| Element 3-14 | Compound 27 | 1.2 | C | B | The present invention |
| Element 3-15 | Compound 30 | 1.2 | B | C | The present invention |
| Element 3-16 | Compound 31 | 1.1 | B | C | The present invention |
| Element 3-17 | Compound 36 | 1.3 | C | C | The present invention |
| Element 3-18 | Compound 41 | 1.5 | A | B | The present invention |
| Element 3-19 | Compound 42 | 1.3 | B | B | The present invention |
| Element 3-20 | Compound 43 | 1.4 | A | B | The present invention |
| Element 3-21 | Compound 46 | 1.1 | A | B | The present invention |

TABLE 4-continued

| Element No. | Light emitting material | Relative external quantum efficiency | Chromaticity | Chromaticity after Deterioration by Driving | Note |
|---|---|---|---|---|---|
| Element 3-22 | Compound 49 | 1.1 | A | B | The present invention |
| Element 3-23 | Compound 53 | 1.5 | A | B | The present invention |
| Element 3-24 | Compound 55 | 1.4 | A | B | The present invention |
| Element 3-25 | Compound 70 | 1.4 | C | C | The present invention |
| Element 3-26 | Compound 71 | 1.3 | B | B | The present invention |
| Element 3-27 | Compound 75 | 1.3 | B | B | The present invention |
| Element 3-28 | Compound 78 | 1.2 | A | B | The present invention |
| Element 3-29 | Compound 83 | 1.4 | A | B | The present invention |
| Element 3-30 | Compound 87 | 1.5 | A | B | The present invention |
| Element 3-31 | Compound 100 | 1.3 | C | B | The present invention |
| Element 3-32 | Compound 101 | 1.4 | A | B | The present invention |
| Element 3-33 | Compound 104 | 1.4 | A | B | The present invention |
| Element 3-34 | Compound 108 | 1.5 | A | B | The present invention |
| Element 3-35 | Compound 114 | 1.4 | A | B | The present invention |
| Element 3-36 | Compound 116 | 1.5 | A | B | The present invention |
| Element 3-37 | Compound 120 | 1.4 | A | B | The present invention |
| Element 3-38 | Compound 121 | 1.4 | A | B | The present invention |
| Element 3-39 | Compound 129 | 1.3 | B | B | The present invention |
| Comparative element 3-1 | Comparative compound 1 | 1.0 | C | D | Comparative Example |
| Comparative element 3-2 | Comparative compound 2 | 0.3 | D | D | Comparative Example |
| Comparative element 3-3 | Comparative compound 3 | 0.8 | C | C | Comparative Example |
| Comparative element 3-4 | Comparative compound 4 | 1.1 | C | D | Comparative Example |

Example 5

An organic electroluminescent element was fabricated in the same manner as in Example 2, except that the layer configurations were changed as follows, and evaluations were carried out in the same manner as in Example 2. The results are shown in Table 5 below. Further, the external quantum efficiency in Table 5 below is shown as a relative value, taking the external quantum efficiency of an organic electroluminescent element using the comparative compound 1 as 1.0.

First layer: HAT-CN: Film thickness of 10 nm
Second layer: HT-1: Film thickness of 30 nm
Third layer: H-3 and the light emitting material described in Table 5 below (mass ratio=93:7): Film thickness of 30 nm
Fourth layer: ET-4: Film thickness of 30 nm

TABLE 5

| Element No. | Light emitting material | Relative external quantum efficiency | Chromaticity | Chromaticity after Deterioration by Driving | Note |
|---|---|---|---|---|---|
| Element 4-1 | Compound 1 | 1.4 | B | C | The present invention |
| Element 4-2 | Compound 2 | 1.5 | B | B | The present invention |
| Element 4-3 | Compound 3 | 1.3 | A | B | The present invention |
| Element 4-4 | Compound 4 | 1.5 | C | C | The present invention |
| Element 4-5 | Compound 5 | 1.5 | C | C | The present invention |
| Element 4-6 | Compound 7 | 1.2 | B | B | The present invention |
| Element 4-7 | Compound 9 | 1.3 | B | C | The present invention |
| Element 4-8 | Compound 13 | 1.3 | B | B | The present invention |
| Element 4-9 | Compound 14 | 1.4 | B | B | The present invention |
| Element 4-10 | Compound 15 | 1.3 | C | C | The present invention |
| Element 4-11 | Compound 20 | 1.3 | C | C | The present invention |
| Element 4-12 | Compound 22 | 1.4 | C | B | The present invention |
| Element 4-13 | Compound 23 | 1.5 | C | B | The present invention |
| Element 4-14 | Compound 27 | 1.2 | C | B | The present invention |
| Element 4-15 | Compound 30 | 1.2 | B | C | The present invention |
| Element 4-16 | Compound 31 | 1.2 | B | C | The present invention |

TABLE 5-continued

| Element No. | Light emitting material | Relative external quantum efficiency | Chromaticity | Chromaticity after Deterioration by Driving | Note |
|---|---|---|---|---|---|
| Element 4-17 | Compound 36 | 1.4 | C | C | The present invention |
| Element 4-18 | Compound 41 | 1.6 | A | B | The present invention |
| Element 4-19 | Compound 42 | 1.4 | B | B | The present invention |
| Element 4-20 | Compound 43 | 1.5 | A | B | The present invention |
| Element 4-21 | Compound 46 | 1.1 | A | B | The present invention |
| Element 4-22 | Compound 49 | 1.2 | A | B | The present invention |
| Element 4-23 | Compound 53 | 1.6 | A | B | The present invention |
| Element 4-24 | Compound 55 | 1.4 | A | B | The present invention |
| Element 4-25 | Compound 70 | 1.3 | C | C | The present invention |
| Element 4-26 | Compound 71 | 1.4 | B | B | The present invention |
| Element 4-27 | Compound 75 | 1.3 | C | B | The present invention |
| Element 4-28 | Compound 78 | 1.2 | A | B | The present invention |
| Element 4-29 | Compound 83 | 1.5 | A | B | The present invention |
| Element 4-30 | Compound 87 | 1.6 | A | B | The present invention |
| Element 4-31 | Compound 100 | 1.3 | C | B | The present invention |
| Element 4-32 | Compound 101 | 1.4 | A | B | The present invention |
| Element 4-33 | Compound 104 | 1.4 | A | B | The present invention |
| Element 4-34 | Compound 108 | 1.6 | A | B | The present invention |
| Element 4-35 | Compound 114 | 1.4 | A | B | The present invention |
| Element 4-36 | Compound 116 | 1.5 | A | B | The present invention |
| Element 4-37 | Compound 120 | 1.4 | A | B | The present invention |
| Element 4-38 | Compound 121 | 1.4 | A | B | The present invention |
| Element 4-39 | Compound 129 | 1.3 | B | B | The present invention |
| Comparative Element 4-1 | Comparative compound 1 | 1.0 | C | D | Comparative Example |
| Comparative Element 4-2 | Comparative compound 2 | 0.6 | C | D | Comparative Example |
| Comparative Element 4-3 | Comparative compound 3 | 0.7 | D | C | Comparative Example |
| Comparative Element 4-4 | Comparative compound 4 | 1.1 | D | D | Comparative Example |

Example 6

An organic electroluminescent element was fabricated in the same manner as in Example 2, except that the layer configurations were changed as follows, and evaluations were carried out in the same manner as in Example 2. The results are shown in Table 6 below. Further, the external quantum efficiency in Table 6 below is shown as a relative value, taking the external quantum efficiency of an organic electroluminescent element using the comparative compound 1 as 1.0.

First layer: HAT-CN: Film thickness of 10 nm
Second layer: HT-2: Film thickness of 60 nm
Third layer: H-4 and the light emitting material described in Table 6 below (mass ratio=97:3): Film thickness of 30 nm
Fourth layer: ET-2: Film thickness of 20 nm

TABLE 6

| Element No. | Light emitting material | Relative external quantum efficiency | Chromaticity | Chromaticity after Deterioration by Driving | Note |
| --- | --- | --- | --- | --- | --- |
| Element 5-1 | Compound 1 | 1.4 | B | C | The present invention |
| Element 5-2 | Compound 2 | 1.4 | B | B | The present invention |
| Element 5-3 | Compound 3 | 1.4 | A | B | The present invention |
| Element 5-4 | Compound 4 | 1.5 | C | C | The present invention |
| Element 5-5 | Compound 5 | 1.4 | C | C | The present invention |
| Element 5-6 | Compound 7 | 1.3 | B | B | The present invention |
| Element 5-7 | Compound 9 | 1.3 | B | C | The present invention |
| Element 5-8 | Compound 13 | 1.3 | B | B | The present invention |
| Element 5-9 | Compound 14 | 1.5 | B | B | The present invention |
| Element 5-10 | Compound 15 | 1.2 | C | C | The present invention |
| Element 5-11 | Compound 20 | 1.3 | C | C | The present invention |
| Element 5-12 | Compound 22 | 1.4 | C | B | The present invention |
| Element 5-13 | Compound 23 | 1.4 | C | B | The present invention |
| Element 5-14 | Compound 27 | 1.1 | C | B | The present invention |
| Element 5-15 | Compound 30 | 1.2 | B | C | The present invention |
| Element 5-16 | Compound 31 | 1.1 | B | C | The present invention |
| Element 5-17 | Compound 36 | 1.3 | C | C | The present invention |
| Element 5-18 | Compound 41 | 1.5 | A | B | The present invention |
| Element 5-19 | Compound 42 | 1.4 | B | B | The present invention |
| Element 5-20 | Compound 43 | 1.5 | A | B | The present invention |
| Element 5-21 | Compound 46 | 1.2 | A | B | The present invention |
| Element 5-22 | Compound 49 | 1.1 | A | B | The present invention |
| Element 5-23 | Compound 53 | 1.5 | A | B | The present invention |
| Element 5-24 | Compound 55 | 1.4 | A | B | The present invention |
| Element 5-25 | Compound 70 | 1.3 | C | C | The present invention |
| Element 5-26 | Compound 71 | 1.4 | B | B | The present invention |
| Element 5-27 | Compound 75 | 1.3 | C | B | The present invention |
| Element 5-28 | Compound 78 | 1.3 | A | B | The present invention |
| Element 5-29 | Compound 83 | 1.5 | A | B | The present invention |
| Element 5-30 | Compound 87 | 1.5 | A | B | The present invention |
| Element 5-31 | Compound 100 | 1.4 | C | B | The present invention |
| Element 5-32 | Compound 101 | 1.3 | A | B | The present invention |
| Element 5-33 | Compound 104 | 1.4 | A | B | The present invention |
| Element 5-34 | Compound 108 | 1.5 | A | B | The present invention |
| Element 5-35 | Compound 114 | 1.5 | A | B | The present invention |
| Element 5-36 | Compound 116 | 1.4 | A | B | The present invention |
| Element 5-37 | Compound 120 | 1.4 | A | B | The present invention |
| Element 5-38 | Compound 121 | 1.4 | A | B | The present invention |
| Element 5-39 | Compound 129 | 1.3 | B | B | The present invention |
| comparative Element 5-1 | Comparative compound 1 | 1.0 | C | D | Comparative Example |
| comparative Element 5-2 | Comparative compound 2 | 0.2 | C | D | Comparative Example |
| Comparative element 5-3 | Comparative compound 3 | 0.6 | D | C | Comparative Example |
| Comparative element 5-4 | Comparative compound 4 | 1.1 | D | D | Comparative Example |

Example 7

(Evaluation of Organic Electroluminescent Element (Coating))
—Preparation of Light Emitting Layer-Forming Coating Liquids—

The compound 7 (0.05% by mass) and the following host material PH-1 (0.95% by mass) were mixed with methyl ethyl ketone (99.0% by mass) to obtain a light emitting layer-forming coating liquid 1.

[Chem. 80]

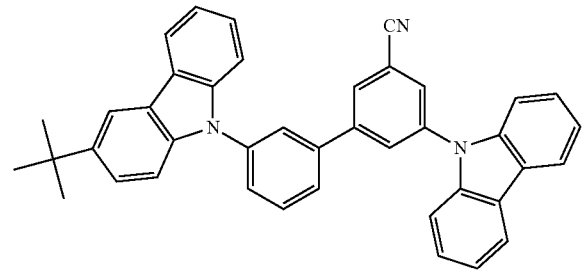

Host material PH-1

In the same manner as for the light emitting layer-forming coating liquid 1, except that the compound 7 was changed to each of compounds 11, 20, 46, and 65 in the light emitting layer-forming coating liquid 1, light emitting layer-forming coating liquids 2 to 5 were prepared.

Furthermore, in the same manner as for the light emitting layer-forming coating liquids 1 to 5, except that the host material PH-1 was changed to the host material H-2 in the light emitting layer-forming coating liquids 1 to 5, light emitting layer-forming coating liquids 6 to 10 were prepared.

In addition, for comparison, in the same manner as for the light emitting layer-forming coating liquid 1, except that the compound 7 was changed to the comparative compound 1 in the light emitting layer-forming coating liquid 1, a comparative light emitting layer-forming coating liquid 1 was prepared. In the same manner as for the light emitting layer-forming coating liquid 1, except that the compound 7 in the light emitting layer-forming coating liquid 6 was changed to the comparative compound 1, a comparative light emitting layer-forming coating liquid 2 was prepared.

(Procedure for Fabrication of Element)
—Fabrication of Organic Electroluminescent Element—
ITO was deposited on a 25 mm×25 mm×0.7 mm glass substrate to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the electronics industry (manufactured by Kanto Chemical Co., Inc.) and spin-coated (2,000 rpm for 20 seconds) to give a thickness of about 40 nm, and then dried at 120° C. for 30 minutes and subjected to an annealing treatment at 160° C. for 10 minutes to form a hole injecting layer.

[Chem. 81]

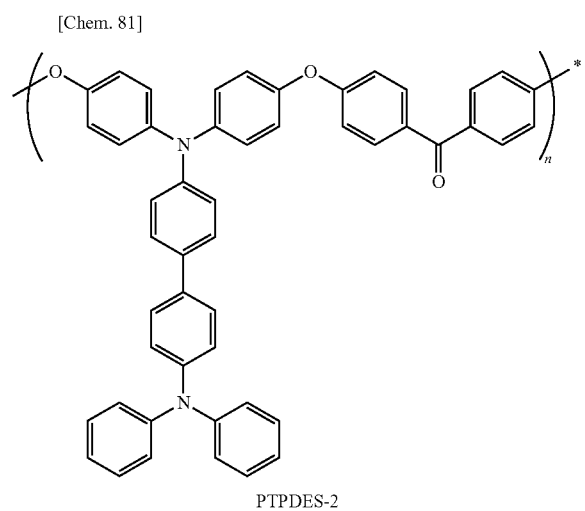

PTPDES-2

The light emitting layer-forming coating liquid 1 was spin-coated on the hole injecting layer (1,300 rpm for 30 seconds) to give a thickness of about 40 nm, thereby obtaining a light emitting layer.

Subsequently, BAlq (bis-(2-methyl-8-quinolinolato)-4-(phenylphenolate)-aluminum(III)) represented by the following structural formula was formed as an electron transporting layer on the light emitting layer to give a thickness of 40 nm by a vacuum deposition method.

[Chem. 82]

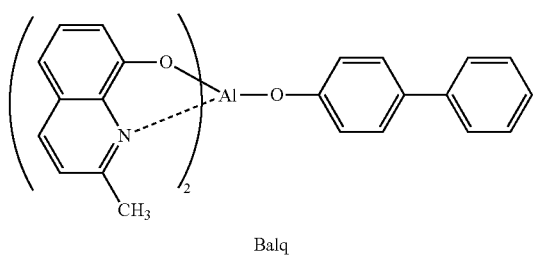

Balq

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a glove box purged with an argon gas, and then sealed with a sealing can made of stainless steel and an ultraviolet-curable adhesive (XNR5516HV, manufactured by Nagase-Chiba, Ltd.) to fabricate an organic electroluminescent element P1.

Organic electroluminescent elements P2 to P10 were fabricated in the same manner as for the organic electroluminescent element P1, except that the light emitting layer-forming coating liquid 1 was changed to the light emitting layer-forming coating liquids 2 to 10 in the organic electroluminescent element P1.

In addition, for comparison, organic electroluminescent elements P11 and P12 were fabricated in the same manner as for the organic electroluminescent element P1, except that the light emitting layer-forming coating liquid 1 was changed to the comparative light emitting layer-forming coating liquids 1 and 2 in the organic electroluminescent element P1.

The same evaluation as in Example 2 was carried out for the fabricated organic electroluminescent elements P1 to P12. The results are shown in Table 7 below. The external quantum efficiency in Table 7 below is shown as a relative value, taking the external quantum efficiency of an organic electroluminescent element using the comparative compound 1 as 1.0 for each type of host materials.

TABLE 7

| Organic electroluminescent element | Light emitting material | Host material | Relative external quantum efficiency | Chromaticity | Chromaticity after Deterioration by Driving | Note |
| --- | --- | --- | --- | --- | --- | --- |
| P1 | Compound 7 | PH-1 | 1.2 | B | C | The present invention |
| P2 | Compound 11 | PH-1 | 1.2 | C | C | The present invention |
| P3 | Compound 20 | PH-1 | 1.3 | A | B | The present invention |
| P4 | Compound 46 | PH-1 | 1.3 | B | B | The present invention |
| P5 | Compound 65 | PH-1 | 1.4 | B | B | The present invention |
| P11 | Comparative compound 1 | PH-1 | 1.0 | C | D | Comparative Example |
| P6 | Compound 7 | H-2 | 1.2 | B | C | The present invention |
| P7 | Compound 11 | H-2 | 1.3 | C | C | The present invention |
| P8 | Compound 20 | H-2 | 1.3 | A | B | The present invention |
| P9 | Compound 46 | H-2 | 1.3 | B | B | The present invention |
| P10 | Compound 65 | H-2 | 1.4 | B | B | The present invention |
| P12 | Comparative compound 1 | H-2 | 1.0 | C | D | Comparative Example |

From the results of Tables 2 to 7, it could be seen that the organic electroluminescent element of the present invention, using the compound of the present invention, has high luminous efficiency and excellent chromaticity.

On the other hand, it could also be seen that the number of carbon atoms of the alkyl group of $R^9$ to $R^{12}$ in the general formula (1) is 8 and each of the comparative elements using the comparative compound 1 described in US2005/202279, which exceeds the upper limit of the range in the present invention has lowered external quantum efficiency.

It could be seen that in $R^1$ to $R^8$ in the general formula (1), each of the comparative elements using the comparative compound 2 described in US2002/132134, which has no substituent represented by the general formula (2), has lowered external quantum efficiency as well as lowered chromaticity.

The total number of carbon atoms of the alkyl group included in $R^9$ and $R^{10}$ and the total number of carbon atoms of the alkyl group included in $R^{11}$ and $R^{12}$ in the general formula (1) are both 14, and each of the comparative elements using the comparative compound 3 described in US2005/202279, which exceeds the upper limit of the range in the present invention, has lowered external quantum efficiency as well as lowered chromaticity.

The total number of carbon atoms of the alkyl group included in $R^9$ and $R^{10}$ and the total number of carbon atoms of the alkyl group included in $R^{11}$ and $R^{12}$ in the general formula (1) are both 10, and each of the comparative elements using the comparative compound 4 which exceeds the upper limit of the range in the present invention, has lowered chromaticity.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUT SURFACE
32: FINE PARTICLES
40: ILLUMINATION DEVICE

The invention claimed is:
1. An organic electroluminescent element comprising:
a substrate;
a pair of electrodes including an anode and a cathode, disposed on the substrate; and
at least one organic layer including a light emitting layer, disposed between the electrodes,
wherein the organic layer(s) contains a compound represented by the following general formula (1):

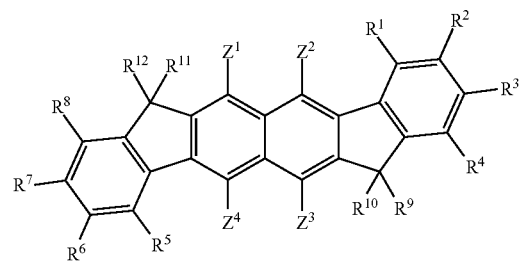

wherein $R^1$ to $R^8$ each independently represent a hydrogen atom or a substituent, these may be bonded to each other to form a ring, and at least one of $R^1$ to $R^8$ is a substituent represented by the following general formula (2);

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Z^1$ and $Z^2$ and $Z^3$ and $Z^4$ may be respectively bonded to each other to form a ring, but they do not form an aromatic ring in any case;

when $Z^1$ and $Z^2$ and $Z^3$ and $Z^4$ are respectively bonded to each other to form a ring, $Z^1$ to $Z^4$ each independently represent an alkyl group, an aryl group, a heteroaryl group, a silyl group, —O—, or —NY—, provided that Y is an alkyl group or an aryl group and provided that $Z^1$ and $Z^2$ are not both alkyl groups in any case and $Z^3$ and $Z^4$ are not both alkyl groups in any case;

when $Z^1$ and $Z^2$ and $Z^3$ and $Z^4$ are not respectively bonded to each other to form a ring, $Z^1$ to $Z^4$ each independently represent a hydrogen atom, a deuterium atom, an alkyl group, an aryl group, a heteroaryl group, a fluorine atom, a silyl group, or a cyano group:

General Formula (2)

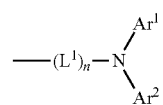

wherein $Ar^1$ and $Ar^2$ each independently represent an alkyl group, an aryl group, or a heteroaryl group and may be bonded to each other to form a ring; $L^1$ represents an arylene group or a heteroarylene group; $Ar^1$ and $Ar^2$, and $L^1$ and $Ar^1$ and/or $L^1$ and $Ar^2$ may be bonded to each other to form a ring; n represents 0 or 1, and when n is 0, $L^1$ represents a single bond.

2. The organic electroluminescent element according to claim 1, wherein at least one of $R^1$ to $R^4$ and at least one of $R^5$ to $R^8$ in the general formula (1) are each a substituent represented by the general formula (2).

3. The organic electroluminescent element according to claim 1, wherein the compound represented by the general formula (1) is a compound represented by the following general formula (3):

General Formula (3)

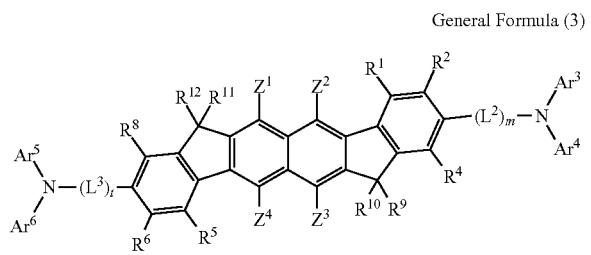

wherein $R^1$, $R^2$, $R^4$ to $R^6$, and $R^8$ each independently represent a hydrogen atom or a substituent, and these may be bonded to each other to form a ring;

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring;

$L^2$ and $L^3$ each independently represent an arylene group or a heteroarylene group, $Ar^3$ and $Ar^4$, $L^2$ and $Ar^3$ and/or $L^2$ and $Ar^4$, $Ar^5$ and $Ar^6$, and $L^3$ and $Ar^5$ and/or $L^3$ and $Ar^6$ may be bonded to each other to form a ring;

m and t each independently represent 0 or 1, and when m and t are 0, each of $L^2$ and $L^3$ represents a single bond;

$Z^1$ and $Z^2$ and $Z^3$ and $Z^4$ may be respectively bonded to each other to form a ring, but they do not form an aromatic ring in any case; when $Z^1$ and $Z^2$ and $Z^3$ and $Z^4$ are bonded to each other to form a ring, $Z^1$ to $Z^4$ each independently represent an alkyl group, an aryl group, a heteroaryl group, a silyl group, —O—, or —NY—, provided that Y is an alkyl group or an aryl group and provided that $Z^1$ and $Z^2$ are not both alkyl groups in any case and $Z^3$ and $Z^4$ are not both alkyl groups in any case; when $Z^1$ and $Z^2$ and $Z^3$ and $Z^4$ are not bonded to each other to form a ring, $Z^1$ to $Z^4$ each independently represent a hydrogen atom, a deuterium atom, an alkyl group, an aryl group, a heteroaryl group, a fluorine atom, a silyl group, or a cyano group.

4. The organic electroluminescent element according to claim 1, wherein the compound represented by the general formula (3) is a compound represented by the following general formula (4):

General Formula (4)

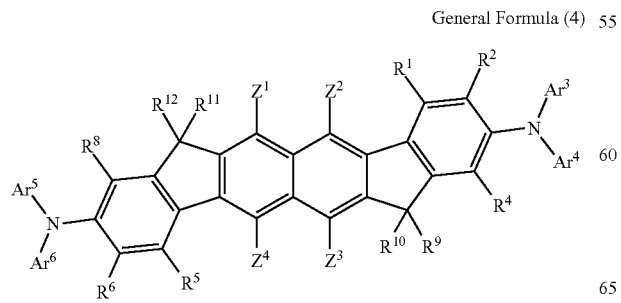

wherein $R^1$, $R^2$, $R^4$ to $R^6$, and $R^8$ each independently represent a hydrogen atom or a substituent, and these may be bonded to each other to form a ring;

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring;

$Z^1$ and $Z^2$ and $Z^3$ and $Z^4$ may be respectively bonded to each other to form a ring, but they do not form an aromatic ring in any case; when $Z^1$ and $Z^2$ and $Z^3$ and $Z^4$ are bonded to each other to form a ring, $Z^1$ to $Z^4$ each independently represent an alkyl group, an aryl group, a heteroaryl group, a silyl group, —O—, or —NY—, provided that Y is an alkyl group or an aryl group and provided that $Z^1$ and $Z^2$ are not both alkyl groups in any case and $Z^3$ and $Z^4$ are not both alkyl groups in any case; when $Z^1$ and $Z^2$ and $Z^3$ and $Z^4$ are not bonded to each other to form a ring, $Z^1$ to $Z^4$ each independently represent a hydrogen atom (including a deuterium atom), an alkyl group, an aryl group, a heteroaryl group, a fluorine atom, a silyl group, or a cyano group.

5. The organic electroluminescent element according to claim 4, wherein $Z^1$ and $Z^2$ and $Z^3$ and $Z^4$ in the general formula (4) are not respectively bonded to each other to form a ring and $Z^1$ to $Z^4$ are each independently a hydrogen atom, a deuterium atom, an alkyl group, a fluorine atom, a silyl group, or a cyano group.

6. The organic electroluminescent element according to claim 1, wherein the compound represented by the general formula (1) is a compound represented by the following general formula (5):

General Formula (5)

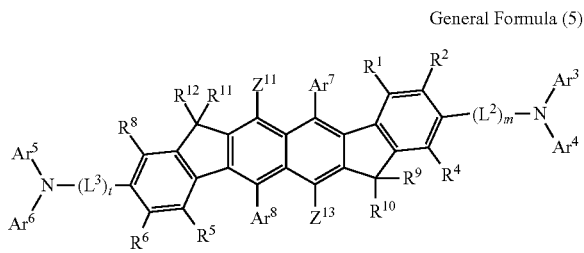

wherein $R^1$, $R^2$, $R^4$ to $R^6$, and $R^8$ each independently represent a hydrogen atom or a substituent, and these may be bonded to each other to form a ring;

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring;

$Ar^7$ and $Ar^8$ each independently represent an aryl group or a heteroaryl group;

$L^2$ and $L^3$ each independently represent an arylene group or a heteroarylene group;

m and t each independently represent 0 or 1, and when m and t are 0, each of $L^2$ and $L^3$ represents a single bond;

$Z^{11}$ and $Ar^7$ and $Z^{13}$ and $Ar^8$ may be respectively bonded to each other to form a ring, but they do not form an aromatic ring in any case; when $Z^{11}$ and $Ar^7$ and $Z^{13}$ and $Ar^8$ are respectively bonded to each other to form a ring, $Z^{11}$ and $Z^{13}$ each independently represent an alkyl group, an aryl group, a heteroaryl group, a silyl group, —O—, or —NY—, provided that Y is an alkyl group or an aryl group; when $Z^{11}$ and $Ar^7$ and $Z^{13}$ and $Ar^8$ are not respectively bonded to each other to form a ring, $Z^{11}$ and $Z^{13}$ each independently represent a hydrogen atom, a deuterium atom, an alkyl group, an aryl group, a heteroaryl group, a fluorine atom, a silyl group, or a cyano group.

7. The organic electroluminescent element according to claim 1, wherein the compound represented by the general formula (1) is a compound represented by the following general formula (6):

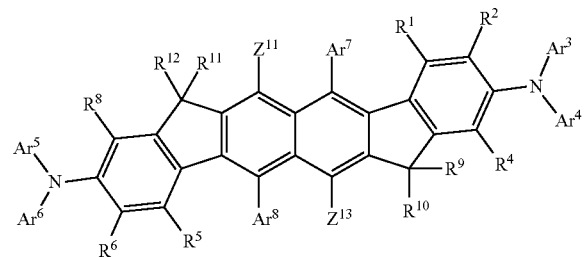

General Formula (6)

wherein $R^1$, $R^2$, $R^4$ to $R^6$, and $R^8$ each independently represent a hydrogen atom or a substituent, and these may be bonded to each other to form a ring;

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring;

$Ar^7$ and $Ar^8$ each independently represent an aryl group or a heteroaryl group;

$Z^{11}$ and $Ar^7$ and $Z^{13}$ and $Ar^8$ may be respectively bonded to each other to form a ring, but they do not form an aromatic ring in any case; when $Z^{11}$ and $Ar^7$ and $Z^{13}$ and $Ar^8$ are respectively bonded to each other to form a ring, $Z^{11}$ and $Z^{13}$ each independently represent an alkyl group, an aryl group, a heteroaryl group, a silyl group, —O—, or —NY—, provided that Y is an alkyl group or an aryl group; when $Z^{11}$ and $Ar^7$ and $Z^{13}$ and $Ar^8$ are not respectively bonded to each other to form a ring, and $Z^{13}$ each independently represent a hydrogen atom, a deuterium atom, an alkyl group, an aryl group, a heteroaryl group, a fluorine atom, a silyl group, or a cyano group.

8. The organic electroluminescent element according to claim 6, wherein $Z^{11}$ and $Ar^7$ and $Z^{13}$ and $Ar^8$ in the general formulae (5) are respectively not bonded to each other to form a ring.

9. The organic electroluminescent element according to claim 6, wherein $Ar^3$ to $Ar^8$ in the general formulae (5) each independently represent an aryl group having 6 to 20 carbon atoms.

10. The organic electroluminescent element according to claim 6, wherein at least two or more of $Ar^3$ to $Ar^8$ in the general formulae (5) are an alkyl group having 1 to 5 carbon atoms, an aryl group having 6 to 12 carbon atoms, a silyl group having 3 to 18 carbon atoms, or an aryl group having a fluorine atom as a substituent.

11. The organic electroluminescent element according to claim 6, wherein $Ar^7$ to $Ar^8$ in the general formulae (5) are an alkyl group having 1 to 5 carbon atoms, an aryl group having 6 to 12 carbon atoms, a silyl group having 3 to 18 carbon atoms, or an aryl group having a fluorine atom as a substituent.

12. The organic electroluminescent element according to claim 6, wherein $Ar^7$ to $Ar^8$ in the general formulae (5) are an aryl group having a fluorine atom as a substituent.

13. The organic electroluminescent element according to claim 4, wherein at least one of $Ar^3$ to $Ar^6$ in the general formula (4) is an alkyl group having 1 to 5 carbon atoms, an aryl group having 6 to 12 carbon atoms, a silyl group having 3 to 18 carbon atoms, or an aryl group having a fluorine atom as a substituent.

14. The organic electroluminescent element according to claim 4, wherein at least one of $Ar^3$ to $Ar^6$ in the general formula (4) is a substituted or unsubstituted β-naphthyl group or biphenyl group.

15. The organic electroluminescent element according to claim 1, wherein at least one layer of the organic layer(s) containing the compound represented by the general formula (1) is a light emitting layer.

16. The organic electroluminescent element according to claim 15, wherein the light emitting layer contains an anthracene-based host material.

17. The organic electroluminescent element according to claim 16, wherein the anthracene-based host material is represented by the following general formula (An-1):

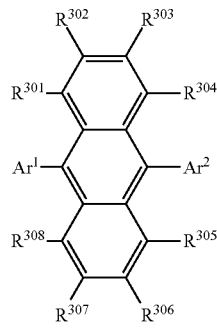

General Formula (An-1)

wherein $Ar^1$ and $Ar^2$ each independently represent an aryl group or a heteroaryl group, and $R^{301}$ to $R^{308}$ each independently represent a hydrogen atom or a substituent; $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be bonded to each other to form a ring.

18. The organic electroluminescent element according to claim 17, wherein the compound represented by the general formula (An-1) is a compound represented by the following general formula (An-2):

General Formula (An-2)

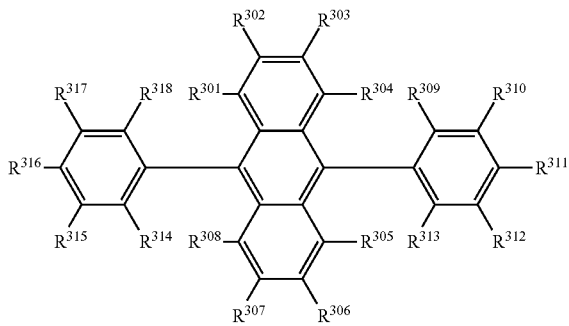

wherein $R^{301}$ to $R^{318}$ each independently represent a hydrogen atom or a substituent; $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{313}$ and $R^{314}$, $R^{315}$, $R^{315}$ and $R^{316}$, $R^{316}$ and $R^{317}$, and $R^{317}$ and $R^{318}$ may be bonded to each other to form a ring.

19. The organic electroluminescent element according to claim 1, wherein at least one of the organic layer(s) contains a compound represented by the following general formula (P):

General Formula (P)

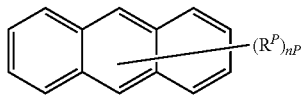

wherein $R^P$ represents an alkyl group, an aryl group, or a heteroaryl group, and these may have a substituent selected from the above-described Substituent Group A; nP represents an integer of 1 to 10, and when there are a plurality of $R^P$s, they may be the same as or different from each other; At least one of $R^P$s is a substituent represented by any of the following general formulae (P-1) to (P-5):

General Formula (P-1)

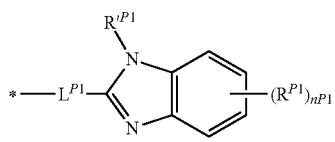

General Formula (P-2)

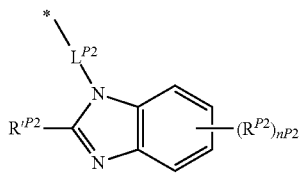

General Formula (P-3)

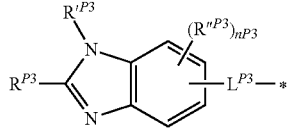

General Formula (P-4)

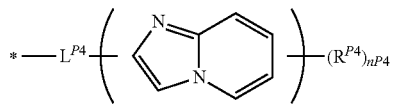

General Formula (P-5)

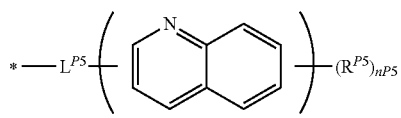

wherein $R^{P1}$ to $R^{P5}$, $R^{\prime P1}$ to $R^{\prime P3}$, $R^{\prime P5}$, and $R^{\prime\prime P3}$ each represent an alkyl group, an aryl group, or a heteroaryl group, and these may have a substituent selected from the above-described Substituent Group A; $n^{P1}$ to $n^{P2}$, $n^{P4}$, and $n^{P5}$ represent an integer of 0 to 4, $n^{P3}$ and $n^{P5}$ each represent an integer of 0 to 2, and there are a plurality of $R^{P1}$ to $R^{P5}$, $R^{\prime P1}$ to $R^{\prime P3}$, and $R^{\prime\prime P3}$, they may be the same as or different from each other; $L^{P1}$ to $L^{P5}$ represents any one of divalent linking groups consisting of a single bond, an aryl ring, and a heteroaryl ring; * represents a binding position with an anthracene ring of the general formula (P).

20. The organic electroluminescent element according to claim 19, wherein the compound represented by the general formula (P) is a compound having a substituent represented by the general formula (P-1) as at least one of $R^P$s.

21. The organic electroluminescent element according to claim 19, wherein the compound represented by the general formula (P) is a compound having a substituent represented by the general formula (P-2) as at least one of $R^P$s.

22. The organic electroluminescent element according to claim 19, wherein the compound represented by the general formula (P) is a compound having a substituent represented by the general formula (P-3) as at least one of $R^P$s.

23. The organic electroluminescent element according to claim 19, wherein the compound represented by the general formula (P) is a compound having a substituent represented by the general formula (P-4) as at least one of $R^P$s.

24. The organic electroluminescent element according to claim 19, wherein the compound represented by the general formula (P) is a compound having a substituent represented by the general formula (P-5) as at least one of $R^P$s.

25. The organic electroluminescent element according to claim 1, wherein the light emitting layer is formed by a vacuum deposition process.

26. The organic electroluminescent element according to claim 1, wherein the light emitting layer is formed by a wet type process.

27. A light emitting device using the organic electroluminescent element according to claim 1.

28. A display device using the organic electroluminescent element according to claim 1.

29. An illumination device using the organic electroluminescent element according to claim 1.

30. A material for an organic electroluminescent element represented by the following general formula (1):

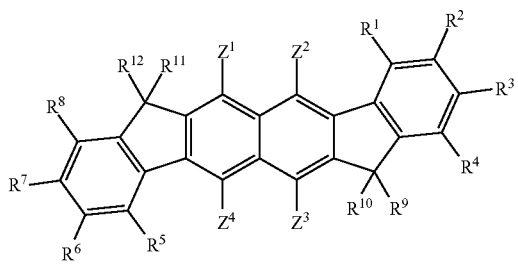

wherein $R^1$ to $R^8$ each independently represent a hydrogen atom or a substituent, these may be bonded to each other to form a ring, and at least one of $R^1$ to $R^8$ is a substituent represented by the following general formula (2);

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Z^1$ and $Z^2$ and $Z^3$ and $Z^4$ may be respectively bonded to each other to form a ring, but they do not form an aromatic ring in any case; $Z^1$ and $Z^2$ and $Z^3$ and $Z^4$ are respectively bonded to each other to form a ring, $Z^1$ to $Z^4$ each independently represent an alkyl group, an aryl group, a heteroaryl group, a silyl group, —O—, or —NY—, provided that Y is an alkyl group or an aryl group and provided that $Z^1$ and $Z^2$ are not both alkyl groups in any case and $Z^3$ and $Z^4$ are not both alkyl groups in any case; when $Z^1$ and $Z^2$ and $Z^3$ and $Z^4$ are not respectively bonded to each other to form a ring, $Z^1$ to $Z^4$ each independently represents a hydrogen atom, a deuterium atom, an alkyl group, an aryl group, a heteroaryl group, a fluorine atom, a silyl group, or a cyano group:

General Formula (2)

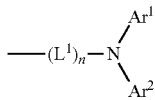

wherein $Ar^1$ and $Ar^2$ each independently represent an alkyl group, an aryl group, or a heteroaryl group and may be bonded to each other to form a ring; $L^1$ represents an arylene group or a heteroarylene group; $L^1$ and $Ar^1$, and/or $L^1$ and $Ar^2$ may be bonded to each other to form a ring; n represents 0 or 1, and when n is 0, $L^1$ represents a single bond.

31. The material for an organic electroluminescent element according to claim 30, wherein at least one of $R^1$ to $R^4$ and at least one of $R^5$ to $R^8$ in the general formula (1) are a substituent represented by the general formula (2).

32. The material for an organic electroluminescent element according to claim 30, represented by the following general formula (3):

General Formula (3)

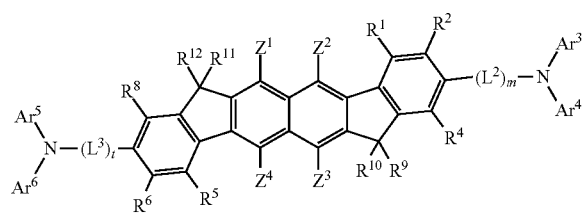

wherein $R^1$, $R^2$, $R^4$ to $R^6$, and $R^8$ each independently represent a hydrogen atom or a substituent, and these may be bonded to each other to form a ring;

$R^9$ to $R^{12}$ each independently represent an aryl group or an alkyl group having 1 to 5 carbon atoms, wherein when $R^9$ and $R^{10}$ are each an alkyl group or an aryl group having an alkyl chain, the total number of carbon atoms in the alkyl groups represented by $R^9$ and $R^{10}$ is from 2 to 8, and wherein when $R^{11}$ and $R^{12}$ are each an alkyl group or an aryl group having an alkyl chain, the total number of carbon atoms in the alkyl groups represented by $R^{11}$ and $R^{12}$ is from 2 to 8;

$Ar^3$ to $Ar^6$ each independently represent an alkyl group, an aryl group, or a heteroaryl group, and $Ar^3$ and $Ar^4$ and $Ar^5$ and $Ar^6$ may be respectively bonded to each other to form a ring;

$L^2$ and $L^3$ each independently represent an arylene group or a heteroarylene group; $L^2$ and $Ar^3$ and/or $L^2$ and $Ar^4$, and $L^3$ and $Ar^5$ and/or $L^3$ and $Ar^6$ may be bonded to each other to form a ring;

m and t each independently represent 0 or 1, and when m and t are 0, each of $L^2$ and $L^3$ represents a single bond;

$Z^1$ and $Z^2$ and $Z^3$ and $Z^4$ may be respectively bonded to each other to form a ring, but they do not form an aromatic ring in any case; $Z^1$ and $Z^2$ and $Z^3$ and $Z^4$ are bonded to each other to form a ring, $Z^1$ to $Z^4$ each independently represent an alkyl group, an aryl group, a heteroaryl group, a silyl group, —O—, or —NY—, provided that Y is an alkyl group or an aryl group and provided that $Z^1$ and $Z^2$ are not both alkyl groups in any case and $Z^3$ and $Z^4$ are not both alkyl groups in any case; when $Z^1$ and $Z^2$ and $Z^3$ and $Z^4$ are not bonded to each other to form a ring, $Z^1$ to $Z^4$ each independently represents a hydrogen atom, a deuterium atom, an alkyl group, an aryl group, a heteroaryl group, a fluorine atom, a silyl group, or a cyano group.

* * * * *